(12) United States Patent
Guba et al.

(10) Patent No.: US 7,135,488 B2
(45) Date of Patent: Nov. 14, 2006

(54) PYRROLYL-THIAZOLE DERIVATIVES

(75) Inventors: Wolgang Guba, Muellheim (DE); Wolfgang Haap, Loerrach (DE); Hans Peter Marty, Basel (CH); Robert Narquizian, St. Louis (FR)

(73) Assignee: Hoffmann-La Roche Inc., Nutley, NJ (US)

( * ) Notice: Subject to any disclaimer, the term of this patent is extended or adjusted under 35 U.S.C. 154(b) by 5 days.

(21) Appl. No.: 10/743,403

(22) Filed: Dec. 22, 2003

(65) Prior Publication Data
US 2004/0147572 A1 Jul. 29, 2004

(30) Foreign Application Priority Data
Jan. 2, 2003 (EP) ................................. 03000002

(51) Int. Cl.
*A61K 31/427* (2006.01)
*C07D 403/04* (2006.01)

(52) U.S. Cl. .................. 514/365; 514/326; 514/342; 514/236.8; 514/255.05; 544/133; 544/405; 546/270.4; 546/269.7; 546/209; 548/202

(58) Field of Classification Search ............... 548/202; 546/270.4, 269.7, 209; 544/133, 405; 514/365, 514/326, 342, 236.8, 255.05
See application file for complete search history.

(56) References Cited

U.S. PATENT DOCUMENTS

| 3,940,418 A | | 2/1976 | Hamilton |
| 5,342,851 A | * | 8/1994 | Sanfilippo et al. .......... 514/370 |
| 5,596,106 A | | 1/1997 | Cullinan et al. |
| 5,624,941 A | | 4/1997 | Barth et al. |
| 2004/0167129 A1 | * | 8/2004 | Mayweg et al. .......... 514/227.8 |

FOREIGN PATENT DOCUMENTS

| EP | 576357 | 12/1993 |
| EP | 656354 | 6/1995 |
| EP | 658546 | 6/1995 |
| WO | WO9602248 | 2/1996 |
| WO | WO9719063 | 5/1997 |
| WO | WO0015609 | 3/2000 |
| WO | WO 00 46209 | 8/2000 |
| WO | WO0046209 | 8/2000 |
| WO | WO0132663 | 5/2001 |
| WO | WO 01 58869 | 8/2001 |
| WO | WO0164632 | 9/2001 |
| WO | WO0164633 | 9/2001 |
| WO | WO0164634 | 9/2001 |
| WO | WO0170700 | 9/2001 |
| WO | WO0228346 | 4/2002 |

OTHER PUBLICATIONS

Pacheco, M., et al., Aminoalkylindoles: Actions on Specific G-Protein-Linked Receptors, Journal of Pharmacology and Experimental Therapeutics, 1991, pp. 170-183, v. 257(1).
Casiano, F.M., et al., Putative Aminoalkylindoles (AAI) Antagonists, Problems of Drug Dependence 1990: Proceedings of the 52nd Annual Scientific Meeting The Committeee on Problems of Drug Dependence, 1991, pp. 295-296, v. 105.
Hosohata, K., et al., AM630 is a Competitive Cannabinoid Receptor Antagonist in the Guinea Pig Brain, Life Sciences, 1997, pp. 115-118, v. 61(9).
Pertwee, R., et al., AM630, A Competitive Cannabinoid Receptor Antagonist, Life Sciences, 1995, pp. 1949-1955, v. 56(23/24).
Felder, C.C., et al., LY320135, a Novel Cannabinoid CB1 Receptor Antagonist, Unmasks Coupling of the CB1 Receptor to Stimulation of cAMP Accumulation, Journal of Pharmacology and Experimental Therapeutics, 1998, pp. 291-297, v. 284(1).
Kanyonyo, M. et al., 3-Alkyl-(5,5'-Diphenyl) Imidazolidinediones As New Cannabinoid Ligands, Bioorganic & Medicinal Chemistry Letters, 1999, pp. 2233-2236, v. 9.
Ooms, F., et al., Exploration of the Pharmacophore of 3-Alkyl-5-Arylimidazolidinediones as New $CB_1$ Cannabinoid Receptor Ligands and Potential Antagonists: Synthesis, Lipophilicity, Affinity, and Molecular Modeling, J. Med. Chem., 2002, pp. 1748-1756, v. 45(9).

* cited by examiner

*Primary Examiner*—Laura L. Stockton
(74) *Attorney, Agent, or Firm*—George W. Johnston; Patricia S. Rocha-Tramaloni; Brian C. Remy

(57) ABSTRACT

The present invention relates to compounds of formula (I)

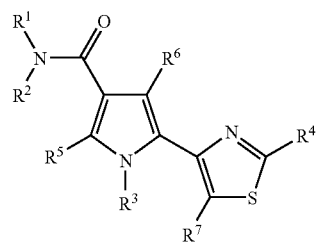

wherein $R^1$, $R^2$, $R^3$, $R^4$, $R^5$, $R^6$ and $R^7$ are as defined in the description and claims, and pharmaceutically acceptable salts thereof. The compounds are useful for the treatment and/or prophylaxis of diseases which are associated with the modulation of CB1 receptors.

34 Claims, No Drawings

1

PYRROLYL-THIAZOLE DERIVATIVES

BACKGROUND OF THE INVENTION

The present invention is concerned with novel pyrrolyl-thiazole derivatives, their manufacture, pharmaceutical compositions containing them and their use as medicaments. The active compounds of the present invention may be useful in treating obesity and other disorders.

Two different subtypes of cannabinoid receptors ($CB_1$ amd $CB_2$) have been isolated and both belong to G protein coupled receptor superfamily. An alternative spliced form of $CB_1$, $CB_{1A}$, has also been described, but it did not exhibit different properties in terms of ligand binding and receptor activation than $CB_1$ (D. Shire, C. Carrillon, M. Kaghad, B. Calandra, M. Rinaldi-Carmona, G. Le Fur, D. Caput, P. Ferrara, J. Biol. Chem. 270 (8) (1995) 3726–31). The $CB_1$ receptor is mainly located in the brain, whereas the $CB_2$ receptor is predominately distributed in the periphery and primarily localized in spleen and cells of the immune system (S. Munro, K. L. Thomas, M. Abu-Shaar, Nature 365 (1993) 61–61). Therefore in order to avoid side effects a $CB_1$-selective compound is desirable.

$\Delta^9$-tetrahydrocannabinol ($\Delta^9$-THC) is the principal psychoactive compound in the Indian hemp (Y. Gaoni, R. Mechoulam, J. Am. Chem. Soc., 86 (1964) 1646), *canabis savita* (marijuanan), which is used in medicine since ages (R. Mechoulam (Ed.) in *"Cannabinoids as therapeutic Agents"*, 1986, pp. 1–20, CRC Press). $\Delta^9$-THC is a nonselective $CB_1/_2$ receptor agonist and is available in the USA as dronabinol (marinol®) for the alleviation of cancer chemotherapy-induced emesis (CIE) and the reversal of body weight loss experienced by AIDS patients through appetite stimulation. In the UK Nabolinone (LY-109514, Cesamet®), a synthetic analogue of $\Delta^9$-THC, is used for CIE (R. G. Pertwee, Pharmaceut. Sci. 3 (11) (1997) 539–545, E. M. Williamson, F. J. Evans, Drugs 60 (6) (2000) 1303–1314).

Anandamide (arachidonylethanolamide) was identified as the endogenous ligand (agonist) for the $CB_1$ receptor (R. G. Pertwee, Curr. Med. Chem., 6 (8) (1999) 635–664; W. A. Devane, L. Hanus, A. Breuer, R. G. Pertwee, L. A. Stevenson, G. Griffin, D. Gibson, A. Mandelbaum, A. Etinger, R. Mechoulam, Science 258 (1992) 1946–9). Anandamide and 2-arachidonoylglycerol (2-AG) modulate at the presynaptic nerve teminal negatively adenylate cyclase and voltage-sensitive $Ca^{2+}$ channels and activates the inwardly rectifying $K^+$ channel (V. Di Marzo, D. Melck, T. Bisogno, L. De Petrocellis, Trends in Neuroscience 21 (12) (1998) 521–8), thereby affecting neurotransmitter release and/or action, which decreases the release of neurotransmitter (A. C. Porter, C. C. Felder, Pharmacol. Ther., 90 (1) (2001) 45–60).

Anandamide as $\Delta^9$-THC also increases feeding through $CB_1$ receptor-mediated mechanism. $CB_1$ receptor selective antagonists block the increase in feeding associated with administration of anandamide (C. M. Williams, T. C. Kirkham, Psychopharmacology 143 (3) (1999) 315–317; C. C. Felder, E. M. Briley, J. Axelrod, J. T. Simpson, K. Mackie, W. A. Devane, Proc. Natl. Acad. Sci. U.S.A. 90 (16) (1993) 7656–60) and caused appetite suppression and weight loss (G. Colombo, R. Agabio, G. Diaz, C. Lobina, R. Reali, G. L. Gessa, Life Sci. 63 (8) (1998) L113–PL117).

Leptin is the primary signal through which the hypothalamus senses nutritional state and modulates food intake and energy balance. Following temporary food restriction, CB1 receptor knockout mice eat less than their wild-type littermates, and the CB1 antagonist SR141716A reduces food intake in wild-type but not knockout mice. Furthermore, defective leptin signaling is associated with elevated hypothalamic, but not cerebellar, levels of endocannabinoids in obese db/db and ob/ob mice and Zucker rats. Acute leptin treatment of normal rats and ob/ob mice reduces anandamide and 2-arachidonoyl glycerol in the hypothalamus. These findings indicate that endocannabinoids in the hypothalamus may tonically activate CB1 receptors to maintain food intake and form part of the neural circuitry regulated by leptin (V. Di Marzo, S. K. Goparaju, L. Wang, J. Liu, S. Bitkai, Z. Jarai, F. Fezza, G. I. Miura, R. D. Palmiter, T. Sugiura, G. Kunos, Nature 410 (6830) 822–825).

SR-141716A, a CB1 selective antagonist/inverse agonist is undergoing currently phase III clinical trials for the treatment of obesity. In a double blind placebo-controlled study, at the doses of 5, 10 and 20 mg daily, SR 141716 significantly reduced body weight when compared to placebo (F. Barth, M. Rinaldi-Carmona, M. Arnone, H. Heshmati, G. Le Fur, "*Cannabinoid antagonists: From research tools to potential new drugs.*" Abstracts of Papers, 222nd ACS National Meeting, Chicago, Ill., United States, Aug. 26–30, 2001).

Other compounds which have been proposed as CB1 receptor antagonists respectively inverse agonists are aminoalkylindols (AAI; M. Pacheco, S. R. Childers, R. Arnold, F. Casiano, S. J. Ward, J. Pharmacol. Exp. Ther. 257 (1) (1991) 170–183), like 6-bromo- (WIN54661; F. M. Casiano, R. Arnold, D. Haycock, J. Kuster, S. J. Ward, NIDA Res. Monogr. 105 (1991) 295–6) or 6-iodopravadoline (AM630, K. Hosohata, R. M. Quock, R. M; Hosohata, T. H. Burkey, A. Makriyannis, P. Consroe, W. R. Roeske, H. I. Yamamura, Life Sci. 61 (1997) 115–118; R. Pertwee, G. Griffin, S. Fernando, X. Li, A. Hill, A. Makriyannis, Life Sci. 56 (23–24) (1995) 1949–55). Arylbenzo[b]thiophene and benzo[b]furan (LY320135, C. C. Felder, K. E. Joyce, E. M. Briley, M. Glass, K. P. Mackie, K. J. Fahey, G. J. Cullinan, D. C. Hunden, D. W. Johnson, M. O. Chaney, G. A. Koppel, M. Brownstein, J. Pharmacol. Exp. Ther. 284 (1) (1998) 291–7) disclosed in WO9602248, U.S. Pat. No. 5,596,106, 3-alkyl-(5,5-diphenyl)imidazolidinediones (M. Kanyonyo, S. J. Govaerts, E. Hermans, J. H. Poupaert, D. M. Lambert, Bioorg. Med. Chem. Lett. 9 (15) (1999) 2233–2236.) as well as 3-alkyl-5-arylimidazolidinediones (F. Ooms, J. Wouters, O. Oscaro. T. Happaerts, G. Bouchard, P.-A. Carrupt, B. Testa, D. M. Lambert, J. Med. Chem. 45 (9) (2002) 1748–1756) are known to antagonize the $CB_1$ receptor respectively act as an inverse agonist on the $hCB_1$ receptor. WO0015609 (FR2783246-A1), WO0164634 (FR2805817-A1), WO0228346, WO0164632 (FR2805818-A1), WO0164633 (FR2805810-A1) disclosed substituted 1-bis(aryl)methyl-azetidines derivatives as antagonists of $CB_1$. In WO0170700 4,5-dihydro-1H-pyrazole derivatives are described as $CB_1$ antagonists. In several patents bridged and non-bridged 1,5-diphenyl-3-pyrazolecarboxamide derivatives are disclosed as $CB_1$ antagonists/inverse agonists (WO0132663, WO0046209, WO9719063, EP658546, EP656354, U.S. Pat. No. 5,624,941, EP576357, U.S. Pat. No. 3,940,418).

SUMMARY OF THE INVENTION

The present invention relates to compounds of formula (I):

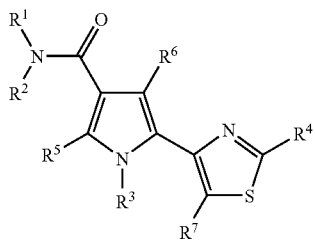

wherein
$R^1$, $R^2$, $R^3$, $R^4$, $R^5$, $R^6$ and $R^7$ are as herein defined, or a pharmaceutically acceptable salt thereof.

According to one aspect of the present invention, compounds of formula (I) may be selective, directly acting CB1 receptor antagonists respectively inverse agonists. Such antagonists/inverse antagonists are useful in medical therapy, particularly in the treatment and/or prevention of diseases which are associated with the modulation of CB1 receptors.

Unless otherwise indicated, the following definitions are set forth to illustrate and define the meaning and scope of the various terms used to describe the invention herein.

In this specification the term "lower" is used to mean a group consisting of one to eight, preferably of one to four carbon atom(s).

The term "halogen" refers to fluorine, chlorine, bromine and iodine, preferably to chlorine and fluorine.

The term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

The term "lower alkyl", alone or in combination with other groups, refers to a branched or straight-chain monovalent alkyl radical of one to eight carbon atoms, preferably one to four carbon atoms. This term is further exemplified by radicals such as methyl, ethyl, n-propyl, isopropyl, n-butyl, s-butyl, isobutyl, t-butyl, n-pentyl, 3-methylbutyl, n-hexyl, 2-ethylbutyl and the like.

The term "alkoxy" refers to the group R'—O—, wherein R' is alkyl. The term "lower alkoxy" refers to the group R'—O—, wherein R' is lower alkyl. Examples of lower alkoxy groups are e.g. methoxy, ethoxy, propoxy, isopropoxy, butoxy, isobutoxy and hexyloxy, with methoxy being especially preferred.

The term "lower alkenyl" refers to a lower alkyl group containing one or more double bond(s) in the alkylene chain. This term is further exemplified by radicals such as vinyl, 1-propenyl, allyl, 1-butenyl, 2-butenyl and 3-butenyl, with allyl being preferred.

The term "lower alkylamino" refers to the group R'—NH—, wherein R' is lower alkyl.

The term "lower alkoxycarbonyl" refers to the group R'—O—C(O)—, wherein R' is lower alkyl.

The term "lower alkoxycarbonylamino" refers to the group R'—O—C(O)NH—, wherein R' is lower alkyl.

The term "halogenated lower alkyl" refers to a lower alkyl group wherein at least one of the hydrogens of the lower alkyl group is replaced by a halogen atom, preferably fluoro or chloro. Among the preferred halogenated lower alkyl groups are trifluoromethyl, difluoromethyl, fluoromethyl and chloromethyl, with trifluoromethyl being especially preferred. The term "fluorinated lower alkyl" refers to a lower alkyl group wherein at least one of the hydrogens of the lower alkyl group is replaced by fluoro. Among the preferred fluorinated lower alkyl groups are trifluoromethyl, difluoromethyl and fluoromethyl, with trifluoromethyl being especially preferred.

The term "halogenated lower alkoxy" refers to a lower alkoxy group wherein at least one of the hydrogens of the lower alkoxy group is replaced by halogen, preferably by fluorine or chlorine. Among the preferred halogenated lower alkoxy groups are fluorinated lower alkoxy groups such as trifluoromethoxy, difluoromethoxy and fluoromethoxy, with trifluoromethoxy being especially preferred. The term "fluorinated lower alkoxy" refers to a lower alkoxy group wherein at least one of the hydrogens of the lower alkoxy group is replaced by fluoro. Among the preferred fluorinated lower alkoxy groups are trifluoromethoxy, difluoromethoxy and fluoromethoxy, with trifluoromethoxy being especially preferred.

The term "di-phenyl-lower alkyl" refers to a lower alkyl group wherein two of the hydrogens of the lower alkyl group is replaced by phenyl. The phenyl moiety may optionally be mono-, di-, or tri-substituted, independently, by lower alkyl, lower alkoxy or halogen.

The term "phenoxy-lower alkyl" refers to a lower alkyl group wherein one of the hydrogens of the lower alkyl group is replaced by phenoxy. The phenyl moiety of the phenoxy-lower alkyl residues may optionally be mono-, di-, or tri-substituted, independently, by lower alkyl, lower alkoxy or halogen.

The term "cycloalkyl" refers to a monovalent carbocyclic radical of three to six, preferably three to five carbon atoms. This term is further exemplified by radicals such as cyclopropyl, cyclobutyl, cyclopentyl and cyclohexyl.

The term "cycloalkenyl" refers to a monovalent carbocyclic radical of three to six, preferably three to five carbon atoms, which carbocyclic ring contains at least on double bond. This term is further exemplified by radicals such as cyclobutenyl, cyclopentenyl and cyclohexenyl, with cyclohexenyl being preferred.

The term "pharmaceutically acceptable salts" embraces salts of the compounds of formula (I) with inorganic or organic acids such as hydrochloric acid, hydrobromic acid, nitric acid, sulphuric acid, phosphoric acid, citric acid, formic acid, maleic acid, acetic acid, fumaric acid, succinic acid, tartaric acid, methanesulphonic acid, salicylic acid, p-toluenesulphonic acid and the like, which are non toxic to living organisms. Preferred salts with acids are formates, maleates, citrates, hydrochlorides, hydrobromides and methanesulfonic acid salts, with hydrochlorides being especially preferred.

DETAILED DESCRIPTION OF THE INVENTION

In particular, the present invention relates to compounds of formula (I):

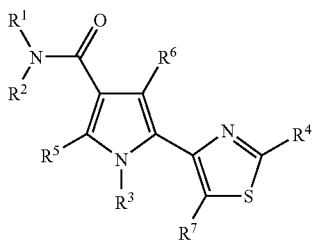

wherein
R¹ is hydrogen, or lower alkyl;
R² is hydrogen, lower alkyl, lower alkenyl, lower alkoxy-lower alkyl, lower alkoxycarbonylamino, —(CH²)ₘ—R²ᵃ or —NHC(O)—R²ᵃ;
or R¹ and R² together with the nitrogen atom to which they are attached form a 5- or 6-membered, saturated heterocyclic ring optionally containing one or two further heteroatom(s) independently selected from nitrogen, oxygen and sulfur, said heterocyclic ring being optionally mono-, di- or tri-substituted, independently, by hydroxy, lower alkyl, lower alkoxy, amino, lower alkylamino, fluorinated lower alkyl or fluorinated lower alkoxy;
R²ᵃ is cycloalkyl, optionally mono-, di-, tri- or tetra-substituted, independently, by hydroxy, lower alkyl, lower alkoxy, fluorinated lower alkyl or fluorinated lower alkoxy; cycloalkenyl, optionally mono-, di- or tri-substituted, independently, by hydroxy, lower alkyl, lower alkoxy, fluorinated lower alkyl or fluorinated lower alkoxy; a 5- or 6-membered monovalent saturated heterocyclic ring containing one to three heteroatoms independently selected from nitrogen, oxygen and sulfur, said heterocyclic ring being optionally mono-, di- or tri-substituted, independently, by hydroxy, lower alkyl, lower alkoxy, amino, lower alkylamino, fluorinated lower alkyl or fluorinated lower alkoxy; a 5- or 6-membered monovalent heteroaromatic ring containing one to three heteroatoms independently selected from nitrogen, oxygen and sulfur, said heteroaromatic ring being optionally mono-, di- or tri-substituted, independently, by hydroxy, lower alkyl, lower alkoxy, halogen, amino, lower alkylamino; or phenyl, which may optionally be mono-, di- or tri-substituted, independently, by hydroxy, lower alkyl, lower alkoxy, halogen, lower alkylamino, halogenated lower alkyl, halogenated lower alkoxy or nitro;
R³ is lower alkyl, lower alkenyl, lower alkoxy-lower alkyl, di-phenyl-lower alkyl, or —(CH₂)ₙ—R³ᵃ;
R³ᵃ is cycloalkyl fused to a phenyl ring; or cycloalkyl which may optionally be mono-, di- or tri-substituted, independently, by hydroxy, lower alkyl, lower alkoxy, fluorinated lower alkyl or fluorinated lower alkoxy; cycloalkenyl, which may optionally be mono-, di- or tri-substituted, independently, by hydroxy, lower alkyl, lower alkoxy, fluorinated lower alkyl or fluorinated lower alkoxy; a 5- or 6-membered monovalent saturated heterocyclic ring containing one to three heteroatoms independently selected from nitrogen, oxygen and sulfur, said heterocyclic ring being optionally mono-, di- or tri-substituted, independently, by hydroxy, lower alkyl, lower alkoxy, amino, lower alkylamino, fluorinated lower alkyl or fluorinated lower alkoxy; a 5- or 6-membered monovalent heteroaromatic ring containing one to three heteroatoms independently selected from nitrogen, oxygen and sulfur, said heteroaromatic ring being optionally mono-, di- or tri-substituted, independently, by hydroxy, lower alkyl, lower alkoxy, halogen, amino or lower alkylamino; or phenyl, which may optionally be mono-, di- or tri-substituted, independently, by hydroxy, lower alkyl, lower alkoxy, halogen, lower alkylamino, halogenated lower alkyl, halogenated lower alkoxy or nitro;
R⁴ is lower alkyl, lower alkoxycarbonyl; cycloalkyl, which may optionally be mono-, di- or tri-substituted, independently, by hydroxy, lower alkyl, lower alkoxy, fluorinated lower alkyl or fluorinated lower alkoxy; a 5- or 6-membered monovalent heteroaromatic ring containing one to three heteroatoms independently selected from nitrogen, oxygen and sulfur, said heteroaromatic ring being optionally mono-, di- or tri-substituted, independently, by hydroxy, lower alkyl, lower alkoxy, halogen, amino, lower alkylamino; phenoxy-lower alkyl, wherein the phenyl moiety may optionally be mono-, di- or tri-substituted, independently, by hydroxy, lower alkyl, lower alkoxy, halogen, lower alkylamino, halogenated lower alkyl, halogenated lower alkoxy or nitro; or phenyl, which may optionally be mono-, di- or tri-substituted, independently, by, hydroxy, lower alkyl, lower alkoxy, halogen, lower alkylamino, halogenated lower alkyl, halogenated lower alkoxy or nitro; or two adjacent substituents of the said phenyl residue together are —O—(CH₂)ₚ—O— or —(CH₂)₂—O—;
R⁵ and R⁶ are each independently selected from hydrogen, lower alkyl, halogen or fluorinated methyl;
R⁷ is hydrogen, lower alkyl or halogen;
m is 0, 1, 2 or 3;
n is 0, 1, 2, 3 or 4;
p is 1, 2 or 3;

or a pharmaceutically acceptable salts thereof.

In one embodiment, the present invention relates to a compound of formula (I) as defined above, wherein R¹ is hydrogen or lower alkyl.

Preferable lower alkyl residues R¹ are methyl and ethyl, with methyl being especially preferred. Most preferably, R¹ is hydrogen.

In another embodiment, the present invention relates to a compound of formula (I) as defined above, wherein R² is hydrogen, lower alkyl, lower alkenyl, lower alkoxy-lower alkyl, lower alkoxycarbonylamino, —(CH₂)ₘ—R²ᵃ or —NHC(O)—R²ᵃ.

Preferable lower alkyl residues R² are branched or straight chain alkyl residues with one to eight, preferably three to five carbon atoms, such as n-propyl, n-butyl, s-butyl, isobutyl, n-pentyl and 2-ethylhexyl. Most preferred lower alkyl residues R² are n-propyl, n-butyl, s-butyl, isobutyl and n-pentyl. Preferable lower alkenyl residues R² are 1-butenyl and allyl, with allyl being especially preferred. Preferable lower alkoxy-lower alkyl residues R² are methoxymethyl, methoxyethyl, methoxypropyl, ethoxymethyl, ethoxyethyl and ethoxypropyl, with methoxyethyl and methoxypropyl being especially preferred. Preferable lower alkoxycarbonylamino groups R² are methoxycarbonylamino, ethoxycarbonylamino, propoxycarbonylamino and butoxycarbonylamino, with ethoxycarbonylamino being especially preferred. Preferable residues R² are lower alkyl as defined above, —(CH₂)ₘ—R²ᵃ or —NHC(O)—R²ᵃ, wherein R²ᵃ is as defined below and m is 0 or 1, preferably 0. Most preferable residues R² are lower alkyl as defined above or —(CH₂)ₘ—R²ᵃ, wherein R²ᵃ is as defined below and m is 0 or 1, preferably 0.

In one embodiment, $R^{2a}$ is cycloalkyl, optionally mono-, di-, tri- or tetra-substituted, independently, by hydroxy, lower alkyl, lower alkoxy, fluorinated lower alkyl or fluorinated lower alkoxy; cycloalkenyl, optionally mono-, di- or tri-substituted, independently, by hydroxy, lower alkyl, lower alkoxy, fluorinated lower alkyl or fluorinated lower alkoxy; a 5- or 6-membered monovalent saturated heterocyclic ring containing one to three heteroatoms independently selected from nitrogen, oxygen and sulfur, said heterocyclic ring being optionally mono-, di- or tri-substituted, independently, by hydroxy, lower alkyl, lower alkoxy, amino, lower alkylamino, fluorinated lower alkyl or fluorinated lower alkoxy; a 5- or 6-membered monovalent heteroaromatic ring containing one to three heteroatoms independently selected from nitrogen, oxygen and sulfur, said heteroaromatic ring being optionally mono-, di- or tri-substituted, independently, by hydroxy, lower alkyl, lower alkoxy, halogen, amino, lower alkylamino; or phenyl, which may optionally be mono-, di- or tri-substituted, independently, by hydroxy, lower alkyl, lower alkoxy, halogen, lower alkylamino, halogenated lower alkyl, halogenated lower alkoxy or nitro.

Preferable cycloalkyl residues $R^{2a}$ are cycloalkyl residues with three to six carbon atoms, such as cyclopropyl, cyclobutyl, cyclopentyl and cyclohexyl, which may optionally be mono-, di-, tri-or tetra-substituted, preferably mono- or tetra-substituted, independently, by hydroxy, lower alkyl, lower alkoxy, fluorinated lower alkyl or fluorinated lower alkoxy, preferably by lower alkyl, such as methyl, and/or hydroxy. Most preferable cycloalkyl residues $R^{2a}$ are cyclopropyl, cyclobutyl, cyclopentyl, cyclohexyl and 2-hydroxy-cyclopentyl.

Preferable cycloalkenyl residues $R^{2a}$ are cyclobutenyl, cyclopentenyl and cyclohexenyl, with cyclohexenyl, preferably cyclohex-1-enyl, being especially preferred. Preferable heterocyclic rings $R^{2a}$ are 5- or 6-memberd, with 5-membered being especially preferred, and contain one to three, preferably one or two, heteroatoms independently selected from nitrogen, oxygen and sulfur, preferably selected form nitrogen and oxygen, said heterocyclic ring being optionally mono-, di- or tri-substituted, independently, by hydroxy, lower alkyl, lower alkoxy, amino, lower alkylamino, fluorinated lower alkyl or fluorinated lower alkoxy. Preferably, heterocyclic rings $R^{2a}$ are unsubstituted. Most preferred heterocyclic rings $R^{2a}$ are piperidinyl, morpholino and tetrahydrofuranyl, with piperidinyl and morpholino being especially preferred. Preferable heteroaromatic rings $R^{2a}$ are 5- or 6-membered and contain one to three, preferably one or two, heteroatoms independently selected from nitrogen, oxygen and sulfur, preferably selected form nitrogen and sulfur, said heteroaromatic ring being optionally mono-, di- or tri-substituted, independently, by hydroxy, lower alkyl, lower alkoxy, halogen, amino or lower alkylamino. Examples of heteroaromatic rings $R^{2a}$ are pyridinyl, pyrimidinyl, thiazolyl and isoxazolyl, optionally substituted as defined above. Preferably, heteroaromatic rings $R^{2a}$ are unsubstituted or mono-substituted by lower alkyl, preferably methyl. Most preferable heteroaromatic rings $R^{2a}$ are pyridinyl, pyrimidinyl, 4-methylthiazolyl or 5-methylisoxazolyl. Preferable phenyl residues $R^{2a}$ are optionally mono-, di- or tri-substituted, preferably mono- or di-substituted, independently, by lower alkoxy, such as methoxy, halogen, such as chloro, halogenated lower alkyl, such as trifluoromethyl, halogenated lower alkoxy, such as trifluoromethoxy, or nitro. Most preferable phenyl residues $R^{2a}$ are unsubstituted phenyl, 4-trifluoromethyl-phenyl, 4-chloro-phenyl, 3,4-dichloro-phenyl, 3,4-dimethoxy-phenyl, 2-nitro-phenyl and 4-trifluoromethoxy-phenyl. Preferably, m is 0, 1 or 2, more preferably m is 0 or 1, most preferably m is 0.

In another embodiment, $R^1$ and $R^2$ together with the nitrogen atom to which they are attached form a 5- or 6-membered, saturated heterocyclic ring optionally containing one or two, preferably one, further heteroatom(s) independently selected from nitrogen, oxygen and sulfur, preferably oxygen, said heterocyclic ring being optionally mono-, di- or tri-substituted, independently, by hydroxy, lower alkyl, lower alkoxy, amino, lower alkylamino, fluorinated lower alkyl or fluorinated lower alkoxy. Preferably, heterocyclic rings formed by $R^1$ and $R^2$ together with the nitrogen atom to which they are attached are unsubstituted, with unsubstituted pyrrolidinyl, piperidinyl and morpholino being especially preferred.

In another embodiment, the present invention relates to a compound of formula (I) as defined above, wherein $R^3$ is lower alkyl, lower alkenyl, lower alkoxy-lower alkyl, di-phenyl-lower alkyl, or —$(CH_2)_n$—$R^{3a}$.

Preferable lower alkyl residues $R^3$ are branched or straight chain alkyl residues with one to six, preferably four carbon atoms, such as ethyl, n-propyl, isopropyl, n-butyl, s-butyl, isobutyl, n-pentyl and n-hexyl. Most preferred lower alkyl residues $R^3$ are n-butyl and s-butyl. Preferable lower alkenyl residues $R^3$ are 1-butenyl and allyl, with allyl being especially preferred. Preferable lower alkoxy-lower alkyl residues $R^3$ are methoxymethyl, methoxyethyl, methoxypropyl, ethoxymethyl, ethoxyethyl and ethoxypropyl, with methoxyethyl and methoxypropyl being especially preferred. Preferable di-phenyl-lower alkyl is di-phenyl-methyl. Most preferably, $R^3$ is a residue —$(CH_2)_n$—$R^{3a}$, wherein $R^{3a}$ is as defined below and n is 1 or 2, preferably 1.

In one embodiment, $R^{3a}$ is cycloalkyl fused to a phenyl ring; or cycloalkyl which may optionally be mono-, di- or tri-substituted, independently, by hydroxy, lower alkyl, lower alkoxy, fluorinated lower alkyl or fluorinated lower alkoxy; cycloalkenyl, which may optionally be mono-, di- or tri-substituted, independently, by hydroxy, lower alkyl, lower alkoxy, fluorinated lower alkyl or fluorinated lower alkoxy; a 5- or 6-membered monovalent saturated heterocyclic ring containing one to three heteroatoms independently selected from nitrogen, oxygen and sulfur, said heterocyclic ring being optionally mono-, di- or tri-substituted, independently, by hydroxy, lower alkyl, lower alkoxy, amino, lower alkylamino, fluorinated lower alkyl or fluorinated lower alkoxy; a 5- or 6-membered monovalent heteroaromatic ring containing one to three heteroatoms independently selected from nitrogen, oxygen and sulfur, said heteroaromatic ring being optionally mono-, di- or tri-substituted, independently, by hydroxy, lower alkyl, lower alkoxy, halogen, amino or lower alkylamino; or phenyl, which may optionally be mono-, di- or tri-substituted, independently, by hydroxy, lower alkyl, lower alkoxy, halogen, lower alkylamino, halogenated lower alkyl, halogenated lower alkoxy or nitro.

Preferable cycloalkyl residues $R^{3a}$ are cycloalkyl residues with five or six carbon atoms, which may optionally be mono-, di- or tri-substituted, independently, by hydroxy, lower alkyl, lower alkoxy, fluorinated lower alkyl or fluorinated lower alkoxy, or which may optionally be fused to a phenyl ring. Preferably, cycloalkyl residues $R^{3a}$ are unsubstituted, such as unsubstituted cyclopentyl or unsubstituted cyclohexyl, with unsubstituted cyclohexyl being preferred, or fused to a phenyl residue, such as indanyl. Preferable cycloalkenyl residues $R^{2a}$ are cyclobutenyl, cyclopentenyl and cyclohexenyl, with cyclohexenyl, preferably cyclohex-1-enyl, being especially preferred. Preferable heterocyclic rings $R^{3a}$ are 5- or 6-membered and contain one to three, preferably one or two, heteroatoms independently selected from nitrogen, oxygen and sulfur, preferably selected form nitrogen and oxygen, said heterocyclic ring being optionally mono-, di- or tri-substituted, independently, by hydroxy, lower alkyl, lower alkoxy, amino, lower alkylamino, fluorinated lower alkyl or fluorinated lower alkoxy. Examples of heterocyclic rings $R^{3a}$ are piperidinyl, morpholino and pyrrolidinyl, optionally substituted as defined above. Preferably, heterocyclic rings $R^{3a}$ are unsubstituted or substituted by lower alkyl, such as methyl or ethyl, with ethyl being especially preferred. Most preferred heterocyclic rings $R^{3a}$ are piperidinyl, morpholino and 1-ethyl-pyrrolidinyl. Preferable heteroaromatic rings $R^{3a}$ are 5- or 6-membered and contain one to three, preferably one, heteroatom(s) independently selected from nitrogen, oxygen and sulfur, said heteroaromatic ring being optionally mono-, di- or tri-substituted, independently, by hydroxy, lower alkyl, lower alkoxy, halogen, amino or lower alkylamino. Examples of heteroaromatic rings $R^{3a}$ are furyl, thienyl and pyridinyl, optionally substituted as defined above. Preferably, heteroaromatic rings $R^{3a}$ are unsubstituted or mono-substituted by lower alkyl, preferably methyl. Most preferable heteroaromatic rings $R^{3a}$ are furyl, thienyl, 3-methylthienyl and pyridinyl. Preferable phenyl residues $R^{3a}$ are optionally mono-, di- or tri-substituted, preferably mono- or di-substituted, most preferably mono-substituted, independently, by hydroxy, lower alkyl, such as methyl or isopropyl, lower alkoxy, such as methoxy, halogen, such as chloro, halogenated lower alkyl, such as trifluoromethyl, halogenated lower alkoxy, such as trifluoromethoxy, or nitro. Most preferable phenyl residues $R^{3a}$ are unsubstituted phenyl, 2-methyl-phenyl, 4-methyl-phenyl, 3,4-dimethyl-phenyl, 3,5-dimethyl-phenyl, 4-isopropyl-phenyl, 4-chloro-phenyl, 3,4-dichloro-phenyl, 3,5-dichloro-phenyl, 3-methoxy-phenyl, 4-methoxy-phenyl, 3,4-dimethoxy-phenyl, 3,5-dimethoxy-phenyl, 2,4-dimethoxy-phenyl, 3,4,5-trimethoxy-phenyl, 3-trifluoromethoxy-phenyl, 4-trifluoromethoxy-phenyl, 3-trifluormethyl-4-chlorophenyl and 4-nitro-phenyl, with 4-methoxy-phenyl being especially preferred. Most preferable residue $R^{3a}$ is a phenyl residue as defined above.

Preferably, n is 0, 1, 2 or 3, more preferably n is 1 or 2, most preferably n is 1.

In another embodiment, the present invention relates to a compound of formula (I) as defined above, wherein $R^4$ is lower alkyl; lower alkoxycarbonyl; cycloalkyl, which may optionally be mono-, di- or tri-substituted, independently, by hydroxy, lower alkyl, lower alkoxy, fluorinated lower alkyl or fluorinated lower alkoxy; a 5- or 6-membered monovalent heteroaromatic ring containing one to three heteroatoms independently selected from nitrogen, oxygen and sulfur, said heteroaromatic ring being optionally mono-, di- or tri-substituted, independently, by hydroxy, lower alkyl, lower alkoxy, halogen, amino, lower alkylamino; phenoxy-lower alkyl, wherein the phenyl moiety may optionally be mono-, di- or tri-substituted, independently, by hydroxy, lower alkyl, lower alkoxy, halogen, lower alkylamino, halogenated lower alkyl, halogenated lower alkoxy or nitro; or phenyl, which may optionally be mono-, di- or tri-substituted, independently, by hydroxy, lower alkyl, lower alkoxy, halogen, lower alkylamino, halogenated lower alkyl, halogenated lower alkoxy or nitro; or two adjacent substituents of the said phenyl residue together are —O—$(CH_2)_p$—O— or —$(CH_2)_2$—O—.

Preferable lower alkyl residues $R^4$ are branched or straight chain alkyl residues with one to six, preferably one to three carbon atoms, such as methyl, ethyl, n-propyl, isopropyl, n-butyl, s-butyl, t-butyl, isobutyl and n-pentyl. Most preferred lower alkyl residue $R^4$ is methyl. Preferable lower alkoxycarbonylamino groups $R^4$ are methoxycarbonylamino, ethoxycarbonylamino, propoxycarbonylamino and butoxycarbonylamino, with ethoxycarbonylamino being especially preferred. Preferable cycloalkyl residues $R^4$ are cycloalkyl residues with three to six carbon atoms, such as cyclopropyl, cyclobutyl, cyclopentyl and cyclohexyl, which may optionally be mono-, di-, tri- or tetra-substituted, preferably mono- or tetra-substituted, independently, by hydroxy, lower alkyl, lower alkoxy, fluorinated lower alkyl or fluorinated lower alkoxy, preferably by lower alkyl, such as methyl, and/or hydroxy. Most preferable cycloalkyl residue $R^4$ is unsubstituted cyclohexyl. Preferable heteroaromatic rings $R^4$ are 5- or 6-membered and contain one to three, preferably one or two, heteroatoms independently selected from nitrogen, oxygen and sulfur, preferably selected form nitrogen and sulfur, said heteroaromatic ring being optionally mono-, di- or tri-substituted, independently, by hydroxy, lower alkyl, lower alkoxy, halogen, amino or lower alkylamino. Examples of heteroaromatic rings $R^4$ are pyridinyl, pyrazinyl and thiazolyl, optionally substituted as defined above. Preferably, heteroaromatic rings $R^4$ are unsubstituted or mono-substituted by lower alkyl, such as methyl and ethyl, or by lower alkoxy, such as methoxy. Most preferable heteroaromatic rings $R^4$ are 2-methoxy-pyridinyl, 2-methyl-pyridinyl, pyrazinyl and 2-methyl-thiazolyl.

Preferable phenoxy-lower alkyl residues $R^4$ are phenoxymethyl and phenoxy ethyl, wherein the phenyl moiety may optionally be mono-substituted by lower alkoxy, such as methoxy. Most preferable phenoxy-lower alkyl residue $R^4$ is 3-methoxy-phenoxy-methyl.

Preferable phenyl residues $R^4$ are mono-, di- or tri-substituted, preferably mono-or di-substituted, most preferably mono-substituted, independently, by hydroxy, lower alkyl, such as methyl, ethyl or t-butyl, lower alkoxy, such as methoxy, halogen, such as chloro or fluoro, halogenated lower alkyl, such as trifluoromethyl, halogenated lower alkoxy, such as trifluoromethoxy or nitro. Alternatively, two adjacent substituents of the said phenyl residue together may be —O—$(CH_2)_p$—O— or —$(CH_2)_2$—O—, wherein p is 1, 2 or 3, preferably 1 or 2, most preferably 1. Preferable substituents of phenyl residues $R^4$ are nitro and lower alkoxy, or two adjacent substituents being —O—$CH_2$—O—. Most preferable substituted phenyl residues $R^4$ are 2-methyl-phenyl, 4-methyl-phenyl, 4-ethyl-phenyl, 4-t-butyl-phenyl, 2-chloro-phenyl, 4-chloro-phenyl, 2,4-dichloro-phenyl, 2-fluoro-phenyl, 4-fluoro-phenyl, 2-methoxy-phenyl, 3-methoxy-phenyl, 4-methoxy-phenyl, 3,4-dimethoxy-phenyl, 3,5-dimethoxy-phenyl, 4-hydroxy-phenyl, 4-trifluoromethyl-phenyl, 4-trifluoromethoxy-phenyl, 4-nitro-phenyl, benzo[1,3]dioxolyl and 2,3-dihydro-benzofuranyl, with 4-methoxyphenyl, 4-nitro-phenyl and benzo[1,3]dioxolyl being especially preferred.

Preferable residues $R^4$ are cycloalkyl residues and substituted phenyl residues as defined above.

In another embodiment, the present invention relates to a compound of formula (I) as defined above, wherein $R^5$ and $R^6$ are each independently selected from hydrogen, lower alkyl, halogen or fluorinated methyl.

Preferable lower alkyl residues $R^5$ and $R^6$ are methyl and ethyl, with methyl being especially preferred. Preferable halogen residues $R^5$ and $R^6$ are fluoro and chloro, with chloro being especially preferred. Preferable residue $R^5$ is lower alkyl, such as methyl. Preferable residues $R^6$ are hydrogen and lower alkyl, such as methyl.

In another embodiment, the present invention relates to a compound of formula (I) as defined above, wherein $R^7$ is hydrogen, lower alkyl or halogen.

Preferable lower alkyl residues $R^7$ are methyl and ethyl, with methyl being especially preferred. Preferable halogen residues $R^7$ are fluoro and chloro, with chloro being especially preferred. Preferable residue $R^7$ are hydrogen and lower alkyl, such as methyl.

Preferred compounds of general formula (I) are the compounds of Examples 1 to 377, preferably 1 to 375 (see section Examples below) and pharmaceutically acceptable salts thereof.

Especially preferred are the compounds selected from the group consisting of:

Cyclohexylmethyl-5-[2-(4-methoxy-phenyl)-thiazol-4-yl]-2-methyl-1H-pyrrole-3-carboxylic acid butylamide,
1-(4-Methoxy-benzyl)-5-[2-(4-methoxy-phenyl)-thiazol-4-yl]-2-methyl-1H-pyrrole-3-carboxylic acid butylamide,
rac-1-Cyclohexylmethyl-5-[2-(4-methoxy-phenyl)-thiazol-4-yl]-2-methyl-1H-pyrrole-3-carboxylic acid sec-butylamide,
rac-1-Cyclohexylmethyl-5-[2-(4-methoxy-phenoxymethyl)-thiazol-4-yl]-2-methyl-1H-pyrrole-3-carboxylic acid sec-butylamide,
Cyclohexylmethyl-5-[2-(4-methoxy-phenyl)-thiazol-4-yl]-2-methyl-1H-pyrrole-3-carboxylic acid isobutyl-amide,
Furan-2-ylmethyl-5-[2-(4-methoxy-phenyl)-thiazol-4-yl]-2-methyl-1H-pyrrole-3-carboxylic acid isobutyl-amide,
1-(4-Methoxy-benzyl)-5-[2-(4-methoxy-phenyl)-thiazol-4-yl]-2-methyl-1H-pyrrole-3-carboxylic acid isobutyl-amide,
Cyclohexylmethyl-5-[2-(4-methoxy-phenyl)-thiazol-4-yl]-2-methyl-1H-pyrrole-3-carboxylic acid allylamide,
Cyclohexylmethyl-5-[2-(4-methoxy-phenyl)-thiazol-4-yl]-2-methyl-1H-pyrrole-3-carboxylic acid cyclohexylmethyl-amide,
Cyclohexylmethyl-2-methyl-5-(2-pyrazin-2-yl-thiazol-4-yl)-1H-pyrrole-3-carboxylic acid cyclohexylmethyl-amide,
1-(4-Methoxy-benzyl)-5-[2-(4-methoxy-phenyl)-thiazol-4-yl]-2-methyl-1H-pyrrole-3-carboxylic acid cyclohexylmethyl-amide,
5-[2-(4-Methoxy-phenoxymethyl)-thiazol-4-yl]-1-(3-methoxy-propyl)-2-methyl-1H-pyrrole-3-carboxylic acid cyclohexylmethyl-amide,
4-[1-[2-(3,4-Dimethoxy-phenyl)-ethyl]-4-(3-methoxy-propylcarbamoyl)-5-methyl-1H-pyrrol-2-yl]-thiazole-2-carboxylic acid ethyl ester,
Cyclohexylmethyl-5-[2-(4-methoxy-phenyl)-thiazol-4-yl]-2-methyl-1H-pyrrole-3-carboxylic acid piperidin-1-ylamide,
N'-{1-Cyclohexylmethyl-5-[2-(4-methoxy-phenyl)-thiazol-4-yl]-2-methyl-1H-pyrrole-3-carbonyl}-hydrazinecarboxylic acid ethyl ester,
rac-1-Cyclohexylmethyl-5-[2-(4-methoxy-phenyl)-thiazol-4-yl]-2-methyl-1H-pyrrole-3-carboxylic acid sec-butylamide,
{1-Cyclohexylmethyl-5-[2-(4-methoxy-phenyl)-thiazol-4-yl]-2-methyl-1H-pyrrol-3-yl}-piperidin-1-yl-methanone,
Cyclohexylmethyl-5-[2-(4-methoxy-phenyl)-thiazol-4-yl]-2-methyl-1H-pyrrole-3-carboxylic acid phenylamide,
Cyclohexylmethyl-5-[2-(4-methoxy-phenyl)-thiazol-4-yl]-2-methyl-1H-pyrrole-3-carboxylic acid pyrimidin-2-ylamide,
rac-1-Cyclohexylmethyl-5-[2-(4-methoxy-phenyl)-thiazol-4-yl]-2-methyl-1H-pyrrole-3-carboxylic acid (5-hydroxy-2,2,6-trimethyl-cyclohexylmethyl)-amide,
5-[2-(4-Methoxy-phenyl)-thiazol-4-yl]-2-methyl-1-(3-trifluoromethoxy-benzyl)-1H-pyrrole-3-carboxylic acid butylamide,
Benzyl-5-[2-(4-methoxy-phenyl)-thiazol-4-yl]-2-methyl-1H-pyrrole-3-carboxylic acid butylamide,
{1-Cyclohexylmethyl-5-[2-(4-methoxy-phenyl)-thiazol-4-yl]-2-methyl-1H-pyrrol-3-yl}-pyrrolidin-1-yl-methanone,
Cyclohexylmethyl-5-[2-(3,4-dimethoxy-phenyl)-thiazol-4-yl]-2-methyl-1H-pyrrole-3-carboxylic acid butylamide,
Cyclohexylmethyl-5-[2-(3-methoxy-phenyl)-thiazol-4-yl]-2-methyl-1H-pyrrole-3-carboxylic acid butylamide,
5-(2-Benzo[1,3]dioxol-5-yl-thiazol-4-yl)-1-cyclohexylmethyl-2-methyl-1H-pyrrole-3-carboxylic acid butylamide,
Cyclohexylmethyl-5-[2-(4-fluoro-phenyl)-thiazol-4-yl]-2-methyl-1H-pyrrole-3-carboxylic acid butylamide,
Cyclohexylmethyl-5-[2-(2-fluoro-phenyl)-thiazol-4-yl]-2-methyl-1H-pyrrole-3-carboxylic acid butylamide,
Cyclohexylmethyl-2-methyl-5-[2-(4-trifluoromethoxy-phenyl)-thiazol-4-yl]-1H-pyrrole-3-carboxylic acid butylamide,
Cyclohexylmethyl-5-[2-(3,5-dimethoxy-phenyl)-thiazol-4-yl]-2-methyl-1H-pyrrole-3-carboxylic acid butylamide,
Cyclohexylmethyl-2-methyl-5-(2-m-tolyl-thiazol-4-yl)-1H-pyrrole-3-carboxylic acid butylamide,
Cyclohexylmethyl-2-methyl-5-(2'-methyl-[2,4']bithiazolyl-4-yl)-1H-pyrrole-3-carboxylic acid butylamide,
Cyclohexylmethyl-5-[2-(4-ethyl-phenyl)-thiazol-4-yl]-2-methyl-1H-pyrrole-3-carboxylic acid butylamide,
5-[2-(4-Chloro-phenyl)-thiazol-4-yl]-1-cyclohexylmethyl-2-methyl-1H-pyrrole-3-carboxylic acid butylamide,
5-[2-(4-tert-Butyl-phenyl)-thiazol-4-yl]-1-cyclohexylmethyl-2-methyl-1H-pyrrole-3-carboxylic acid butylamide,
Cyclohexylmethyl-5-[2-(2,3-dihydro-benzofuran-5-yl)-thiazol-4-yl]-2-methyl-1H-pyrrole-3-carboxylic acid butylamide,
Cyclohexylmethyl-2-methyl-5-(2-p-tolyl-thiazol-4-yl)-1H-pyrrole-3-carboxylic acid butylamide,
Cyclohexylmethyl-5-[2-(6-methoxy-pyridin-3-yl)-thiazol-4-yl]-2-methyl-1H-pyrrole-3-carboxylic acid butylamide,
Cyclohexylmethyl-5-[2-(2,4-dichloro-phenyl)-thiazol-4-yl]-2-methyl-1H-pyrrole-3-carboxylic acid butylamide,
Cyclohexylmethyl-2-methyl-5-[2-(4-nitro-phenyl)-thiazol-4-yl]-1H-pyrrole-3-carboxylic acid butylamide,
Cyclohexylmethyl-5-[2-(4-methoxy-phenyl)-thiazol-4-yl]-2-methyl-1H-pyrrole-3-carboxylic acid pentylamide,
Cyclohexylmethyl-5-[2-(4-methoxy-phenyl)-thiazol-4-yl]-2-methyl-1H-pyrrole-3-carboxylic acid propylamide,
Cyclohexylmethyl-5-[2-(4-methoxy-phenyl)-thiazol-4-yl]-2-methyl-1H-pyrrole-3-carboxylic acid cyclohexylamide,
Cyclohexylmethyl-5-[2-(4-methoxy-phenyl)-thiazol-4-yl]-2-methyl-1H-pyrrole-3-carboxylic acid cyclopentylamide,
Cyclohexylmethyl-5-[2-(4-methoxy-phenyl)-thiazol-4-yl]-2-methyl-1H-pyrrole-3-carboxylic acid cyclopropylamide,
Cyclohexylmethyl-5-[2-(4-methoxy-phenyl)-thiazol-4-yl]-2-methyl-1H-pyrrole-3-carboxylic acid cyclobutylamide,
(trans) rac-1-Cyclohexylmethyl-5-[2-(4-methoxy-phenyl)-thiazol-4-yl]-2-methyl-1H-pyrrole-3-carboxylic acid (2-hydroxy-cyclopentyl)-amide,
1-(4-Chloro-benzyl)-5-[2-(4-methoxy-phenyl)-thiazol-4-yl]-2-methyl-1H-pyrrole-3-carboxylic acid butylamide,
1-(3,4-Dichloro-benzyl)-5-[2-(4-methoxy-phenyl)-thiazol-4-yl]-2-methyl-1H-pyrrole-3-carboxylic acid butylamide,
1-(3,4-Dimethyl-benzyl)-5-[2-(4-methoxy-phenyl)-thiazol-4-yl]-2-methyl-1H-pyrrole-3-carboxylic acid butylamide, 1-(3,4-Dimethoxy-benzyl)-5-[2-(4-methoxy-phenyl)-thiazol-4-yl]-2-methyl-1H-pyrrole-3-carboxylic acid butylamide,
Cyclohexylmethyl-5-[2-(4-hydroxy-phenyl)-thiazol-4-yl]-2-methyl-1H-pyrrole-3-carboxylic acid butylamide,
1-(4-Isopropyl-benzyl)-5-[2-(4-methoxy-phenyl)-thiazol-4-yl]-2-methyl-1H-pyrrole-3-carboxylic acid butylamide,
5-[2-(4-Methoxy-phenyl)-thiazol-4-yl]-2-methyl-1-pyridin-2-ylmethyl-1H-pyrrole-3-carboxylic acid butylamide,
Cyclohexylmethyl-5-(2-cyclohexyl-thiazol-4-yl)-2-methyl-1H-pyrrole-3-carboxylic acid butylamide, and pharmaceutically acceptable salts thereof.

Most preferred compounds of general formula (I) are those selected from the group consisting of:
Cyclohexylmethyl-5-[2-(4-methoxy-phenyl)-thiazol-4-yl]-2-methyl-1H-pyrrole-3-carboxylic acid butylamide,
rac-1-Cyclohexylmethyl-5-[2-(4-methoxy-phenyl)-thiazol-4-yl]-2-methyl-1H-pyrrole-3-carboxylic acid sec-butylamide,
{1-Cyclohexylmethyl-5-[2-(4-methoxy-phenyl)-thiazol-4-yl]-2-methyl-1H-pyrrol-3-yl}-piperidin-1-yl-methanone,
5-(2-Benzo[1,3]dioxol-5-yl-thiazol-4-yl)-1-cyclohexylmethyl-2-methyl-1H-pyrrole-3-carboxylic acid butylamide,
Cyclohexylmethyl-5-[2-(4-fluoro-phenyl)-thiazol-4-yl]-2-methyl-1H-pyrrole-3-carboxylic acid butylamide,
Cyclohexylmethyl-2-methyl-5-(2-p-tolyl-thiazol-4-yl)-1H-pyrrole-3-carboxylic acid butylamide,
Cyclohexylmethyl-5-[2-(6-methoxy-pyridin-3-yl)-thiazol-4-yl]-2-methyl-1H-pyrrole-3-carboxylic acid butylamide,
Cyclohexylmethyl-2-methyl-5-[2-(4-nitro-phenyl)-thiazol-4-yl]-1H-pyrrole-3-carboxylic acid butylamide,
Cyclohexylmethyl-5-[2-(4-methoxy-phenyl)-thiazol-4-yl]-2-methyl-1H-pyrrole-3-carboxylic acid pentylamide,
Cyclohexylmethyl-5-[2-(4-methoxy-phenyl)-thiazol-4-yl]-2-methyl-1H-pyrrole-3-carboxylic acid cyclohexylamide,
Cyclohexylmethyl-5-[2-(4-methoxy-phenyl)-thiazol-4-yl]-2-methyl-1H-pyrrole-3-carboxylic acid cyclopentylamide,
Cyclohexylmethyl-5-[2-(4-methoxy-phenyl)-thiazol-4-yl]-2-methyl-1H-pyrrole-3-carboxylic acid cyclopropylamide,
Cyclohexylmethyl-5-[2-(4-hydroxy-phenyl)-thiazol-4-yl]-2-methyl-1H-pyrrole-3-carboxylic acid butylamide,
Cyclohexylmethyl-5-(2-cyclohexyl-thiazol-4-yl)-2-methyl-1H-pyrrole-3-carboxylic acid butylamide, or a pharmaceutically acceptable salt thereof.

The present invention also relates to a process for the manufacture of compounds of formula (I) as defined above. The compounds of formula (I) can be manufactured by the methods given below, by the methods given in the Examples or by analogous methods. Appropriate reaction conditions for the individual reaction steps are known to the person skilled in the art. Starting materials are either commercially available or can be prepared by methods analogous to the methods given below or in the Examples or by methods known in the art.

The compounds of formula (I) may be prepared using the general methods described below:

Compounds of formula (I), wherein $R^1$ to $R^7$ and m are as previously defined, can be prepared by reaction of enamines of formula A with alfa-bromoketones of formula B according to methods known in the art (Scheme 1). For example, the reaction can be performed in an inert solvent such as DMF in the presence of a hindered base such as 2,6-di-tert-butylpyridine or 2,6-lutidine.

Scheme 1:

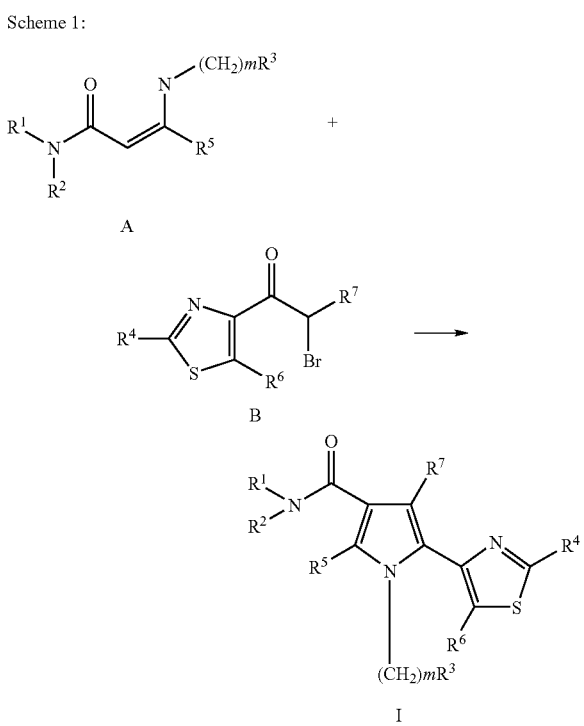

Compounds of formula I can be purified by methods known in the art such as precipitation from mixtures of solvents (e.g. acetonitrile and water) or by column chromatography using $SiO_2$ with eluents know in the art (e.g. n-heptane/Ethyl acetate, dichloromethane/methanol and dichloromethane/(1% $NH_3$ in MeOH)).

Thiazole derivatives of formula B can be prepared from dibromodiketones of formula C and thioamides of formula C by methods known in the art (Scheme 2). For example, the reaction can be performed by addition of thioamides of formula C to dibromo-diketones of formula D in an inert solvent such as DMF.

Scheme 2:

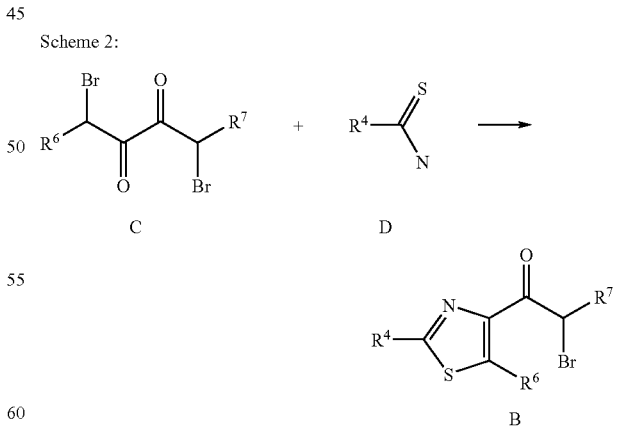

Enamines of formula A can be prepared from beta-ketoamides of formula E and amines of formula F by methods known in the art (Scheme 3). For example a beta-keto amide of formula E can be reacted with an amine of formula B in a suitable inert solvent (e.g. DMF) in the presence of a hindered base (e.g. 2,6-di-tert-butylpyridine) to yield enamine of formula A.

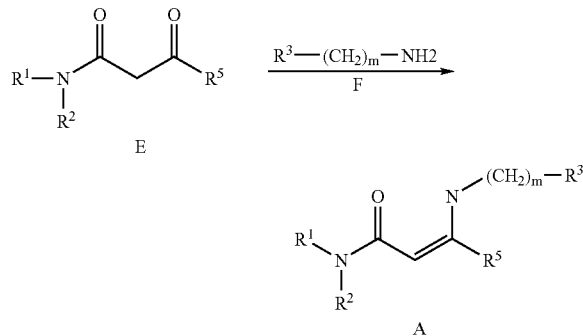

Scheme 3

Beta-ketoamides of formula E are either known form the literature or can be purchased from commercial sources or else can be prepared by methods known in the art. For example, beta-ketoamides of formula E wherein $R^5$=methyl can be prepared by reaction of amines of formula G with diketene in an inert solvent such as dichloromethane (Scheme 4).

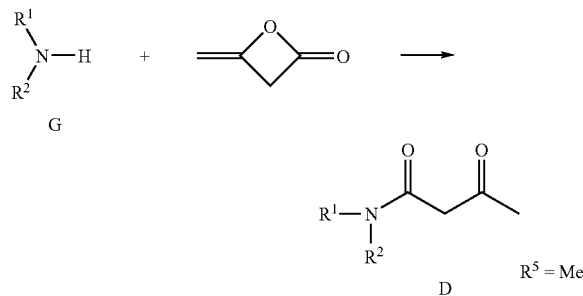

Scheme 4

Compounds of formula D, F and G are either known from the literature or can be purchased from commercial sources or else can be synthesized by methods known in the art.

The invention further relates to compounds of formula (I) as defined above, when manufactured according to a process as defined above.

Some compounds of formula (I) may possess asymmetric centres and are therefore capable of existing in more than one stereoisomeric form. The invention thus also relates to compounds in substantially pure isomeric form at one or more asymmetric centres as well as mixtures, including racemic mixtures, thereof. Such isomers may be prepared by asymmetric synthesis, for example using chiral intermediate, or mixtures may be resolved by conventional methods, eg., chromatography (chromatography with a chiral adsorbens or eluent), or use of a solving agent.

It will be appreciated, that the compounds of general formula (I) in this invention may be derivatised at functional groups to provide derivatives which are capable of conversion back to the parent compound in vivo.

As described above, the compounds of formula (I) or pharmaceutically acceptable salts thereof can be used as medicaments for the treatment and/or prophylaxis of diseases which are associated with the modulation of the CB1 receptors.

The invention therefore also relates to pharmaceutical compositions comprising a compound as defined above and a pharmaceutically acceptable carrier and/or adjuvant.

Further, the invention relates to compounds as defined above for use as therapeutic active substances, particularly as therapeutic active substances for the treatment and/or prophylaxis of diseases which are associated with the modulation of CB1 receptors.

In another embodiment, the invention relates to a method for the treatment and/or prophylaxis of diseases which are associated with the modulation of CB1 receptors, which method comprises administering a compound as defined above to a human being or animal.

The invention further relates to the use of compounds as defined above for the treatment and/or prophylaxis of diseases which are associated with the modulation of CB1 receptors.

In addition, the invention relates to the use of compounds as defined above for the preparation of medicaments for the treatment and/or prophylaxis of diseases which are associated with the modulation of CB1 receptors. Such medicaments comprise a compound as defined above.

In this context, the expression 'diseases associated with modulation of CB1 receptors' means diseases which can be treated and/or prevented by modulation of CB1 receptors. Such diseases encompass, but are not limited to, psychic disorders, especially anxiety, psychosis, schizophrenia, depression, abuse of psychotropes, for example for the abuse and/or dependence of a substances, including alcohole dependency and nicotine dependency, neuropathies, migraine, stress, epilepsy, dyskinesias, Parkinson's disease, amnesia, cognitive disorders, senile dementia, Alzheimer's disease, eating disorders, obesity, diabetes type II or non insulin dependent diabetes (NIDD), gastrointestinal diseases, vomiting, diarrhea, urinary disorders, cardiovascular disorders, infertility disorders, inflammations, infections, cancer, neuroinflammation, in particular in atherosclerosis, or the Guillain-Barré syndrome, viral encephalitis, cerebral vascular incidents and cranial trauma.

In a preferable aspect, the expression 'diseases associated with modulation of CB1 receptors' relates to eating disorders, obesity, diabetes type II or non insulin dependent diabetes (NIDD), neuroinflammation, diarrhea, abuse and/or dependence of a substances, including alcohole dependency and nicotine dependency. In a more preferable aspect, the said term related to eating disorders, obesity, diabetes type II or non insulin dependent diabetes (NIDD), abuse and/or dependence of a substances, including alcohole dependency and nicotine dependency, with obesity being especially preferred.

It is a further preferred object to provide a method of treatment or prevention of Type II diabetes (non-insulin dependent diabetes mellitus (NIDDM) in a human which comprises administration of a therapeutically effective amount of a compound according to formula (I) in combination or association with a therapeutically effective amount of a lipase inhibitor, particularly, wherein the lipase inhibitor is orlistat. Also an object of the invention is the method as described above for the simultaneous, separate or sequential administration of a compound according to formula (I) and a lipase inhibitor, particularly tetrahydrolipstatin.

It is a further preferred object to provide a method for the treatment or prevention of obesity and obesity related disorders which comprises administration of a therapeutically effective amount of a compound according to formula (I) in combination or association with a therapeutically effective amount of other drugs for the treatment of obesity or eating disorders so that together they give effective relief. Suitable other drugs include but are not limited to anorectic agents, lipase inhibitors and selective serotonin reuptake inhibitors (SSRI). Combinations or associations of the above agents may be encompassing separate, sequential or simultaneous administration.

Preferable lipase inhibitor is tetrahydrolipstatin.

Suitable anorectic agents of use in combination with a compound of the present invention include, but are not limited to, aminorex, amphechloral, amphetamine, benzphetamine, chlorphentermine, clobenzorex, cloforex, clominorex, clortermine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phentermine, phenylpropanolamine, picilorex and sibutramine, and pharmaceutically acceptable salts thereof.

Most preferable anorectic agents are sibutramine and phentermine.

Suitable selective serotonin reuptake inhibitors of use in combination with a compound of the present invention include: fluoxetine, fluvoxamine, paroxetine and sertraline, and pharmaceutically acceptable salts thereof.

Demonstration of additional biological activities of the compounds of the present invention may be accomplished through in vitro, ex vivo, and in vivo assays that are well known in the art. For example, to demonstrate the efficacy of a pharmaceutical agent for the treatment of obesity-related disorders such as diabetes, Syndrome X, or atherosclerotic disease and related disorders such as hypertriglyceridemia and hypercholesteremia, the following assays may be used.

Method for Measuring Blood Glucose Levels db/db mice (obtained from Jackson Laboratories, Bar Harbor, Me.) are bled (by either eye or tail vein) and grouped according to equivalent mean blood glucose levels. They are dosed orally (by gavage in a pharmaceutically acceptable vehicle) with the test compound once daily for 7 to 14 days. At this point, the animals are bled again by eye or tail vein and blood glucose levels are determined.

Method for Measuring Triglyceride Levels hApoAl mice (obtained from Jackson Laboratories, Bar Harbor, Me.) are bled (by either eye or tail vein) and grouped according to equivalent mean serum triglyceride levels. They are dosed orally (by gavage in a pharmaceutically acceptable vehicle) with the test compound once daily for 7 to 14 days. The animals are then bled again by eye or tail vein, and serum triglyceride levels are determined.

Method for Measuring HDL-Cholesterol Levels

To determine plasma HDL-cholesterol levels, hApoAl mice are bled and grouped with equivalent mean plasma HDL-cholesterol levels. The mice are orally dosed once daily with vehicle or test compound for 7 to 14 days, and then bled on the following day. Plasma is analyzed for HDL-cholesterol.

In addition, to demonstrate CNS activities of the compounds of the present invention, the following in vivo assays may be used.

Method for Testing Task Learning and Spatial Memory

The Morris Water Maze is routinely used to assess task learning and spatial memory (Jaspers et al., Neurosci. Lett. 117:149–153, 1990; Morris, J. Neurosci. Methods 11:47–60, 1984). In this assay, animals are placed in a water pool which is divided into quadrants. One platform is hidden in one of the quadrants. The animal is placed in the water pool and is expected to locate the hidden platform within a predetermined time. During a number of training trials, the animal learns the location of the platform and escape from the pool. The animal receives multiple trials in this task. Total distance traveled, number of trials to locate platform, latency to find platform, and the swimming path is recorded for each animal. The animal's learning ability is measured by the length of time or number of trials required to find the hidden platform. Memory deficit or improvement is determined by the number of trials or the latency to find the platform at predetermined delay time after acquisition. Leaning and memory may be measured by the number of times that the animal crosses the quadrant where the platform was located during the acquisition phase.

Method for Testing Drug Dependence

Self-administration in animals is a predictor of a compound's abuse potential in humans. Modifications to this procedure may also be used to identify compounds that prevent or block the reinforcing properties of drugs that have abuse potential. A compound that extinguishes the self-administration of a drug may prevent that drug's abuse or its dependence. (Ranaldi et al., Psychopharmacol. 161:442–448, 2002; Campbell et al., Exp. Clin. Psychopharmacol. 8:312–25, 2000). In a self-administration test, animals are placed in the operant chambers containing both an active and inactive lever. Each response on the active lever produces an infusion of either the test compound or a drug known to be self-administered. Presses on the inactive lever have no effect, but are also recorded. Animals are then trained to self-administer compound/drug over a set period of time by having drug access during each daily session. Illumination of the chamber house light signals the beginning of the session and the availability of the compound/drug. When the session ends, the house light is turned off. Initially, a drug infusion occurs with every press of the active lever. Once lever-pressing behavior has been established, the number of presses to produce a drug infusion is increased. After stable compound/drug self-administration is obtained, the effect of a second compound on the drug-reinforced behavior may be evaluated. Administration of this second compound prior to the session can either potentiate, extinguish, or produce no change to the self-administrating behavior.

The following tests were carried out in order to determine the activity of the compounds of formula (I).

The affinity of the compounds of the invention for cannabinoid CB1 receptors was determined using membrane preparations of human embryonic kidney (HEK) cells in which the human cannabis CB1 receptor is transiently transfected using the Semliki Forest Virus system in conjunction with [3H]-CP-55,940 as radioligand. After incubation of a freshly prepared cell membrane preparation with the [3H]-ligand, with or without addition of compounds of the invention, separation of bound and free ligand was performed by filtration over glassfiber filters. Radioactivity on the filter was measured by liquid scintillation counting.

The affinity of the compounds of the invention for cannabinoid CB2 receptors was determined using membrane preparations of human embryonic kidney (HEK) cells in which the human cannabis CB2 receptor is transiently transfected using the Semliki Forest virus system in conjunction with [3H]-CP-55,940 as radioligand. After incubation of a freshly prepared cell membrane preparation with the [3H]-ligand, with or without addition of compounds of the invention, separation of bound of bound and free ligand was performed by filtration over glassfiber filters. Radioactivity on the filter was measured by liquid scintillation counting.

The cannabinoid CB1 antagonistic activity of compounds of the invention was determined by functional studies using CHO cells in which human cannabinoid CB1 receptors are stably expressed (see M. Rinaldi-Carmona et. al., J. Pharmacol. Exp. Ther. 278 (1996) 871).

The stable expression of the human cannabinoid receptor in cell systems was first described in Nature 1990, 346, 561–564 (CB1) and Nature 1993, 365, 61–65 (CB2) respectively. Adenylyl cyclase was stimulated using forskolin and measured by quantifying the amount of accumulated cyclic AMP. Concomitant activation of CB1 receptors by CB1 receptor agonist (e.g., CP-55,940 or (R)-WIN-55212-2) can attenuate the forskolin-induced accumulation of cAMP in a concentration dependent manner. This CB1 receptor mediated response can be antagonised by CB1 receptor antagonists such as the compounds of the invention.

The compounds of formula (I) show an excellent affinity for the CB1 receptor, determined with the experimental conditions described in Devane et. al. Mol. Pharmacol. 34 (1988) 605–613. The compounds of the present invention or the pharmaceutically acceptable salts or sovants are antagonists and selective for the CB1 receptor with affinites below $IC_{50}=2$ µM. They exhibit at least a 10 fold selectivity against the CB2 receptor.

| Compound of Example | $IC_{50}$ [µM] |
|---|---|
| 8 | <2 |
| 299 | <2 |
| 305 | <2 |
| 311 | <2 |
| 315 | <2 |
| 324 | <2 |
| 333 | <2 |
| 340 | <2 |
| 356 | <2 |
| 371 | <2 |
| 375 | <2 |

Effect of CB1 receptor antagonist/inverse agonist on CP 55,940-induced Hypothermia in NMRI mice Animals Male NMRI mice were used in this study and were obtained from Research Consulting Company Ltd (RCC) of Füllinsdorf (Switzerland). Mice, weighing 30–31 g were used in this study. Ambient temperature is approximately 20–21° C. and relative humidity 55–65%. A 12 hours light-dark cycle is maintained in the rooms with all tests being performed during the light phase. Access to tap water and food are ad libitum.

Method

All measurements were made between 12:00 am and 5:00 pm. Mice were brought in this environment and habituated for at least two hours before the start of the experiment. They had always free access to food and water. For each dose, 8 mice were used. Rectal body temperature measurements were recorded by mean of a rectal probe (RET2 of Physitemp) and digital thermometer (Digi-sense n°8528-20 of Cole Parmer, Chicago USA). The probe was inserted about 3.5 cm in each mouse.

The body temperature was taken 15 min before administration of either Vehicle or CB1 receptor antagonist/inverse agonist. 30 or 90 min after i.p. or p.o. administration of this compound, respectively, rectal body temperature was recorded in order to evaluate any influence of the compound itself. The CB receptor agonist CP 55,940 (0.3 mg/kg) was immediately administered intravenously, then 20 min after i.v. administration of CP 55940, body temperature was again measured.

The in vivo activity of compounds of formula (1) was assessed for their ability to regulate feeding behaviour by recording food consumption in food deprived animals.

Rats were trained to have access to food for 2 h per day and were food deprived for 22 h. When they were trained under this schedule, the amount of food taken every day during these 2 h food intake session was consistent day after day.

To test the ability of compounds of formula (1) to decrease food intake, 8 animals were used in a cross-over study. Rats were individually housed in Plexiglas boxes with a grid on the floor and a paper was placed below the cage floor to collect any spillage. A food dispenser (becher) filled with a pre-weighed amount of food was presented to them for 2 h. At the end of the food intake session, rats returned to their home cage. Each rat was weighed before the start of the experiment and the amount of food consumed during this 2 h food intake session was recorded. Either various doses of test compound or vehicle was administered orally 60 min before the 2 h food intake session. A positive control Rimonabant (SR141716) was included in the experiment. An Anova analysis with repeated measures was used followed by a posthoc test Student Neumann-Keuls. *$P<0.05$ compared to Saline-treated rats.

Furthermore the utility of compounds of formula (1) in diseases or disorders may be demonstrated in animal disease models that have been reported in the literature. The following are examples of such animal disease models: a) reduction of sweet food intake in marmosets (Behavioural Pharm, 1998, 9,179–181); b) reduction of sucrose and ethanol intake in mice (Psychopharm. 1997, 132, 104–106); c) increased motor activity and place conditioning in rats (Psychopharm. 1998, 135, 324–332; Psychopharmacol 2000, 151: 25–30); d) spontaneous locomotor activity in mice (J. Pharm. Exp. Ther. 1996, 277, 586–594); e) reduction in opiate self-administration in mice (Sci. 1999, 283, 401–404);

The compounds of formula (I) and/or their pharmaceutically acceptable salts can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils. Oral administration is preferred.

The production of the pharmaceutical preparations can be effected in a manner which will be familiar to any person skilled in the art by bringing the described compounds of formula (I) and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules).

Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula (I) can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 100 mg, comes into consideration. Depending on severity of the disease and the precise pharmacokinetic profile the compound could be administered with one or several daily dosage units, e.g. in 1 to 3 dosage units.

The pharmaceutical preparations conveniently contain about 1–500 mg, preferably 1–100 mg, of a compound of formula (I).

The following Examples serve to illustrate the present invention in more detail. They are, however, not intended to limit its scope in any manner.

EXAMPLES

MS=mass spectrometry; ISP=ion spray (positive ion), corresponds to ESI and ES+ (electrospray, positive ion); mp=melting point.

Example 1

Cyclohexylmethyl-2-methyl-5-[2-(4-nitro-phenyl)-thiazol-4-yl]-1H-pyrrole-3-carboxylic acid butylamide

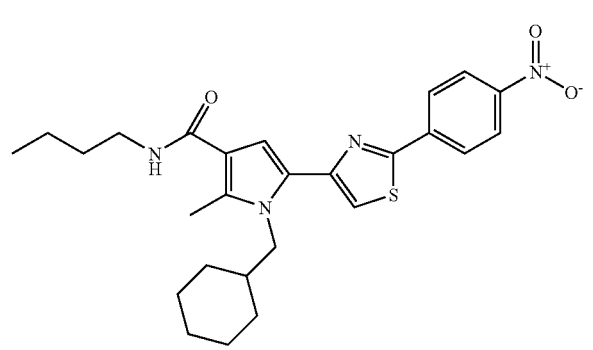

The title compound was obtained using butylamine as $R^1R^2NH$, aminomethylcyclohexane as $R^3$—$(CH_2)_m$—$NH_2$ and 4-nitrophenyl thioamide as $R^4C(S)NH_2$, as follows:

Synthesis of 2-bromo-1-[2-(4-nitro-phenyl)-thiazol-4-yl]-ethanone (Compound B)

To a solution of 1.4 g of 1,4-dibromo-2,3-butanedione in dimethylformamide (110 ml) at room temperature was added 1.4 ml of 2,6-di-tert-butylpyridine. Then a solution of 1.0 g of 4-nitro-phenyl-thiobenzamide in 20 ml of dimethylformamide was slowly added to the reaction mixture over 1 hour. The reaction mixture was then allowed to stir for an additional hour at room temperature before being concentrated in vacuo. The residue was then purified by chromatography over a short column ($SiO_2$, 120 g, $CH_2Cl_2$ 100%). The isolated compound was triturated with isopropylether to yield 771 mg of the title compound as a yellow solid, mp=186–187° C., MS (EI) 326(M).

Synthesis of 1-Cyclohexylmethyl-2-methyl-5-[2-(4-nitro-phenyl)-thiazol-4-yl]-1H-pyrrole-3-carboxylic acid butylamide To a solution of 4.2 g of diketene in dichloromethane (70 ml) cooled at 0° C. was added over 1 hour a solution of 3.7 g of butylamine in 50 ml of dichloromethane. The reaction mixture was then stirred for one hour at 0° C. and then let to stir at room temperature for another hour. The reaction mixture was then concentrated in vacuo and the crude residue was partitioned in batches which were directly used in the next step.

To 180 mg of the previous crude material in 5 ml of dimethylformamide was added 0.15 ml of cyclohexylmethylamine together with 0.13 ml of trimethyl orthoformate and the reaction mixture was stirred for 24 hours at room temperature. After such time, 260 mg of 2-bromo-1-[2-(4-nitro-phenyl)-thiazol-4-yl]-ethanone was added together with 0.14 ml of 2,6-lutidine and the reaction mixture was stirred for another 24 hours at room temperature. After such time, 5 ml of a MeCN—$H_2O$ (1:1) solution is added to the reaction mixture, the precipitate is filtrated and washed with MeCN—$H_2O$ (1:1) and isopropylether to yield 264 mg of the title compound as a yellow solid, mp=184–187° C., MS (ISP) 481.3 $(M+H)^+$.

Examples 2–375 were synthesized in analogy to Example 1, using the indicated educts.

Example 2

Butyl-5-[2-(2-chloro-phenyl)-thiazol-4-yl]-2-methyl-1H-pyrrole-3-carboxylic acid butylamide

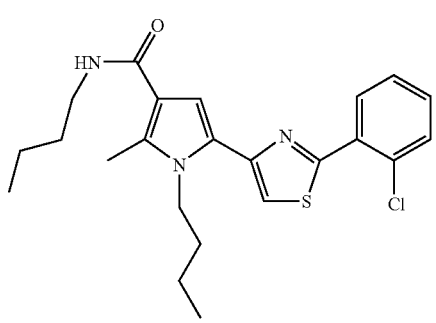

The title compound was obtained using butylamine as $R^1R^2NH$, butylamine as $R^3$—$(CH_2)_m$—$NH_2$ and 2-chlorophenyl thiobenzamide as $R^4C(S)NH_2$, MS(ES+) 430 $(M+H)^+$.

Example 3

Butyl-5-[2-(4-methoxy-phenyl)-thiazol-4-yl]-2-methyl-1H-pyrrole-3-carboxylic acid Butylamide

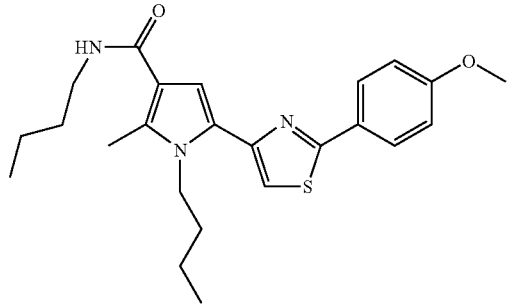

The title compound was obtained using butylamine as $R^1R^2NH$, butylamine as $R^3$—$(CH_2)_m$—$NH_2$ and 4-methoxy-phenyl thiobenzamide as $R^4C(S)NH_2$, MS(ES+) 426 (M+H)⁺.

Example 4

5-[2-(2-Chloro-phenyl)-thiazol-4-yl]-1-isobutyl-2-methyl-1H-pyrrole-3-carboxylic acid butylamide

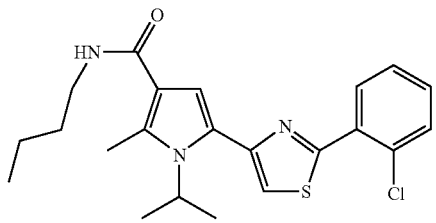

The title compound was obtained using butylamine as $R^1R^2NH$, isobutylamine as $R^3$—$(CH_2)_m$—$NH_2$ and 2-chloro-phenyl thiobenzamide as $R^4C(S)NH_2$, MS(ES+) (M+H)⁺.

Example 5

Isobutyl-5-[2-(4-methoxy-phenyl)-thiazol-4-yl]-2-methyl-1H-pyrrole-3-carboxylic acid butylamide

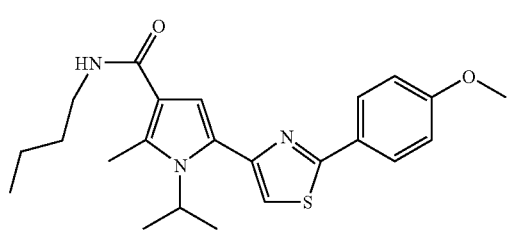

The title compound was obtained using butylamine as $R^1R^2NH$, isobutylamine as $R^3$—$(CH_2)_m$—$NH_2$ and 4-methoxy-phenyl thiobenzamide as $R^4C(S)NH_2$, MS(ES+) 426 (M+H)⁺.

Example 6

Isobutyl-2-methyl-5-(2-pyrazin-2-yl-thiazol-4-yl)-1H-pyrrole-3-carboxylic acid butylamide

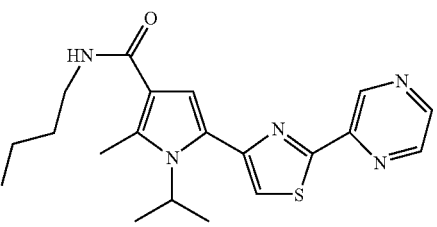

The title compound was obtained using butylamine as $R^1R^2NH$, isobutylamine as $R^3$—$(CH_2)_m$—$NH_2$ and pyrazine-2-carbothioamide as $R^4C(S)NH_2$, MS(ES+) 398 (M+H)⁺.

Example 7

5-[2-(2-Chloro-phenyl)-thiazol-4-yl]-1-cyclohexylmethyl-2-methyl-1H-pyrrole-3-carboxylic acid butylamide

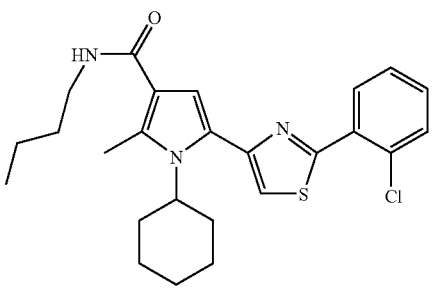

The title compound was obtained using butylamine as $R^1R^2NH$, aminomethylcyclohexane as $R^3$—$(CH_2)_m$—$NH_2$ and 2-chloro-phenyl thiobenzamide as $R^4C(S)NH_2$, MS(ES+) 470 (M+H)⁺.

Example 8

Cyclohexylmethyl-5-[2-(4-methoxy-phenyl)-thiazol-4-yl]-2-methyl-1H-pyrrole-3-carboxylic acid butylamide

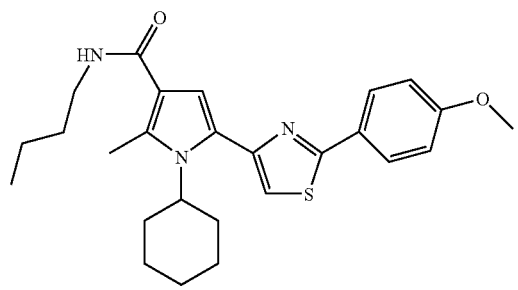

The title compound was obtained using butylamine as $R^1R^2NH$, aminomethylcyclohexane as $R^3$—$(CH_2)_m$—$NH_2$ and 4-methoxy-phenyl thiobenzamide as $R^4C(S)NH_2$, MS(ES+) 466 (M+H)⁺.

Example 9

Cyclohexylmethyl-5-[2-(4-methoxy-phenoxymethyl)-thiazol-4-yl]-2-methyl-1H-pyrrole-3-carboxylic acid butylamide

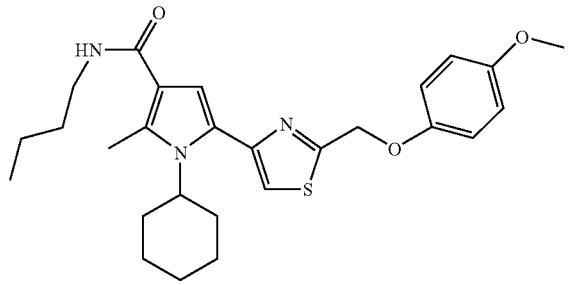

The title compound was obtained using butylamine as $R^1R^2NH$, aminomethylcyclohexane as $R^3$—$(CH_2)_m$—$NH_2$ and 2-(4-methoxyphenoxy)ethanethioamide as $R^4C(S)NH_2$, MS(ES+) 496 (M+H)$^+$.

Example 10

Cyclohexylmethyl-5-[2-(2-ethyl-pyridin-4-yl)-thiazol-4-yl]-2-methyl-1H-pyrrole-3-carboxylic acid butylamide

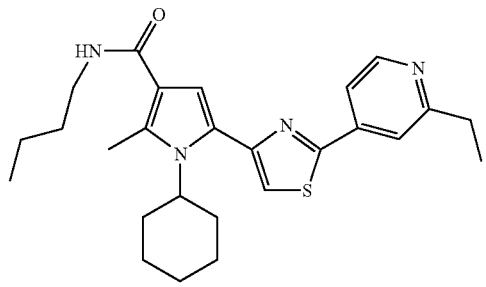

The title compound was obtained using butylamine as $R^1R^2NH$, aminomethylcyclohexane as $R^3$—$(CH_2)_m$—$NH_2$ and 2-ethyl-4-pyridinecarbothioamide as $R^4C(S)NH_2$, MS(ES+) 465 (M+H)$^+$.

Example 11

Cyclohexylmethyl-2-methyl-5-(2-pyrazin-2-yl-thiazol-4-yl)-1H-pyrrole-3-carboxylic acid butylamide

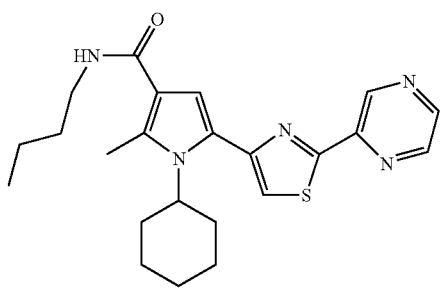

The title compound was obtained using butylamine as $R^1R^2NH$, aminomethylcyclohexane as $R^3$—$(CH_2)_m$—$NH_2$ and pyrazine-2-carbothioamide as $R^4C(S)NH_2$, MS(ES+) 438 (M+H)$^+$.

Example 12

5-[2-(2-Chloro-phenyl)-thiazol-4-yl]-2-methyl-1-(tetrahydro-furan-2-ylmethyl)-1H-pyrrole-3-carboxylic acid butylamide

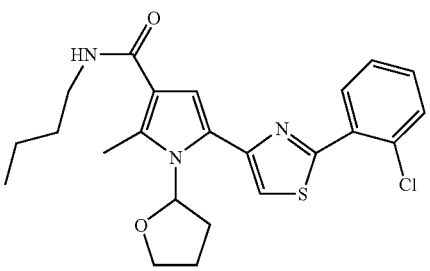

The title compound was obtained using butylamine as $R^1R^2NH$, tetrahydrofurfurylamine as $R^3$—$(CH_2)_m$—$NH_2$ and 2-chlorophenyl thioamide as $R^4C(S)NH_2$, MS(ES+) 458 (M+H)$^+$.

Example 13

5-[2-(4-Methoxy-phenyl)-thiazol-4-yl]-2-methyl-1-(tetrahydro-furan-2-ylmethyl)-1H-pyrrole-3-carboxylic acid butylamide

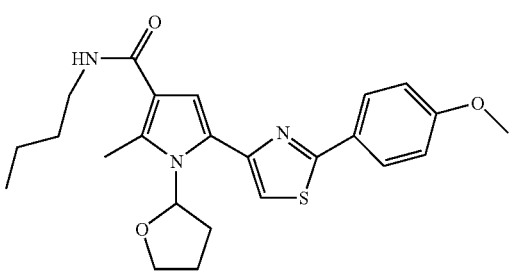

The title compound was obtained using butylamine as $R^1R^2NH$, tetrahydrofurfurylamine as $R^3$—$(CH_2)_m$—$NH_2$ and 4-methoxy-phenyl thioamide as $R^4C(S)NH_2$, MS(ES+) 454 (M+H)$^+$.

Example 14

5-[2-(4-Methoxy-phenoxymethyl)-thiazol-4-yl]-2-methyl-1-(tetrahydro-furan-2-ylmethyl)-1H-pyrrole-3-carboxylic acid butylamide

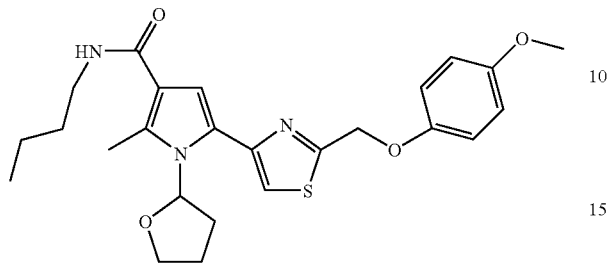

The title compound was obtained using butylamine as $R^1R^2NH$, tetrahydrofurfurylamine as $R^3$—$(CH_2)_m$—$NH_2$ and 2-(4-methoxyphenoxy)ethanethioamide as $R^4C(S)NH_2$, MS(ES+) 484 (M+H)$^+$.

Example 15

5-[2-(2-Ethyl-pyridin-4-yl)-thiazol-4-yl]-2-methyl-1-(tetrahydro-furan-2-ylmethyl)-1H-pyrrole-3-carboxylic acid butylamide

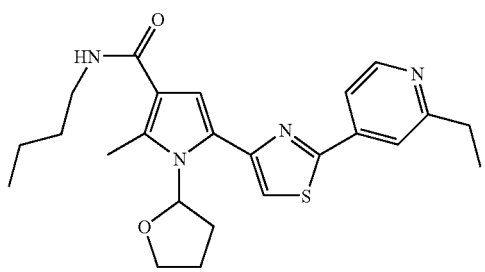

The title compound was obtained using butylamine as $R^1R^2NH$, tetrahydrofurfurylamine as $R^3$—$(CH_2)_m$—$NH_2$ and 2-ethyl-4-pyridine carbothioamide as $R^4C(S)NH_2$, MS(ES+) 453 (M+H)$^+$.

Example 16

Methyl-5-[2-(6-methyl-pyridin-3-yl)-thiazol-4-yl]-1-(tetrahydro-furan-2-ylmethyl)-1H-pyrrole-3-carboxylic acid butylamide

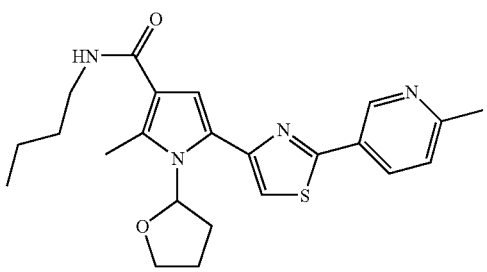

The title compound was obtained using butylamine as $R^1R^2NH$, tetrahydrofurfurylamine as $R^3$—$(CH_2)_m$—$NH_2$ and 6-methyl-pyridine-3-carbothiamide as $R^4C(S)NH_2$, MS(ES+) 439 (M+H)$^+$.

Example 17

Methyl-5-(2-pyrazin-2-yl-thiazol-4-yl)-1-(tetrahydro-furan-2-ylmethyl)-1H-pyrrole-3-carboxylic acid butylamide

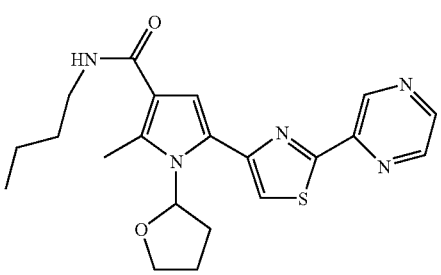

The title compound was obtained using butylamine as $R^1R^2NH$, tetrahydrofurfurylamine as $R^3$—$(CH_2)_m$—$NH_2$ and pyrazine-2-carbothiamide as $R^4C(S)NH_2$, MS(ES+) 426 (M+H)$^+$.

Example 18

1-(2-Methoxy-ethyl)-5-[2-(4-methoxy-phenyl)-thiazol-4-yl]-2-methyl-1H-pyrrole-3-carboxylic acid butylamide

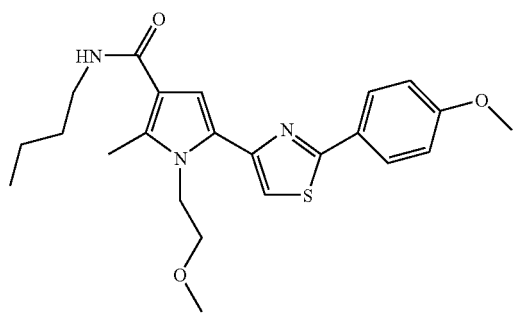

The title compound was obtained using butylamine as $R^1R^2NH$, 2-methoxyethylamine as $R^3$—$(CH_2)_m$—$NH_2$ and 4-methoxy-phenyl thioamide as $R^4C(S)NH_2$, MS(ES+) 428 (M+H)$^+$.

Example 19

1-(2-Methoxy-ethyl)-2-methyl-5-(2-pyrazin-2-yl-thiazol-4-yl)-1H-pyrrole-3-carboxylic acid butylamide

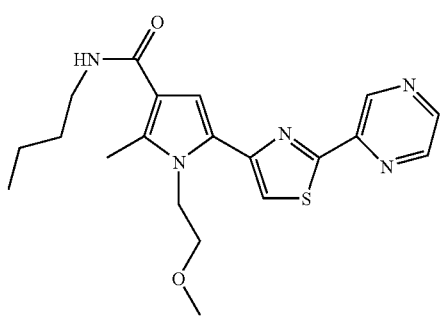

The title compound was obtained using butylamine as $R^1R^2NH$, 2-methoxyethylamine as $R^3$—$(CH_2)_m$—$NH_2$ and pyrazine-2-carbothioamide as $R^4C(S)NH_2$, MS(ES+) 400 (M+H)$^+$.

Example 20

5-[2-(2-Chloro-phenyl)-thiazol-4-yl]-1-furan-2-ylmethyl-2-methyl-1H-pyrrole-3-carboxylic acid butylamide

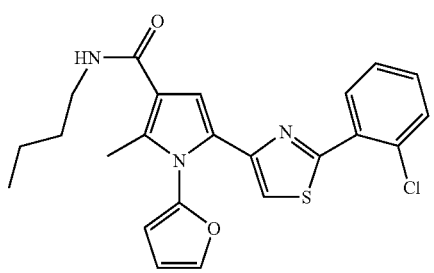

The title compound was obtained using butylamine as $R^1R^2NH$, tetrahydrofurfurylamine as $R^3$—$(CH_2)_m$—$NH_2$ and 2-chlorophenyl thioamide as $R^4C(S)NH_2$, MS(ES+) 454 (M+H)$^+$.

Example 21

Furan-2-ylmethyl-5-[2-(4-methoxy-phenyl)-thiazol-4-yl]-2-methyl-1H-pyrrole-3-carboxylic acid butylamide

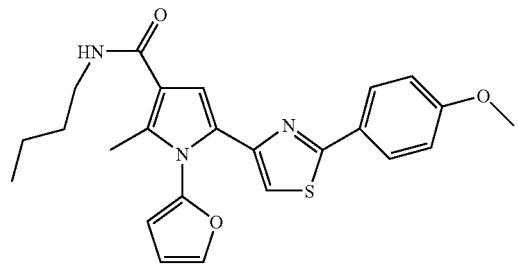

The title compound was obtained using butylamine as $R^1R^2NH$, 3-(aminomethyl)-thiophene as $R^3$—$(CH_2)_m$—$NH_2$ and 4-methoxy-phenyl thioamide as $R^4C(S)NH_2$, MS(ES+) 450 (M+H)$^+$.

Example 22

5-[2-(2-Ethyl-pyridin-4-yl)-thiazol-4-yl]-1-furan-2-ylmethyl-2-methyl-1H-pyrrole-3-carboxylic acid butylamide

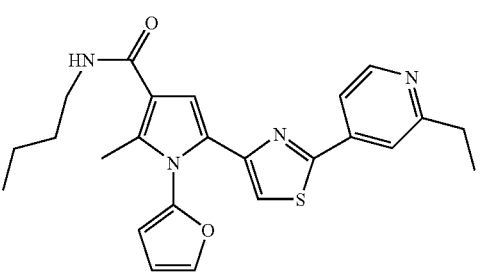

The title compound was obtained using butylamine as $R^1R^2NH$, 3-furyl methylamine as $R^3$—$(CH_2)_m$—$NH_2$ and 2-ethyl-4-pyridine carbothioamide as $R^4C(S)NH_2$, MS(ES+) 449 (M+H)$^+$.

Example 23

5-[2-(2-Chloro-phenyl)-thiazol-4-yl]-1-(4-methoxy-benzyl)-2-methyl-1H-pyrrole-3-carboxylic acid butylamide

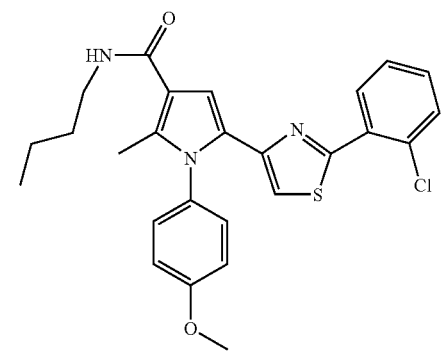

The title compound was obtained using butylamine as $R^1R^2NH$, 4-methoxybenzylamine as $R^3$—$(CH_2)_m$—$NH_2$ and 2-chlorophenyl thioamide as $R^4C(S)NH_2$, MS(ES+) 494 (M+H)$^+$.

Example 24

1-(4-Methoxy-benzyl)-5-[2-(4-methoxy-phenyl)-thiazol-4-yl]-2-methyl-1H-pyrrole-3-carboxylic acid butylamide

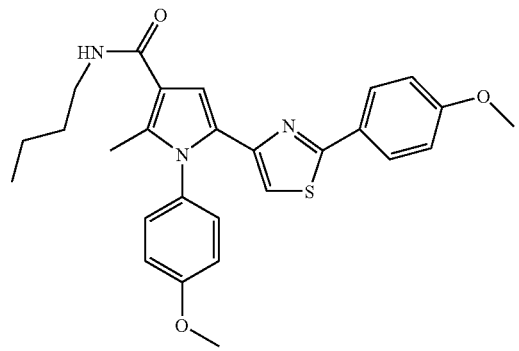

The title compound was obtained using butylamine as $R^1R^2NH$, 4-methoxybenzylamine as $R^3—(CH_2)_m—NH_2$ and 4-methoxyphenyl thioamide as $R^4C(S)NH_2$, MS(ES+) 490 (M+H)$^+$.

Example 25

1-(4-Methoxy-benzyl)-5-[2-(4-methoxy-phenoxymethyl)-thiazol-4-yl]-2-methyl-1H-pyrrole-3-carboxylic acid butylamide

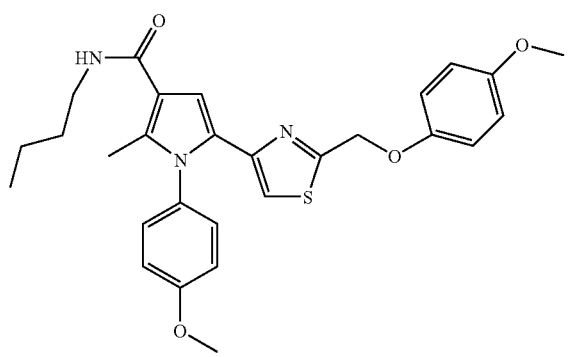

The title compound was obtained using butylamine as $R^1R^2NH$, 4-methoxybenzylamine as $R^3—(CH_2)_m—NH_2$ and 2-(4-methoxyphenoxy)ethanethioamide as $R^4C(S)NH_2$, MS(ES+) 520 (M+H)$^+$.

Example 26

5-[2-(2-Ethyl-pyridin-4-yl)-thiazol-4-yl]-1-(4-methoxy-benzyl)-2-methyl-1H-pyrrole-3-carboxylic acid butylamide

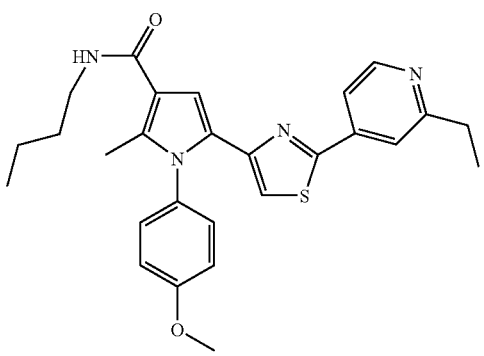

The title compound was obtained using butylamine as $R^1R^2NH$, 4-methoxybenzylamine as $R^3—(CH_2)_m—NH_2$ and 2-ethyl-4-pyridine carbothiamide as $R^4C(S)NH_2$, MS(ES+) 489 (M+H)$^+$.

Example 27

4-[4-Butylcarbamoyl-1-(4-methoxy-benzyl)-5-methyl-1H-pyrrol-2-yl]-thiazole-2-carboxylic acid ethyl ester

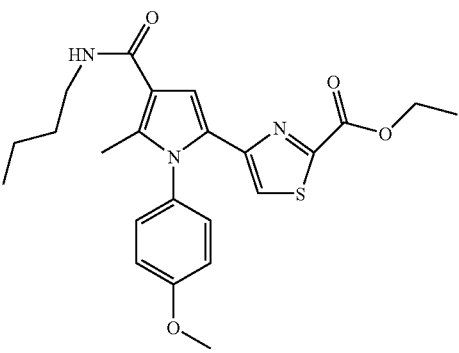

The title compound was obtained using butylamine as $R^1R^2NH$, 4-methoxybenzylamine as $R^3—(CH_2)_m—NH_2$ and ethylthiooxamate as $R^4C(S)NH_2$, MS(ES+) 456 (M+H)$^+$.

Example 28

1-(4-Methoxy-benzyl)-2-methyl-5-[2-(6-methyl-pyridin-3-yl)-thiazol-4-yl]-1H-pyrrole-3-carboxylic acid butylamide

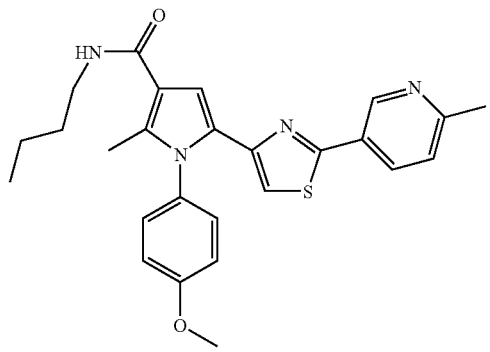

The title compound was obtained using butylamine as $R^1R^2NH$, 4-methoxybenzylamine as $R^3$—$(CH_2)_m$—$NH_2$ and 6-methyl-pyridine-3-carbothioamide as $R^4C(S)NH_2$, MS(ES+) 475 (M+H)$^+$.

Example 29

1-(4-Methoxy-benzyl)-2-methyl-5-(2-pyrazin-2-yl-thiazol-4-yl)-1H-pyrrole-3-carboxylic acid butylamide

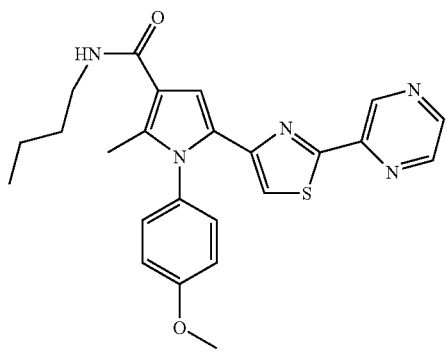

The title compound was obtained using butylamine as $R^1R^2NH$, 4-methoxybenzylamine as $R^3$—$(CH_2)_m$—$NH_2$ and pyrazine-2-carbothiamide as $R^4C(S)NH_2$, MS(ES+) 462 (M+H)$^+$.

Example 30

5-[2-(4-Methoxy-phenyl)-thiazol-4-yl]-1-(3-methoxy-propyl)-2-methyl-1H-pyrrole-3-carboxylic acid butylamide

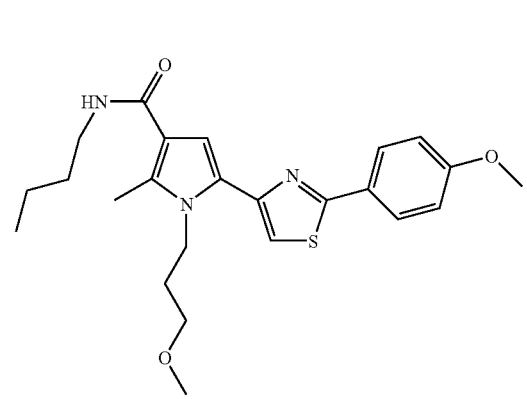

The title compound was obtained using butylamine as $R^1R^2NH$, methoxypropylamine as $R^3$—$(CH_2)_m$—$NH_2$ and 4-methoxyphenyl thioamide as $R^4C(S)NH_2$, MS(ES+) 442 (M+H)$^+$.

Example 31

5-[2-(4-Methoxy-phenoxymethyl)-thiazol-4-yl]-1-(3-methoxy-propyl)-2-methyl-1H-pyrrole-3-carboxylic acid butylamide

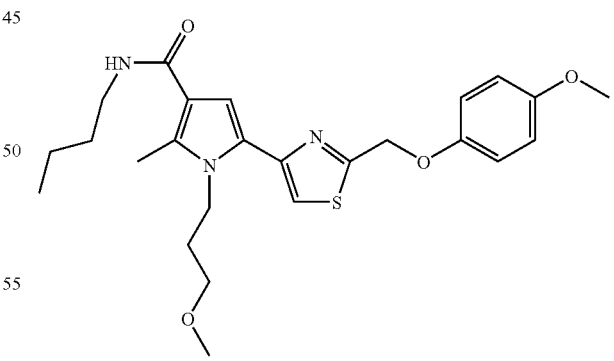

The title compound was obtained using butylamine as $R^1R^2NH$, methoxypropylamine as $R^3$—$(CH_2)_m$—$NH_2$ and 2-(4-methoxyphenoxy)ethane thioamide as $R^4C(S)NH_2$, MS(ES+) 472 (M+H)$^+$.

Example 32

4-[4-Butylcarbamoyl-1-(3-methoxy-propyl)-5-methyl-1H-pyrrol-2-yl]-thiazole-2-carboxylic acid ethyl ester

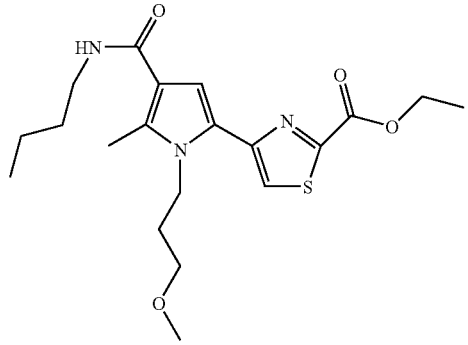

The title compound was obtained using butylamine as $R^1R^2NH$, methoxypropylamine as $R^3$—$(CH_2)_m$—$NH_2$ and ethylthiooxamate as $R^4C(S)NH_2$, MS(ES+) 408 (M+H)$^+$.

Example 33

5-[2-(2-Chloro-phenyl)-thiazol-4-yl]-2-methyl-1-thiophen-2-ylmethyl-1H-pyrrole-3-carboxylic acid butylamide

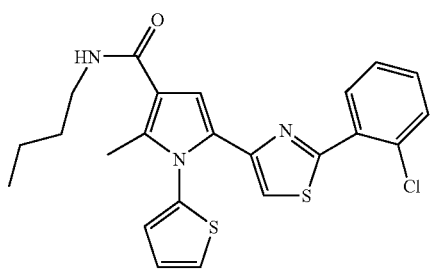

The title compound was obtained using butylamine as $R^1R^2NH$, 3-(aminomethyl)thiophene as $R^3$—$(CH_2)_m$—$NH_2$ and 2-chloro-phenyl thioamide as $R^4C(S)NH_2$, MS(ES+) 470 (M+H)$^+$.

Example 34

5-[2-(4-Methoxy-phenyl)-thiazol-4-yl]-2-methyl-1-thiophen-2-ylmethyl-1H-pyrrole-3-carboxylic acid butylamide

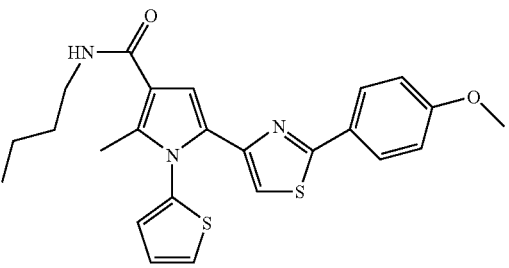

The title compound was obtained using butylamine as $R^1R^2NH$, 3-(aminomethyl)thiophene as $R^3$—$(CH_2)_m$—$NH_2$ and 4-methoxyphenyl thioamide as $R^4C(S)NH_2$, MS(ES+) 466 (M+H)$^+$.

Example 35

5-[2-(4-Methoxy-phenoxymethyl)-thiazol-4-yl]-2-methyl-1-thiophen-2-ylmethyl-1H-pyrrole-3-carboxylic acid butylamide

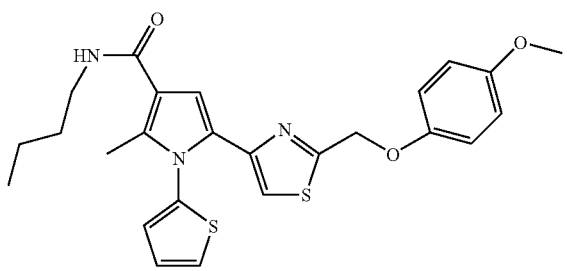

The title compound was obtained using butylamine as $R^1R^2NH$, 3-(aminomethyl)thiophene as $R^3$—$(CH_2)_m$—$NH_2$ and 2-(4-methoxyphenoxy)ethanethioamide as $R^4C(S)NH_2$, MS(ES+) 496 (M+H)$^+$.

Example 36

5-[2-(2-Ethyl-pyridin-4-yl)-thiazol-4-yl]-2-methyl-1-thiophen-2-ylmethyl-1H-pyrrole-3-carboxylic acid butylamide

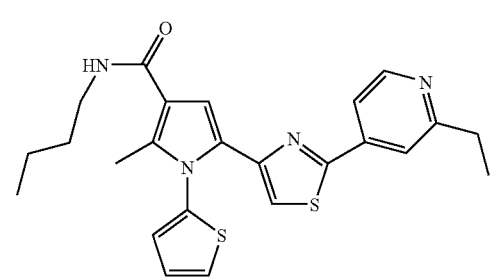

The title compound was obtained using butylamine as $R^1R^2NH$, 3-(aminomethyl)thiophene as $R^3$—$(CH_2)_m$—$NH_2$ and 2-ethyl-4-pyridine carbothiamide as $R^4C(S)NH_2$, MS(ES+) 465 (M+H)$^+$.

Example 37

1-[2-(3,4-Dimethoxy-phenyl)-ethyl]-5-[2-(2-ethyl-pyridin-4-yl)-thiazol-4-yl]-2-methyl-1H-pyrrole-3-carboxylic acid butylamide

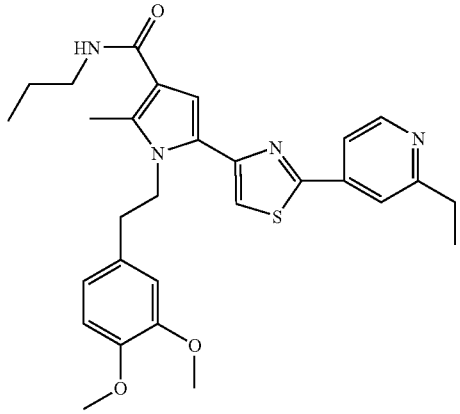

The title compound was obtained using butylamine as $R^1R^2NH$, homoveratrylamine as $R^3$—$(CH_2)_m$—$NH_2$ and 2-ethyl-4-pyridine carbothiamide as $R^4C(S)NH_2$, MS(ES+) 533 (M+H)+.

Example 38 rac-1-Butyl-5-[2-(2-chloro-phenyl)-thiazol-4-yl]-2-methyl-1H-pyrrole-3-carboxylic acid sec-butylamide

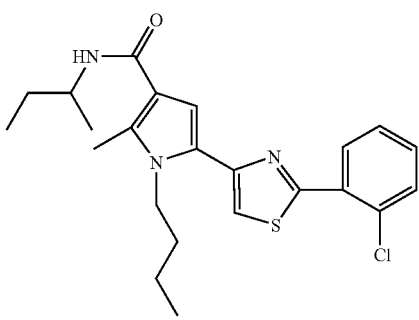

The title compound was obtained using sec-butylamine as $R^1R^2NH$, butylamine as $R^3$—$(CH_2)_m$—$NH_2$ and 2-chlorophenyl thioamide as $R^4C(S)NH_2$, MS(ES+) 430 (M+H)+.

Example 39 rac-1-Butyl-5-[2-(4-methoxy-phenyl)-thiazol-4-yl]-2-methyl-1H-pyrrole-3-carboxylic acid sec-butylamide

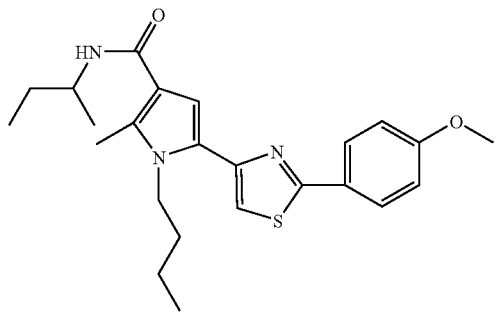

The title compound was obtained using sec-butylamine as $R^1R^2NH$, butylamine as $R^3$—$(CH_2)_m$—$NH_2$ and 4-methoxyphenyl thioamide as $R^4C(S)NH_2$, MS(ES+) 426 (M+H)+.

Example 40 rac-1-Butyl-5-[2-(4-methoxy-phenoxymethyl)-thiazol-4-yl]-2-methyl-1H-pyrrole-3-carboxylic acid sec-butylamide

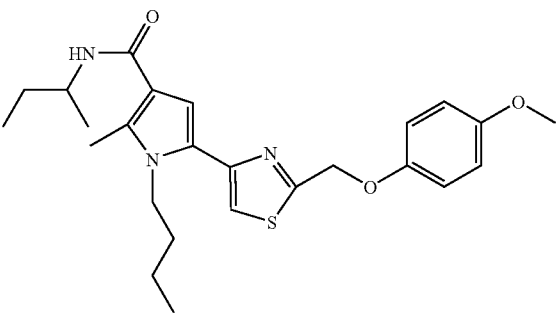

The title compound was obtained using sec-butylamine as $R^1R^2NH$, butylamine as $R^3$—$(CH_2)_m$—$NH_2$ and 2-(4-methoxyphenoxy)ethanethioamide as $R^4C(S)NH_2$, MS(ES+) 456 (M+H)+.

Example 41 rac-1-Butyl-5-[2-(2-ethyl-pyridin-4-yl)-thiazol-4-yl]-2-methyl-1H-pyrrole-3-carboxylic acid sec-butylamide

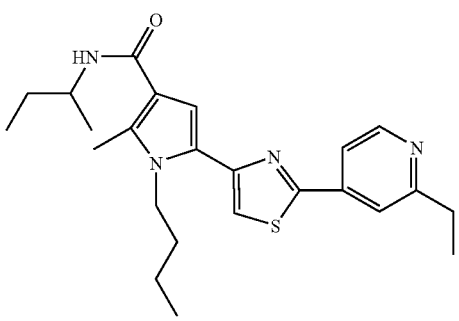

The title compound was obtained using sec-butylamine as R¹R²NH, butylamine as R³—(CH₂)ₘ—NH₂ and 2-ethyl-4-pyridine carbothiamide as R⁴C(S)NH₂, MS(ES+) 425 (M+H)⁺.

Example 42 rac-5-[2-(2-Chloro-phenyl)-thiazol-4-yl]-1-isobutyl-2-methyl-1H-pyrrole-3-carboxylic acid sec-butylamide

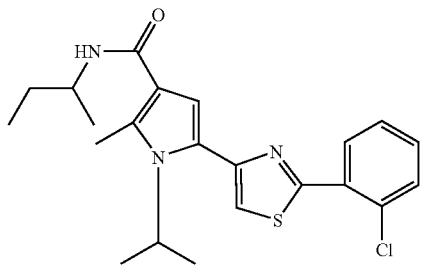

The tile compound was obtained using sec-butylamine as R¹R²NH, isobutylamine as R³—(CH₂)ₘ—NH₂ and 2-chloro-phenyl thioamide as R⁴C(S)NH₂, MS(ES+) 430 (M+H)⁺.

Example 43 rac-1-Isobutyl-5-[2-(4-methoxy-phenyl)-thiazol-4-yl]-2-methyl-1H-pyrrole-3-carboxylic acid sec-butylamide

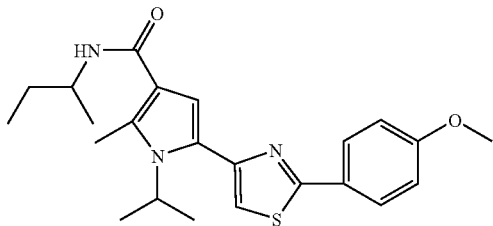

The title compound was obtained using sec-butylamine as R¹R²NH, isobutylamine as R³—(CH₂)ₘ—NH₂ and 4-methoxyphenyl thioamide as R⁴C(S)NH₂, MS(ES+) 426 (M+H)⁺.

Example 44 rac-1-Isobutyl-5-[2-(4-methoxy-phenoxymethyl)-thiazol-4-yl]-2-methyl-1H-pyrrole-3-carboxylic acid sec-butylamide

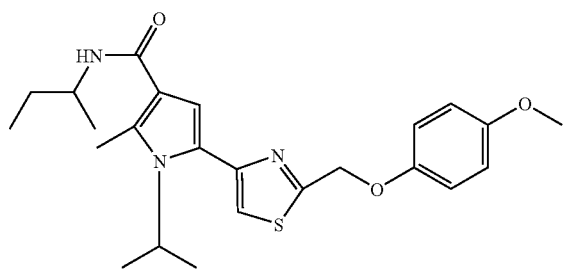

The title compound was obtained using sec-butylamine as R¹R²NH, isobutylamine as R³—(CH₂)ₘ—NH₂ and 2-(4-methoxyphenoxy)ethanethioamide as R⁴C(S)NH₂, MS(ES+) 456 (M+H)⁺.

Example 45 rac-5-[2-(2-Chloro-phenyl)-thiazol-4-yl]-1-cyclo-hexylmethyl-2-methyl-1H-pyrrole-3-carboxylic acid sec-butylamide

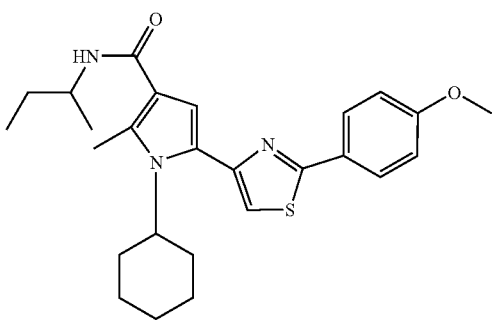

The title compound was obtained using sec-butylamine as R¹R²NH, aminomethylcyclohexane as R³—(CH₂)ₘ—NH₂ and 2-chloro-phenyl thioamide as R⁴C(S)NH₂, MS(ES+) 470 (M+H)⁺.

Example 46 rac-1-Cyclohexylmethyl-5-[2-(4-methoxy-phenyl)-thiazol-4-yl]-2-methyl-1H-pyrrole-3-carboxylic acid sec-butylamide The title compound was obtained using sec-butylamine as R¹R²NH, aminomethylcyclohexane as R³—(CH₂)ₘ—NH₂ and 4-methoxyphenyl thioamide as R⁴C(S)NH₂, MS(ES+) 466 (M+H)⁺.

Example 47 rac-1-Cyclohexylmethyl-5-[2-(4-methoxy-phenoxymethyl)-thiazol-4-yl]-2-methyl-1H-pyrrole-3-carboxylic acid sec-butylamide

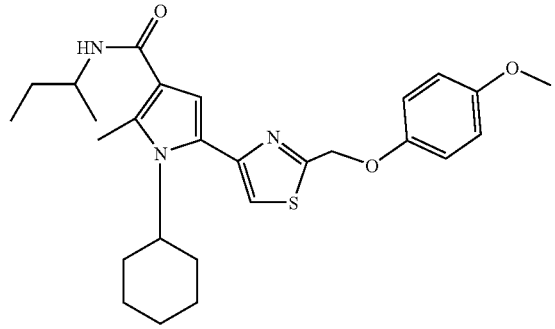

The title compound was obtained using sec-butylamine as $R^1R^2NH$, aminomethylcyclohexane as $R^3$—$(CH_2)_m$—$NH_2$ and 2-(4-methoxyphenoxy)ethanethioamide as $R^4C(S)NH_2$, MS(ES+) 496 (M+H)$^+$.

Example 48 rac-1-Cyclohexylmethyl-5-[2-(2-ethyl-pyridin-4-yl)-thiazol-4-yl]-2-methyl-1H-pyrrole-3-carboxylic acid sec-butylamide

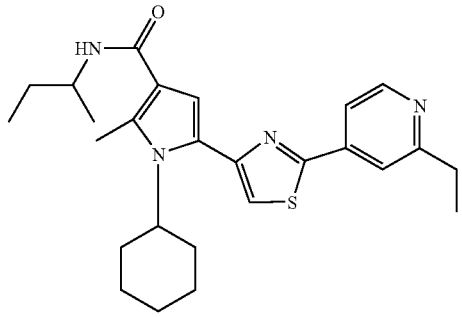

The title compound was obtained using sec-butylamine as $R^1R^2NH$, aminomethylcyclohexane as $R^3$—$(CH_2)_m$—$NH_2$ and 2-ethyl-4-pyridine carbothiamide as $R^4C(S)NH_2$, MS(ES+) 465 (M+H)$^+$.

Example 49 rac-1-Cyclohexylmethyl-2-methyl-5-(2-pyrazin-2-yl-thiazol-4-yl)-1H-pyrrole-3-carboxylic acid sec-butylamide

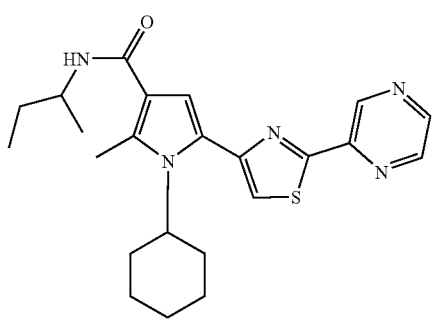

The title compound was obtained using sec-butylamine as $R^1R^2NH$, aminomethylcyclohexane as $R^3$—$(CH_2)_m$—$NH_2$ and pyrazine-2-carbothioamide as $R^4C(S)NH_2$, MS(ES+) 438 (M+H)$^+$.

Example 50 rac-5-[2-(2-Chloro-phenyl)-thiazol-4-yl]-2-methyl-1-(tetrahydro-furan-2-ylmethyl)-1H-pyrrole-3-carboxylic acid sec-butylamide

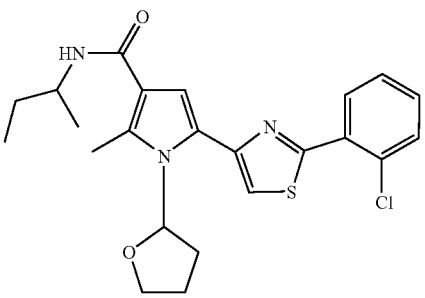

The title compound was obtained using sec-butylamine as $R^1R^2NH$, tetrahydrofurfurylamine as $R^3$—$(CH_2)_m$—$NH_2$ and 2-chloro-phenyl thioamide as $R^4C(S)NH_2$, MS(ES+) 458 (M+H)$^+$.

Example 51 rac-5-[2-(4-Methoxy-phenyl)-thiazol-4-yl]-2-methyl-1-(tetrahydro-furan-2-ylmethyl)-1H-pyrrole-3-carboxylic acid sec-butylamide

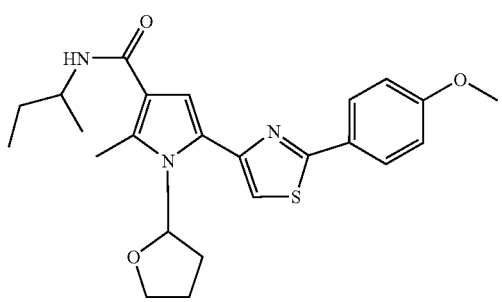

The title compound was obtained using sec-butylamine as $R^1R^2NH$, tetrahydrofurfurylamine as $R^3$—$(CH_2)_m$—$NH_2$ and 4-methoxyphenyl thioamide as $R^4C(S)NH_2$, MS(ES+) 454 (M+H)$^+$.

Example 52 rac-5-[2-(4-Methoxy-phenoxymethyl)-thiazol-4-yl]-2-methyl-1-(tetrahydro-furan-2-ylmethyl)-1H-pyrrole-3-carboxylic acid sec-butylamide

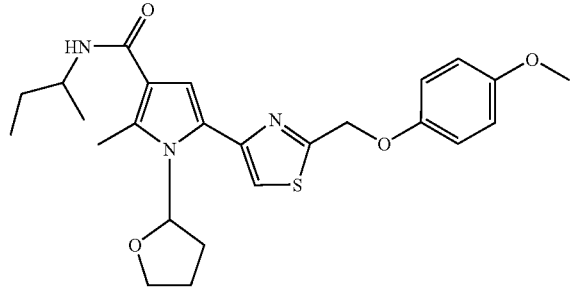

The title compound was obtained using sec-butylamine as R¹R²NH, tetrahydrofurfurylamine as R³—(CH$_2$)$_m$—NH$_2$ and 2-(4-methoxyphenoxy)ethanethioamide as R⁴C(S)NH$_2$, MS(ES+) 484 (M+H)⁺.

Example 53 rac-2-Methyl-5-(2-pyrazin-2-yl-thiazol-4-yl)-1-(tetrahydro-furan-2-ylmethyl)-1H-pyrrole-3-carboxylic acid sec-butylamide

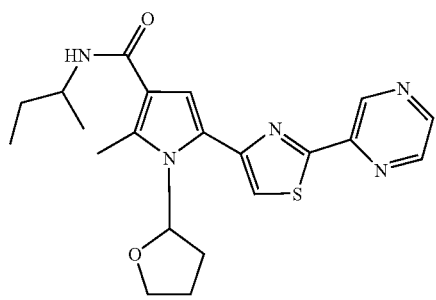

The title compound was obtained using sec-butylamine as R¹R²NH, tetrahydrofurfurylamine as R³—(CH$_2$)$_m$—NH$_2$ and pyrazine-2-carbothioamide as R⁴C(S)NH$_2$, MS(ES+) 426 (M+H)⁺.

Example 54 rac 1-(2-Methoxy-ethyl)-5-[2-(4-methoxy-phenyl)-thiazol-4-yl]-2-methyl-1H-pyrrole-3-carboxylic acid sec-butylamide

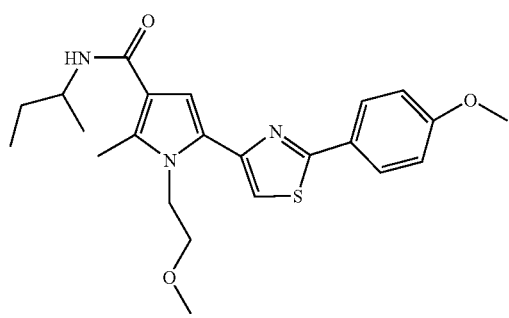

The title compound was obtained using sec-butylamine as R¹R²NH, methoxyethylamine as R³—(CH$_2$)$_m$—NH$_2$ and 4-methoxyphenyl thioamide as R⁴C(S)NH$_2$, MS(ES+) 428 (M+H)⁺.

Example 55 rac-5-[2-(2-Chloro-phenyl)-thiazol-4-yl]-1-furan-2-ylmethyl-2-methyl-1H-pyrrole-3-carboxylic acid sec-butylamide

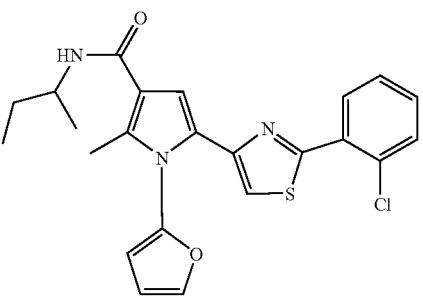

The title compound was obtained using sec-butylamine as R¹R²NH, 3-furylmethylamine as R³—(CH$_2$)$_m$—NH$_2$ and 2-chloro-phenyl thioamide as R⁴C(S)NH$_2$, MS(ES+) 454 (M+H)⁺.

Example 56 rac-1-Furan-2-ylmethyl-5-[2-(4-methoxy-phenyl)-thiazol-4-yl]-2-methyl-1H-pyrrole-3-carboxylic acid sec-butylamide

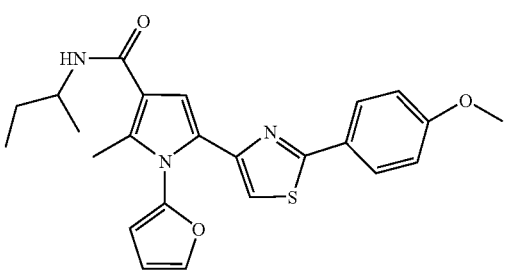

The title compound was obtained using sec-butylamine as R¹R²NH, 3-furylmethylamine as R³—(CH$_2$)$_m$—NH$_2$ and 4-methoxyphenyl thioamide as R⁴C(S)NH$_2$, MS(ES+) 450 (M+H)⁺.

Example 57 rac-5-[2-(2-Ethyl-pyridin-4-yl)-thiazol-4-yl]-1-furan-2-ylmethyl-2-methyl-1H-pyrrole-3-carboxylic acid sec-butylamide

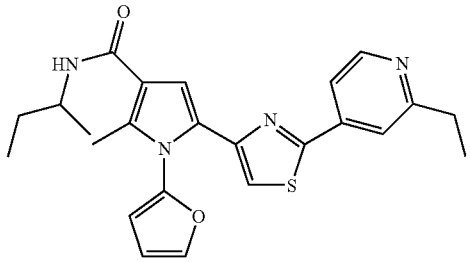

The title compound was obtained using sec-butylamine as $R^1R^2NH$, 3-furylmethylamine as $R^3$—$(CH_2)_m$—$NH_2$ and 2-ethyl-4-pyridine carbothiamide as $R^4C(S)NH_2$, MS(ES+) 449 (M+H)$^+$.

Example 58 rac-5-[2-(2-Chloro-phenyl)-thiazol-4-yl]-1-(4-methoxy-benzyl)-2-methyl-1H-pyrrole-3-carboxylic acid sec-butylamide

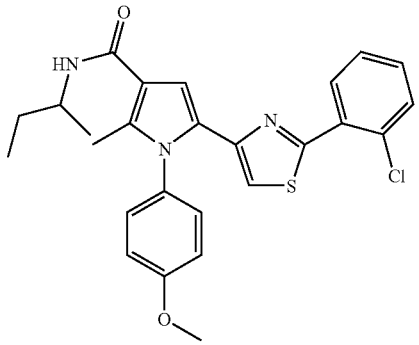

The title compound was obtained using sec-butylamine as $R^1R^2NH$, 4-methoxybenzyl-amine as $R^3$—$(CH_2)_m$—$NH_2$ and 2-chloro-phenyl thioamide as $R^4C(S)NH_2$, MS(ES+) 494 (M+H)$^+$.

Example 59 rac-1-(4-Methoxy-benzyl)-5-[2-(4-methoxy-phenyl)-thiazol-4-yl]-2-methyl-1H-pyrrole-3-carboxylic acid sec-butylamide

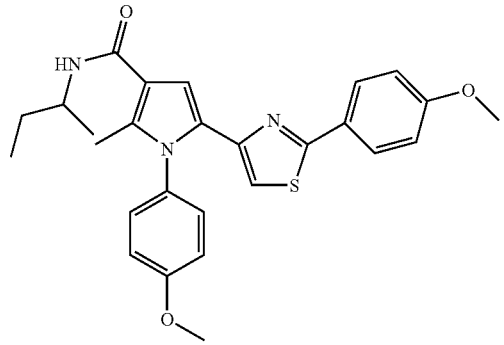

The title compound was obtained using sec-butylamine as $R^1R^2NH$, 4-methoxybenzyl-amine as $R^3$—$(CH_2)_m$—$NH_2$ and 4-methoxyphenyl thioamide as $R^4C(S)NH_2$, MS(ES+) 490 (M+H)$^+$.

Example 60 rac-1-(4-Methoxy-benzyl)-5-[2-(4-methoxy-phenoxymethyl)-thiazol-4-yl]-2-methyl-1H-pyrrole-3-carboxylic acid sec-butylamide

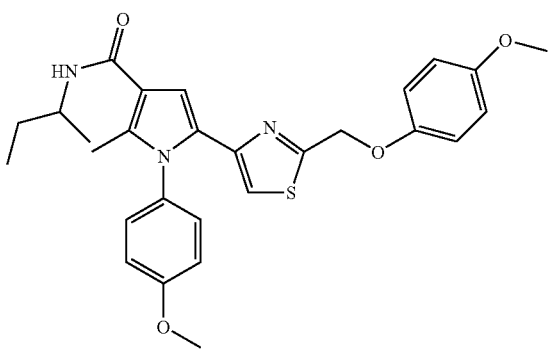

The title compound was obtained using sec-butylamine as $R^1R^2NH$, 4-methoxybenzyl-amine as $R^3$—$(CH_2)_m$—$NH_2$ and 2-(4-methoxyphenoxy)ethanethioamide as $R^4C(S)NH_2$, MS(ES+) 520 (M+H)$^+$.

Example 61 rac-5-[2-(2-Ethyl-pyridin-4-yl)-thiazol-4-yl]-1-(4-methoxy-benzyl)-2-methyl-1H-pyrrole-3-carboxylic acid sec-butylamide

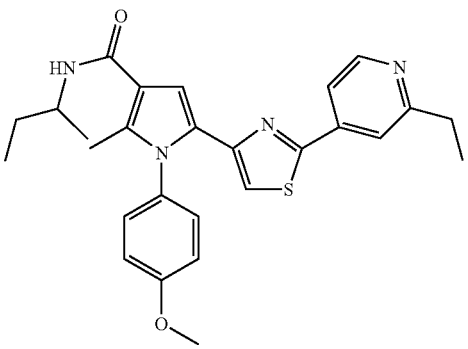

The title compound was obtained using sec-butylamine as $R^1R^2NH$, 4-methoxybenzyl-amine as $R^3$—$(CH_2)_m$—$NH_2$ and 2-ethyl-4-pyridine carbothiamide as $R^4C(S)NH_2$, MS(ES+) 489 (M+H)$^+$.

Example 62 rac-1-(4-Methoxy-benzyl)-2-methyl-5-(2-pyrazin-2-yl-thiazol-4-yl)-1H-pyrrole-3-carboxylic acid sec-butylamide

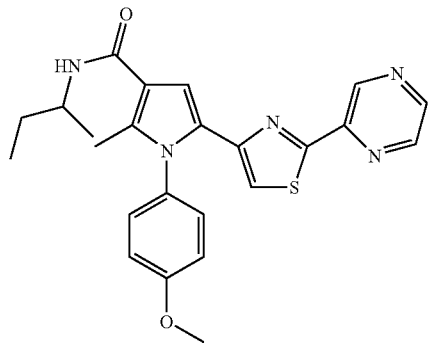

The title compound was obtained using sec-butylamine as $R^1R^2NH$, 4-methoxybenzyl-amine as $R^3$—$(CH_2)_m$—$NH_2$ and pyrazine-2-carbothioamide as $R^4C(S)NH_2$, MS(ES+) 462 (M+H)$^+$.

Example 63 rac-5-[2-(4-Methoxy-phenyl)-thiazol-4-yl]-1-(3-methoxy-propyl)-2-methyl-1H-pyrrole-3-carboxylic acid sec-butylamide

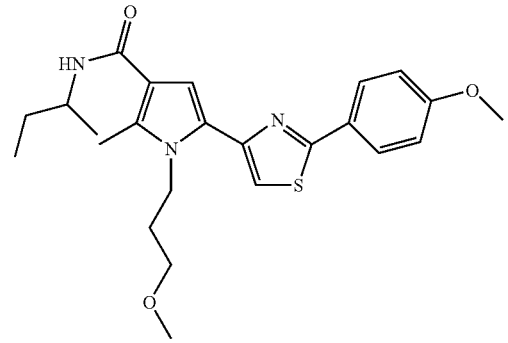

The title compound was obtained using sec-butylamine as $R^1R^2NH$, methoxyethylamine as $R^3$—$(CH_2)_m$—$NH_2$ and 4-methoxyphenyl thioamide as $R^4C(S)NH_2$, MS(ES+) 442 (M+H)$^+$.

Example 64 rac-5-[2-(4-Methoxy-phenoxymethyl)-thiazol-4-yl]-1-(3-methoxy-propyl)-2-methyl-1H-pyrrole-3-carboxylic acid sec-butylamide

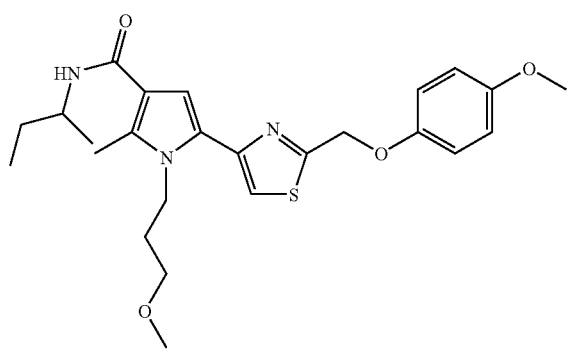

The title compound was obtained using sec-butylamine as $R^1R^2NH$, methoxyethylamine as $R^3$—$(CH_2)_m$—$NH_2$ and 2-(4-methoxyphenoxy)ethanethioamide as $R^4C(S)NH_2$, MS(ES+) 472 (M+H)$^+$.

Example 65 rac-5-[2-(2-Chloro-phenyl)-thiazol-4-yl]-2-methyl-1-thiophen-2-ylmethyl-1H-pyrrole-3-carboxylic acid sec-butylamide

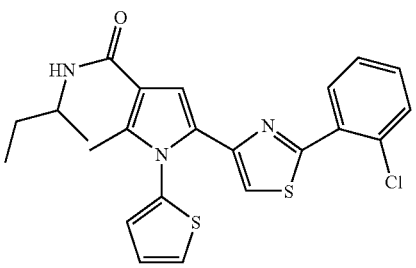

The title compound was obtained using sec-butylamine as $R^1R^2NH$, 3-(aminomethyl)-thiophene as $R^3$—$(CH_2)_m$—$NH_2$ and 2-chloro-phenyl thioamide as $R^4C(S)NH_2$, MS(ES+) 470 (M+H)$^+$.

Example 66 rac-5-[2-(4-Methoxy-phenyl)-thiazol-4-yl]-2-methyl-1-thiophen-2-ylmethyl-1H-pyrrole-3-carboxylic acid sec-butylamide

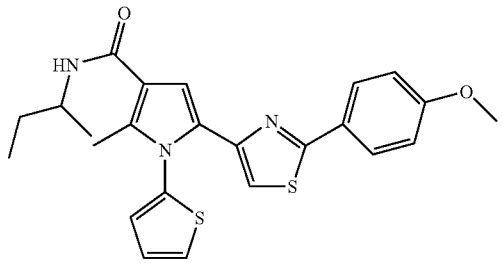

The title compound was obtained using sec-butylamine as $R^1R^2NH$, 3-(aminomethyl)-thiophene as $R^3$—$(CH_2)_m$—$NH_2$ and 4-methoxyphenyl thioamide as $R^4C(S)NH_2$, MS(ES+) 466 (M+H)$^+$.

Example 67 rac-5-[2-(4-Methoxy-phenoxymethyl)-thiazol-4-yl]-2-methyl-1-thiophen-2-ylmethyl-1H-pyrrole-3-carboxylic acid sec-butylamide

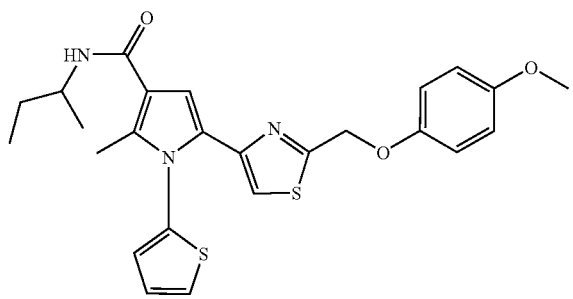

The title compound was obtained using sec-butylamine as $R^1R^2NH$, 3-(aminomethyl)-thiophene as $R^3$—$(CH_2)_m$—$NH_2$ and 2-(4-methoxyphenoxy)ethanethioamide as $R^4C(S)NH_2$, MS(ES+) 496 (M+H)$^+$.

Example 68 rac-5-[2-(2-Ethyl-pyridin-4-yl)-thiazol-4-yl]-2-methyl-1-thiophen-2-ylmethyl-1H-pyrrole-3-carboxylic acid sec-butylamide

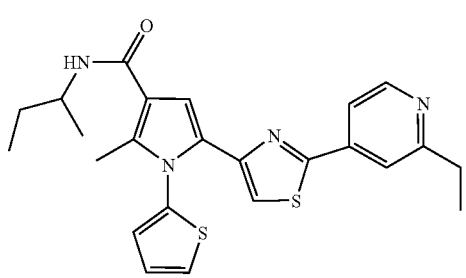

The title compound was obtained using sec-butylamine as $R^1R^2NH$, 3-(aminomethyl)-thiophene as $R^3$—$(CH_2)_m$—$NH_2$ and 2-ethyl-4-pyridine carbothiamide as $R^4C(S)NH_2$, MS(ES+) 465 (M+H)$^+$.

Example 69 rac-5-[2-(2-Chloro-phenyl)-thiazol-4-yl]-1-[2-(3,4-dimethoxy-phenyl)-ethyl]-2-methyl-1H-pyrrole-3-carboxylic acid sec-butylamide

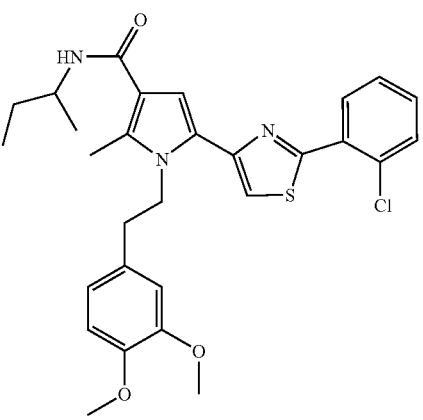

The title compound was obtained using sec-butylamine as $R^1R^2NH$, homoveratrylamine as $R^3$—$(CH_2)_m$—$NH_2$ and 2-chloro-phenyl thioamide as $R^4C(S)NH_2$, MS(ES+) 538 (M+H)$^+$.

Example 70

Butyl-5-[2-(2-chloro-phenyl)-thiazol-4-yl]-2-methyl-1H-pyrrole-3-carboxylic acid isobutyl-amide

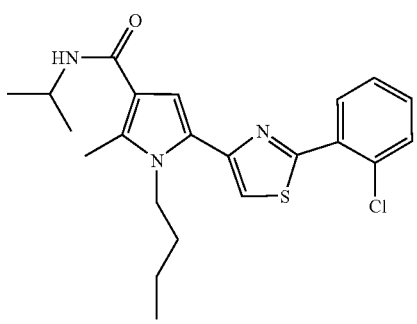

The title compound was obtained using iso-butylamine as $R^1R^2NH$, butylamine as $R^3$—$(CH_2)_m$—$NH_2$ and 2-chloro-phenyl thioamide as $R^4C(S)NH_2$, MS(ES+) 430 (M+H)$^+$.

Example 71

Butyl-5-[2-(4-methoxy-phenyl)-thiazol-4-yl]-2-methyl-1H-pyrrole-3-carboxylic acid isobutyl-amide

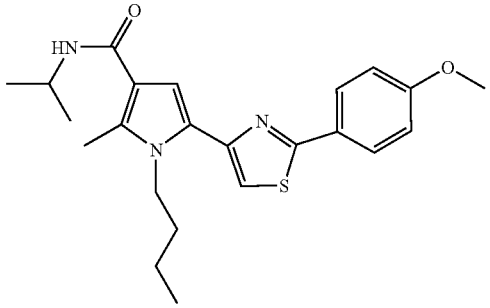

The title compound was obtained using iso-butylamine as $R^1R^2NH$, butylamine as $R^3$—$(CH_2)_m$—$NH_2$ and 4-methoxyphenyl thioamide as $R^4C(S)NH_2$, MS(ES+) 426 (M+H)$^+$.

Example 72

Butyl-5-[2-(4-methoxy-phenoxymethyl)-thiazol-4-yl]-2-methyl-1H-pyrrole-3-carboxylic acid isobutyl-amide

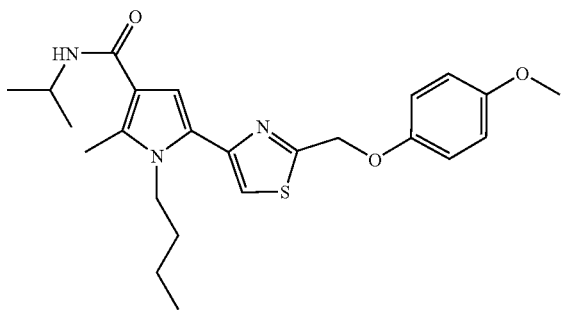

The title compound was obtained using iso-butylamine as $R^1R^2NH$, butylamine as $R^3$—$(CH_2)_m$—$NH_2$ and 2-(4-methoxyphenoxy)ethanethioamide as $R^4C(S)NH_2$, MS(ES+) 456 (M+H)$^+$.

Example 73

Butyl-5-[2-(2-ethyl-pyridin-4-yl)-thiazol-4-yl]-2-methyl-1H-pyrrole-3-carboxylic acid isobutyl-amide

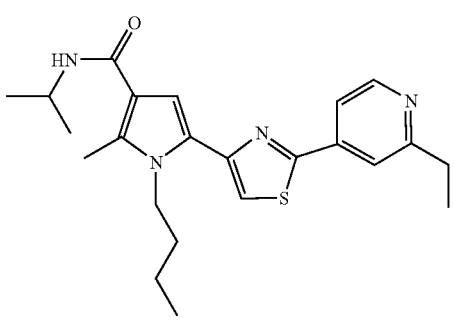

The title compound was obtained using iso-butylamine as $R^1R^2NH$, butylamine as $R^3$—$(CH_2)_m$—$NH_2$ and 2-ethyl-4-pyridine carbothiamide as $R^4C(S)NH_2$, MS(ES+) 425 (M+H)$^+$.

Example 74

Butyl-2-methyl-5-[2-(6-methyl-pyridin-3-yl)-thiazol-4-yl]-1H-pyrrole-3-carboxylic acid isobutyl-amide

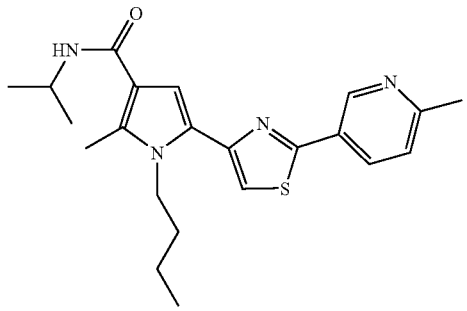

The title compound was obtained using iso-butylamine as $R^1R^2NH$, butylamine as $R^3$—$(CH_2)_m$—$NH_2$ and 6-methyl-pyridine-3-carbothioamide as $R^4C(S)NH_2$, MS(ES+) 411 (M+H)$^+$.

Example 75

Isobutyl-5-[2-(4-methoxy-phenyl)-thiazol-4-yl]-2-methyl-1H-pyrrole-3-carboxylic acid isobutyl-amide

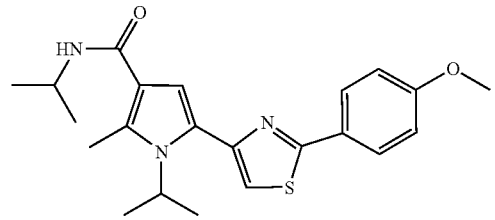

The title compound was obtained using isobutylamine as $R^1R^2NH$, isobutylamine as $R^3$—$(CH_2)_m$—$NH_2$ and 4-methoxyphenyl thioamide as $R^4C(S)NH_2$, MS(ES+) 426 (M+H)$^+$.

Example 76

Isobutyl-5-[2-(4-methoxy-phenoxymethyl)-thiazol-4-yl]-2-methyl-1H-pyrrole-3-carboxylic acid isobutyl-amide

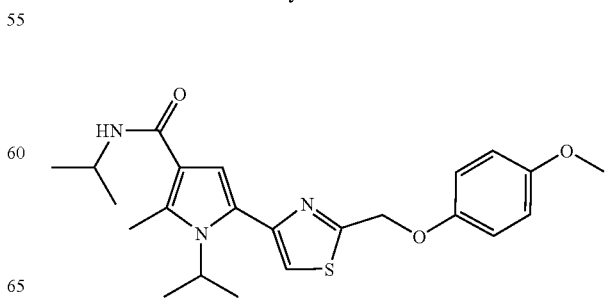

The title compound was obtained using iso-butylamine as R$^1$R$^2$NH, isobutylamine as R$^3$—(CH$_2$)$_m$—NH$_2$ and 2-(4-methoxyphenoxy)ethanethioamide as R$^4$C(S)NH$_2$, MS(ES+) 456 (M+H)$^+$.

Example 77

5-[2-(2-Ethyl-pyridin-4-yl)-thiazol-4-yl]-1-isobutyl-2-methyl-1H-pyrrole-3-carboxylic acid isobutyl-amide

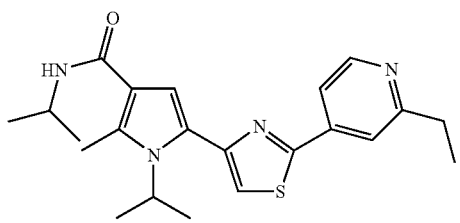

The title compound was obtained using iso-butylamine as R$^1$R$^2$NH, isobutylamine as R$^3$—(CH$_2$)$_m$—NH$_2$ and 2-ethyl-4-pyridine carbothiamide as R$^4$C(S)NH$_2$, MS(ES+) 425 (M+H)$^+$.

Example 78

5-[2-(2-Ethyl-pyridin-4-yl)-thiazol-4-yl]-1-[2-(4-methoxy-phenyl)-ethyl]-2-methyl-1H-pyrrole-3-carboxylic acid isobutyl-amide

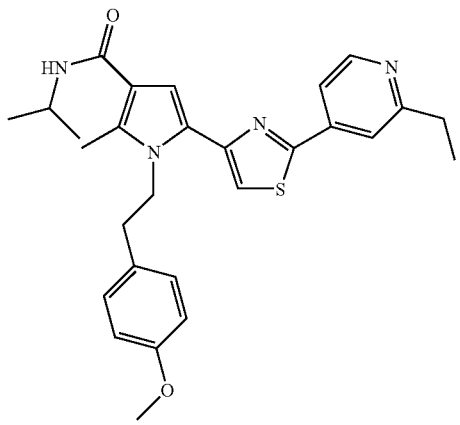

The title compound was obtained using iso-butylamine as R$^1$R$^2$NH, 2-(4-methoxyphenyl)ethylamine as R$^3$—(CH$_2$)$_m$—NH$_2$ and 2-ethyl-4-pyridine carbothiamide as R$^4$C(S)NH$_2$, MS(ES+) 503 (M+H)$^+$.

Example 79

5-[2-(2-Chloro-phenyl)-thiazol-4-yl]-1-cyclohexylmethyl-2-methyl-1H-pyrrole-3-carboxylic acid isobutyl-amide

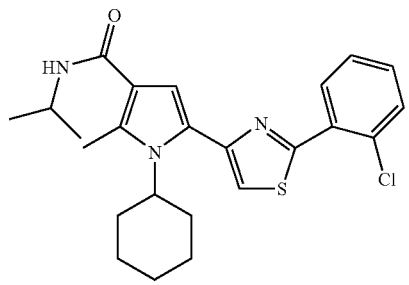

The title compound was obtained using iso-butylamine as R$^1$R$^2$NH, aminomethylcyclohexane as R$^3$—(CH$_2$)$_m$—NH$_2$ and 2-chloro-phenyl thioamide as R$^4$C(S)NH$_2$, MS(ES+) 470 (M+H)$^+$.

Example 80

Cyclohexylmethyl-5-[2-(4-methoxy-phenyl)-thiazol-4-yl]-2-methyl-1H-pyrrole-3-carboxylic acid isobutyl-amide

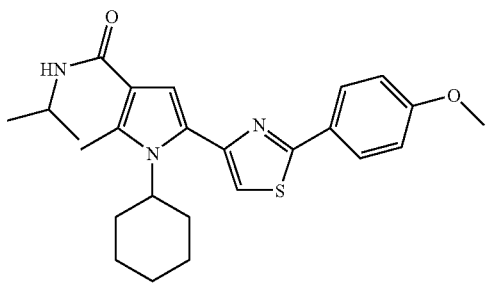

The title compound was obtained using iso-butylamine as R$^1$R$^2$NH, aminomethylcyclohexane as R$^3$—(CH$_2$)$_m$—NH$_2$ and 4-methoxyphenyl thioamide as R$^4$C(S)NH$_2$, MS(ES+) 466 (M+H)$^+$.

Example 81

Cyclohexylmethyl-5-[2-(4-methoxy-phenoxymethyl)-thiazol-4-yl]-2-methyl-1H-pyrrole-3-carboxylic acid isobutyl-amide

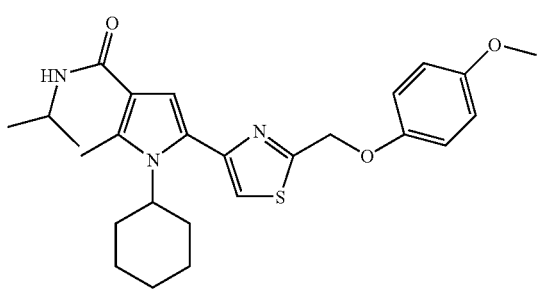

The title compound was obtained using iso-butylamine as R¹R²NH, aminomethylcyclohexane as R³—(CH₂)$_m$—NH₂ and 2-(4-methoxyphenoxy)ethanethioamide as R⁴C(S)NH₂, MS(ES+) 496 (M+H)⁺.

Example 82

Cyclohexylmethyl-5-[2-(2-ethyl-pyridin-4-yl)-thiazol-4-yl]-2-methyl-1H-pyrrole-3-carboxylic acid isobutyl-amide

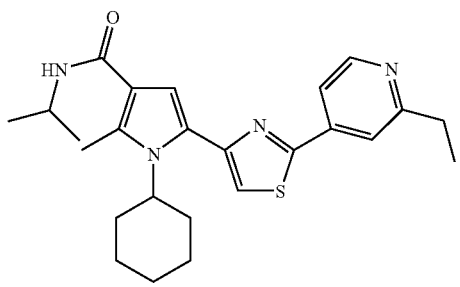

The title compound was obtained using iso-butylamine as R¹R²NH, aminomethylcyclohexane as R³—(CH₂)$_m$—NH₂ and 2-ethyl-4-pyridine carbothiamide as R⁴C(S)NH₂, MS(ES+) 465 (M+H)⁺.

Example 83

5-[2-(2-Chloro-phenyl)-thiazol-4-yl]-2-methyl-1-(tetrahydro-furan-2-ylmethyl)-1H-pyrrole-3-carboxylic acid isobutyl-amide

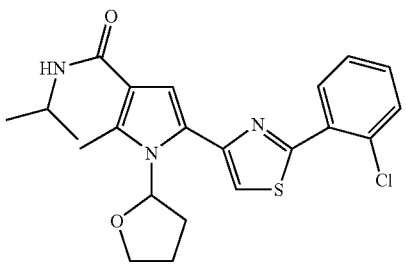

The title compound was obtained using iso-butylamine as R¹R²NH, tetrahydrofurfurylamine as R³—(CH₂)$_m$—NH₂ and 2-chloro-phenyl thioamide as R⁴C(S)NH₂, MS(ES+) 458 (M+H)⁺.

Example 84

5-[2-(4-Methoxy-phenyl)-thiazol-4-yl]-2-methyl-1-(tetrahydro-furan-2-ylmethyl)-1H-pyrrole-3-carboxylic acid isobutyl-amide

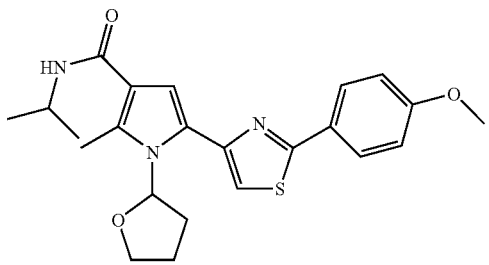

The title compound was obtained using iso-butylamine as R¹R²NH, tetrahydrofurfurylamine as R³—(CH₂)$_m$—NH₂ and 4-methoxyphenyl thioamide as R⁴C(S)NH₂, MS(ES+) 454 (M+H)⁺.

Example 85

5-[2-(4-Methoxy-phenoxymethyl)-thiazol-4-yl]-2-methyl-1-(tetrahydro-furan-2-ylmethyl)-1H-pyrrole-3-carboxylic acid isobutyl-amide

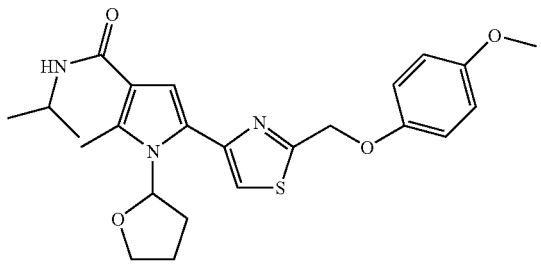

The title compound was obtained using iso-butylamine as R¹R²NH, tetrahydrofurfurylamine as R³—(CH₂)$_m$—NH₂ and 2-(4-methoxyphenoxy)ethanethioamide as R⁴C(S)NH₂, MS(ES+) 484 (M+H)⁺.

Example 86

4-[4-Isobutylcarbamoyl-5-methyl-1-(tetrahydro-furan-2-ylmethyl)-1H-pyrrol-2-yl]-thiazole-2-carboxylic acid ethyl ester

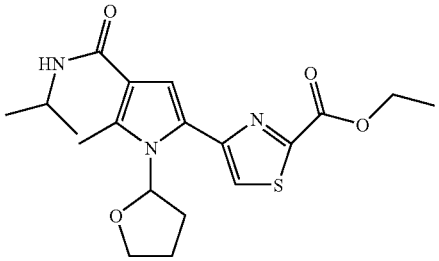

The title compound was obtained using iso-butylamine as R¹R²NH, tetrahydrofurfurylamine as R³—(CH₂)ₘ—NH₂ and ethylthiooxamate as R⁴C(S)NH₂, MS(ES+) 420 (M+H)⁺.

Example 87

Methyl-5-[2-(6-methyl-pyridin-3-yl)-thiazol-4-yl]-1-(tetrahydro-furan-2-ylmethyl)-1H-pyrrole-3-carboxylic acid isobutyl-amide

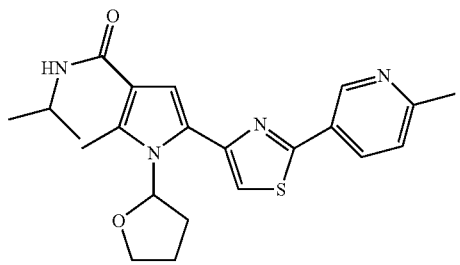

The title compound was obtained using iso-butylamine as R¹R²NH, tetrahydrofurfurylamine as R³—(CH₂)ₘ—NH₂ and 6-methyl-pyridine-3-carbothioamide as R⁴C(S)NH₂, MS(ES+) 439 (M+H)⁺.

Example 88

Methyl-5-(2-pyrazin-2-yl-thiazol-4-yl)-1-(tetrahydro-furan-2-ylmethyl)-1H-pyrrole-3-carboxylic acid isobutyl-amide

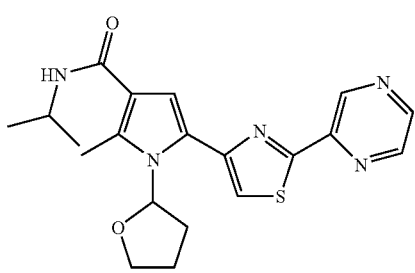

The title compound was obtained using iso-butylamine as R¹R²NH, tetrahydrofurfurylamine as R³—(CH₂)ₘ—NH₂ and pyrazine-2-carbothioamide as R⁴C(S)NH₂, MS(ES+) 426 (M+H)⁺.

Example 89

1-(2-Methoxy-ethyl)-5-[2-(4-methoxy-phenyl)-thiazol-4-yl]-2-methyl-1H-pyrrole-3-carboxylic acid isobutyl-amide

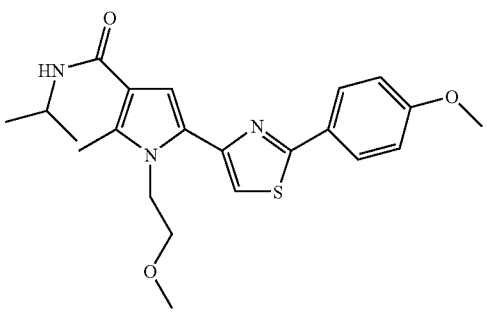

The title compound was obtained using iso-butylamine as R¹R²NH, methoxyethylamine as R³—(CH₂)ₘ—NH₂ and 4-methoxyphenyl thioamide as R⁴C(S)NH₂, MS(ES+) 428 (M+H)⁺.

Example 90

1-(2-Methoxy-ethyl)-2-methyl-5-(2-pyrazin-2-yl-thiazol-4-yl)-1H-pyrrole-3-carboxylic acid isobutyl-amide

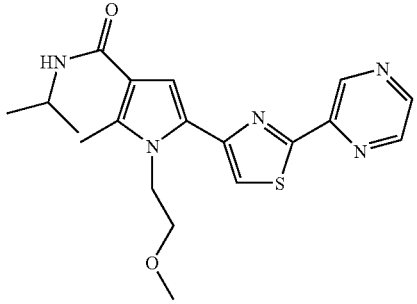

The title compound was obtained using iso-butylamine as R¹R²NH, methoxyethylamine as R³—(CH₂)ₘ—NH₂ and pyrazine-2-carbothioamide as R⁴C(S)NH₂, MS(ES+) 400 (M+H)⁺.

Example 91

5-[2-(2-Chloro-phenyl)-thiazol-4-yl]-1-furan-2-ylmethyl-2-methyl-1H-pyrrole-3-carboxylic acid isobutyl-amide

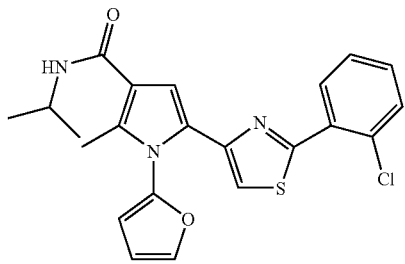

The title compound was obtained using iso-butylamine as $R^1R^2NH$, 3-furylmethylamine as $R^3$—$(CH_2)_m$—$NH_2$ and 2-chloro-phenyl thioamide as $R^4C(S)NH_2$, MS(ES+) 454 $(M+H)^+$.

Example 92

Furan-2-ylmethyl-5-[2-(4-methoxy-phenyl)-thiazol-4-yl]-2-methyl-1H-pyrrole-3-carboxylic acid isobutyl-amide

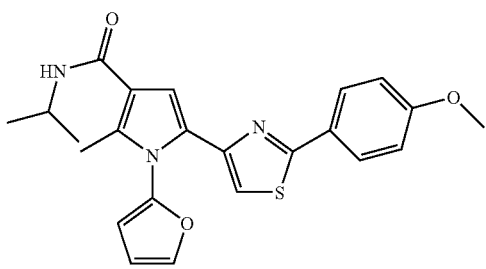

The title compound was obtained using iso-butylamine as $R^1R^2NH$, 3-furylmethylamine as $R^3$—$(CH_2)_m$—$NH_2$ and 4-methoxyphenyl thioamide as $R^4C(S)NH_2$, MS(ES+) 450 $(M+H)^+$.

Example 93

5-[2-(2-Ethyl-pyridin-4-yl)-thiazol-4-yl]-1-furan-2-ylmethyl-2-methyl-1H-pyrrole-3-carboxylic acid isobutyl-amide

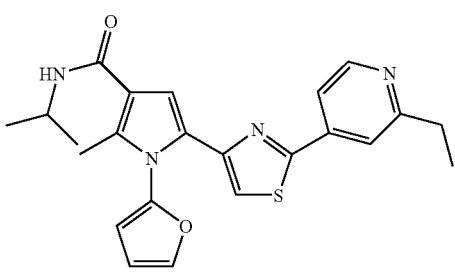

The title compound was obtained using iso-butylamine as $R^1R^2NH$, 3-furylmethylamine as $R^3$—$(CH_2)_m$—$NH_2$ and 2-ethyl-4-pyridine carbothiamide as $R^4C(S)NH_2$, MS(ES+) 449 $(M+H)^+$.

Example 94

1-(4-Methoxy-benzyl)-5-[2-(4-methoxy-phenyl)-thiazol-4-yl]-2-methyl-1H-pyrrole-3-carboxylic acid isobutyl-amide

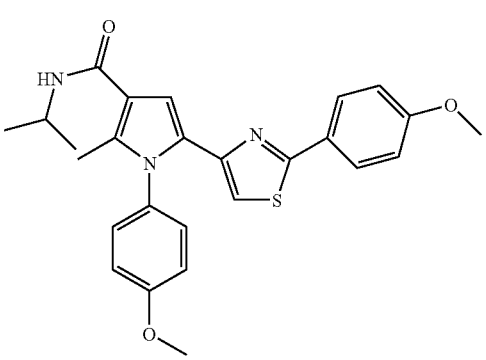

The title compound was obtained using iso-butylamine as $R^1R^2NH$, 4-methoxybenzylamine as $R^3$—$(CH_2)_m$—$NH_2$ and 4-methoxyphenyl thioamide as $R^4C(S)NH_2$, MS(ES+) 490 $(M+H)^+$.

Example 95

1-(4-Methoxy-benzyl)-5-[2-(4-methoxy-phenoxymethyl)-thiazol-4-yl]-2-methyl-1H-pyrrole-3-carboxylic acid isobutyl-amide

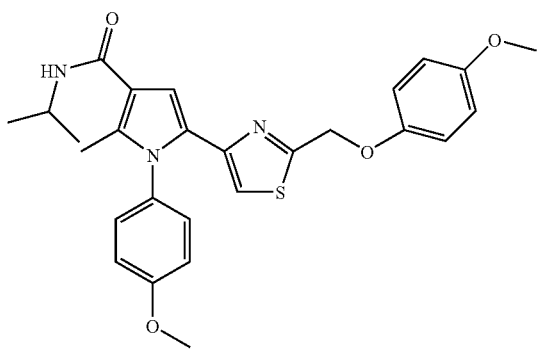

The title compound was obtained using iso-butylamine as $R^1R^2NH$, 4-methoxybenzylamine as $R^3$—$(CH_2)_m$—$NH_2$ and 2-(4-methoxyphenoxy)ethanethioamide as $R^4C(S)NH_2$, MS(ES+) 520 $(M+H)^+$.

Example 96

5-[2-(2-Ethyl-pyridin-4-yl)-thiazol-4-yl]-1-(4-methoxy-benzyl)-2-methyl-1H-pyrrole-3-carboxylic acid isobutyl-amide

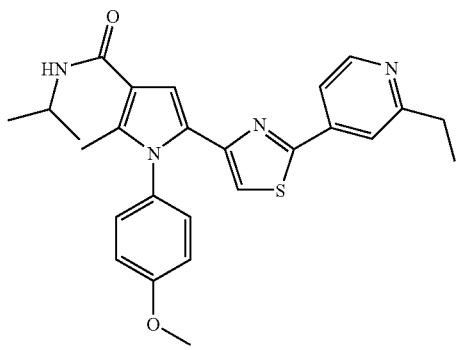

The title compound was obtained using iso-butylamine as $R^1R^2NH$, 4-methoxybenzylamine as $R^3$—$(CH_2)_m$—$NH_2$ and 2-ethyl-4-pyridine carbothiamide as $R^4C(S)NH_2$, MS(ES+) 489 (M+H)$^+$.

Example 97

4-[4-Isobutylcarbamoyl-1-(4-methoxy-benzyl)-5-methyl-1H-pyrrol-2-yl]-thiazole-2-carboxylic acid ethyl ester

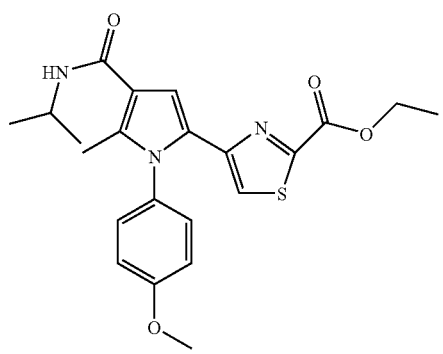

The title compound was obtained using iso-butylamine as $R^1R^2NH$, 4-methoxybenzylamine as $R^3$—$(CH_2)_m$—$NH_2$ and ethylthiooxamate as $R^4C(S)NH_2$, MS(ES+) 456 (M+H)$^+$.

Example 98

1-(4-Methoxy-benzyl)-2-methyl-5-[2-(6-methyl-pyridin-3-yl)-thiazol-4-yl]-1H-pyrrole-3-carboxylic acid isobutyl-amide

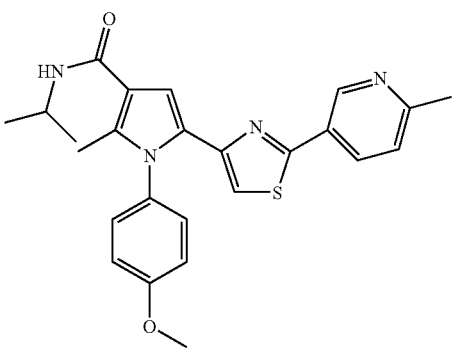

The title compound was obtained using iso-butylamine as $R^1R^2NH$, 4-methoxybenzylamine as $R^3$—$(CH_2)_m$—$NH_2$ and 6-methyl-pyridine-3-carbothioamide as $R^4C(S)NH_2$, MS(ES+) 475 (M+H)$^+$.

Example 99

1-(4-Methoxy-benzyl)-2-methyl-5-(2-pyrazin-2-yl-thiazol-4-yl)-1H-pyrrole-3-carboxylic acid isobutyl-amide

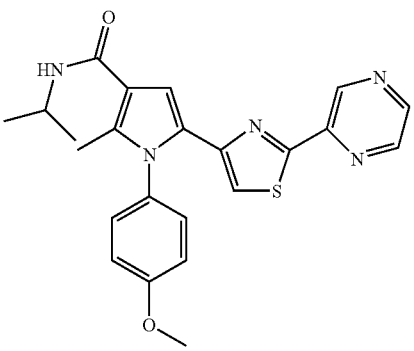

The title compound was obtained using iso-butylamine as $R^1R^2NH$, 4-methoxybenzylamine as $R^3$—$(CH_2)_m$—$NH_2$ and pyrazine-2-carbothioamide as $R^4C(S)NH_2$, MS(ES+) 462 (M+H)$^+$.

Example 100

5-[2-(4-Methoxy-phenyl)-thiazol-4-yl]-1-(3-methoxy-propyl)-2-methyl-1H-pyrrole-3-carboxylic acid isobutyl-amide

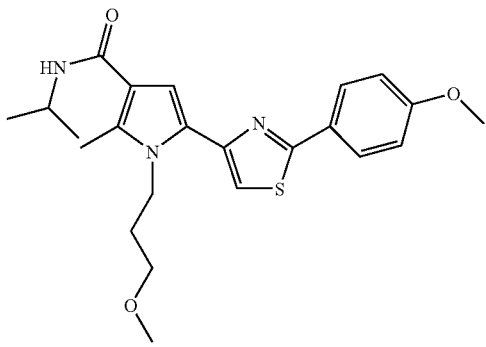

The title compound was obtained using iso-butylamine as $R^1R^2NH$, methoxyethylamine as $R^3$—$(CH_2)_m$—$NH_2$ and 4-methoxyphenyl thioamide as $R^4C(S)NH_2$, MS(ES+) 442 $(M+H)^+$.

Example 101

5-[2-(2-Chloro-phenyl)-thiazol-4-yl]-2-methyl-1-thiophen-2-ylmethyl-1H-pyrrole-3-carboxylic acid isobutyl-amide

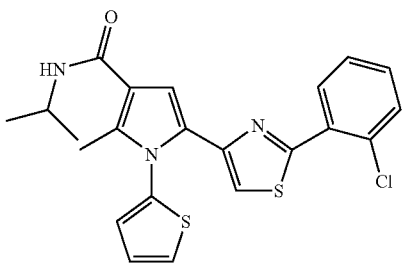

The title compound was obtained using iso-butylamine as $R^1R^2NH$, 3-(aminomethyl)thiophene as $R^3$—$(CH_2)_m$—$NH_2$ and 2-chloro-phenyl thioamide as $R^4C(S)NH_2$, MS(ES+) 470 $(M+H)^+$.

Example 102

5-[2-(4-Methoxy-phenyl)-thiazol-4-yl]-2-methyl-1-thiophen-2-ylmethyl-1H-pyrrole-3-carboxylic acid isobutyl-amide

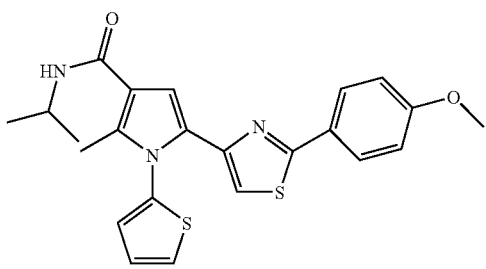

The title compound was obtained using iso-butylamine as $R^1R^2NH$, 3-(aminomethyl)thiophene as $R^3$—$(CH_2)_m$—$NH_2$ and 4-methoxyphenyl thioamide as $R^4C(S)NH_2$, MS(ES+) 466 $(M+H)^+$.

Example 103

5-[2-(4-Methoxy-phenoxymethyl)-thiazol-4-yl]-2-methyl-1-thiophen-2-ylmethyl-1H-pyrrole-3-carboxylic acid isobutyl-amide

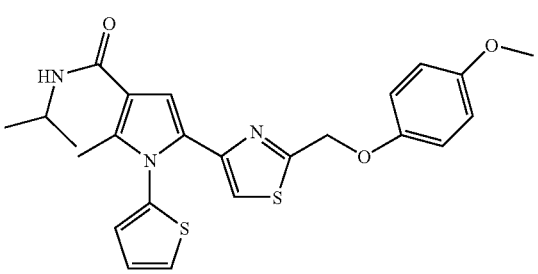

The title compound was obtained using iso-butylamine as $R^1R^2NH$, 3-(aminomethyl)thiophene as $R^3$—$(CH_2)_m$—$NH_2$ and 2-(4-methoxyphenoxy)ethanethioamide as $R^4C(S)NH_2$, MS(ES+) 496 $(M+H)^+$.

Example 104

5-[2-(2-Ethyl-pyridin-4-yl)-thiazol-4-yl]-2-methyl-1-thiophen-2-ylmethyl-1H-pyrrole-3-carboxylic acid isobutyl-amide

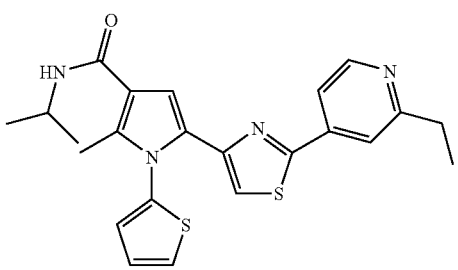

The title compound was obtained using iso-butylamine as $R^1R^2NH$, 3-(aminomethyl)thiophene as $R^3$—$(CH_2)_m$—$NH_2$ and 2-ethyl-4-pyridine carbothiamide as $R^4C(S)NH_2$, MS(ES+) 465 $(M+H)^+$.

Example 105

Butyl-5-[2-(4-methoxy-phenyl)-thiazol-4-yl]-2-methyl-1H-pyrrole-3-carboxylic acid allylamide

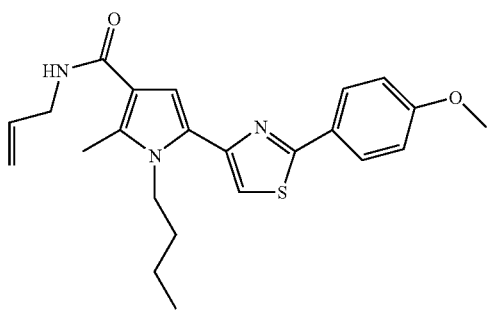

The title compound was obtained using allylamine as $R^1R^2NH$, butylamine as $R^3$—$(CH_2)_m$—$NH_2$ and 4-methoxyphenyl thioamide as $R^4C(S)NH_2$, MS(ES+) 410 (M+H)$^+$.

Example 106

Butyl-5-[2-(4-methoxy-phenoxymethyl)-thiazol-4-yl]-2-methyl-1H-pyrrole-3-carboxylic acid allylamide

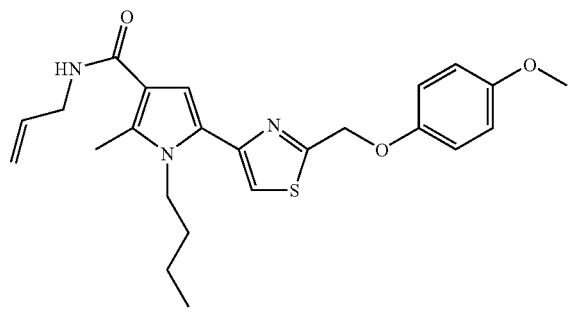

The title compound was obtained using allylamine as $R^1R^2NH$, butylamine as $R^3$—$(CH_2)_m$—$NH_2$ and 2-(4-methoxyphenoxy)ethanethioamide as $R^4C(S)NH_2$, MS(ES+) 440 (M+H)$^+$.

Example 107

Isobutyl-5-[2-(4-methoxy-phenyl)-thiazol-4-yl]-2-methyl-1H-pyrrole-3-carboxylic acid allylamide

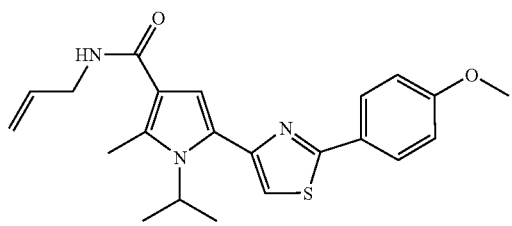

The title compound was obtained using allylamine as $R^1R^2NH$, isobutylamine as $R^3$—$(CH_2)_m$—$NH_2$ and 4-methoxyphenyl thioamide as $R^4C(S)NH_2$, MS(ES+) 410 (M+H)$^+$.

Example 108

5-[2-(4-Methoxy-phenoxymethyl)-thiazol-4-yl]-1-[2-(4-methoxy-phenyl)-ethyl]-2-methyl-1H-pyrrole-3-carboxylic acid allylamide

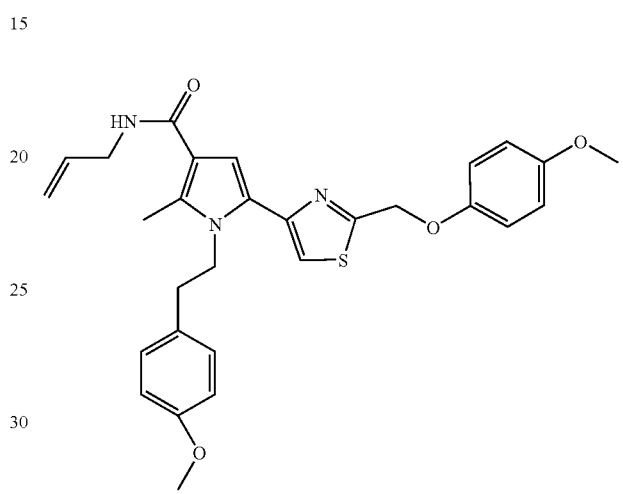

The title compound was obtained using allylamine as $R^1R^2NH$, 2-(4-methoxyphenyl)-ethylamine as $R^3$—$(CH_2)_m$—$NH_2$ and 2-(4-methoxyphenoxy)ethanethioamide as $R^4C(S)NH_2$, MS(ES+) 518 (M+H)$^+$.

Example 109

5-[2-(2-Chloro-phenyl)-thiazol-4-yl]-1-cyclohexylmethyl-2-methyl-1H-pyrrole-3-carboxylic acid allylamide

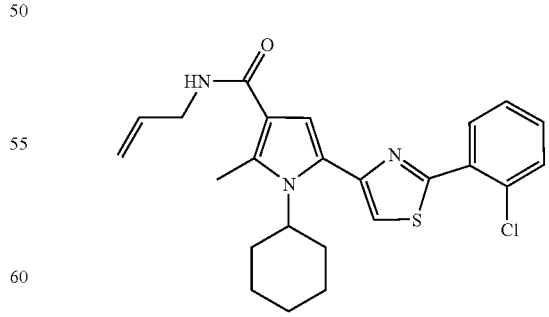

The title compound was obtained using allylamine as $R^1R^2NH$, aminomethylcyclohexane as $R^3$—$(CH_2)_m$—$NH_2$ and 2-chloro-phenyl thioamide as $R^4C(S)NH_2$, MS(ES+) 454 (M+H)$^+$.

Example 110

Cyclohexylmethyl-5-[2-(4-methoxy-phenyl)-thiazol-4-yl]-2-methyl-1H-pyrrole-3-carboxylic acid allylamide

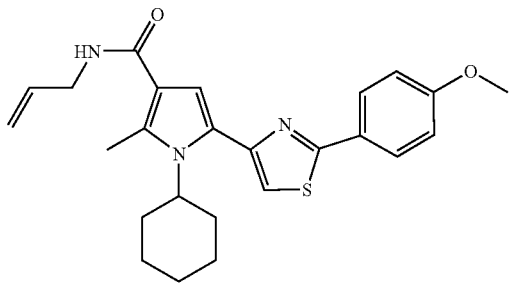

The title compound was obtained using allylamine as R¹R²NH, aminomethylcyclohexane as $R^3$—$(CH_2)_m$—$NH_2$ and 4-methoxyphenyl thioamide as $R^4C(S)NH_2$, MS(ES+) 450 (M+H)⁺.

Example 111

Cyclohexylmethyl-5-[2-(4-methoxy-phenoxymethyl)-thiazol-4-yl]-2-methyl-1H-pyrrole-3-carboxylic acid allylamide

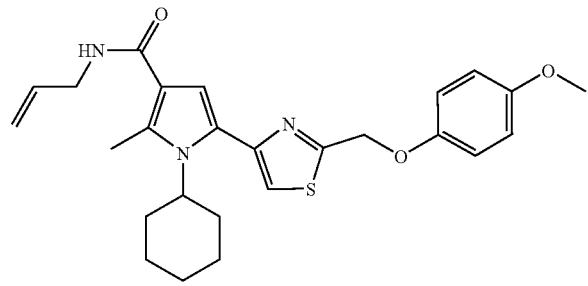

The title compound was obtained using allylamine as R¹R²NH, aminomethylcyclohexane as $R^3$—$(CH_2)_m$—$NH_2$ and 2-(4-methoxyphenoxy)ethanethioamide as $R^4C(S)NH_2$, MS(ES+) 480 (M+H)⁺.

Example 112

Cyclohexylmethyl-5-[2-(2-ethyl-pyridin-4-yl)-thiazol-4-yl]-2-methyl-1H-pyrrole-3-carboxylic acid allylamide

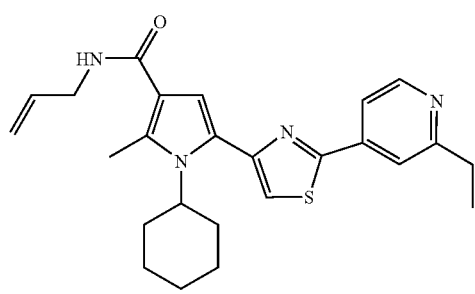

The title compound was obtained using allylamine as R¹R²NH, aminomethylcyclohexane as $R^3$—$(CH_2)_m$—$NH_2$ and 2-ethyl-4-pyridine carbothiamide as $R^4C(S)NH_2$, MS(ES+) 449 (M+H)⁺.

Example 113

Cyclohexylmethyl-2-methyl-5-(2-pyrazin-2-yl-thiazol-4-yl)-1H-pyrrole-3-carboxylic acid allylamide

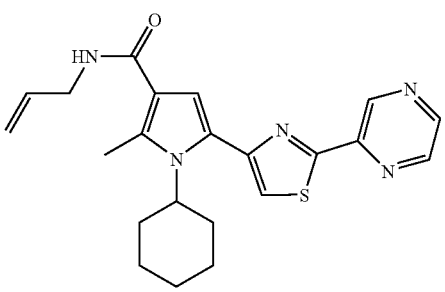

The title compound was obtained using allylamine as R¹R²NH, aminomethylcyclohexane as $R^3$—$(CH_2)_m$—$NH_2$ and pyrazine-2-carbothioamide as $R^4C(S)NH_2$, MS(ES+) 422 (M+H)⁺.

Example 114

5-[2-(4-Methoxy-phenyl)-thiazol-4-yl]-2-methyl-1-(tetrahydro-furan-2-ylmethyl)-1H-pyrrole-3-carboxylic acid allylamide

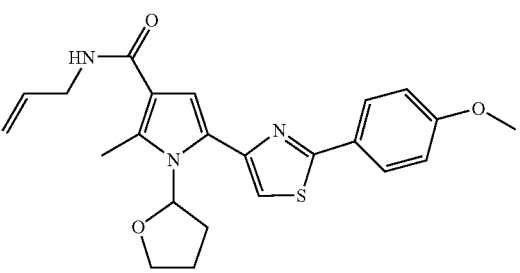

The title compound was obtained using allylamine as R¹R²NH, tetrahydrofurfurylamine as $R^3$—$(CH_2)_m$—$NH_2$ and 4-methoxyphenyl thioamide as $R^4C(S)NH_2$, MS(ES+) 438 (M+H)⁺.

Example 115

5-[2-(2-Chloro-phenyl)-thiazol-4-yl]-1-(2-methoxy-ethyl)-2-methyl-1H-pyrrole-3-carboxylic acid allylamide

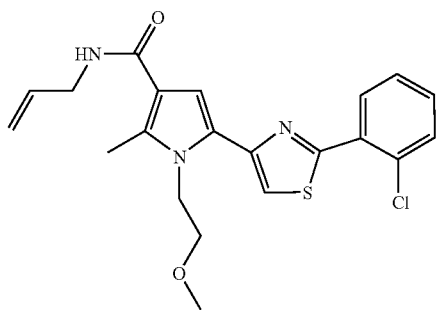

The title compound was obtained using allylamine as $R^1R^2NH$, methoxyethylamine as $R^3$—$(CH_2)_m$—$NH_2$ and 2-chloro-phenyl thioamide as $R^4C(S)NH_2$, MS(ES+) 416 (M+H)$^+$.

Example 116

Furan-2-ylmethyl-5-[2-(4-methoxy-phenyl)-thiazol-4-yl]-2-methyl-1H-pyrrole-3-carboxylic acid allylamide

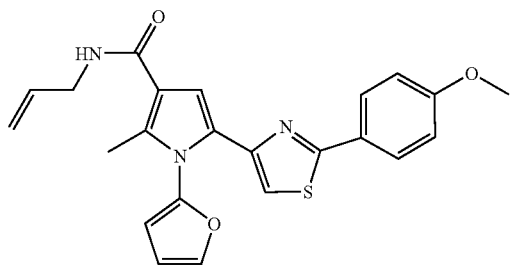

The title compound was obtained using allylamine as $R^1R^2NH$, 3-furylmethylamine as $R^3$—$(CH_2)_m$—$NH_2$ and 4-methoxyphenyl thioamide as $R^4C(S)NH_2$, MS(ES+) 434 (M+H)$^+$.

Example 117

5-[2-(2-Ethyl-pyridin-4-yl)-thiazol-4-yl]-1-furan-2-ylmethyl-2-methyl-1H-pyrrole-3-carboxylic acid allylamide

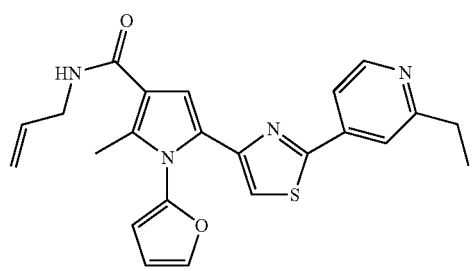

The title compound was obtained using allylamine as $R^1R^2NH$, 3-furylmethylamine as $R^3$—$(CH_2)_m$—$NH_2$ and 2-ethyl-4-pyridine carbothiamide as $R^4C(S)NH_2$, MS(ES+) 433 (M+H)$^+$.

Example 118

5-[2-(2-Chloro-phenyl)-thiazol-4-yl]-1-(4-methoxy-benzyl)-2-methyl-1H-pyrrole-3-carboxylic acid allylamide

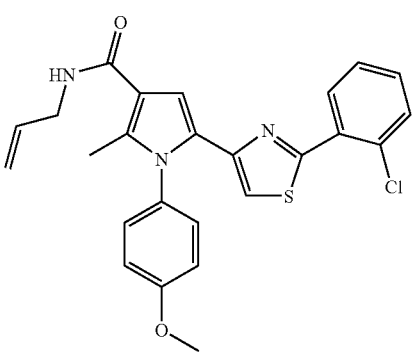

The title compound was obtained using allylamine as $R^1R^2NH$, 4-methoxybenzylamine as $R^3$—$(CH_2)_m$—$NH_2$ and 2-chloro-phenyl thioamide as $R^4C(S)NH_2$, MS(ES+) 478 (M+H)$^+$.

Example 119

1-(4-Methoxy-benzyl)-5-[2-(4-methoxy-phenyl)-thiazol-4-yl]-2-methyl-1H-pyrrole-3-carboxylic acid allylamide

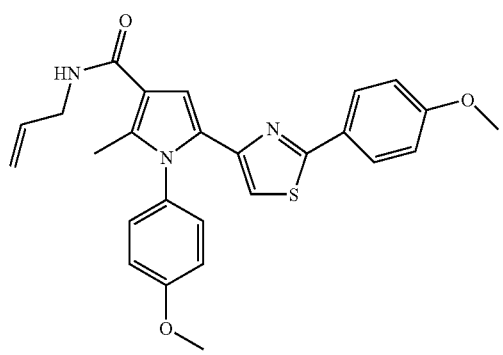

The title compound was obtained using allylamine as $R^1R^2NH$, 4-methoxybenzylamine as $R^3$—$(CH_2)_m$—$NH_2$ and 4-methoxyphenyl thioamide as $R^4C(S)NH_2$, MS(ES+) 474 (M+H)$^+$.

Example 120

1-(4-Methoxy-benzyl)-5-[2-(4-methoxy-phenoxymethyl)-thiazol-4-yl]-2-methyl-1H-pyrrole-3-carboxylic acid allylamide

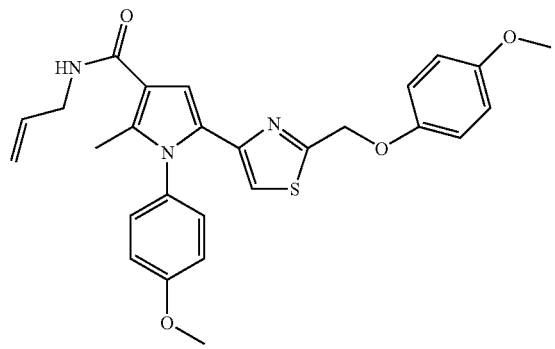

The title compound was obtained using allylamine as $R^1R^2NH$, 4-methoxybenzylamine as $R^3$—$(CH_2)_m$—$NH_2$ and 2-(4-methoxyphenoxy)ethanethioamide as $R^4C(S)NH_2$, MS(ES+) 504 (M+H)$^+$.

Example 121

5-[2-(2-Ethyl-pyridin-4-yl)-thiazol-4-yl]-1-(4-methoxy-benzyl)-2-methyl-1H-pyrrole-3-carboxylic acid allylamide

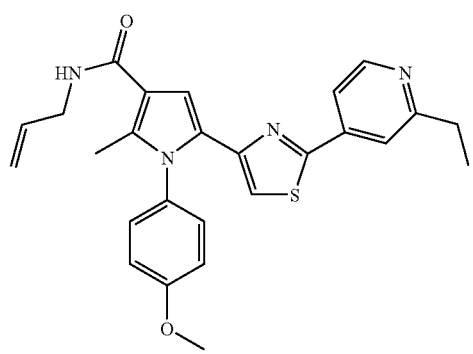

The title compound was obtained using allylamine as $R^1R^2NH$, 4-methoxybenzylamine as $R^3$—$(CH_2)_m$—$NH_2$ and 2-ethyl-4-pyridine carbothiamide as $R^4C(S)NH_2$, MS(ES+) 473 (M+H)$^+$.

Example 122

4-[4-Allylcarbamoyl-1-(4-methoxy-benzyl)-5-methyl-1H-pyrrol-2-yl]-thiazole-2-carboxylic acid ethyl ester

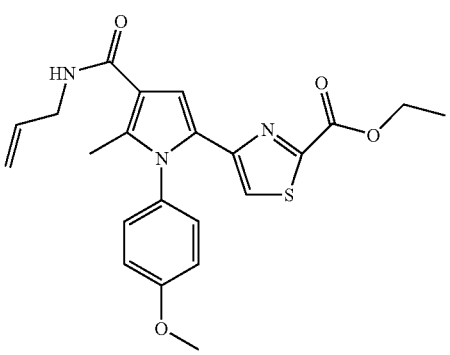

The title compound was obtained using allylamine as $R^1R^2NH$, 4-methoxybenzylamine as $R^3$—$(CH_2)_m$—$NH_2$ and ethylthiooxamate as $R^4C(S)NH_2$, MS(ES+) 440 (M+H)$^+$.

Example 123

1-(4-Methoxy-benzyl)-2-methyl-5-[2-(6-methyl-pyridin-3-yl)-thiazol-4-yl]-1H-pyrrole-3-carboxylic acid allylamide

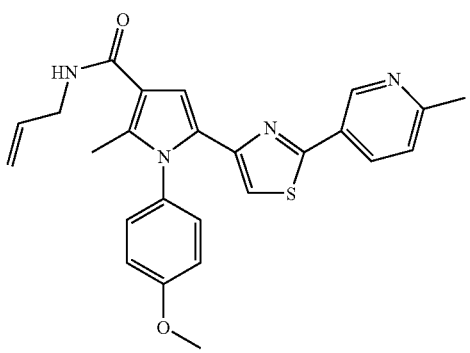

The title compound was obtained using allylamine as $R^1R^2NH$, 4-methoxybenzylamine as $R^3$—$(CH_2)_m$—$NH_2$ and 6-methyl-pyridine-3-carbothioamide as $R^4C(S)NH_2$, MS(ES+) 459 (M+H)$^+$.

Example 124

1-(4-Methoxy-benzyl)-2-methyl-5-(2-pyrazin-2-yl-thiazol-4-yl)-1H-pyrrole-3-carboxylic acid allylamide

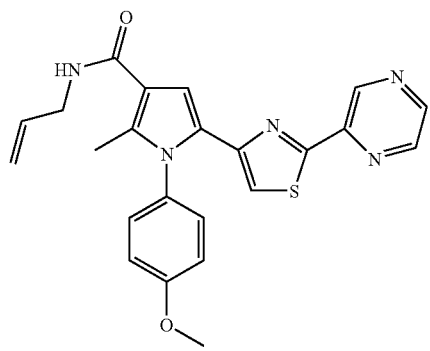

The title compound was obtained using allylamine as R¹R²NH, 4-methoxybenzylamine as R³—(CH₂)ₘ—NH₂ and pyrazine-2-carbothioamide as R⁴C(S)NH₂, MS(ES+) 446 (M+H)⁺.

Example 125

5-[2-(4-Methoxy-phenyl)-thiazol-4-yl]-2-methyl-1-thiophen-2-ylmethyl-1H-pyrrole-3-carboxylic acid allylamide

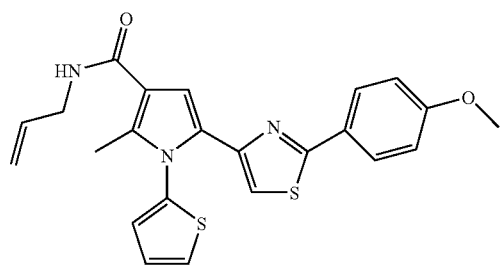

The title compound was obtained using allylamine as R¹R²NH, 3-(aminomethyl)thiophene as R³—(CH₂)ₘ—NH₂ and 4-methoxyphenyl thioamide as R⁴C(S)NH₂, MS(ES+) 450 (M+H)⁺.

Example 126

1-[2-(3,4-Dimethoxy-phenyl)-ethyl]-2-methyl-5-(2-pyrazin-2-yl-thiazol-4-yl)-1H-pyrrole-3-carboxylic acid allylamide

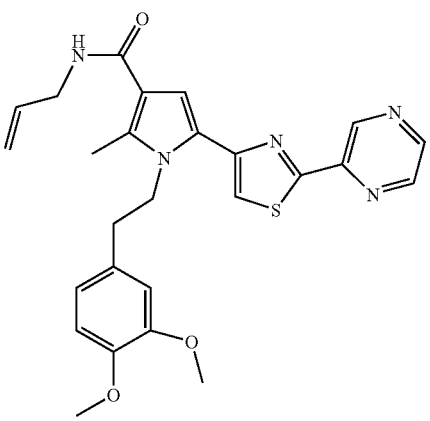

The title compound was obtained using allylamine as R¹R²NH, homoveratrylamine as R³—(CH₂)ₘ—NH₂ and pyrazine-2-carbothioamide as R⁴C(S)NH₂, MS(ES+) 490 (M+H)⁺.

Example 127

Butyl-5-[2-(4-methoxy-phenyl)-thiazol-4-yl]-2-methyl-1H-pyrrole-3-carboxylic acid cyclohexylmethyl-amide

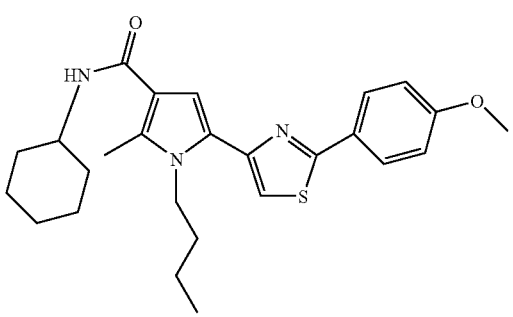

The title compound was obtained using aminomethylcyclohexane as R¹R²NH, butylamine as R³—(CH₂)ₘ—NH₂ and 4-methoxyphenyl thioamide as R⁴C(S)NH₂, MS(ES+) 466 (M+H)⁺.

Example 128

Butyl-5-[2-(4-methoxy-phenoxymethyl)-thiazol-4-yl]-2-methyl-1H-pyrrole-3-carboxylic acid cyclohexylmethyl-amide

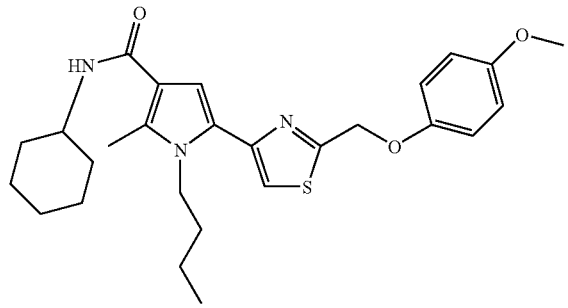

The title compound was obtained using aminomethylcyclohexane as $R^1R^2NH$, butylamine as $R^3$—$(CH_2)_m$—$NH_2$ and 2-(4-methoxyphenoxy)ethanethioamide as $R^4C(S)NH_2$, MS(ES+) 496 (M+H)$^+$.

Example 129

Butyl-5-[2-(2-ethyl-pyridin-4-yl)-thiazol-4-yl]-2-methyl-1H-pyrrole-3-carboxylic acid cyclohexylmethyl-amide

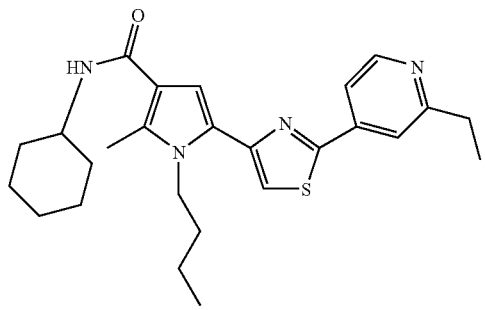

The title compound was obtained using aminomethylcyclohexane as $R^1R^2NH$, butylamine as $R^3$—$(CH_2)_m$—$NH_2$ and 2-ethyl-4-pyridine carbothiamide as $R^4C(S)NH_2$, MS(ES+) 465 (M+H)$^+$.

Example 130

5-[2-(2-Chloro-phenyl)-thiazol-4-yl]-1-isobutyl-2-methyl-1H-pyrrole-3-carboxylic acid cyclohexylmethyl-amide

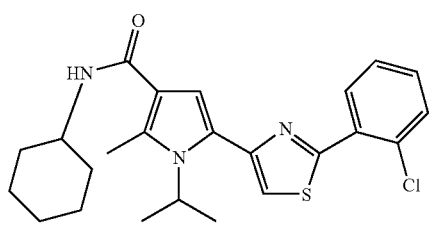

The title compound was obtained using aminomethylcyclohexane as $R^1R^2NH$, isobutylamine as $R^3$—$(CH_2)_m$—$NH_2$ and 2-chloro-phenyl thioamide as $R^4C(S)NH_2$, MS(ES+) 470 (M+H)$^+$.

Example 131

Isobutyl-5-[2-(4-methoxy-phenyl)-thiazol-4-yl]-2-methyl-1H-pyrrole-3-carboxylic acid cyclohexylmethyl-amide

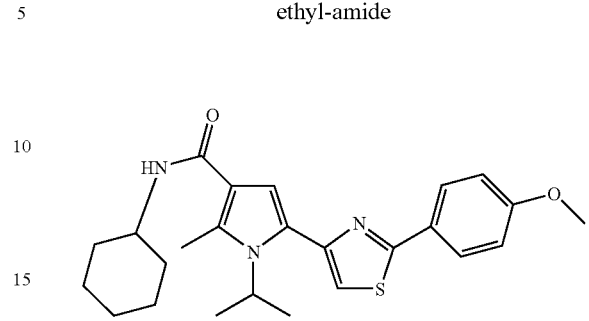

The title compound was obtained using aminomethylcyclohexane as $R^1R^2NH$, isobutylamine as $R^3$—$(CH_2)_m$—$NH_2$ and 4-methoxyphenyl thioamide as $R^4C(S)NH_2$, MS(ES+) 466 (M+H)$^+$.

Example 132

Isobutyl-5-[2-(4-methoxy-phenoxymethyl)-thiazol-4-yl]-2-methyl-1H-pyrrole-3-carboxylic acid cyclohexylmethyl-amide

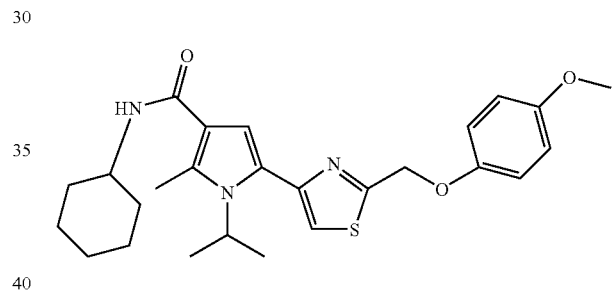

The title compound was obtained using aminomethylcyclohexane as $R^1R^2NH$, isobutylamine as $R^3$—$(CH_2)_m$—$NH_2$ and 2-(4-methoxyphenoxy)ethanethioamide as $R^4C(S)NH_2$, MS(ES+) 496 (M+H)$^+$.

Example 133

Isobutyl-2-methyl-5-(2-pyrazin-2-yl-thiazol-4-yl)-1H-pyrrole-3-carboxylic acid cyclohexylmethyl-amide

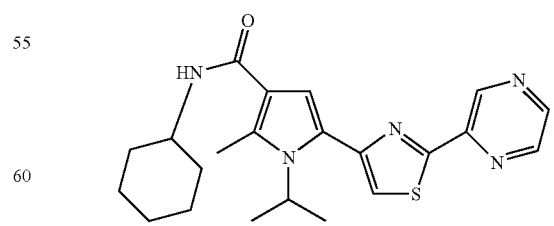

The title compound was obtained using aminomethylcyclohexane as $R^1R^2NH$, isobutylamine as $R^3$—$(CH_2)_m$—$NH_2$ and pyrazine-2-carbothioamide as $R^4C(S)NH_2$, MS(ES+) 438 (M+H)$^+$.

Example 134

Cyclohexylmethyl-5-[2-(4-methoxy-phenyl)-thiazol-4-yl]-2-methyl-1H-pyrrole-3-carboxylic acid cyclohexylmethyl-amide

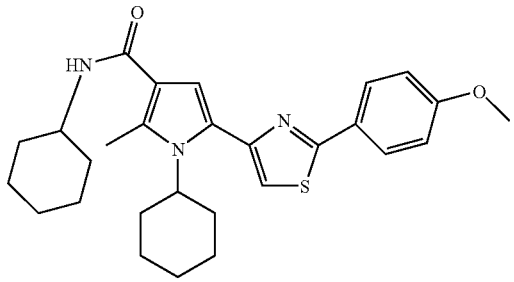

The title compound was obtained using aminomethylcyclohexane as $R^1R^2NH$, aminomethylcyclohexane as $R_3$—$(CH_2)_m$—$NH_2$ and 4-methoxyphenyl thioamide as $R^4C(S)NH_2$, MS(ES+) 506 (M+H)$^+$.

Example 135

Cyclohexylmethyl-5-[2-(2-ethyl-pyridin-4-yl)-thiazol-4-yl]-2-methyl-1H-pyrrole-3-carboxylic acid cyclohexylmethyl-amide

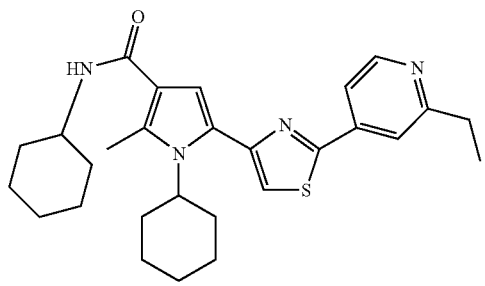

The title compound was obtained using aminomethylcyclohexane as $R^1R^2NH$, aminomethylcyclohexane as $R_3$—$(CH_2)_m$—$NH_2$ and 2-ethyl-4-pyridine carbothiamide as $R^4C(S)NH_2$, MS(ES+) 505 (M+H)$^+$.

Example 136

Cyclohexylmethyl-2-methyl-5-(2-pyrazin-2-yl-thiazol-4-yl)-1H-pyrrole-3-carboxylic acid cyclohexylmethyl-amide

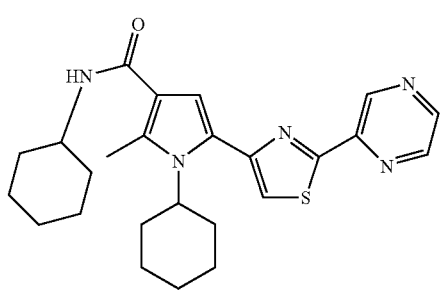

The title compound was obtained using aminomethylcyclohexane as $R^1R^2NH$, aminomethylcyclohexane as $R_3$—$(CH_2)_m$—$NH_2$ and pyrazine-2-carbothioamide as $R^4C(S)NH_2$, MS(ES+) 478 (M+H)$^+$.

Example 137

5-[2-(2-Chloro-phenyl)-thiazol-4-yl]-2-methyl-1-(tetrahydro-furan-2-ylmethyl)-1H-pyrrole-3-carboxylic acid cyclohexylmethyl-amide

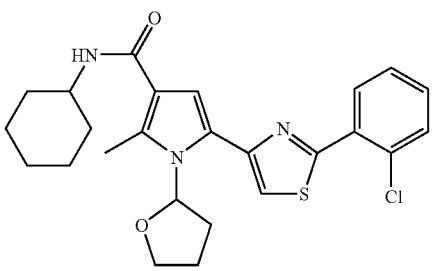

The title compound was obtained using aminomethylcyclohexane as $R^1R^2NH$, tetrahydrofurfurylamine as $R_3$—$(CH_2)_m$—$NH_2$ and 2-chloro-phenyl thioamide as $R^4C(S)NH_2$, MS(ES+) 498 (M+H)$^+$.

Example 138

5-[2-(4-Methoxy-phenyl)-thiazol-4-yl]-2-methyl-1-(tetrahydro-furan-2-ylmethyl)-1H-pyrrole-3-carboxylic acid cyclohexylmethyl-amide

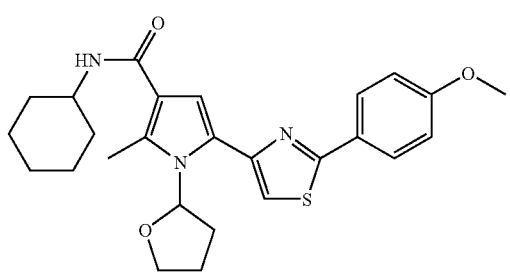

The title compound was obtained using aminomethylcyclohexane as $R^1R^2NH$, tetrahydrofurfurylamine as $R_3$—$(CH_2)_m$—$NH_2$ and 4-methoxyphenyl thioamide as $R^4C(S)NH_2$, MS(ES+) 494 (M+H)$^+$.

Example 139

5-[2-(4-Methoxy-phenoxymethyl)-thiazol-4-yl]-2-methyl-1-(tetrahydro-furan-2-ylmethyl)-1H-pyrrole-3-carboxylic acid cyclohexylmethyl-amide

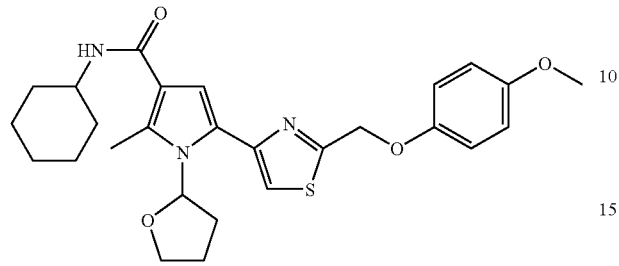

The title compound was obtained using aminomethylcyclohexane as $R^1R^2NH$, tetrahydrofurfurylamine as $R_3$—$(CH_2)_m$—$NH_2$ and 2-(4-methoxyphenoxy)ethanethioamide as $R^4C(S)NH_2$, MS(ES+) 524 (M+H)$^+$.

Example 140

5-[2-(2-Ethyl-pyridin-4-yl)-thiazol-4-yl]-2-methyl-1-(tetrahydro-furan-2-ylmethyl)-1H-pyrrole-3-carboxylic acid cyclohexylmethyl-amide

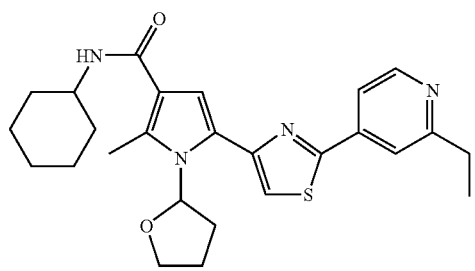

The title compound was obtained using aminomethylcyclohexane as $R^1R^2NH$, tetrahydrofurfurylamine as $R_3$—$(CH_2)_m$—$NH_2$ and 2-ethyl-4-pyridine carbothiamide as $R^4C(S)NH_2$, MS(ES+) 493 (M+H)$^+$.

Example 141

4-[4-(Cyclohexylmethyl-carbamoyl)-5-methyl-1-(tetrahydro-furan-2-ylmethyl)-1H-pyrrol-2-yl]-thiazole-2-carboxylic acid ethyl ester

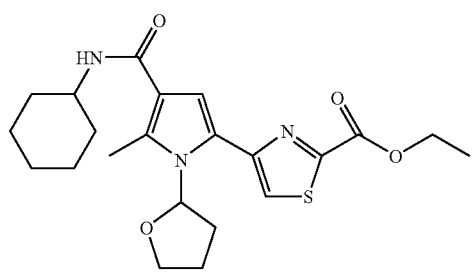

The title compound was obtained using aminomethylcyclohexane as $R^1R^2NH$, tetrahydrofurfurylamine as $R_3$—$(CH_2)_m$—$NH_2$ and ethylthiooxamate, MS(ES+) 460 (M+H)$^+$.

Example 142

Methyl-5-[2-(6-methyl-pyridin-3-yl)-thiazol-4-yl]-1-(tetrahydro-furan-2-ylmethyl)-1H-pyrrole-3-carboxylic acid cyclohexylmethyl-amide

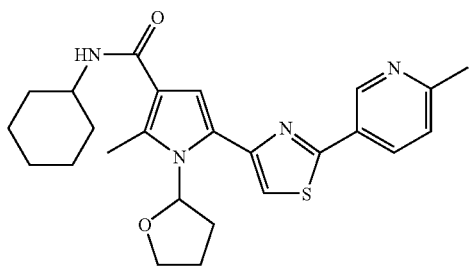

The title compound was obtained using aminomethylcyclohexane as $R^1R^2NH$, tetrahydrofurfirylamine as $R_3$—$(CH_2)_m$—$NH_2$ and 6-methyl-pyridine-3-carbothioamide as $R^4C(S)NH_2$. xx479

Example 143

Methyl-5-(2-pyrazin-2-yl-thiazol-4-yl)-1-(tetrahydro-furan-2-ylmethyl)-1H-pyrrole-3-carboxylic acid cyclohexylmethyl-amide

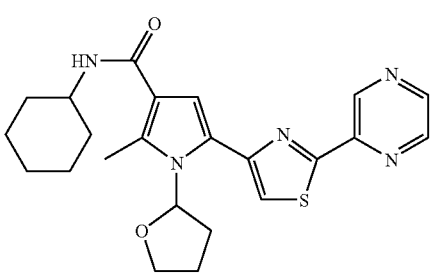

The title compound was obtained using aminomethylcyclohexane as $R^1R^2NH$, tetrahydrofurfurylamine as $R_3$—$(CH_2)_m$—$NH_2$ and pyrazine-2-carbothioamide as $R^4C(S)NH_2$, MS(ES+) 466 (M+H)$^+$.

Example 144

5-[2-(2-Chloro-phenyl)-thiazol-4-yl]-1-(2-methoxy-ethyl)-2-methyl-1H-pyrrole-3-carboxylic acid cyclohexylmethyl-amide

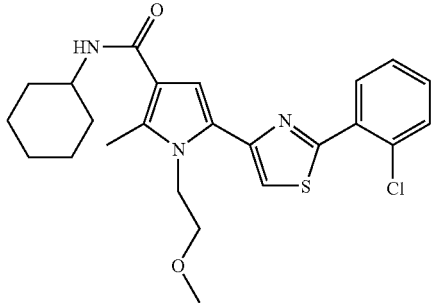

The title compound was obtained using aminomethylcyclohexane as $R^1R^2NH$, methoxyethylamine as $R^3$—$(CH_2)_m$—$NH_2$ and 2-chloro-phenyl thioamide as $R^4C(S)NH_2$, MS(ES+) 472 (M+H)⁺.

Example 145

1-(2-Methoxy-ethyl)-5-[2-(4-methoxy-phenyl)-thiazol-4-yl]-2-methyl-1H-pyrrole-3-carboxylic acid cyclohexylmethyl-amide

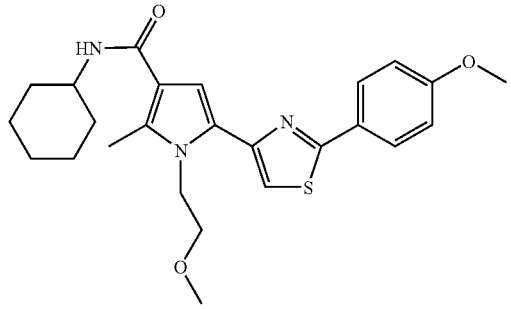

The title compound was obtained using aminomethylcyclohexane as $R^1R^2NH$, methoxyethylamine as $R^3$—$(CH_2)_m$—$NH_2$ and 4-methoxyphenyl thioamide as $R^4C(S)NH_2$, MS(ES+) 468 (M+H)⁺.

Example 146

1-(2-Methoxy-ethyl)-5-[2-(4-methoxy-phenoxymethyl)-thiazol-4-yl]-2-methyl-1H-pyrrole-3-carboxylic acid cyclohexylmethyl-amide

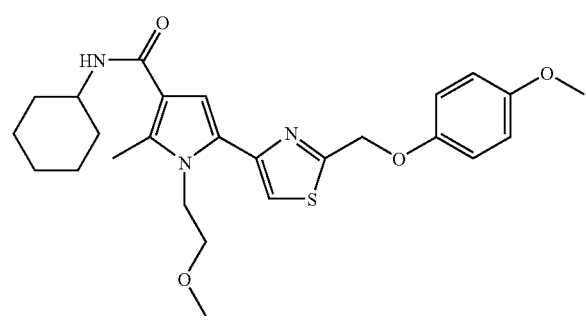

The title compound was obtained using aminomethylcyclohexane as $R^1R^2NH$, methoxyethylamine as $R^3$—$(CH_2)_m$—$NH_2$ and 2-(4-methoxyphenoxy)ethanethioamide as $R^4C(S)NH_2$, MS(ES+) 498 (M+H)⁺.

Example 147

5-[2-(2-Ethyl-pyridin-4-yl)-thiazol-4-yl]-1-(2-methoxy-ethyl)-2-methyl-1H-pyrrole-3-carboxylic acid cyclohexylmethyl-amide

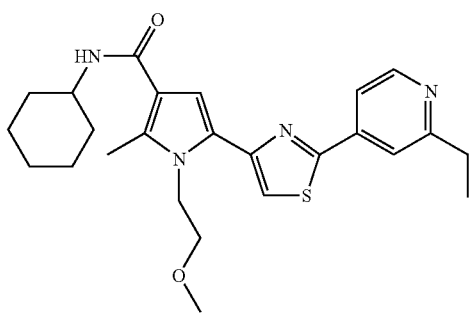

The title compound was obtained using aminomethylcyclohexane as $R^1R^2NH$, methoxyethylamine as $R^3$—$(CH_2)_m$—$NH_2$ and 2-ethyl-4-pyridine carbothiamide as $R^4C(S)NH_2$, MS(ES+) 467 (M+H)⁺.

Example 148

4-[4-(Cyclohexylmethyl-carbamoyl)-1-(2-methoxy-ethyl)-5-methyl-1H-pyrrol-2-yl]-thiazole-2-carboxylic acid ethyl ester

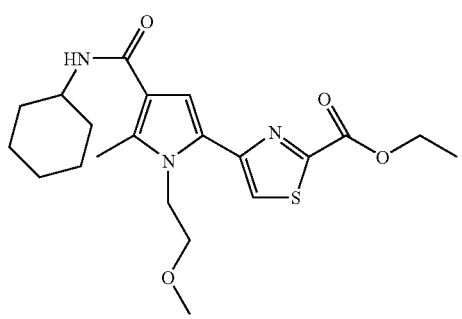

The title compound was obtained using aminomethylcyclohexane as $R^1R^2NH$, methoxyethylamine as $R^3$—$(CH_2)_m$—$NH_2$ and ethylthiooxamate as $R^4C(S)NH_2$, MS(ES+) 434 (M+H)⁺.

Example 149

1-(2-Methoxy-ethyl)-2methyl-5-[2-(6-methyl-pyridin-3-yl)-thiazol-4-yl]-1H-pyrrole-3-carboxylic acid cyclohexylmethyl-amide

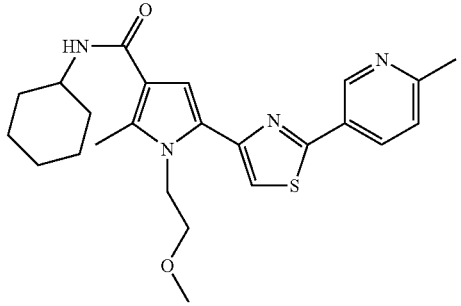

The title compound was obtained using aminomethylcyclohexane as $R^1R^2NH$, methoxyethylamine as $R^3$—$(CH_2)_m$—$NH_2$ and 6-methyl-pyridine-3-carbothioamide as $R^4C(S)NH_2$, MS(ES+) 453 (M+H)$^+$.

Example 150

1-(2-Methoxy-ethyl)-2-methyl-5-(2-pyrazin-2-yl-thiazol-4-yl)-1H-pyrrole-3-carboxylic acid cyclohexylmethyl-amide

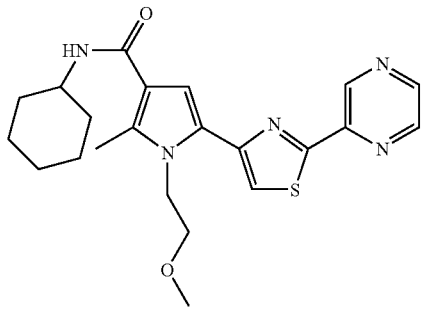

The title compound was obtained using aminomethylcyclohexane as $R^1R^2NH$, methoxyethylamine as $R^3$—$(CH_2)_m$—$NH_2$ and pyrazine-2-carbothioamide as $R^4C(S)NH_2$, MS(ES+) 440 (M+H)$^+$.

Example 151

1-(2-Cyclohex-1-enyl-ethyl)-5-[2-(2-ethyl-pyridin-4-yl)-thiazol-4-yl]-2-methyl-1H-pyrrole-3-carboxylic acid cyclohexylmethyl-amide

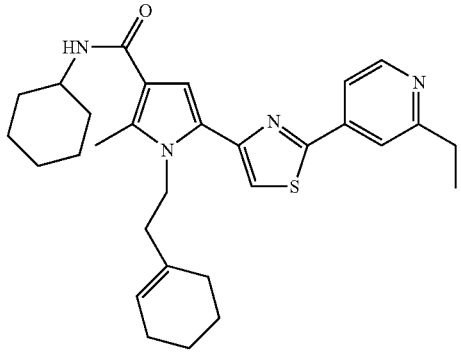

The title compound was obtained using aminomethylcyclohexane as $R^1R^2NH$, 2-(1-cyclohexenyl)ethylamine as $R^3$—$(CH_2)_m$—$NH_2$ and 2-ethyl-4-pyridine carbothiamide as $R^4C(S)NH_2$, MS(ES+) 517 (M+H)$^+$.

Example 152

Furan-2-ylmethyl-5-[2-(4-methoxy-phenyl)-thiazol-4-yl]-2-methyl-1H-pyrrole-3-carboxylic acid cyclohexylmethyl-amide

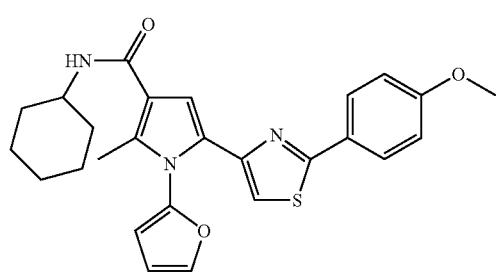

The tide compound was obtained using aminomethylcyclohexane as $R^1R^2NH$, 3-furylmethylamine as $R^3$—$(CH_2)_m$—$NH_2$ and 4-methoxyphenyl thioamide as $R^4C(S)NH_2$, MS(ES+) 490 (M+H)$^+$.

Example 153

5-[2-(2-Chloro-phenyl)-thiazol-4-yl]-1-(4-methoxy-benzyl)-2-methyl-1H-pyrrole-3-carboxylic acid cyclohexylmethyl-amide

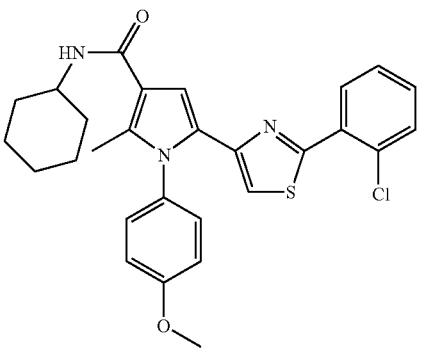

The title compound was obtained using aminomethylcyclohexane as $R^1R^2NH$, 4-methoxybenzylamine as $R^3$—$(CH_2)_m$—$NH_2$ and 2-chloro-phenyl thioamide as $R^4C(S)NH_2$, MS(ES+) 534 (M+H)$^+$.

Example 154

1-(4-Methoxy-benzyl)-5-[2-(4-methoxy-phenyl)-thiazol-4-yl]-2-methyl-1H-pyrrole-3-carboxylic acid cyclohexylmethyl-amide

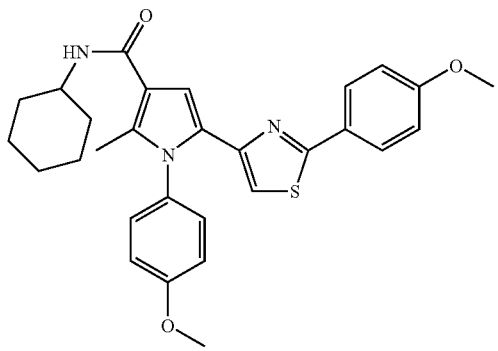

The title compound was obtained using aminomethylcyclohexane as $R^1R^2NH$, 4-methoxybenzylamine as $R^3$—$(CH_2)_m$—$NH_2$ and 4-methoxyphenyl thioamide as $R^4C(S)NH_2$, MS(ES+) 530 (M+H)$^+$.

Example 155

5-[2-(2-Ethyl-pyridin-4-yl)-thiazol-4-yl]-1-(4-methoxy-benzyl)-2-methyl-1H-pyrrole-3-carboxylic acid cyclohexylmethyl-amide

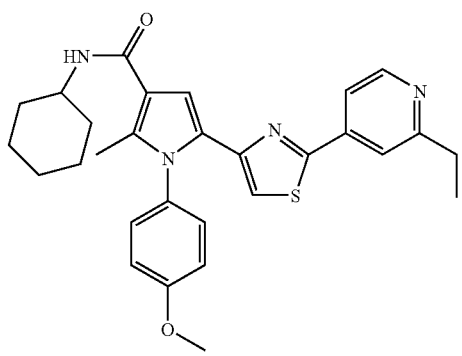

The title compound was obtained using aminomethylcyclohexane as $R^1R^2NH$, 4-methoxybenzylamine as $R^3$—$(CH_2)_m$—$NH_2$ and 2-ethyl-4-pyridine carbothiamide as $R^4C(S)NH_2$, MS(ES+) 529 (M+H)$^+$.

Example 156

5-[2-(2-Chloro-phenyl)-thiazol-4-yl]-1-(3-methoxy-propyl)-2-methyl-1H-pyrrole-3-carboxylic acid cyclohexylmethyl-amide

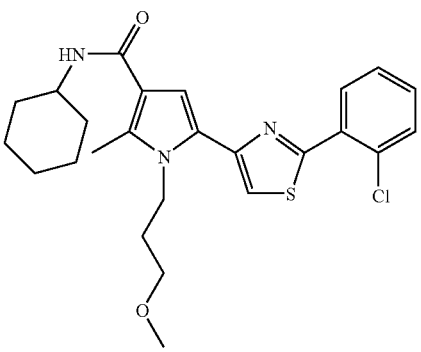

The title compound was obtained using aminomethylcyclohexane as $R^1R^2NH$, methoxyethylamine as $R^3$—$(CH_2)_m$—$NH_2$ and 2-chloro-phenyl thioamide as $R^4C(S)NH_2$, MS(ES+) 486 (M+H)$^+$.

Example 157

5-[2-(4-Methoxy-phenyl)-thiazol-4-yl]-1-(3-methoxy-propyl)-2-methyl-1H-pyrrole-3-carboxylic acid cyclohexylmethyl-amide

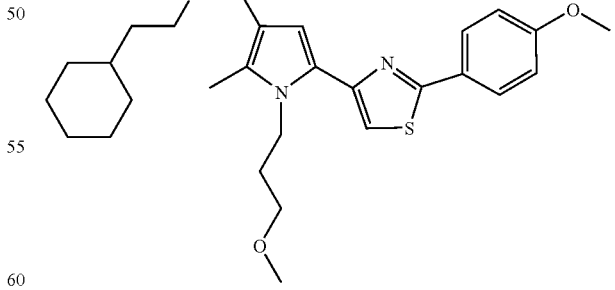

The title compound was obtained using aminomethylcyclohexane as $R^1R^2NH$, methoxyethylamine as $R^3$—$(CH_2)_m$—$NH_2$ and 4-methoxyphenyl thioamide as $R^4C(S)NH_2$, MS(ES+) 482 (M+H)$^+$.

Example 158

5-[2-(4-Methoxy-phenoxymethyl)-thiazol-4-yl]-1-(3-methoxy-propyl)-2-methyl-1H-pyrrole-3-carboxylic acid cyclohexylmethyl-amide

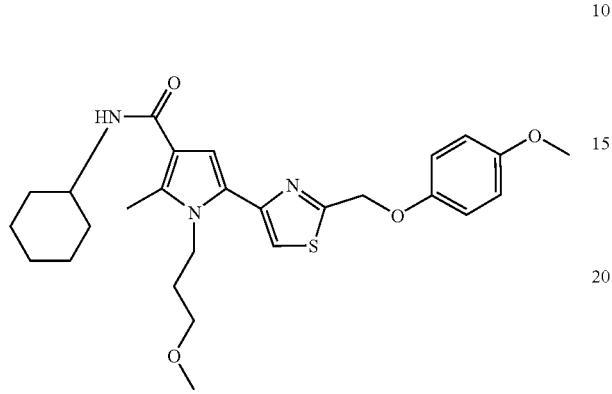

The title compound was obtained using aminomethylcyclohexane as $R^1R^2NH$, methoxyethylamine as $R^3$—$(CH_2)_m$—$NH_2$ and 2-(4-methoxyphenoxy)ethanethioamide as $R^4C(S)NH_2$, MS(ES+) 512 (M+H)$^+$.

Example 159

5-[2-(2-Ethyl-pyridin-4-yl)-thiazol-4-yl]-1-(3-methoxy-propyl)-2-methyl-1H-pyrrole-3-carboxylic acid cyclohexylmethyl-amide

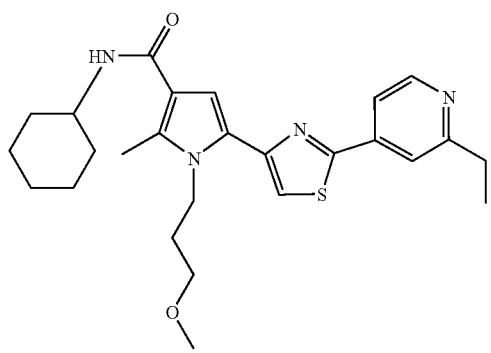

The title compound was obtained using aminomethylcyclohexane as $R^1R^2NH$, methoxyethylamine as $R^3$—$(CH_2)_m$—$NH_2$ and 2-ethyl-4-pyridine carbothiamide as $R^4C(S)NH_2$, MS(ES+) 481 (M+H)$^+$.

Example 160

4-[4-(Cyclohexylmethyl-carbamoyl)-1-(3-methoxy-propyl)-5-methyl-1H-pyrrol-2-yl]-thiazole-2-carboxylic acid ethyl ester

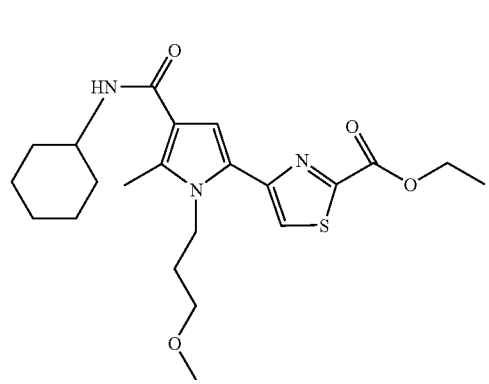

The title compound was obtained using aminomethylcyclohexane as $R^1R^2NH$, methoxyethylamine as $R^3$—$(CH_2)_m$—$NH_2$ and ethylthiooxamate as $R^4C(S)NH_2$, MS(ES+) 448 (M+H)$^+$.

Example 161

1-(3-Methoxy-propyl)-2-methyl-5-(2-pyrazin-2-yl-thiazol-4-yl)-1H-pyrrole-3-carboxylic acid cyclohexylmethyl-amide

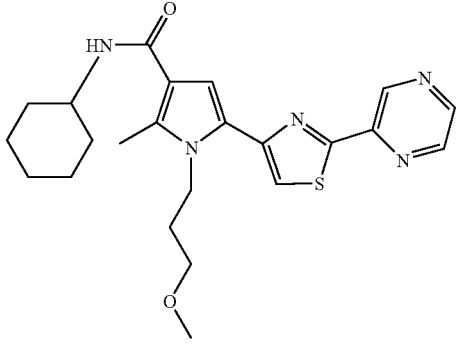

The title compound was obtained using aminomethylcyclohexane as $R^1R^2NH$, methoxyethylamine as $R^3$—$(CH_2)_m$—$NH_2$ and pyrazine-2-carbothioamide as $R^4C(S)NH_2$, MS(ES+) 454 (M+H)$^+$.

Example 162

5-[2-(4-Methoxy-phenyl)-thiazol-4-yl]-2-methyl-1-thiophen-2-ylmethyl-1H-pyrrole-3-carboxylic acid cyclohexylmethyl-amide

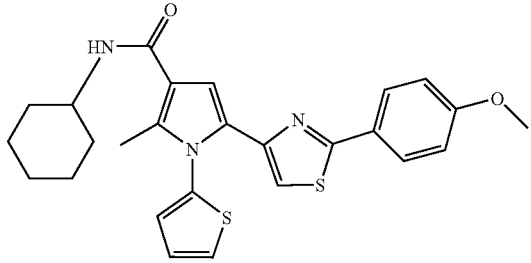

The title compound was obtained using aminomethylcyclohexane as $R^1R^2NH$, 3-(aminomethyl)thiophene as $R^3$—$(CH_2)_m$—$NH_2$ and 4-methoxyphenyl thioamide as $R^4C(S)NH_2$, MS(ES+) 506 (M+H)+.

Example 163

5-[2-(2-Ethyl-pyridin-4-yl)-thiazol-4-yl]-2-methyl-1-thiophen-2-ylmethyl-1H-pyrrole-3-carboxylic acid cyclohexylmethyl-amide

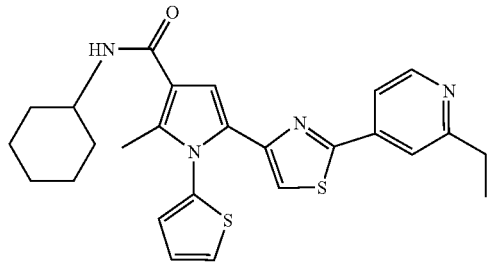

The title compound was obtained using aminomethylcyclohexane as $R^1R^2NH$, 3-(aminomethyl)thiophene as $R^3$—$(CH_2)_m$—$NH_2$ and 2-ethyl-4-pyridine carbothiamide as $R^4C(S)NH_2$, MS(ES+) 505 (M+H)+.

Example 164

5-[2-(2-Chloro-phenyl)-thiazol-4-yl]-1-[2-(3,4-dimethoxy-phenyl)-ethyl]-2-methyl-1H-pyrrole-3-carboxylic acid cyclohexylmethyl-amide

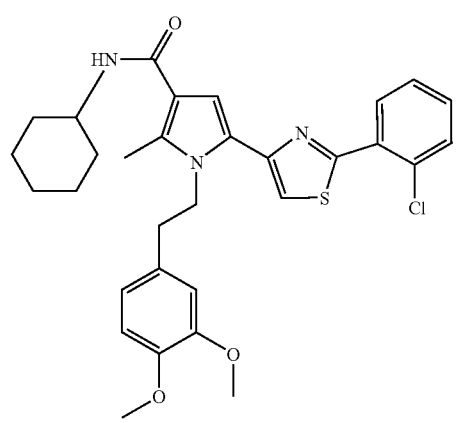

The title compound was obtained using aminomethylcyclohexane as $R^1R^2NH$, homoveratrylamine as $R^3$—$(CH_2)_m$—$NH_2$ and 2-chloro-phenyl thioamide as $R^4C(S)NH_2$, MS(ES+) 578 (M+H)+.

Example 165

Butyl-5-[2-(4-methoxy-phenyl)-thiazol-4-yl]-2-methyl-1H-pyrrole-3-carboxylic acid (tetrahydro-furan-2-ylmethyl)-amide

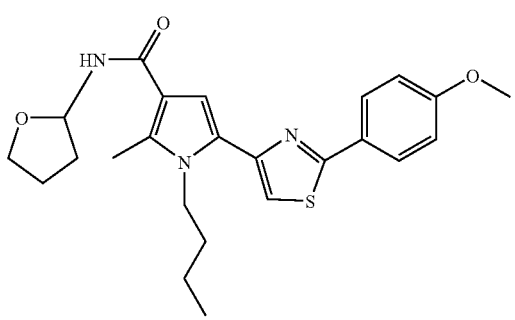

The title compound was obtained using tetrahydrofurfurylamine as $R^1R^2NH$, butylamine as $R^3$—$(CH_2)_m$—$NH_2$ and 4-methoxyphenyl thioamide as $R^4C(S)NH_2$, MS(ES+) 454 (M+H)+.

Example 166

4-{1-Isobutyl-5-methyl-4-[(tetrahydro-furan-2-ylmethyl)-carbamoyl]-1H-pyrrol-2-yl}-thiazole-2-carboxylic acid ethyl ester

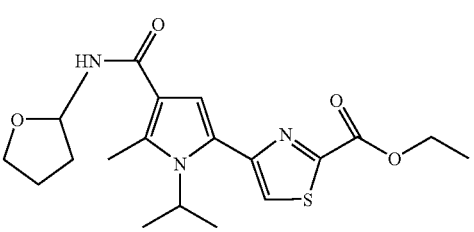

The title compound was obtained using tetrahydrofurfurylamine as $R^1R^2NH$, isobutylamine as $R^3$—$(CH_2)_m$—$NH_2$ and ethylthiooxamate as $R^4C(S)NH_2$, MS(ES+) 420. (M+H)+.

Example 167

Isobutyl-2-methyl-5-(2-pyrazin-2-yl-thiazol-4-yl)-1H-pyrrole-3-carboxylic acid (tetrahydro-furan-2-ylmethyl)-amide

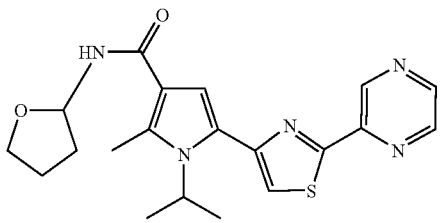

The title compound was obtained using tetrahydrofurfurylamine as $R^1R^2NH$, isobutylamine as $R^3$—$(CH_2)_m$—$NH_2$ and pyrazine-2-carbothioamide as $R^4C(S)NH_2$, MS(ES+) 426 (M+H)$^+$.

Example 168

5-[2-(2-Chloro-phenyl)-thiazol-4-yl]-1-cyclohexylmethyl-2-methyl-1H-pyrrole-3-carboxylic acid (tetrahydro-furan-2-ylmethyl)-amide

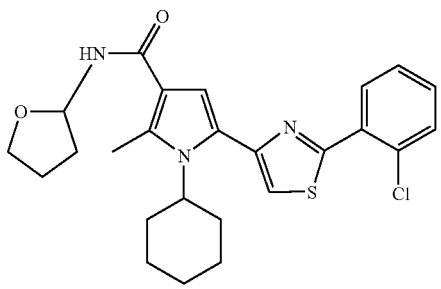

The title compound was obtained using tetrahydrofurfurylamine as $R^1R^2NH$, aminomethylcyclohexane as $R^3$—$(CH_2)_m$—$NH_2$ and 2-chloro-phenyl thioamide as $R^4C(S)NH_2$, MS(ES+) 498 (M+H)$^+$.

Example 169

Cyclohexylmethyl-5-[2-(4-methoxy-phenyl)-thiazol-4-yl]-2-methyl-1H-pyrrole-3-carboxylic acid (tetrahydro-furan-2-ylmethyl)-amide

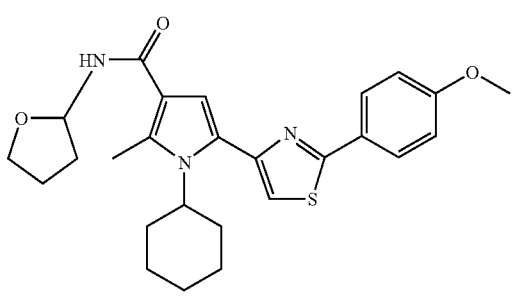

The title compound was obtained using tetrahydrofurfurylamine as $R^1R^2NH$, aminomethylcyclohexane as $R^3$—$(CH_2)_m$—$NH_2$ and 4-methoxyphenyl thioamide as $R^4C(S)NH_2$, MS(ES+) 494 (M+H)$^+$.

Example 170

Cyclohexylmethyl-5-[2-(4-methoxy-phenoxymethyl)-thiazol-4-yl]-2-methyl-1H-pyrrole-3-carboxylic acid (tetrahydro-furan-2-ylmethyl)-amide

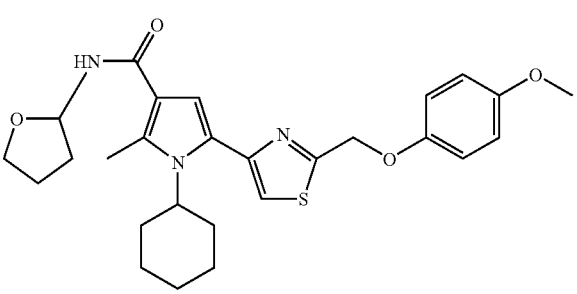

The title compound was obtained using tetrahydrofurfurylamine as $R^1R^2NH$, aminomethylcyclohexane as $R^3$—$(CH_2)_m$—$NH_2$ and 2-(4-methoxyphenoxy)ethanethioamide as $R^4C(S)NH_2$, MS(ES+) 524 (M+H)$^+$.

Example 171

Cyclohexylmethyl-5-[2-(2-ethyl-pyridin-4-yl)-thiazol-4-yl]-2-methyl-1H-pyrrole-3-carboxylic acid (tetrahydro-furan-2-ylmethyl)-amide

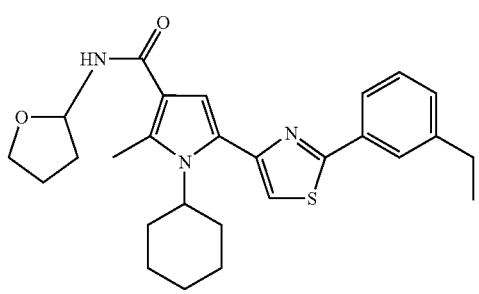

The title compound was obtained using tetrahydrofurfurylamine as $R^1R^2NH$, aminomethylcyclohexane as $R^3$—$(CH_2)_m$—$NH_2$ and 2-ethyl-4-pyridine carbothiamide as $R^4C(S)NH_2$, MS(ES+) 493 (M+H)$^+$.

Example 172

Cyclohexylmethyl-2-methyl-5-(2-pyrazin-2-yl-thiazol-4-yl)-1H-pyrrole-3-carboxylic acid (tetrahydro-furan-2-ylmethyl)-amide

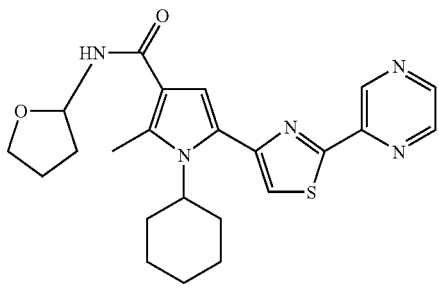

The title compound was obtained using tetrahydrofurfurylamine as $R^1R^2NH$, aminomethylcyclohexane as $R_3$—$(CH_2)_m$—$NH_2$ and pyrazine-2-carbothioamide as $R^4C(S)NH_2$, MS(ES+) 466 (M+H)$^+$.

Example 173

5-[2-(2-Chloro-phenyl)-thiazol-4-yl]-2-methyl-1-(tetrahydro-furan-2-ylmethyl)-1H-pyrrole-3-carboxylic acid (tetrahydro-furan-2-ylmethyl)-amide

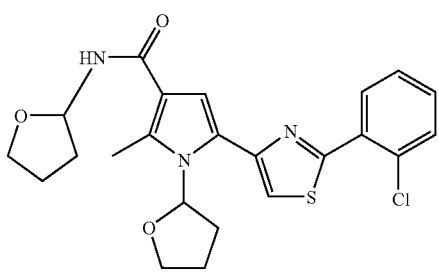

The title compound was obtained using tetrahydrofurfurylamine as $R^1R^2NH$, tetrahydrofurfurylamine as $R_3$—$(CH_2)_m$—$NH_2$ and 2-chloro-phenyl thioamide as $R^4C(S)NH_2$, MS(ES+) 486 (M+H)$^+$.

Example 174

Methyl-5-(2-pyrazin-2-yl-thiazol-4-yl)-1-(tetrahydro-furan-2-ylmethyl)-1H-pyrrole-3-carboxylic acid (tetrahydro-furan-2-ylmethyl)-amide

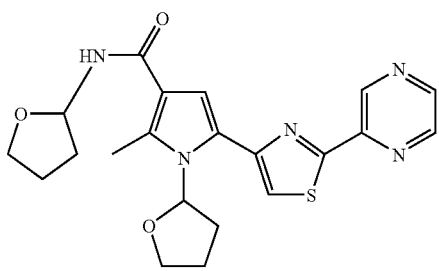

The title compound was obtained using tetrahydrofurfurylamine as $R^1R^2NH$, tetrahydrofurfurylamine as $R_3$—$(CH_2)_m$—$NH_2$ and pyrazine-2-carbothioamide as $R^4C(S)NH_2$, MS(ES+) 454 (M+H)$^+$.

Example 175

5-[2-(2-Ethyl-pyridin-4-yl)-thiazol-4-yl]-1-(2-methoxy-ethyl)-2-methyl-1H-pyrrole-3-carboxylic acid (tetrahydro-furan-2-ylmethyl)-amide

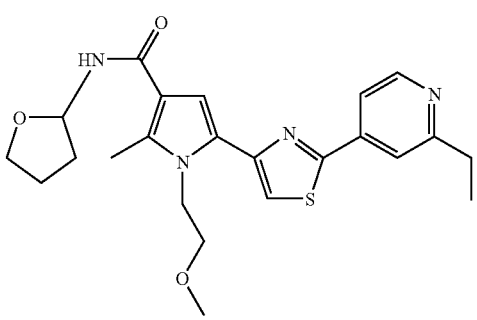

The title compound was obtained using tetrahydrofurfurylamine as $R^1R^2NH$, methoxyethylamine as $R_3$—$(CH_2)_m$—$NH_2$ and 2-ethyl-4-pyridine carbothiamide as $R^4C(S)NH_2$, MS(ES+) 455 (M+H)$^+$.

Example 176

5-[2-(2-Chloro-phenyl)-thiazol-4-yl]-1-furan-2-ylmethyl-2-methyl-1H-pyrrole-3-carboxylic acid (tetrahydro-furan-2-ylmethyl)-amide

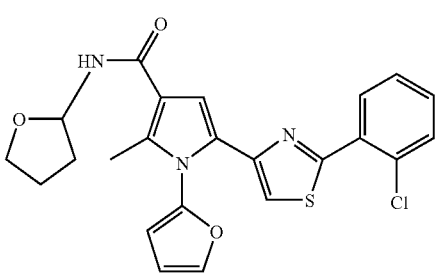

The title compound was obtained using tetrahydrofurfurylamine as $R^1R^2NH$, 3-furylmethylamine as $R_3$—$(CH_2)_m$—$NH_2$ and 2-chloro-phenyl thioamide as $R^4C(S)NH_2$, MS(ES+) 482 (M+H)$^+$.

Example 177

Furan-2-ylmethyl-5-[2-(4-methoxy-phenyl)-thiazol-4-yl]-2-methyl-1H-pyrrole-3-carboxylic acid (tetrahydro-furan-2-ylmethyl)-amide

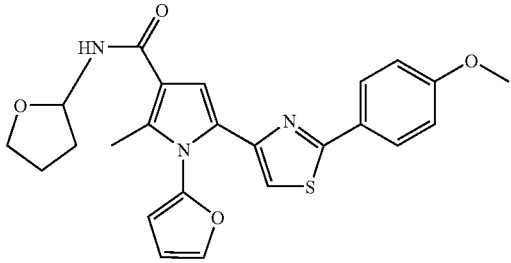

The title compound was obtained using tetrahydrofurfurylamine as $R^1R^2NH$, 3-furylmethylamine as $R^3$—$(CH_2)_m$—$NH_2$ and 4-methoxyphenyl thioamide as $R^4C(S)NH_2$, MS(ES+) 478 (M+H)⁺.

Example 178

5-[2-(2-Ethyl-pyridin-4-yl)-thiazol-4-yl]-1-furan-2-ylmethyl-2-methyl-1H-pyrrole-3-carboxylic acid (tetrahydro-furan-2-ylmethyl)-amide

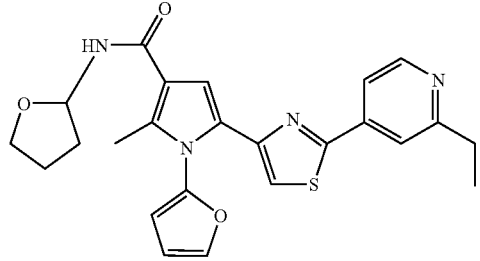

The title compound was obtained using tetrahydrofurfurylamine as $R^1R^2NH$, 3-furylmethylamine as $R^3$—$(CH_2)_m$—$NH_2$ and 2-ethyl-4-pyridine carbothiamide as $R^4C(S)NH_2$, MS(ES+) 477 (M+H)⁺.

Example 179

1-(4-Methoxy-benzyl)-2-methyl-5-(2-methyl-thiazol-4-yl)-1H-pyrrole-3-carboxylic acid (tetrahydro-furan-2-ylmethyl)-amide

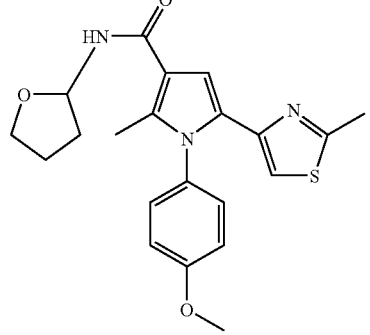

The title compound was obtained using tetrahydrofurfurylamine as $R^1R^2NH$, 4-methoxybenzylamine as $R^3$—$(CH_2)_m$—$NH_2$ and thioacetamide as $R^4C(S)NH_2$, MS(ES+) 426 (M+H)⁺.

Example 180

5-[2-(2-Chloro-phenyl)-thiazol-4-yl]-1-(4-methoxy-benzyl)-2-methyl-1H-pyrrole-3-carboxylic acid (tetrahydro-furan-2-ylmethyl)-amide

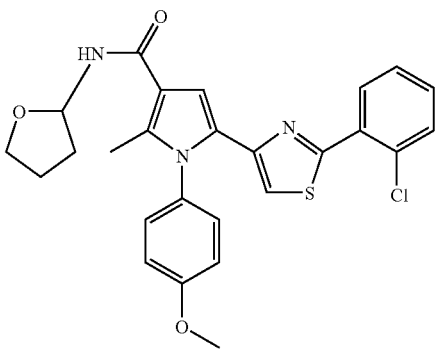

The title compound was obtained using tetrahydrofurfurylamine as $R^1R^2NH$, 4-methoxybenzylamine as $R^3$—$(CH_2)_m$—$NH_2$ and 2-chloro-phenyl thioamide as $R^4C(S)NH_2$, MS(ES+) 522 (M+H)⁺.

Example 181

1-(4-Methoxy-benzyl)-5-[2-(4-methoxy-phenyl)-thiazol-4-yl]-2-methyl-1H-pyrrole-3-carboxylic acid (tetrahydro-furan-2-ylmethyl)-amide

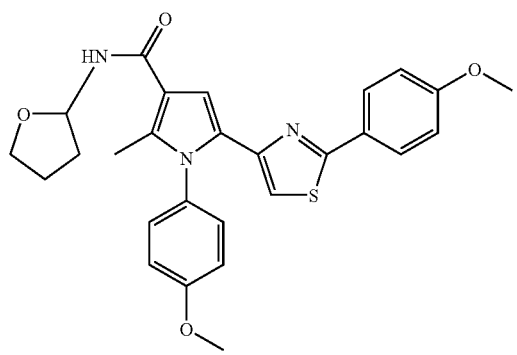

The title compound was obtained using tetrahydrofurfurylamine as $R^1R^2NH$, 4-methoxybenzylamine as $R^3$—$(CH_2)_m$—$NH_2$ and 4-methoxyphenyl thioamide as $R^4C(S)NH_2$, MS(ES+) 518 (M+H)⁺.

Example 182

1-(4-Methoxy-benzyl)-5-[2-(4-methoxy-phenoxymethyl)-thiazol-4-yl]-2-methyl-1H-pyrrole-3-carboxylic acid (tetrahydro-furan-2-ylmethyl)-amide

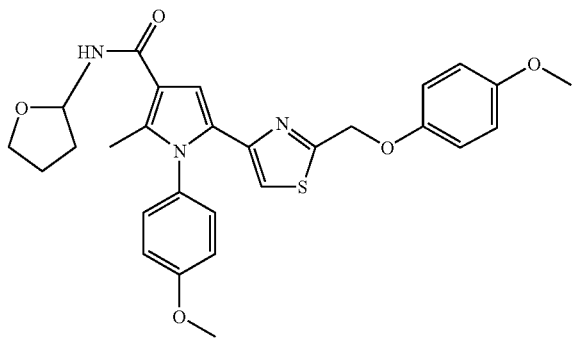

The title compound was obtained using tetrahydrofurfurylamine as $R^1R^2NH$, 4-methoxybenzylamine as $R^3$—$(CH_2)_m$—$NH_2$ and 2-(4-methoxyphenoxy)ethanethioamide as $R^4C(S)NH_2$, MS(ES+) 548 (M+H)$^+$.

Example 183

4-{1-(4-Methoxy-benzyl)-5-methyl-4-[(tetrahydro-furan-2-ylmethyl)-carbamoyl]-1H-pyrrol-2-yl}-thiazole-2-carboxylic acid ethyl ester

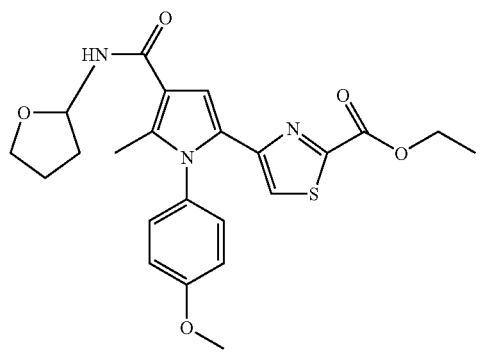

The title compound was obtained using tetrahydrofurfurylamine as $R^1R^2NH$, 4-methoxybenzylamine as $R^3$—$(CH_2)_m$—$NH_2$ and ethylthiooxamate as $R^4C(S)NH_2$, MS(ES+) 484 (M+H)$^+$.

Example 184

1-(4-Methoxy-benzyl)-2-methyl-5-[2-(6-methyl-pyridin-3-yl)-thiazol-4-yl]-1H-pyrrole-3-carboxylic acid (tetrahydro-furan-2-ylmethyl)-amide

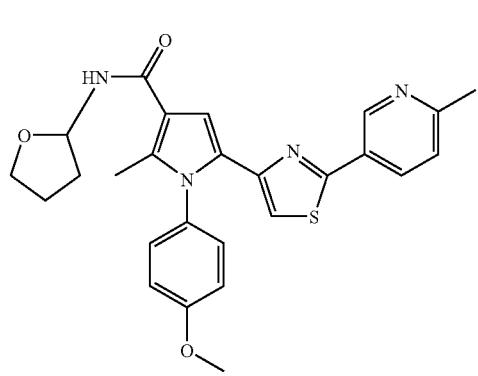

The title compound was obtained using tetrahydrofurfurylamine as $R^1R^2NH$, 4-methoxybenzylamine as $R^3$—$(CH_2)_m$—$NH_2$ and 6-methyl-pyridine-3-carbothioamide as $R^4C(S)NH_2$, MS(ES+) 503 (M+H)$^+$.

Example 185

1-(4-Methoxy-benzyl)-2-methyl-5-(2-pyrazin-2-yl-thiazol-4-yl)-1H-pyrrole-3-carboxylic acid (tetrahydro-furan-2-ylmethyl)-amide

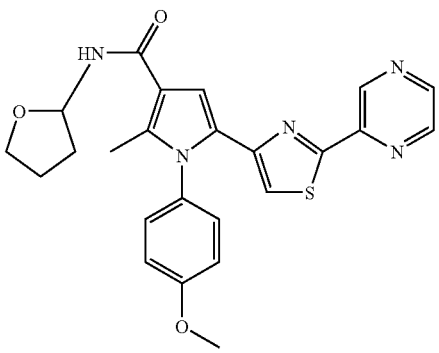

The title compound was obtained using tetrahydrofurfurylamine as $R^1R^2NH$, 4-methoxybenzylamine as $R^3$—$(CH_2)_m$—$NH_2$ and pyrazine-2-carbothioamide as $R^4C(S)NH_2$, MS(ES+) 490 (M+H)$^+$.

Example 186

5-[2-(2-Ethyl-pyridin-4-yl)-thiazol-4-yl]-1-(3-methoxy-propyl)-2-methyl-1H-pyrrole-3-carboxylic acid (tetrahydro-furan-2-ylmethyl)-amide

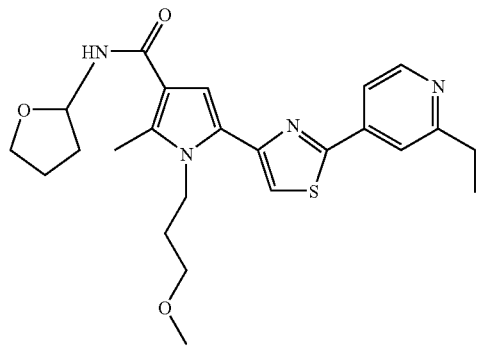

The title compound was obtained using tetrahydrofurfurylamine as $R^1R^2NH$, methoxyethylamine as $R_3$—$(CH_2)_m$—$NH_2$ and 2-ethyl-4-pyridine carbothiamide as $R^4C(S)NH_2$, MS(ES+) 469 (M+H)$^+$.

Example 187

1-(3-Methoxy-propyl)-2-methyl-5-[2-(6-methyl-pyridin-3-yl)-thiazol-4-yl]-1H-pyrrole-3-carboxylic acid (tetrahydro-furan-2-ylmethyl)-amide

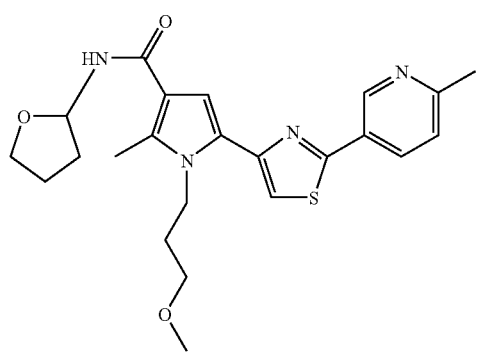

The title compound was obtained using tetrahydrofurfurylamine as $R^1R^2NH$, methoxyethylamine as $R_3$—$(CH_2)_m$—$NH_2$ and 6-methyl-pyridine-3-carbothioamide as $R^4C(S)NH_2$, MS(ES+) 455 (M+H)$^+$.

Example 188

1-(3-Methoxy-propyl)-2-methyl-5-(2-pyrazin-2-yl-thiazol-4-yl)-1H-pyrrole-3-carboxylic acid (tetrahydro-furan-2-ylmethyl)-amide

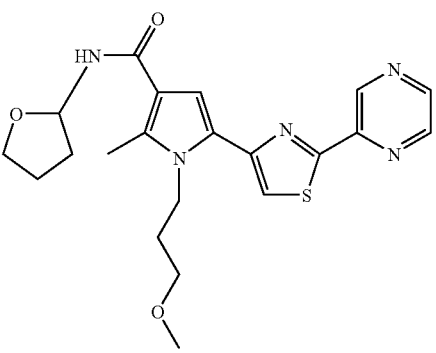

The title compound was obtained using tetrahydrofurfurylamine as $R^1R^2NH$, methoxyethylamine as $R_3$—$(CH_2)_m$—$NH_2$ and pyrazine-2-carbothioamide as $R^4C(S)NH_2$, MS(ES+) 442 (M+H)$^+$.

Example 189

5-[2-(2-Chloro-phenyl)-thiazol-4-yl]-2-methyl-1-thiophen-2-ylmethyl-1H-pyrrole-3-carboxylic acid (tetrahydro-furan-2-ylmethyl)-amide

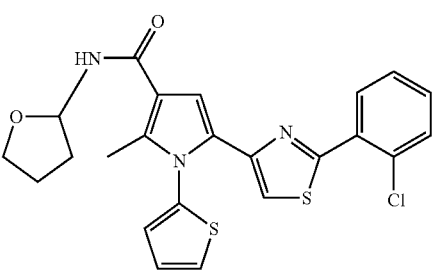

The title compound was obtained using tetrahydrofurfurylamine as $R^1R^2NH$, 3-(aminomethyl)thiophene as $R_3$—$(CH_2)_m$—$NH_2$ and 2-chloro-phenyl thioamide as $R^4C(S)NH_2$, MS(ES+) 498 (M+H)$^+$.

Example 190

5-[2-(4-Methoxy-phenyl)-thiazol-4-yl]-2-methyl-1-thiophen-2-ylmethyl-1H-pyrrole-3-carboxylic acid (tetrahydro-furan-2-ylmethyl)-amide

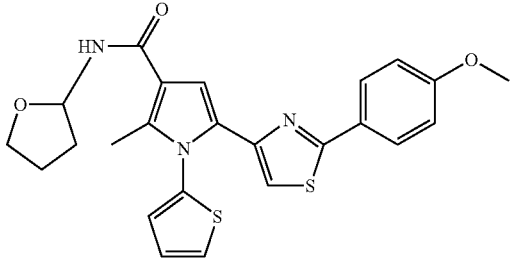

The title compound was obtained using tetrahydrofurfurylamine as $R^1R^2NH$, 3-(aminomethyl)thiophene as $R^3$—$(CH_2)_m$—$NH_2$ and 4-methoxyphenyl thioamide as $R^4C(S)NH_2$, MS(ES+) 494 (M+H)$^+$.

Example 191

5-[2-(2-Ethyl-pyridin-4-yl)-thiazol-4-yl]-2-methyl-1-thiophen-2-ylmethyl-1H-pyrrole-3-carboxylic acid (tetrahydro-furan-2-ylmethyl)-amide

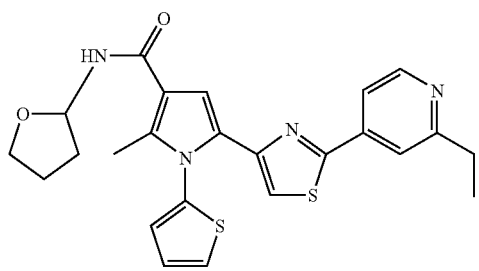

The title compound was obtained using tetrahydrofurfurylamine as $R^1R^2NH$, 3-(aminomethyl)thiophene as $R^3$—$(CH_2)_m$—$NH_2$ and 2-ethyl-4-pyridine carbothiamide as $R^4C(S)NH_2$, MS(ES+) 493 (M+H)$^+$.

Example 192

1-[2-(3,4-Dimethoxy-phenyl)-ethyl]-5-[2-(2-ethyl-pyridin-4-yl)-thiazol-4-yl]-2-methyl-1H-pyrrole-3-carboxylic acid (tetrahydro-furan-2-ylmethyl)-amide

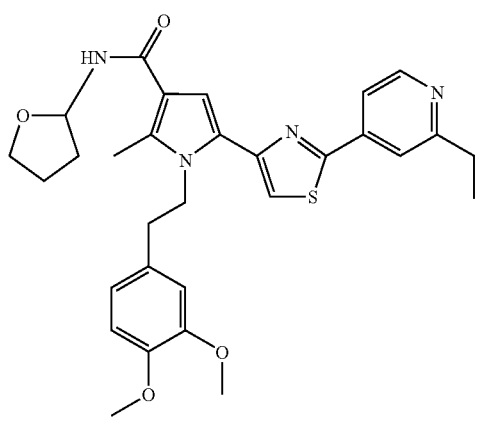

The title compound was obtained using tetrahydrofurfurylamine as $R^1R^2NH$, homoveratrylamine as $R^3$—$(CH_2)_m$—$NH_2$ and 2-ethyl-4-pyridine carbothiamide as $R^4C(S)NH_2$, MS(ES+) 561 (M+H)$^+$.

Example 193

Butyl-5-[2-(4-methoxy-phenyl)-thiazol-4-yl]-2-methyl-1H-pyrrole-3-carboxylic acid (2-methoxy-ethyl)-amide

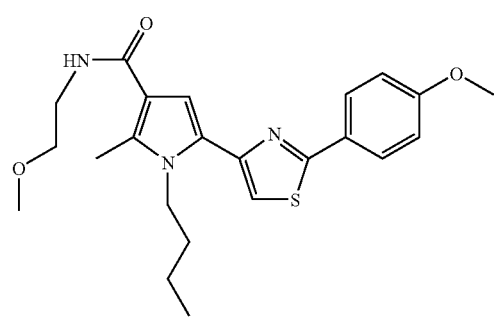

The title compound was obtained using methoxyethylamine as $R^1R^2NH$, butylamine as $R^3$—$(CH_2)_m$—$NH_2$ and 4-methoxyphenyl thioamide as $R^4C(S)NH_2$, MS(ES+) 428 (M+H)$^+$.

Example 194

5-[2-(2-Chloro-phenyl)-thiazol-4-yl]-1-cyclohexylmethyl-2-methyl-1H-pyrrole-3-carboxylic acid (2-methoxy-ethyl)-amide

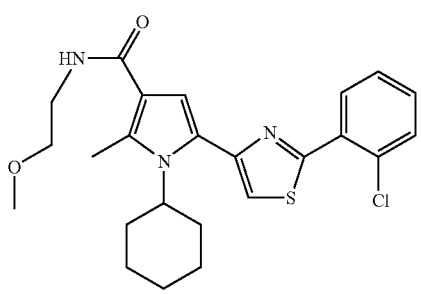

The title compound was obtained using methoxyethylamine as $R^1R^2NH$, aminomethylcyclohexane as $R^3$—$(CH_2)_m$—$NH_2$ and 2-chloro-phenyl thioamide as $R^4C(S)NH_2$, MS(ES+) 472 (M+H)$^+$.

Example 195

Cyclohexylmethyl-5-[2-(4-methoxy-phenyl)-thiazol-4-yl]-2-methyl-1H-pyrrole-3-carboxylic acid (2-methoxy-ethyl)-amide

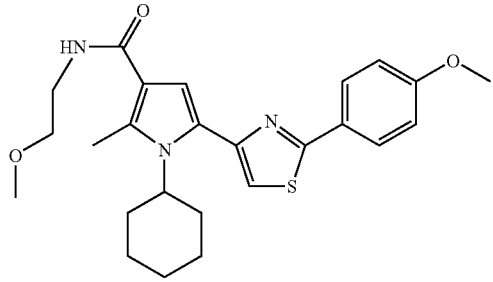

The title compound was obtained using methoxyethylamine as $R^1R^2NH$, aminomethylcyclohexane as $R^3$—$(CH_2)_m$—$NH_2$ and 4-methoxyphenyl thioamide as $R^4C(S)NH_2$, MS(ES+) 468 (M+H)$^+$.

Example 196

Cyclohexylmethyl-5-[2-(4-methoxy-phenoxymethyl)-thiazol-4-yl]-2-methyl-1H-pyrrole-3-carboxylic acid (2-methoxy-ethyl)-amide

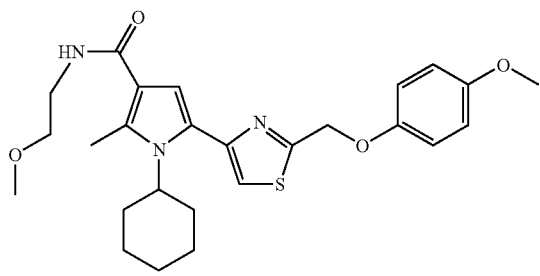

The title compound was obtained using methoxyethylamine as $R^1R^2NH$, aminomethylcyclohexane as $R^3$—$(CH_2)_m$—$NH_2$ and 2-(4-methoxyphenoxy)ethanethioamide as $R^4C(S)NH_2$, MS(ES+) 498 (M+H)$^+$.

Example 197

Cyclohexylmethyl-2-methyl-5-(2-pyrazin-2-yl-thiazol-4-yl)-1H-pyrrole-3-carboxylic acid (2-methoxy-ethyl)-amide

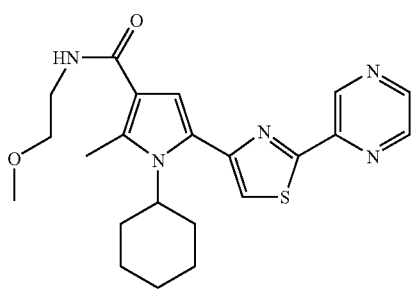

The title compound was obtained using methoxyethylamine as $R^1R^2NH$, aminomethylcyclohexane as $R^3$—$(CH_2)_m$—$NH_2$ and pyrazine-2-carbothioamide as $R^4C(S)NH_2$, MS(ES+) 440 (M+H)$^+$.

Example 198

5-[2-(4-Methoxy-phenyl)-thiazol-4-yl]-2-methyl-1-(tetrahydro-furan-2-ylmethyl)-1H-pyrrole-3-carboxylic acid (2-methoxy-ethyl)-amide

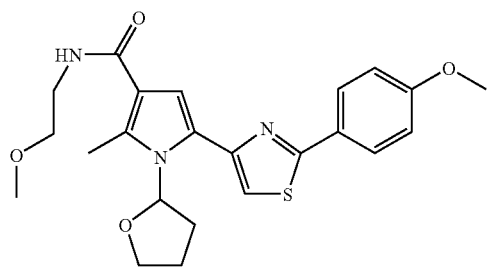

The title compound was obtained using methoxyethylamine as $R^1R^2NH$, tetrahydrofurfurylamine as $R^3$—$(CH_2)_m$—$NH_2$ and 4-methoxyphenyl thioamide as $R^4C(S)NH_2$, MS(ES+) 456 (M+H)$^+$.

Example 199

1-(2-Methoxy-ethyl)-5-[2-(4-methoxy-phenyl)-thiazol-4-yl]-2-methyl-1H-pyrrole-3-carboxylic acid (2-methoxy-ethyl)-amide

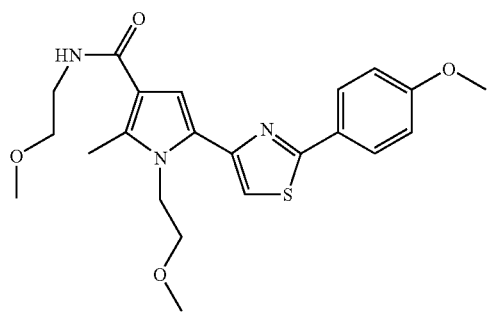

The title compound was obtained using methoxyethylamine as $R^1R^2NH$, methoxyethylamine as $R^3$—$(CH_2)_m$—$NH_2$ and 4-methoxyphenyl thioamide as $R^4C(S)NH_2$, MS(ES+) 430 (M+H)$^+$.

Example 200

5-[2-(2-Chloro-phenyl)-thiazol-4-yl]-1-furan-2-ylm-
ethyl-2-methyl-1H-pyrrole-3-carboxylic acid
(2-methoxy-ethyl)-amide

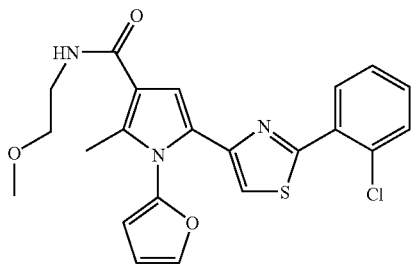

The title compound was obtained using methoxyethy-
lamine as $R^1R^2NH$, 3-furylmethylamine as $R^3$—$(CH_2)_m$—
$NH_2$ and 2-chloro-phenyl thioamide as $R^4C(S)NH_2$,
MS(ES+) 456 (M+H)+.

Example 201

Furan-2-ylmethyl-5-[2-(4-methoxy-phenyl)-thiazol-
4-yl]-2-methyl-1H-pyrrole-3-carboxylic acid
(2-methoxy-ethyl)-amide

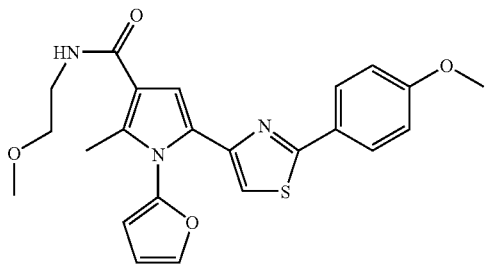

The title compound was obtained using methoxyethy-
lamine as $R^1R^2NH$, 3-furylmethylamine as $R^3$—$(CH_2)_m$—
$NH_2$ and 4-methoxyphenyl thioamide as $R^4C(S)NH_2$,
MS(ES+) 452 (M+H)+.

Example 202

5-[2-(2-Chloro-phenyl)-thiazol-4-yl]-1-(4-methoxy-
benzyl)-2-methyl-1H-pyrrole-3-carboxylic acid
(2-methoxy-ethyl)-amide

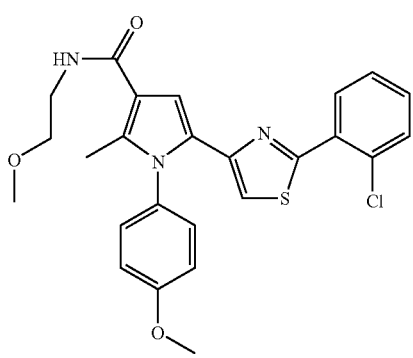

The title compound was obtained using methoxyethy-
lamine as $R^1R^2NH$, 4-methoxybenzylamine as $R^3$—$(CH_2)_m$
—$NH_2$ and 2-chloro-phenyl thioamide as $R^4C(S)NH_2$,
MS(ES+) 496 (M+H)+.

Example 203

1-(4-Methoxy-benzyl)-5-[2-(4-methoxy-phenyl)-
thiazol-4-yl]-2-methyl-1H-pyrrole-3-carboxylic acid
(2-methoxy-ethyl)-amide

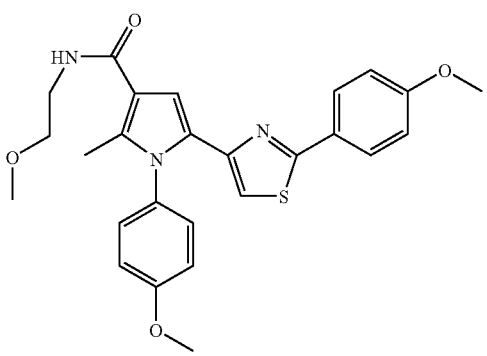

The title compound was obtained using methoxyethy-
lamine as $R^1R^2NH$, 4-methoxybenzylamine as $R^3$—$(CH_2)_m$
—$NH_2$ and 4-methoxyphenyl thioamide as $R^4C(S)NH_2$,
MS(ES+) 492 (M+H)+.

Example 204

1-(4-Methoxy-benzyl)-5-[2-(4-methoxy-phenoxym-
ethyl)-thiazol-4-yl]-2-methyl-1H-pyrrole-3-carboxy-
lic acid (2-methoxy-ethyl)-amide

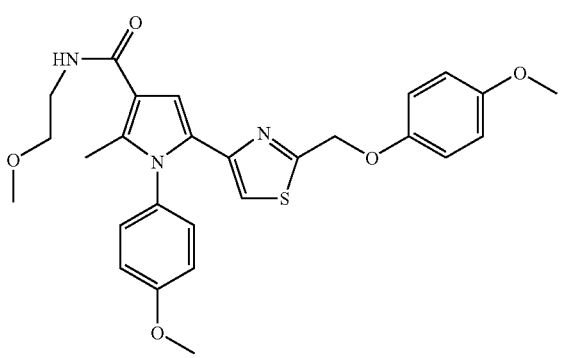

The title compound was obtained using methoxyethy-
lamine as $R^1R^2NH$, 4-methoxybenzylamine as $R^3$—$(CH_2)_m$
—$NH_2$ and 2-(4-methoxyphenoxy)ethanethioamide as $R^4C$
$(S)NH_2$, MS(ES+) 522 (M+H)+.

Example 205

5-[2-(2-Ethyl-pyridin-4-yl)-thiazol-4-yl]-1-(4-methoxy-benzyl)-2-methyl-1H-pyrrole-3-carboxylic acid (2-methoxy-ethyl)-amide

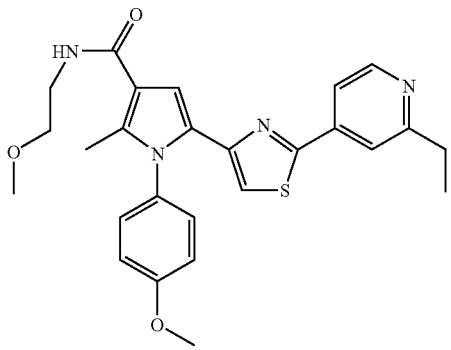

The title compound was obtained using methoxyethylamine as R¹R²NH, 4-methoxybenzylamine as R³—(CH$_2$)$_m$—NH$_2$ and 2-ethyl-4-pyridine carbothiamide as R⁴C(S)NH$_2$, MS(ES+) 491 (M+H)⁺.

Example 206

4-[1-(4-Methoxy-benzyl)-4-(2-methoxy-ethylcarbamoyl)-5-methyl-1H-pyrrol-2-yl]-thiazole-2-carboxylic acid ethyl ester

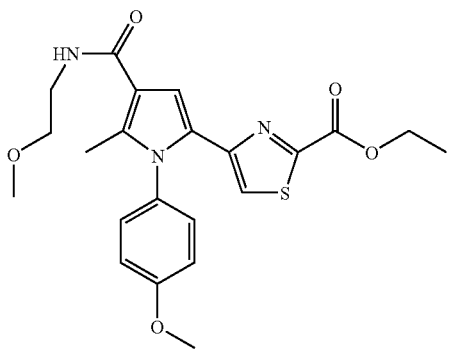

The title compound was obtained using methoxyethylamine as R¹R²NH, 4-methoxybenzylamine as R³—(CH$_2$)$_m$—NH$_2$ and ethylthiooxamate as R⁴C(S)NH$_2$., MS(ES+) 458 (M+H)⁺.

Example 207

1-(4-Methoxy-benzyl)-2-methyl-5-[2-(6-methylpyridin-3-yl)-thiazol-4-yl]-1H-pyrrole-3-carboxylic acid (2-methoxy-ethyl)-amide

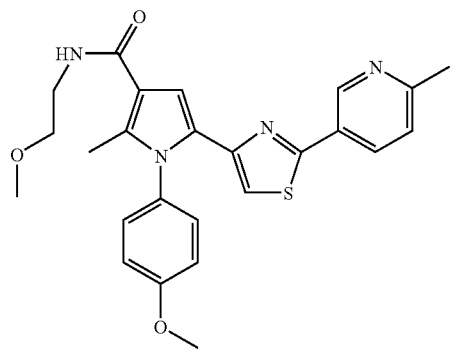

The title compound was obtained using methoxyethylamine as R¹R²NH, 4-methoxybenzylamine as R³—(CH$_2$)$_m$—NH$_2$ and 6-methyl-pyridine-3-carbothioamide as R⁴C(S)NH$_2$, MS(ES+) 477 (M+H)⁺.

Example 208

1-(4-Methoxy-benzyl)-2-methyl-5-(2-pyrazin-2-yl-thiazol-4-yl)-1H-pyrrole-3-carboxylic acid (2-methoxy-ethyl)-amide

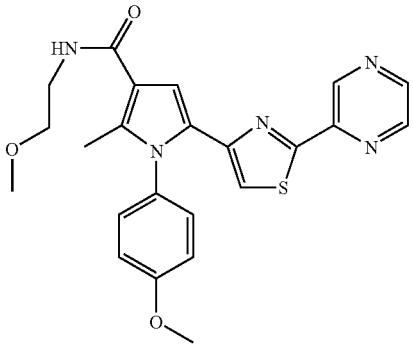

The title compound was obtained using methoxyethylamine as R¹R²NH, 4-methoxybenzylamine as R³—(CH$_2$)$_m$—NH$_2$ and pyrazine-2-carbothioamide as R⁴C(S)NH$_2$, MS(ES+) 464 (M+H)⁺.

Example 209

1-[2-(3,4-Dimethoxy-phenyl)-ethyl]-5-[2-(2-ethyl-pyridin-4-yl)-thiazol-4-yl]-2-methyl-1H-pyrrole-3-carboxylic acid (2-methoxy-ethyl)-amide

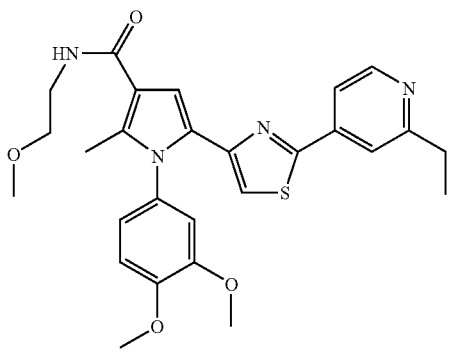

The title compound was obtained using methoxyethylamine as $R^1R^2NH$, homoveratrylamine as $R^3—(CH_2)_m—NH_2$ and 2-ethyl-4-pyridine carbothiamide as $R^4C(S)NH_2$, MS(ES+) 535 (M+H)$^+$.

Example 210

Butyl-5-[2-(4-methoxy-phenyl)-thiazol-4-yl]-2-methyl-1H-pyrrole-3-carboxylic acid (2-cyclohex-1-enyl-ethyl)-amide

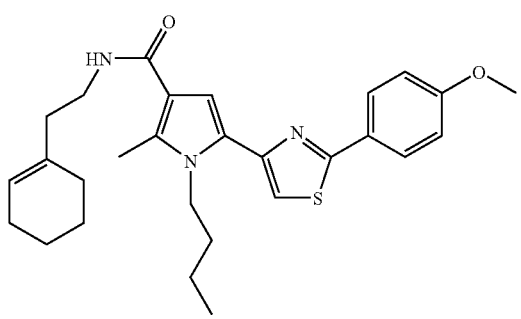

The title compound was obtained using 2-cyclohex-1-enyl-ethylamine as $R^1R^2NH$, butylamine as $R^3—(CH_2)_m—NH_2$ and 4-methoxyphenyl thioamide as $R^4C(S)NH_2$, MS(ES+) 478 (M+H)$^+$.

Example 211

Cyclohexylmethyl-5-[2-(4-methoxy-phenyl)-thiazol-4-yl]-2-methyl-1H-pyrrole-3-carboxylic acid (2-cyclohex-1-enyl-ethyl)-amide

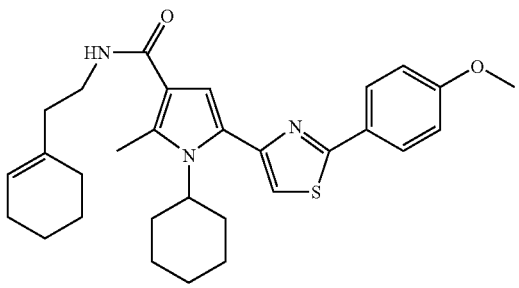

The title compound was obtained using 2-cyclohex-1-enyl-ethylamine as $R^1R^2NH$, aminomethylcyclohexane as $R^3—(CH_2)_m—NH_2$ and 4-methoxyphenyl thioamide as $R^4C(S)NH_2$, MS(ES+) 518 (M+H)$^+$.

Example 212

Cyclohexylmethyl-5-[2-(2-ethyl-pyridin-4-yl)-thiazol-4-yl]-2-methyl-1H-pyrrole-3-carboxylic acid (2-cyclohex-1-enyl-ethyl)-amide

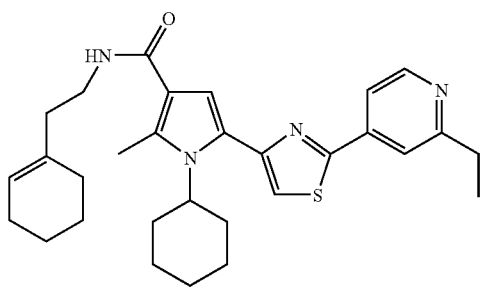

The title compound was obtained using 2-cyclohex-1-enyl-ethylamine as $R^1R^2NH$, aminomethylcyclohexane as $R^3—(CH_2)_m—NH_2$ and 2-ethyl-4-pyridine carbothiamide as $R^4C(S)NH_2$, MS(ES+) 517 (M+H)$^+$.

Example 213

5-[2-(4-Methoxy-phenyl)-thiazol-4-yl]-2-methyl-1-(tetrahydro-furan-2-ylmethyl)-1H-pyrrole-3-carboxylic acid (2-cyclohex-1-enyl-ethyl)-amide

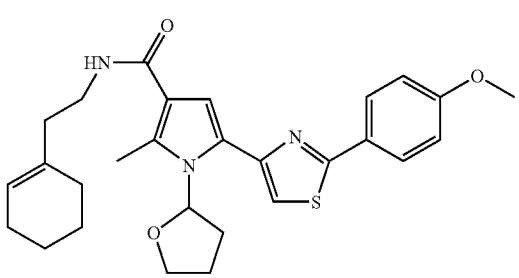

The title compound was obtained using 2-cyclohex-1-enyl-ethylamine as $R^1R^2NH$, tetrahydrofurfurylamine as $R^3$—$(CH_2)_m$—$NH_2$ and 4-methoxyphenyl thioamide as $R^4C(S)NH_2$, MS(ES+) 506 (M+H)$^+$.

Example 214

5-[2-(2-Ethyl-pyridin-4-yl)-thiazol-4-yl]-2-methyl-1-(tetrahydro-furan-2-ylmethyl)-1H-pyrrole-3-carboxylic acid (2-cyclohex-1-enyl-ethyl)-amide

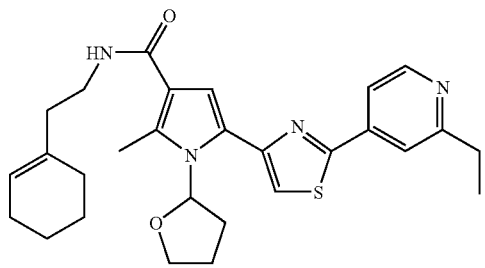

The title compound was obtained using 2-cyclohex-1-enyl-ethylamine as $R^1R^2NH$, tetrahydrofurfurylamine as $R^3$—$(CH_2)_m$—$NH_2$ and 2-ethyl-4-pyridine carbothiamide as $R^4C(S)NH_2$, MS(ES+) 505 (M+H)$^+$.

Example 215

Methyl-5-[2-(6-methyl-pyridin-3-yl)-thiazol-4-yl]-1-(tetrahydro-furan-2-ylmethyl)-1H-pyrrole-3-carboxylic acid (2-cyclohex-1-enyl-ethyl)-amide

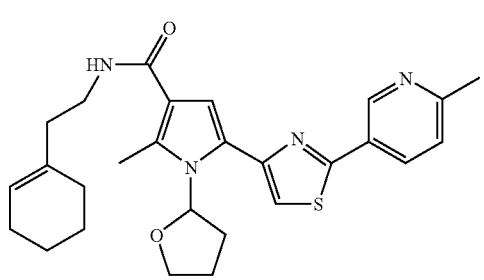

The title compound was obtained using 2-cyclohex-1-enyl-ethylamine as $R^1R^2NH$, tetrahydrofurfurylamine as $R^3$—$(CH_2)_m$—$NH_2$ and 6-methyl-pyridine-3-carbothioamide as $R^4C(S)NH_2$, MS(ES+) 491 (M+H)$^+$.

Example 216

1-(2-Methoxy-ethyl)-2-methyl-5-[2-(6-methyl-pyridin-3-yl)-thiazol-4-yl]-1H-pyrrole-3-carboxylic acid (2-cyclohex-1-enyl-ethyl)-amide

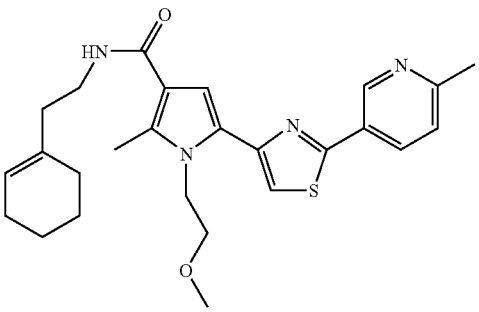

The title compound was obtained using 2-cyclohex-1-enyl-ethylamine as $R^1R^2NH$, methoxyethylamine as $R^3$—$(CH_2)_m$—$NH_2$ and 6-methyl-pyridine-3-carbothioamide as $R^4C(S)NH_2$, MS(ES+) 465 (M+H)$^+$.

Example 217

5-[2-(2-Ethyl-pyridin-4-yl)-thiazol-4-yl]-1-furan-2-ylmethyl-2-methyl-1H-pyrrole-3-carboxylic acid (2-cyclohex-1-enyl-ethyl)-amide

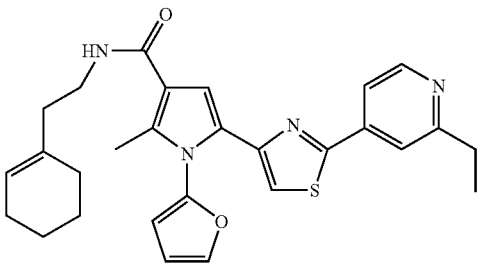

The title compound was obtained using 2-cyclohex-1-enyl-ethylamine as $R^1R^2NH$, 3-furylmethylamine as $R^3$—$(CH_2)_m$—$NH_2$ and 2-ethyl-4-pyridine carbothiamide as $R^4C(S)NH_2$, MS(ES+) 501 (M+H)$^+$.

Example 218

5-[2-(2-Ethyl-pyridin-4-yl)-thiazol-4-yl]-1-(4-methoxy-benzyl)-2-methyl-1H-pyrrole-3-carboxylic acid (2-cyclohex-1-enyl-ethyl)-amide

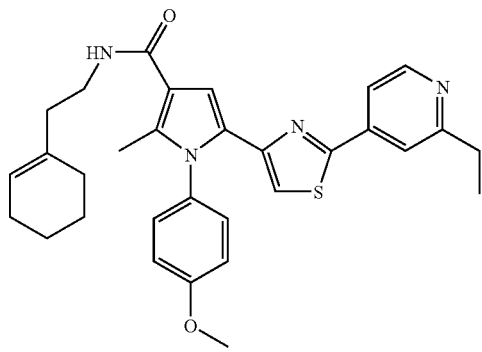

The title compound was obtained using 2-cyclohex-1-enyl-ethylamine as $R^1R^2NH$, 4-methoxybenzylamine as $R^3$—$(CH_2)_m$—$NH_2$ and 2-ethyl-4-pyridine carbothiamide as $R^4C(S)NH_2$, MS(ES+) 541 $(M+H)^+$.

Example 219

1-(4-Methoxy-benzyl)-2-methyl-5-[2-(6-methyl-pyridin-3-yl)-thiazol-4-yl]-1H-pyrrole-3-carboxylic acid (2-cyclohex-1-enyl-ethyl)-amide

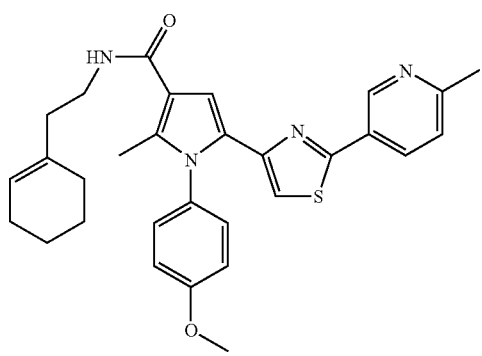

The title compound was obtained using 2-cyclohex-1-enyl-ethylamine as $R^1R^2NH$, 4-methoxybenzylamine as $R^3$—$(CH_2)_m$—$NH_2$ and 6-methyl-pyridine-3-carbothioamide as $R^4C(S)NH_2$, MS(ES+) 527 $(M+H)^+$.

Example 220

5-[2-(2-Ethyl-pyridin-4-yl)-thiazol-4-yl]-2-methyl-1-thiophen-2-ylmethyl-1H-pyrrole-3-carboxylic acid (2-cyclohex-1-enyl-ethyl)-amide

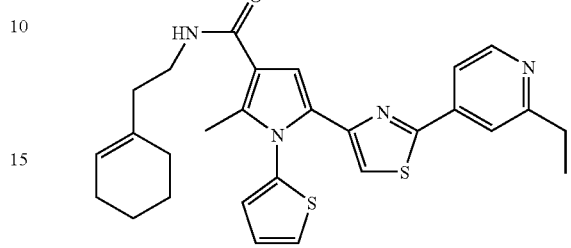

The title compound was obtained using 2-cyclohex-1-enyl-ethylamine as $R^1R^2NH$, 3-(aminomethyl)thiophene as $R^3$—$(CH_2)_m$—$NH_2$ and 2-ethyl-4-pyridine carbothiamide as $R^4C(S)NH_2$, MS(ES+) 517 $(M+H)^+$.

Example 221 rac-1-Butyl-5-[2-(4-methoxy-phenyl)-thiazol-4-yl]-2-methyl-1H-pyrrole-3-carboxylic acid (2-ethyl-hexyl)-amide

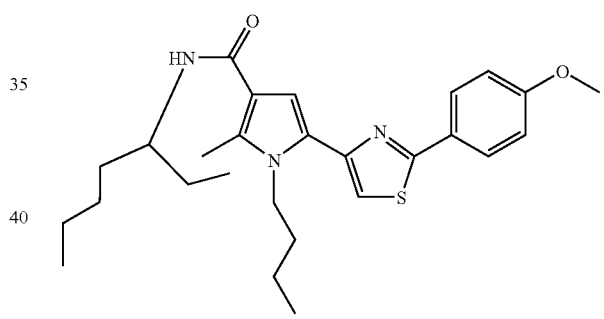

The title compound was obtained using 2-ethyl-hexylamine as $R^1R^2NH$, butylamine as $R^3$—$(CH_2)_m$—$NH_2$ and 4-methoxyphenyl thioamide as $R^4C(S)NH_2$, MS(ES+) 482 $(M+H)^+$.

Example 222 rac-1-Butyl-5-[2-(4-methoxy-phenoxymethyl)-thiazol-4-yl]-2-methyl-1H-pyrrole-3-carboxylic acid (2-ethyl-hexyl)-amide

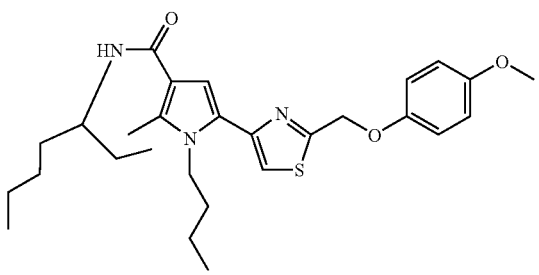

The title compound was obtained using 2-ethyl-hexylamine as $R^1R^2NH$, butylamine as $R^3$—$(CH_2)_m$—$NH_2$ and 2-(4-methoxyphenoxy)ethanethioamide as $R^4C(S)NH_2$, MS(ES+) 512 (M+H)$^+$.

Example 223 rac-1-Butyl-5-[2-(2-ethyl-pyridin-4-yl)-thiazol-4-yl]-2-methyl-1H-pyrrole-3-carboxylic acid (2-ethyl-hexyl)-amide

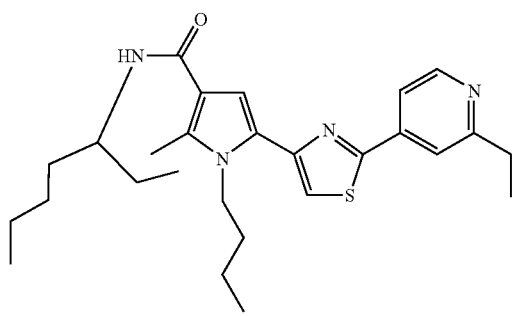

The title compound was obtained using 2-ethyl-hexylamine as $R^1R^2NH$, butylamine as $R^3$—$(CH_2)_m$—$NH_2$ and 2-ethyl-4-pyridine carbothiamide as $R^4C(S)NH_2$, MS(ES+) 481 (M+H)$^+$.

Example 224 rac-4-[1-Butyl-4-(2-ethyl-hexylcarbamoyl)-5-methyl-1H-pyrrol-2-yl]-thiazole-2-carboxylic acid ethyl ester

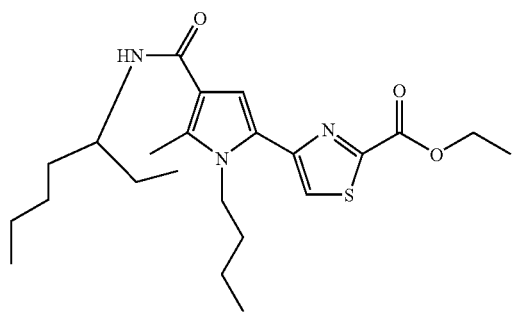

The title compound was obtained using 2-ethyl-hexylamine as $R^1R^2NH$, butylamine as $R^3$—$(CH_2)_m$—$NH_2$ and ethylthiooxamate as $R^4C(S)NH_2$, MS(ES+) 448 (M+H)$^+$.

Example 225 rac-5-[2-(2-Chloro-phenyl)-thiazol-4-yl]-1-isobutyl-2-methyl-1H-pyrrole-3-carboxylic acid (2-ethyl-hexyl)-amide

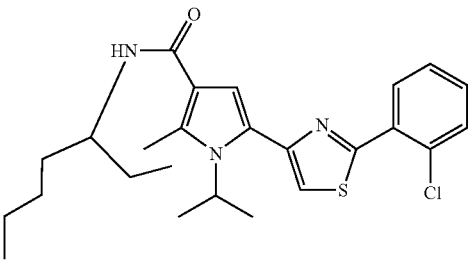

The title compound was obtained using 2-ethyl-hexylamine as $R^1R^2NH$, isobutylamine as $R^3$—$(CH_2)_m$—$NH_2$ and 2-chloro-phenyl thioamide as $R^4C(S)NH_2$, MS(ES+) 486 (M+H)$^+$.

Example 226 rac-1-Isobutyl-5-[2-(4-methoxy-phenyl)-thiazol-4-yl]-2-methyl-1H-pyrrole-3-carboxylic acid (2-ethyl-hexyl)-amide

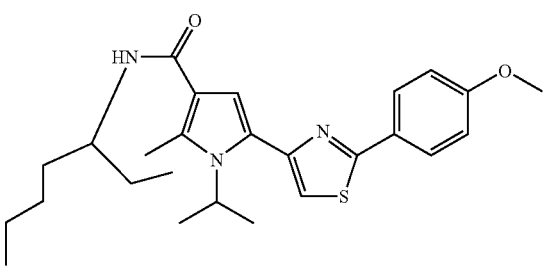

The title compound was obtained using 2-ethyl-hexylamine as $R^1R^2NH$, isobutylamine as $R^3$—$(CH_2)_m$—$NH_2$ and 4-methoxyphenyl thioamide as $R^4C(S)NH_2$, MS(ES+) 482 (M+H)$^+$.

Example 227 rac-1-Isobutyl-5-[2-(4-methoxy-phenoxymethyl)-thiazol-4-yl]-2-methyl-1H-pyrrole-3-carboxylic acid (2-ethyl-hexyl)-amide

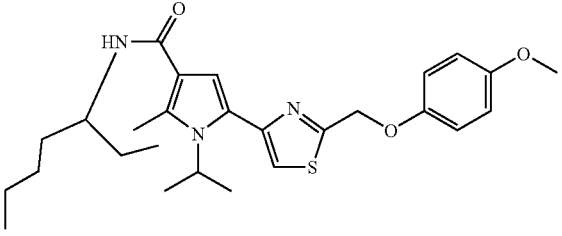

The title compound was obtained using 2-ethyl-hexylamine as $R^1R^2NH$, isobutylamine as $R^3$—$(CH_2)_m$—$NH_2$ and 2-(4-methoxyphenoxy)ethanethioamide as $R^4C(S)NH_2$, MS(ES+) 512 (M+H)$^+$.

Example 228 rac-4-[4-(2-Ethyl-hexylcarbamoyl)-1-isobutyl-5-methyl-1H-pyrrol-2-yl]-thiazole-2-carboxylic acid ethyl ester

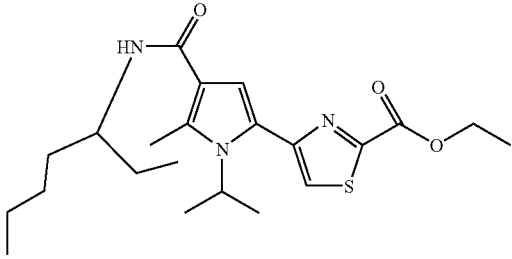

The title compound was obtained using 2-ethyl-hexylamine as $R^1R^2NH$, isobutylamine as $R^3$—$(CH_2)_m$—$NH_2$ and ethylthiooxamate as $R^4C(S)NH_2$, MS(ES+) 44 (M+H)$^+$ 0.8

Example 229 rac-1-Isobutyl-2-methyl-5-(2-pyrazin-2-yl-thiazol-4-yl)-1H-pyrrole-3-carboxylic acid (2-ethyl-hexyl)-amide

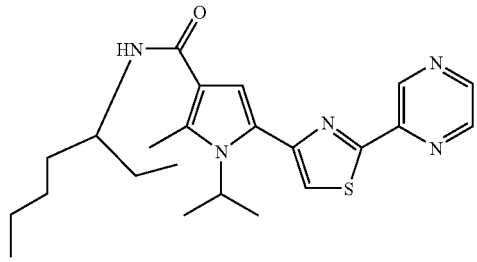

The title compound was obtained using 2-ethyl-hexylamine as $R^1R^2NH$, isobutylamine as $R^3$—$(CH_2)_m$—$NH_2$ and pyrazine-2-carbothioamide as $R^4C(S)NH_2$, MS(ES+) 454 (M+H)$^+$.

Example 230 rac-5-[2-(4-Methoxy-phenoxymethyl)-thiazol-4-yl]-1-[2-(4-methoxy-phenyl)-ethyl]-2-methyl-1H-pyrrole-3-carboxylic acid (2-ethyl-hexyl)-amide

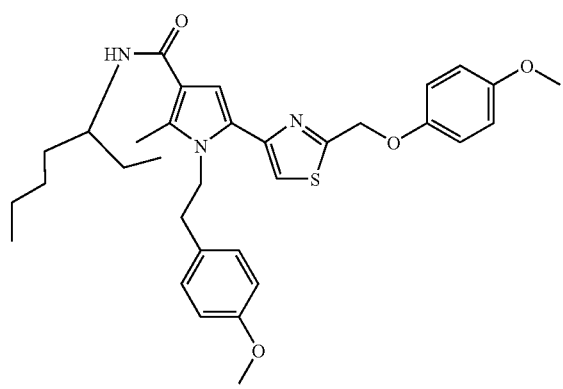

The title compound was obtained using 2-ethyl-hexylamine as $R^1R^2NH$, 2-(1-cyclohexenyl)ethylamine as $R^3$—$(CH_2)_m$—$NH_2$ and 2-(4-methoxyphenoxy)ethanethioamide as $R^4C(S)NH_2$, MS(ES+) 590 (M+H)$^+$.

Example 231 rac-5-[2-(2-Ethyl-pyridin-4-yl)-thiazol-4-yl]-1-[2-(4-methoxy-phenyl)-ethyl]-2-methyl-1H-pyrrole-3-carboxylic acid (2-ethyl-hexyl)-amide

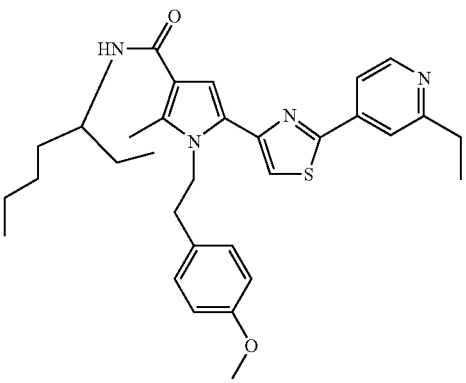

The title compound was obtained using 2-ethyl-hexylamine as $R^1R^2NH$, 2-(1-cyclohexenyl)ethylamine as $R^3$—$(CH_2)_m$—$NH_2$ and 2-ethyl-4-pyridine carbothiamide as $R^4C(S)NH_2$, MS(ES+) 559 (M+H)$^+$.

Example 232 rac-5-[2-(2-Chloro-phenyl)-thiazol-4-yl]-1-cyclohexylmethyl-2-methyl-1H-pyrrole-3-carboxylic acid (2-ethyl-hexyl)-amide

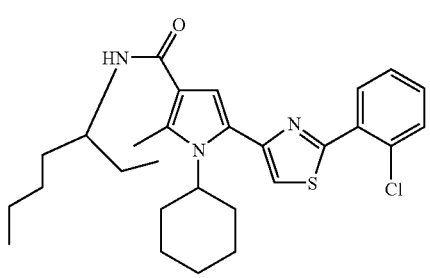

The title compound was obtained using 2-ethyl-hexylamine as $R^1R^2NH$, aminomethylcyclohexane as $R^3$—$(CH_2)_m$—$NH_2$ and 2-chloro-phenyl thioamide as $R^4C(S)NH_2$, MS(ES+) 526 (M+H)$^+$.

Example 233 rac-1-Cyclohexylmethyl-5-[2-(4-methoxy-phenyl)-thiazol-4-yl]-2-methyl-1H-pyrrole-3-carboxylic acid (2-ethyl-hexyl)-amide

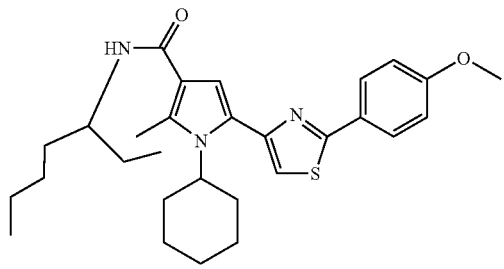

The title compound was obtained using 2-ethyl-hexylamine as $R^1R^2NH$, aminomethylcyclohexane as $R^3$—$(CH_2)_m$—$NH_2$ and 4-methoxyphenyl thioamide as $R^4C(S)NH_2$, MS(ES+) 522 (M+H)$^+$.

Example 234 rac-1-Cyclohexylmethyl-5-[2-(2-ethyl-pyridin-4-yl)-thiazol-4-yl]-2-methyl-1H-pyrrole-3-carboxylic acid (2-ethyl-hexyl)-amide

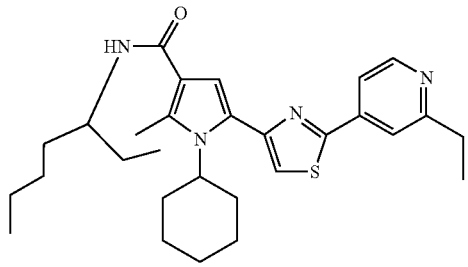

The title compound was obtained using 2-ethyl-hexylamine as $R^1R^2NH$, aminomethylcyclohexane as $R^3$—$(CH_2)_m$—$NH_2$ and 2-ethyl-4-pyridine carbothiamide as $R^4C(S)NH_2$, MS(ES+) 521 (M+H)$^+$.

Example 235 rac-4-[1-Cyclohexylmethyl-4-(2-ethyl-hexylcarbamoyl)-5-methyl-1H-pyrrol-2-yl]-thiazole-2-carboxylic acid ethyl ester

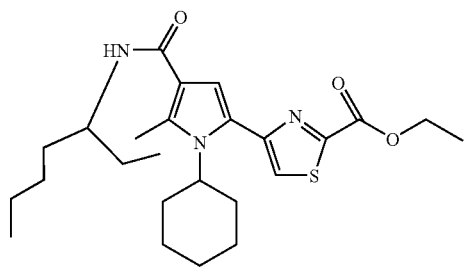

The title compound was obtained using 2-ethyl-hexylamine as $R^1R^2NH$, aminomethylcyclohexane as $R^3$—$(CH_2)_m$—$NH_2$ and ethylthiooxamate as $R^4C(S)NH_2$., MS(ES+) 488 (M+H)$^+$.

Example 236 rac-1-Cyclohexylmethyl-2-methyl-5-[2-(6-methyl-pyridin-3-yl)-thiazol-4-yl]-1H-pyrrole-3-carboxylic acid (2-ethyl-hexyl)-amide

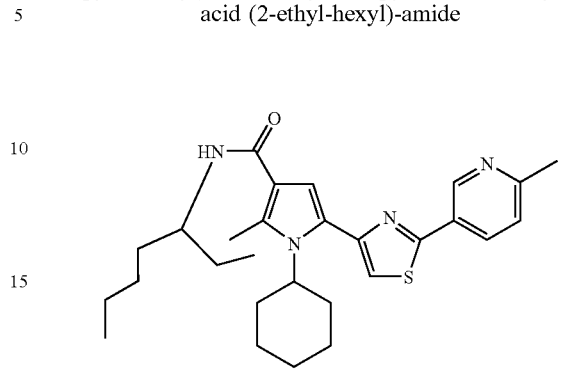

The title compound was obtained using 2-ethyl-hexylamine as $R^1R^2NH$, aminomethylcyclohexane as $R^3$—$(CH_2)_m$—$NH_2$ and 6-methyl-pyridine-3-carbothioamide as $R^4C(S)NH_2$, MS(ES+) 507 (M+H)$^+$.

Example 237 rac-1-Cyclohexylmethyl-2-methyl-5-(2-pyrazin-2-yl-thiazol-4-yl)-1H-pyrrole-3-carboxylic acid (2-ethyl-hexyl)-amide

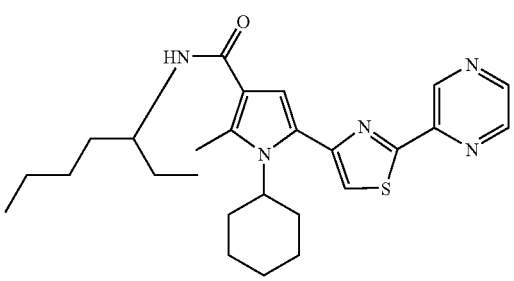

The title compound was obtained using 2-ethyl-hexylamine as $R^1R^2NH$, aminomethylcyclohexane as $R^3$—$(CH_2)_m$—$NH_2$ and pyrazine-2-carbothioamide as $R^4C(S)NH_2$, MS(ES+) 494 (M+H)$^+$.

Example 238 rac-5-[2-(2-Chloro-phenyl)-thiazol-4-yl]-2-methyl-1-(tetrahydro-furan-2-ylmethyl)-1H-pyrrole-3-carboxylic acid (2-ethyl-hexyl)-amide

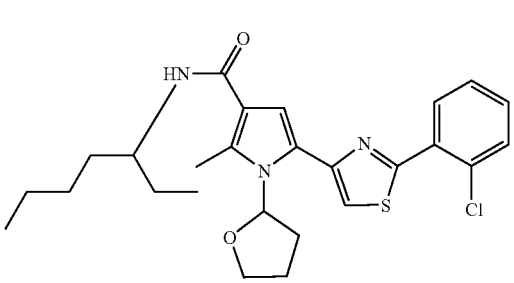

The title compound was obtained using 2-ethyl-hexylamine as $R^1R^2NH$, tetrahydrofurfurylamine as $R^3$—$(CH_2)_m$—$NH_2$ and 2-chloro-phenyl thioamide as $R^4C(S)NH_2$, MS(ES+) 514 (M+H)$^+$.

Example 239 rac-5-[2-(4-Methoxy-phenyl)-thiazol-4-yl]-2-methyl-1-(tetrahydro-furan-2-ylmethyl)-1H-pyrrole-3-carboxylic acid (2-ethyl-hexyl)-amide

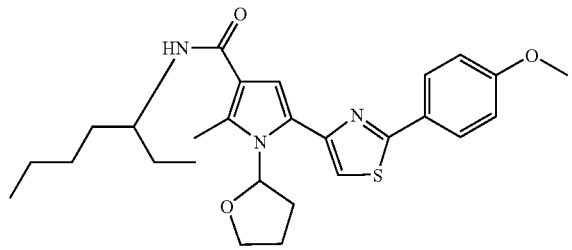

The title compound was obtained using 2-ethyl-hexylamine as $R^1R^2NH$, tetrahydrofurfurylamine as $R^3$—$(CH_2)_m$—$NH_2$ and 4-methoxyphenyl thioamide as $R^4C(S)NH_2$, MS(ES+) 510 (M+H)$^+$.

Example 240 rac-5-[2-(4-Methoxy-phenoxymethyl)-thiazol-4-yl]-2-methyl-1-(tetrahydro-furan-2-ylmethyl)-1H-pyrrole-3-carboxylic acid (2-ethyl-hexyl)-amide

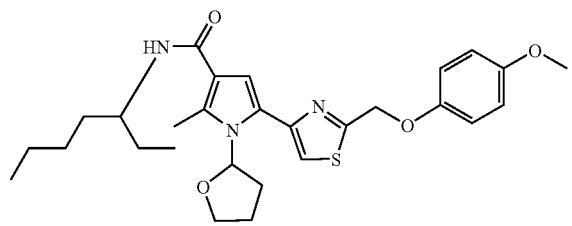

The title compound was obtained using 2-ethyl-hexylamine as $R^1R^2NH$, tetrahydrofurfurylamine as $R^3$—$(CH_2)_m$—$NH_2$ and 2-(4-methoxyphenoxy)ethanethioamide as $R^4C(S)NH_2$, MS(ES+) 540 (M+H)$^+$.

Example 241 rac-5-[2-(2-Ethyl-pyridin-4-yl)-thiazol-4-yl]-2-methyl-1-(tetrahydro-furan-2-ylmethyl)-1H-pyrrole-3-carboxylic acid (2-ethyl-hexyl)-amide

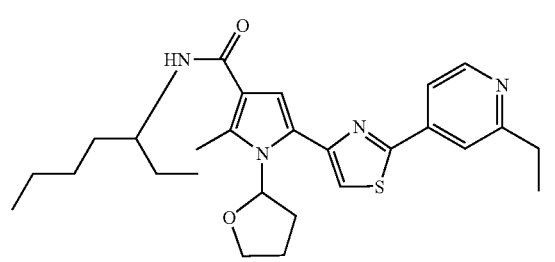

The title compound was obtained using 2-ethyl-hexylamine as $R^1R^2NH$, tetrahydrofurfurylamine as $R^3$—$(CH_2)_m$—$NH_2$ and 2-ethyl-4-pyridine carbothiamide as $R^4C(S)NH_2$, MS(ES+) 509 (M+H)$^+$.

Example 242 rac-4-[4-(2-Ethyl-hexylcarbamoyl)-5-methyl-1-(tetrahydro-furan-2-ylmethyl)-1H-pyrrol-2-yl]-thiazole-2-carboxylic acid ethyl ester

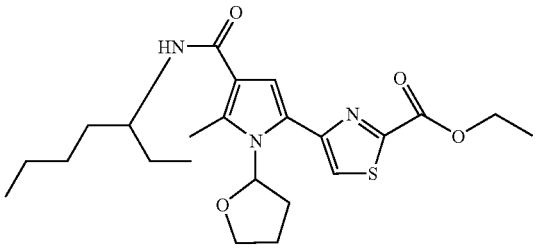

The title compound was obtained using 2-ethyl-hexylamine as $R^1R^2NH$, tetrahydrofurfurylamine as $R^3$—$(CH_2)_m$—$NH_2$ and ethylthiooxamate as $R^4C(S)NH_2$, MS(ES+) 476 (M+H)$^+$.

Example 243 rac-2-Methyl-5-[2-(6-methyl-pyridin-3-yl)-thiazol-4-yl]-1-(tetrahydro-furan-2-ylmethyl)-1H-pyrrole-3-carboxylic acid (2-ethyl-hexyl)-amide

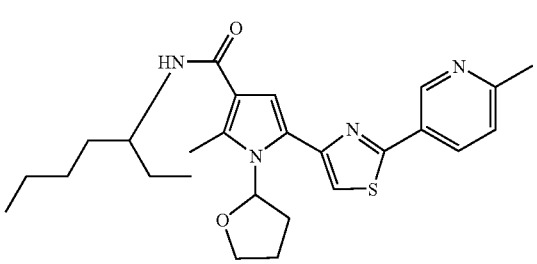

The title compound was obtained using 2-ethyl-hexylamine as $R^1R^2NH$, tetrahydrofurfurylamine as $R^3$—$(CH_2)_m$—$NH_2$ and 6-methyl-pyridine-3-carbothioamide as $R^4C(S)NH_2$, MS(ES+) 495 (M+H)$^+$.

Example 244 rac-2-Methyl-5-(2-pyrazin-2-yl-thiazol-4-yl)-1-(tetrahydro-furan-2-ylmethyl)-1H-pyrrole-3-carboxylic acid (2-ethyl-hexyl)-amide

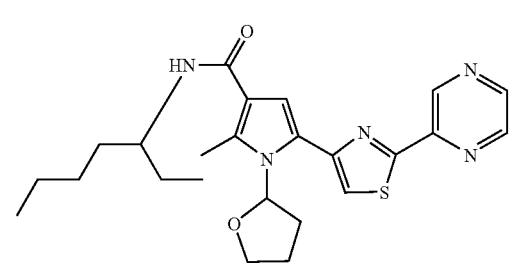

The title compound was obtained using 2-ethyl-hexylamine as R¹R²NH, tetrahydrofurfurylamine as R³—(CH₂)ₘ—NH₂ and pyrazine-2-carbothioamide as R⁴C(S)NH₂, MS(ES+) 482 (M+H)⁺.

Example 245 rac-1-(2-Methoxy-ethyl)-5-[2-(4-methoxy-phenyl)-thiazol-4-yl]-2-methyl-1H-pyrrole-3-carboxylic acid (2-ethyl-hexyl)-amide

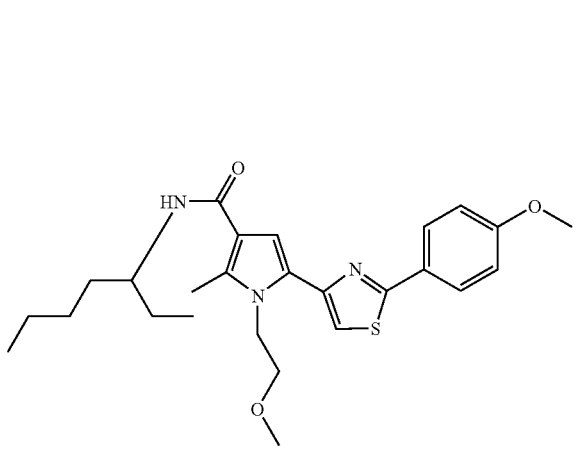

The title compound was obtained using 2-ethyl-hexylamine as R¹R²NH, methoxyethylamine as R³—(CH₂)ₘ—NH₂ and 4-methoxyphenyl thioamide as R⁴C(S)NH₂, MS(ES+) 484 (M+H)⁺.

Example 246 rac-1-(2-Methoxy-ethyl)-5-[2-(4-methoxy-phenoxymethyl)-thiazol-4-yl]-2-methyl-1H-pyrrole-3-carboxylic acid (2-ethyl-hexyl)-amide

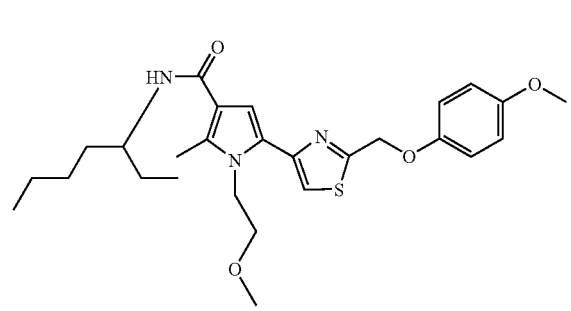

The title compound was obtained using 2-ethyl-hexylamine as R¹R²NH, methoxyethylamine as R³—(CH₂)ₘ—NH₂ and 2-(4-methoxyphenoxy)ethanethioamide as R⁴C(S)NH₂, MS(ES+) 514 (M+H)⁺.

Example 247 rac-1-(2-Methoxy-ethyl)-2-methyl-5-[2-(6-methyl-pyridin-3-yl)-thiazol-4-yl]-1H-pyrrole-3-carboxylic acid (2-ethyl-hexyl)-amide

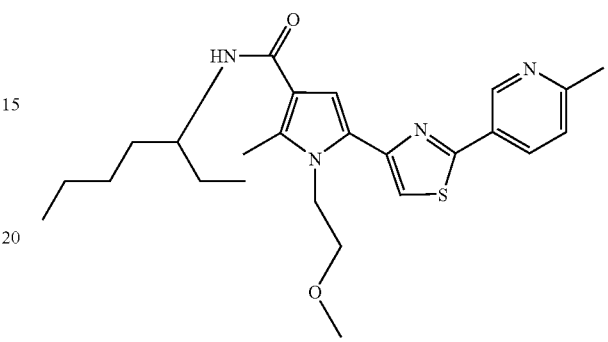

The title compound was obtained using 2-ethyl-hexylamine as R¹R²NH, methoxyethylamine as R³—(CH₂)ₘ—NH₂ and 6-methyl-pyridine-3-carbothioamide as R⁴C(S)NH₂, MS(ES+) 469 (M+H)⁺.

Example 248 rac-1-(2-Methoxy-ethyl)-2-methyl-5-(2-pyrazin-2-yl-thiazol-4-yl)-1H-pyrrole-3-carboxylic acid (2-ethyl-hexyl)-amide

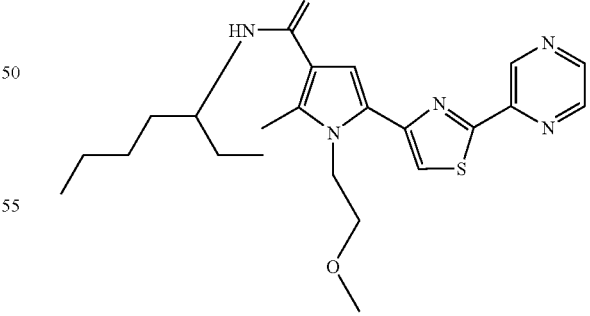

The title compound was obtained using 2-ethyl-hexylamine as R¹R²NH, methoxyethylamine as R³—(CH₂)ₘ—NH₂ and pyrazine-2-carbothioamide as R⁴C(S)NH₂, MS(ES+) 456 (M+H)⁺.

Example 249 rac-1-(2-Cyclohex-1-enyl-ethyl)-5-[2-(2-ethyl-pyridin-4-yl)-thiazol-4-yl]-2-methyl-1H-pyrrole-3-carboxylic acid (2-ethyl-hexyl)-amide

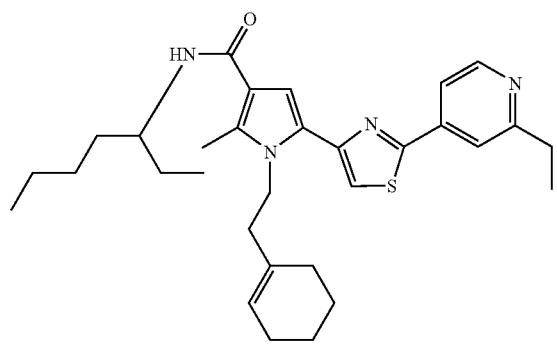

The title compound was obtained using 2-ethyl-hexylamine as $R^1R^2NH$, 2-(1-cyclohexenyl)ethylamine as $R^3$—$(CH_2)_m$—$NH_2$ and 2-ethyl-4-pyridine carbothiamide as $R^4C(S)NH_2$, MS(ES+) 533 (M+H)+.

Example 250 rac-5-[2-(2-Chloro-phenyl)-thiazol-4-yl]-1-furan-2-ylmethyl-2-methyl-1H-pyrrole-3-carboxylic acid (2-ethyl-hexyl)-amide

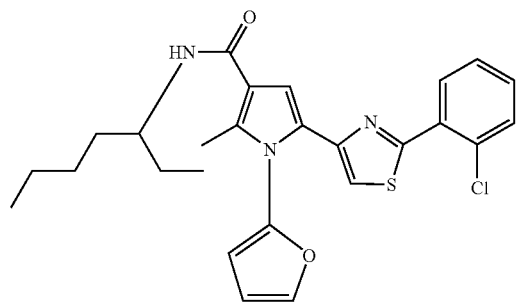

The title compound was obtained using 2-ethyl-hexylamine as $R^1R^2NH$, 3-furylmethylamine as $R^3$—$(CH_2)_m$—$NH_2$ and 2-chloro-phenyl thioamide as $R^4C(S)NH_2$, MS(ES+) 510 (M+H)+.

Example 251 rac-1-Furan-2-ylmethyl-5-[2-(4-methoxy-phenyl)-thiazol-4-yl]-2-methyl-1H-pyrrole-3-carboxylic acid (2-ethyl-hexyl)-amide

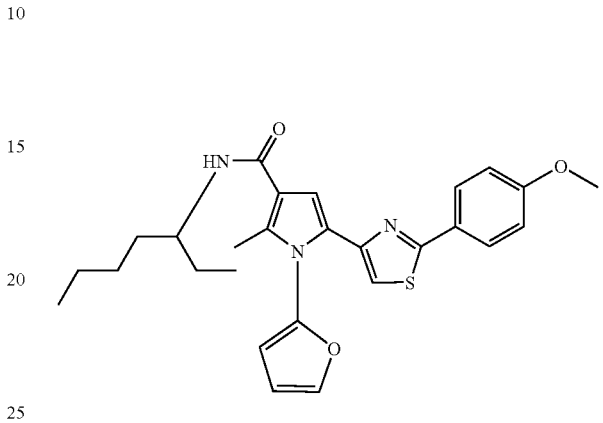

The title compound was obtained using 2-ethyl-hexylamine as $R^1R^2NH$, 3-furylmethylamine as $R^3$—$(CH_2)_m$—$NH_2$ and 4-methoxyphenyl thioamide as $R^4C(S)NH_2$, MS(ES+) 506 (M+H)+.

Example 252 rac-5-[2-(2-Ethyl-pyridin-4-yl)-thiazol-4-yl]-1-furan-2-ylmethyl-2-methyl-1H-pyrrole-3-carboxylic acid (2-ethyl-hexyl)-amide

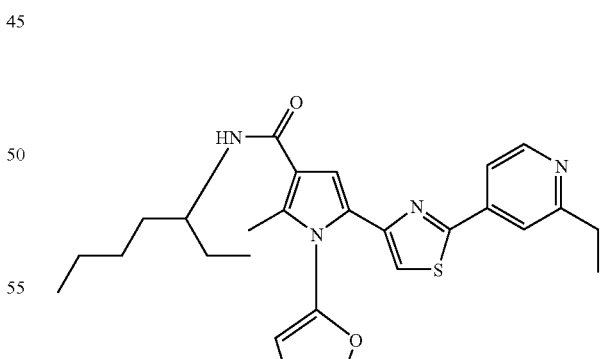

The title compound was obtained using 2-ethyl-hexylamine as $R^1R^2NH$, 3-furylmethylamine as $R^3$—$(CH_2)_m$—$NH_2$ and 2-ethyl-4-pyridine carbothiamide as $R^4C(S)NH_2$, MS(ES+) 505 (M+H)+.

Example 253 rac-1-(4-Methoxy-benzyl)-2-methyl-5-(2-methyl-thiazol-4-yl)-1H-pyrrole-3-carboxylic acid (2-ethyl-hexyl)-amide

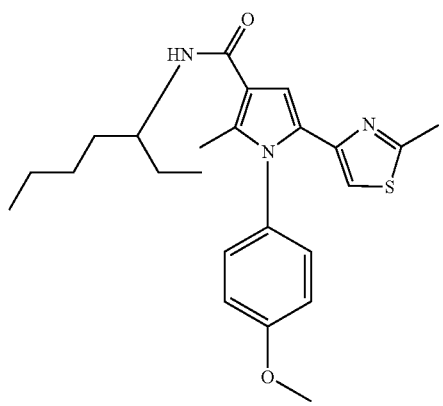

The title compound was obtained using 2-ethyl-hexylamine as $R^1R^2NH$, 4-methoxybenzylamine as $R^3$—$(CH_2)_m$—$NH_2$ and thioacetamide as $R^4C(S)NH_2$, MS(ES+) 454 (M+H)$^+$.

Example 254 rac-5-[2-(2-Chloro-phenyl)-thiazol-4-yl]-1-(4-methoxy-benzyl)-2-methyl-1H-pyrrole-3-carboxylic acid (2-ethyl-hexyl)-amide

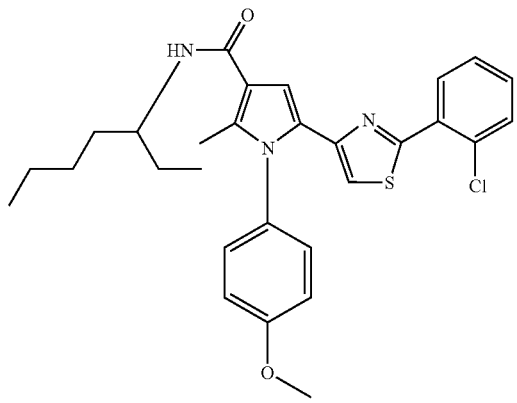

The title compound was obtained using 2-ethyl-hexylamine as $R^1R^2NH$, 4-methoxybenzylamine as $R^3$—$(CH_2)_m$—$NH_2$ and 2-chloro-phenyl thioamide as $R^4C(S)NH_2$, MS(ES+) 550 (M+H)$^+$.

Example 255 rac-1-(4-Methoxy-benzyl)-5-[2-(4-methoxy-phenyl)-thiazol-4-yl]-2-methyl-1H-pyrrole-3-carboxylic acid (2-ethyl-hexyl)-amide

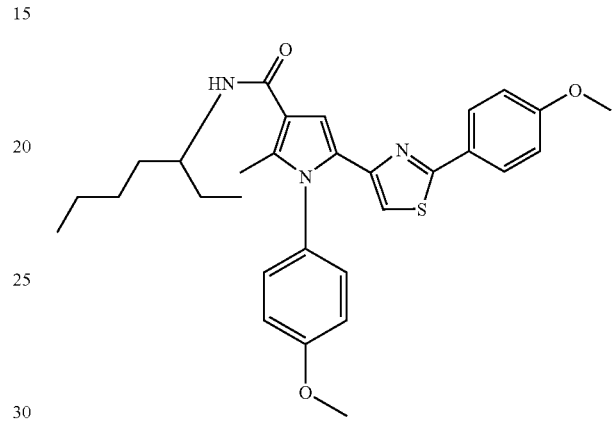

The title compound was obtained using 2-ethyl-hexylamine as $R^1R^2NH$, 4-methoxybenzylamine as $R^3$—$(CH_2)_m$—$NH_2$ and 4-methoxyphenyl thioamide as $R^4C(S)NH_2$, MS(ES+) 546 (M+H)$^+$.

Example 256 rac-1-(4-Methoxy-benzyl)-5-[2-(4-methoxy-phenoxymethyl)-thiazol-4-yl]-2-methyl-1H-pyrrole-3-carboxylic acid (2-ethyl-hexyl)-amide

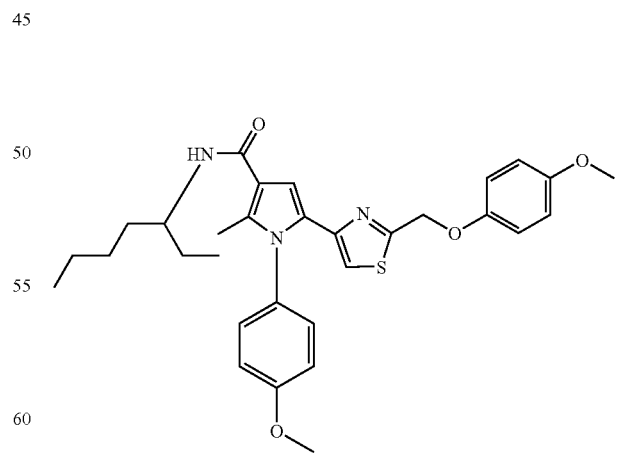

The title compound was obtained using 2-ethyl-hexylamine as $R^1R^2NH$, 4-methoxybenzylamine as $R^3$—$(CH_2)_m$—$NH_2$ and 2-(4-methoxyphenoxy)ethanethioamide as $R^4C(S)NH_2$, MS(ES+) 576 (M+H)$^+$.

Example 257 rac-5-[2-(2-Ethyl-pyridin-4-yl)-thiazol-4-yl]-1-(4-methoxy-benzyl)-2-methyl-1H-pyrrole-3-carboxylic acid (2-ethyl-hexyl)-amide

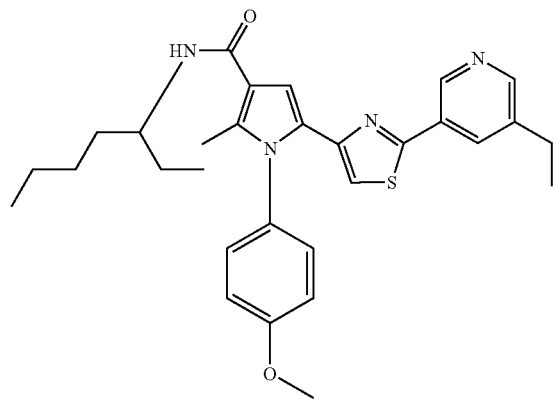

The title compound was obtained using 2-ethyl-hexylamine as R¹R²NH, 4-methoxybenzylamine as R³—(CH₂)ₘ—NH₂ and 2-ethyl-4-pyridine carbothiamide as R⁴C(S)NH₂, MS(ES+) 545 (M+H)⁺.

Example 258 rac-1-(4-Methoxy-benzyl)-2-methyl-5-[2-(6-methyl-pyridin-3-yl)-thiazol-4-yl]-1H-pyrrole-3-carboxylic acid (2-ethyl-hexyl)-amide

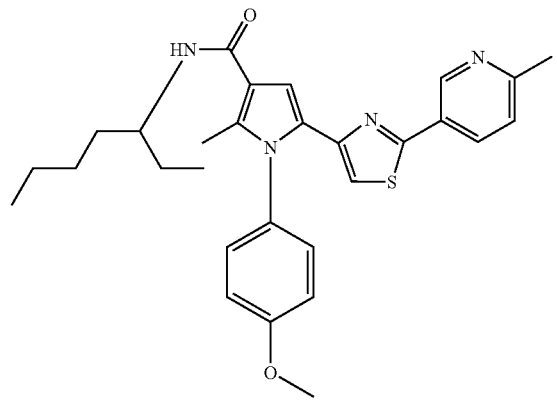

The title compound was obtained using 2-ethyl-hexylamine as R¹R²NH, 4-methoxybenzylamine as R³—(CH₂)ₘ—NH₂ and 6-methyl-pyridine-3-carbothioamide as R⁴C(S)NH₂, MS(ES+) 531 (M+H)⁺.

Example 259 rac-1-(4-Methoxy-benzyl)-2-methyl-5-(2-pyrazin-2-yl-thiazol-4-yl)-1H-pyrrole-3-carboxylic acid (2-ethyl-hexyl)-amide

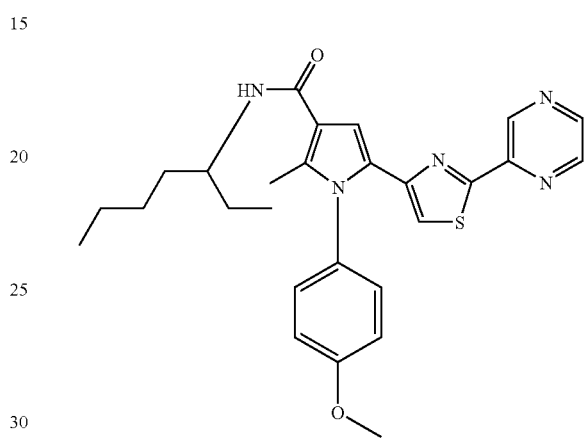

The title compound was obtained using 2-ethyl-hexylamine as R¹R²NH, 4-methoxybenzylamine as R³—(CH₂)ₘ—NH₂ and pyrazine-2-carbothioamide as R⁴C(S)NH₂, MS(ES+) 518 (M+H)⁺.

Example 260 rac-1-(3-Methoxy-propyl)-2-methyl-5-(2-methyl-thiazol-4-yl)-1H-pyrrole-3-carboxylic acid (2-ethyl-hexyl)-amide

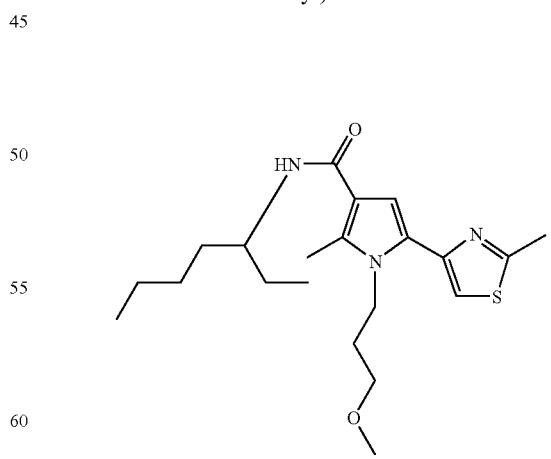

The title compound was obtained using 2-ethyl-hexylamine as R¹R²NH, methoxyethylamine as R³—(CH₂)ₘ—NH₂ and thioacetamide as R⁴C(S)NH₂, MS(ES+) 406 (M+H)⁺.

Example 261 rac-5-[2-(4-Methoxy-phenyl)-thiazol-4-yl]-1-(3-methoxy-propyl)-2-methyl-1H-pyrrole-3-carboxylic acid (2-ethyl-hexyl)-amide

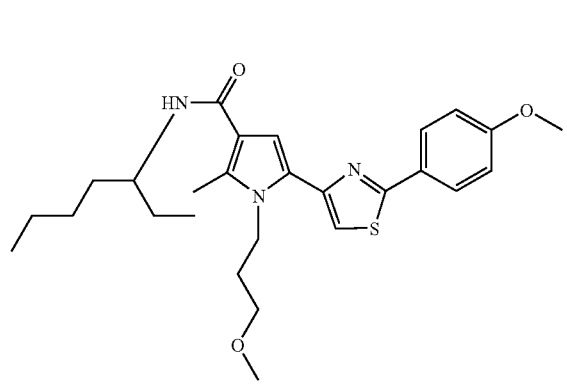

The title compound was obtained using 2-ethyl-hexylamine as $R^1R^2NH$, methoxyethylamine as $R_3—(CH_2)_m—NH_2$ and 4-methoxyphenyl thioamide as $R^4C(S)NH_2$, MS(ES+) 498 (M+H)+.

Example 262 rac-5-[2-(4-Methoxy-phenoxymethyl)-thiazol-4-yl]-1-(3-methoxy-propyl)-2-methyl-1H-pyrrole-3-carboxylic acid (2-ethyl-hexyl)-amide

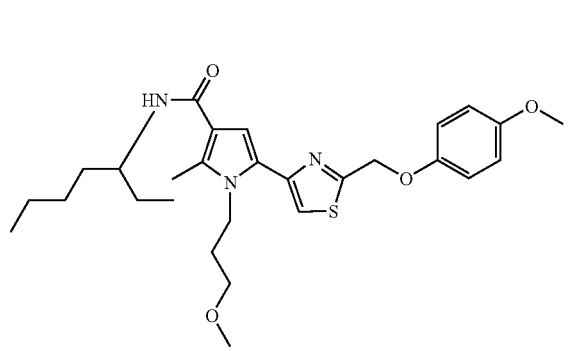

The title compound was obtained using 2-ethyl-hexylamine as $R^1R^2NH$, methoxyethylamine as $R_3—(CH_2)_m—NH_2$ and 2-(4-methoxyphenoxy)ethanethioamide as $R^4C(S)NH_2$, MS(ES+) 528 (M+H)+.

Example 263 rac-4-[4-(2-Ethyl-hexylcarbamoyl)-1-(3-methoxy-propyl)-5-methyl-1H-pyrrol-2-yl]-thiazole-2-carboxylic acid ethyl ester

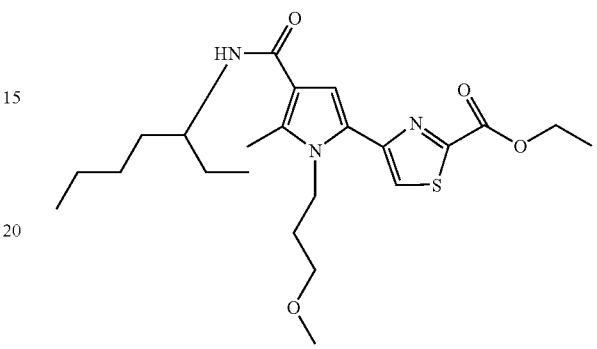

The title compound was obtained using 2-ethyl-hexylamine as $R^1R^2NH$, methoxyethyl-amine as $R_3—(CH_2)_m—NH_2$ and ethylthiooxamate as $R^4C(S)NH_2$, MS (ES+) 564 (M+H)+.

Example 264 rac-1-(3-Methoxy-propyl)-2-methyl-5-(2-pyrazin-2-yl-thiazol-4-yl)-1H-pyrrole-3-carboxylic acid (2-ethyl-hexyl)-amide

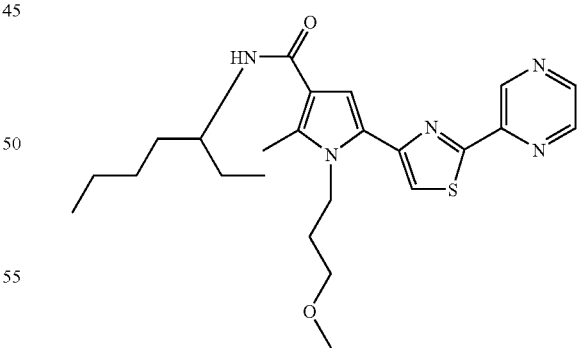

The title compound was obtained using 2-ethyl-hexylamine as $R^1R^2NH$, methoxyethylamine as $R_3—(CH_2)_m—NH_2$ and pyrazine-2-carbothioamide as $R^4C(S)NH_2$, MS(ES+) 470 (M+H)+.

Example 265 rac-5-[2-(2-Chloro-phenyl)-thiazol-4-yl]-2-methyl-1-thiophen-2-ylmethyl-1H-pyrrole-3-carboxylic acid (2-ethyl-hexyl)-amide

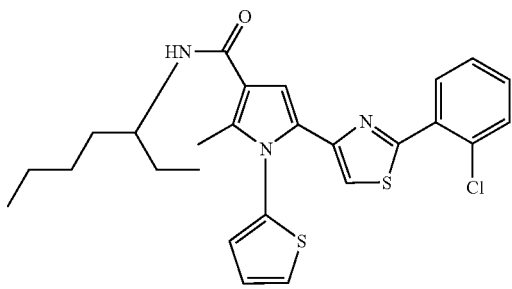

The title compound was obtained using 2-ethyl-hexylamine as $R^1R^2NH$, 3-(aminomethyl)thiophene as $R_3$—$(CH_2)_m$—$NH_2$ and 2-chloro-phenyl thioamide as $R^4C(S)NH_2$, MS(ES+) 526 (M+H)$^+$.

Example 266 rac-5-[2-(4-Methoxy-phenyl)-thiazol-4-yl]-2-methyl-1-thiophen-2-ylmethyl-1H-pyrrole-3-carboxylic acid (2-ethyl-hexyl)-amide

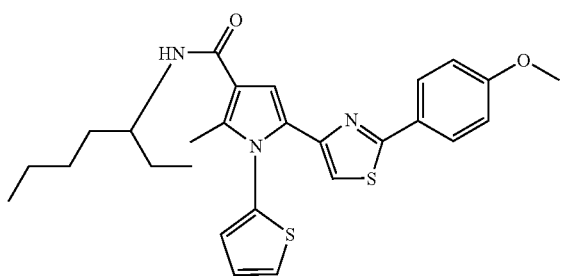

The title compound was obtained using 2-ethyl-hexylamine as $R^1R^2NH$, 3-(aminomethyl)thiophene as $R_3$—$(CH_2)_m$—$NH_2$ and 4-methoxyphenyl thioamide as $R^4C(S)NH_2$, MS(ES+) 522 (M+H)$^+$.

Example 267 rac-5-[2-(4-Methoxy-phenoxymethyl)-thiazol-4-yl]-2-methyl-1-thiophen-2-ylmethyl-1H-pyrrole-3-carboxylic acid (2-ethyl-hexyl)-amide

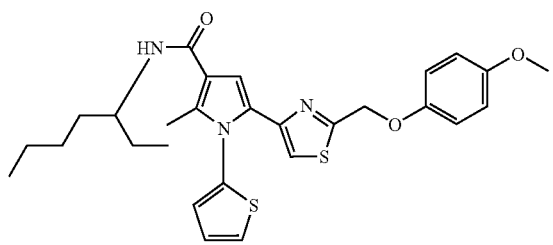

The title compound was obtained using 2-ethyl-hexylamine as $R^1R^2NH$, 3-(aminomethyl)thiophene as $R_3$—$(CH_2)_m$—$NH_2$ and 2-(4-methoxyphenoxy)ethanethioamide as $R^4C(S)NH_2$, MS(ES+) 552 (M+H)$^+$.

Example 268 rac-5-[2-(2-Ethyl-pyridin-4-yl)-thiazol-4-yl]-2-methyl-1-thiophen-2-ylmethyl-1H-pyrrole-3-carboxylic acid (2-ethyl-hexyl)-amide

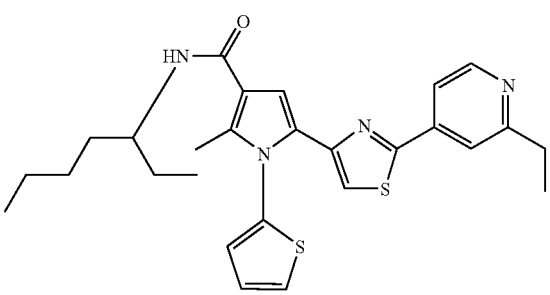

The title compound was obtained using 2-ethyl-hexylamine as $R^1R^2NH$, 3-(aminomethyl)thiophene as $R_3$—$(CH_2)_m$—$NH_2$ and 2-ethyl-4-pyridine carbothiamide as $R^4C(S)NH_2$, MS(ES+) 521 (M+H)$^+$.

Example 269 rac-1-[2-(3,4-Dimethoxy-phenyl)-ethyl]-2-methyl-5-(2-methyl-thiazol-4-yl)-1H-pyrrole-3-carboxylic acid (2-ethyl-hexyl)-amide

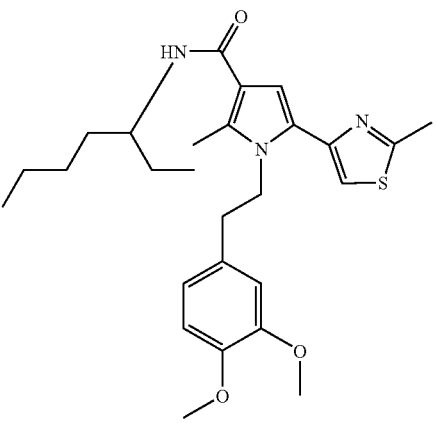

The title compound was obtained using 2-ethyl-hexylamine as $R^1R^2NH$, homoveratrylamine as $R_3$—$(CH_2)_m$—$NH_2$ and thioacetamide as $R^4C(S)NH_2$, MS(ES+) 498 (M+H)$^+$.

Example 270 rac-1-[2-(3,4-Dimethoxy-phenyl)-ethyl]-5-[2-(4-methoxy-phenoxymethyl)-thiazol-4-yl]-2-methyl-1H-pyrrole-3-carboxylic acid (2-ethyl-hexyl)-amide

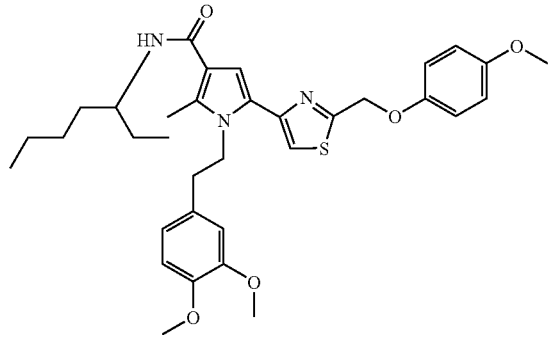

The title compound was obtained using 2-ethyl-hexylamine as $R^1R^2NH$, homoveratrylamine as $R^3$—$(CH_2)_m$—$NH_2$ and 2-(4-methoxyphenoxy)ethanethioamide as $R^4C(S)NH_2$, MS(ES+) 620 (M+H)$^+$.

Example 271

Butyl-5-[2-(4-methoxy-phenyl)-thiazol-4-yl]-2-methyl-1H-pyrrole-3-carboxylic acid (3-methoxy-propyl)-amide

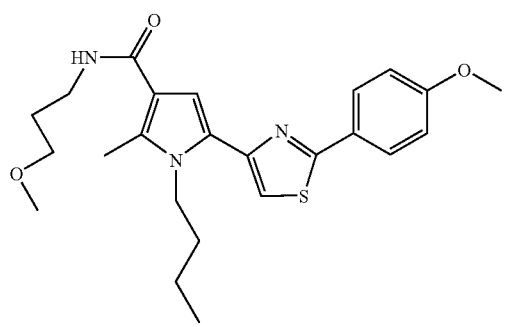

The title compound was obtained using methoxypropylamine as $R^1R^2NH$, butylamine as $R^3$—$(CH_2)_m$—$NH_2$ and 4-methoxyphenyl thioamide as $R^4C(S)NH_2$, MS(ES+) 442 (M+H)$^+$.

Example 272

Butyl-2-methyl-5-(2-pyrazin-2-yl-thiazol-4-yl)-1H-pyrrole-3-carboxylic acid (3-methoxy-propyl)-amide

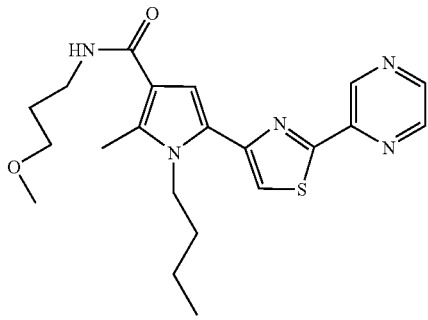

The title compound was obtained using methoxypropylamine as $R^1R^2NH$, butylamine as $R^3$—$(CH_2)_m$—$NH_2$ and pyrazine-2-carbothioamide as $R^4C(S)NH_2$, MS(ES+) 414 (M+H)$^+$.

Example 273

Isobutyl-2-methyl-5-(2-pyrazin-2-yl-thiazol-4-yl)-1H-pyrrole-3-carboxylic acid (3-methoxy-propyl)-amide

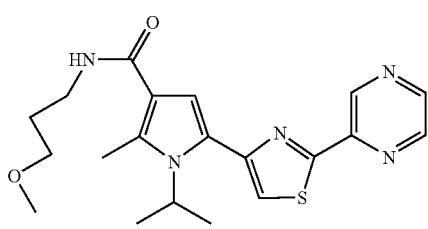

The title compound was obtained using methoxypropylamine as $R^1R^2NH$, isobutylamine as $R^3$—$(CH_2)_m$—$NH_2$ and pyrazine-2-carbothioamide as $R^4C(S)NH_2$, MS(ES+) 414 (M+H)$^+$.

Example 274

5-[2-(2-Chloro-phenyl)-thiazol-4-yl]-1-cyclohexylmethyl-2-methyl-1H-pyrrole-3-carboxylic acid (3-methoxy-propyl)-amide

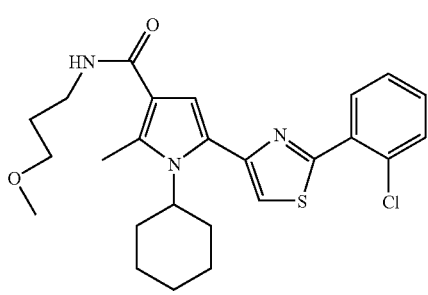

The title compound was obtained using methoxypropylamine as $R^1R^2NH$, aminomethylcyclohexane as $R^3$—$(CH_2)_m$—$NH_2$ and 2-chloro-phenyl thioamide as $R^4C(S)NH_2$, MS(ES+) 486 (M+H)$^+$.

Example 275

Cyclohexylmethyl-5-[2-(4-methoxy-phenyl)-thiazol-4-yl]-2-methyl-1H-pyrrole-3-carboxylic acid (3-methoxy-propyl)-amide

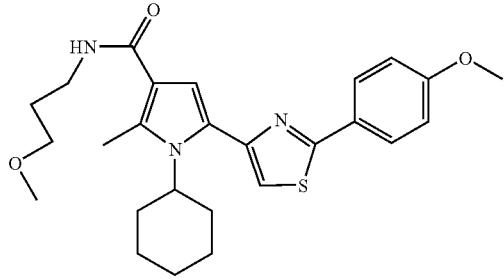

The title compound was obtained using methoxypropylamine as $R^1R^2NH$, aminomethylcyclohexane as $R^3$—$(CH_2)_m$—$NH_2$ and 4-methoxyphenyl thioamide as $R^4C(S)NH_2$, MS(ES+) 482 (M+H)+.

Example 276

Cyclohexylmethyl-5-[2-(4-methoxy-phenoxymethyl)-thiazol-4-yl]-2-methyl-1H-pyrrole-3-carboxylic acid (3-methoxy-propyl)-amide

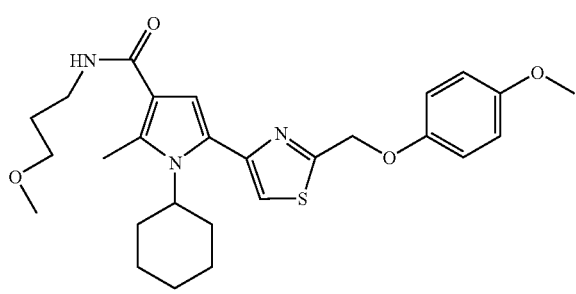

The title compound was obtained using methoxypropylamine as $R^1R^2NH$, aminomethylcyclohexane as $R^3$—$(CH_2)_m$—$NH_2$ and 2-(4-methoxyphenoxy)ethanethioamide as $R^4C(S)NH_2$, MS(ES+) 512 (M+H)+.

Example 277

Cyclohexylmethyl-5-[2-(2-ethyl-pyridin-4-yl)-thiazol-4-yl]-2-methyl-1H-pyrrole-3-carboxylic acid (3-methoxy-propyl)-amide

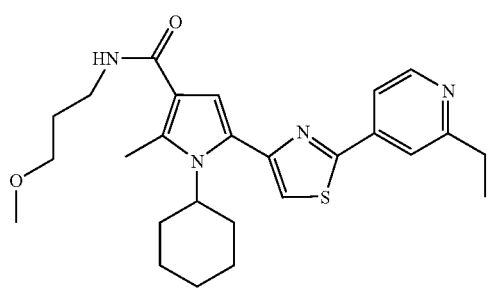

The title compound was obtained using methoxypropylamine as $R^1R^2NH$, aminomethylcyclohexane as $R^3$—$(CH_2)_m$—$NH_2$ and 2-ethyl-4-pyridine carbothiamide as $R^4C(S)NH_2$, MS(ES+) 481 (M+H)+.

Example 278

Cyclohexylmethyl-2-methyl-5-(2-pyrazin-2-yl-thiazol-4-yl)-1H-pyrrole-3-carboxylic acid (3-methoxy-propyl)-amide

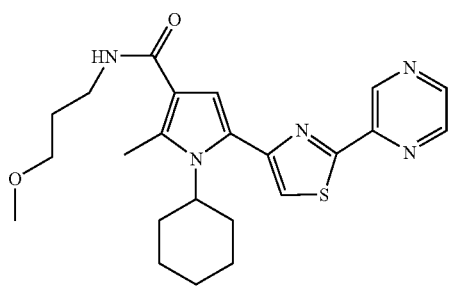

The title compound was obtained using methoxypropylamine as $R^1R^2NH$, aminomethylcyclohexane as $R^3$—$(CH_2)_m$—$NH_2$ and pyrazine-2-carbothioamide as $R^4C(S)NH_2$, MS(ES+) 454 (M+H)+.

Example 279

5-[2-(4-Methoxy-phenyl)-thiazol-4-yl]-2-methyl-1-(tetrahydro-furan-2-ylmethyl)-1H-pyrrole-3-carboxylic acid (3-methoxy-propyl)-amide

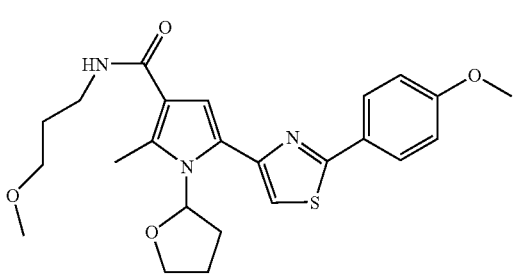

The title compound was obtained using methoxypropylamine as $R^1R^2NH$, tetrahydrofurfurylamine as $R^3$—$(CH_2)_m$—$NH_2$ and 4-methoxyphenyl thioamide as $R^4C(S)NH_2$, MS(ES+) 470 (M+H)+.

Example 280

5-[2-(4-Methoxy-phenoxymethyl)-thiazol-4-yl]-2-methyl-1-(tetrahydro-furan-2-ylmethyl)-1H-pyrrole-3-carboxylic acid (3-methoxy-propyl)-amide

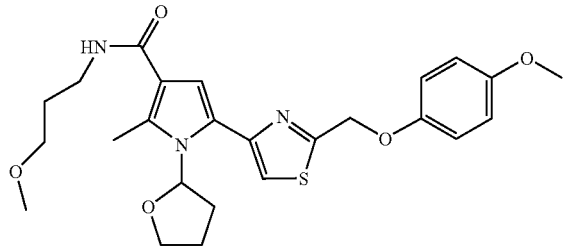

The title compound was obtained using methoxypropylamine as $R^1R^2NH$, tetrahydrofurfurylamine as $R^3$—$(CH_2)_m$—$NH_2$ and 2-(4-methoxyphenoxy)ethanethioamide as $R^4C(S)NH_2$, MS(ES+) 500 (M+H)$^+$.

Example 281

1-(2-Cyclohex-1-enyl-ethyl)-5-[2-(2-ethyl-pyridin-4-yl)-thiazol-4-yl]-2-methyl-1H-pyrrole-3-carboxylic acid (3-methoxy-propyl)-amide

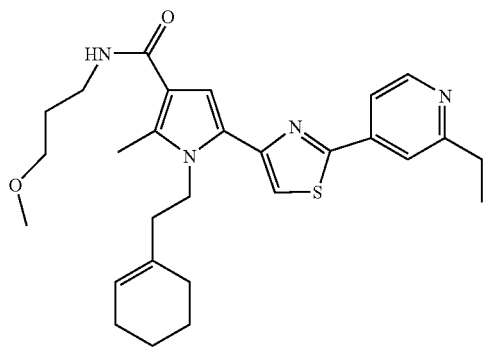

The title compound was obtained using methoxypropylamine as $R^1R^2NH$, 2-(1-cyclohexenyl)ethylamine as $R^3$—$(CH_2)_m$—$NH_2$ and 2-ethyl-4-pyridine carbothiamide as $R^4C(S)NH_2$, MS(ES+) 493 (M+H)$^+$.

Example 282

5-[2-(2-Chloro-phenyl)-thiazol-4-yl]-1-furan-2-ylmethyl-2-methyl-1H-pyrrole-3-carboxylic acid (3-methoxy-propyl)-amide

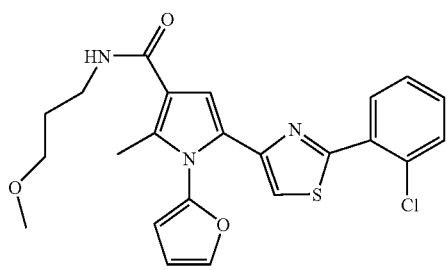

The title compound was obtained using methoxypropylamine as $R^1R^2NH$, 3-furylmethylamine as $R^3$—$(CH_2)_m$—$NH_2$ and 2-chloro-phenyl thioamide as $R^4C(S)NH_2$, MS(ES+) 470 (M+H)$^+$.

Example 283

Furan-2-ylmethyl-5-[2-(4-methoxy-phenyl)-thiazol-4-yl]-2-methyl-1H-pyrrole-3-carboxylic acid (3-methoxy-propyl)-amide

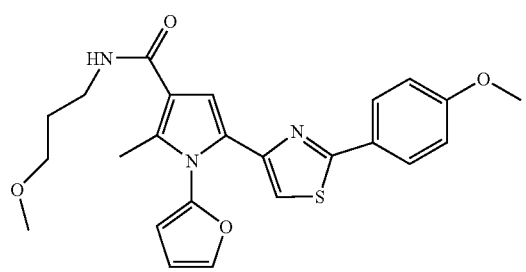

The title compound was obtained using methoxypropylamine as $R^1R^2NH$, 3-furylmethylamine as $R^3$—$(CH_2)_m$—$NH_2$ and 4-methoxyphenyl thioamide as $R^4C(S)NH_2$, MS(ES+) 466 (M+H)$^+$.

Example 284

Furan-2-ylmethyl-5-[2-(4-methoxy-phenoxymethyl)-thiazol-4-yl]-2-methyl-1H-pyrrole-3-carboxylic acid (3-methoxy-propyl)-amide

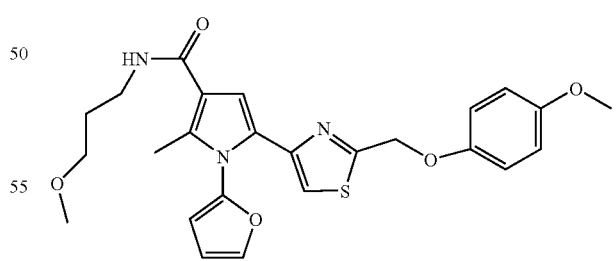

The title compound was obtained using methoxypropylamine as $R^1R^2NH$, 3-furylmethylamine as $R^3$—$(CH_2)_m$—$NH_2$ and 2-(4-methoxyphenoxy)ethanethioamide as $R^4C(S)NH_2$, MS(ES+) 496 (M+H)$^+$.

Example 285

1-(4-Methoxy-benzyl)-2-methyl-5-(2-methyl-thiazol-4-yl)-1H-pyrrole-3-carboxylic acid (3-methoxy-propyl)-amide

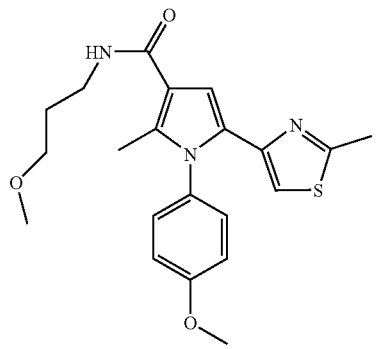

The title compound was obtained using methoxypropylamine as $R^1R^2NH$, 4-methoxybenzylamine as $R^3$—$(CH_2)_m$—$NH_2$ and thioacetamide as $R^4C(S)NH_2$, MS(ES+) 414 (M+H)$^+$.

Example 286

5-[2-(2-Chloro-phenyl)-thiazol-4-yl]-1-(4-methoxy-benzyl)-2-methyl-1H-pyrrole-3-carboxylic acid (3-methoxy-propyl)-amide

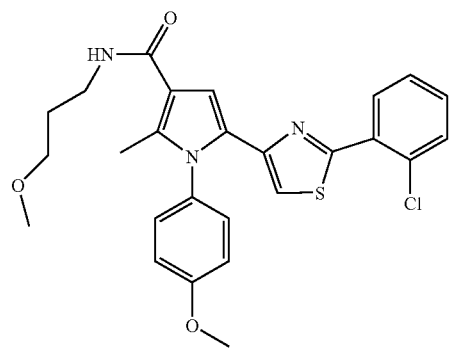

The title compound was obtained using methoxypropylamine as $R^1R^2NH$, 4-methoxybenzylamine as $R^3$—$(CH_2)_m$—$NH_2$ and 2-chloro-phenyl thioamide as $R^4C(S)NH_2$, MS(ES+) 510 (M+H)$^+$.

Example 287

1-(4-Methoxy-benzyl)-5-[2-(4-methoxy-phenyl)-thiazol-4-yl]-2-methyl-1H-pyrrole-3-carboxylic acid (3-methoxy-propyl)-amide

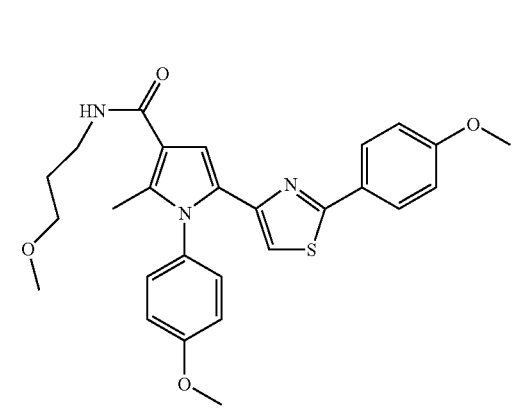

The title compound was obtained using methoxypropylamine as $R^1R^2NH$, 4-methoxybenzylamine as $R^3$—$(CH_2)_m$—$NH_2$ and 4-methoxyphenyl thioamide as $R^4C(S)NH_2$. 506

Example 288

1-(4-Methoxy-benzyl)-5-[2-(4-methoxy-phenoxymethyl)-thiazol-4-yl]-2-methyl-1H-pyrrole-3-carboxylic acid (3-methoxy-propyl)-amide

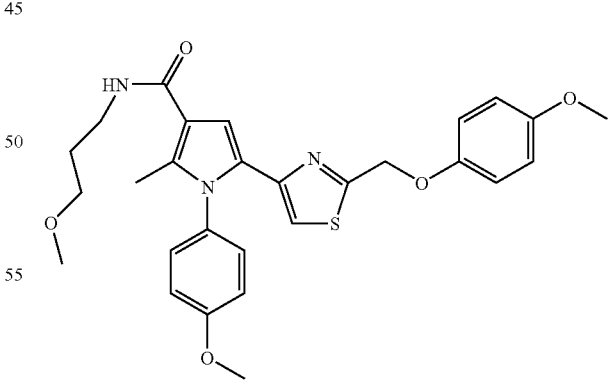

The title compound was obtained using methoxypropylamine as $R^1R^2NH$, 4-methoxybenzylamine as $R^3$—$(CH_2)_m$—$NH_2$ and 2-(4-methoxyphenoxy)ethanethioamide as $R^4C(S)NH_2$, MS(ES+) 536 (M+H)$^+$.

Example 289

5-[2-(2-Ethyl-pyridin-4-yl)-thiazol-4-yl]-1-(4-methoxy-benzyl)-2-methyl-1H-pyrrole-3-carboxylic acid (3-methoxy-propyl)-amide

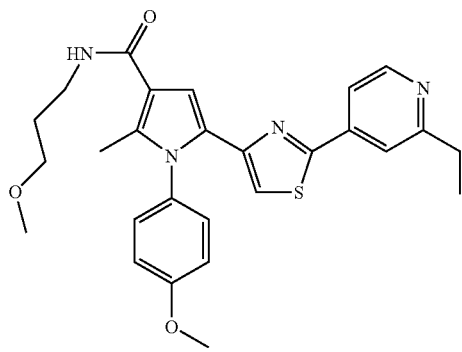

The title compound was obtained using methoxypropylamine as $R^1R^2NH$, 4-methoxybenzylamine as $R^3—(CH_2)_m—NH_2$ and 2-ethyl-4-pyridine carbothiamide as $R^4C(S)NH_2$, MS(ES+) 289 (M+H)+.

Example 290

4-[1-(4-Methoxy-benzyl)-4-(3-methoxy-propylcarbamoyl)-5-methyl-1H-pyrrol-2-yl]-thiazole-2-carboxylic acid ethyl ester

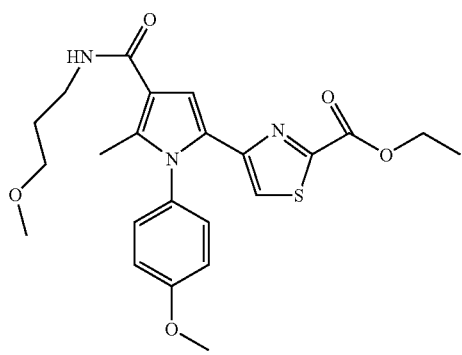

The title compound was obtained using methoxypropylamine as $R^1R^2NH$, 4-methoxybenzylamine as $R^3—(CH_2)_m—NH_2$ and ethylthiooxamate as $R^4C(S)NH_2$, MS(ES+) 472 (M+H)+.

Example 291

1-(4-Methoxy-benzyl)-2-methyl-5-[2-(6-methyl-pyridin-3-yl)-thiazol-4-yl]-1H-pyrrole-3-carboxylic acid (3-methoxy-propyl)-amide

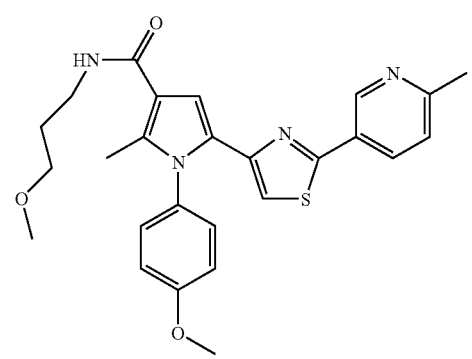

The title compound was obtained using methoxypropylamine as $R^1R^2NH$, 4-methoxybenzylamine as $R^3—(CH_2)_m—NH_2$ and 6-methyl-pyridine-3-carbothioamide as $R^4C(S)NH_2$, MS(ES+) 491 (M+H)+.

Example 292

1-(4-Methoxy-benzyl)-2-methyl-5-(2-pyrazin-2-yl-thiazol-4-yl)-1H-pyrrole-3-carboxylic acid (3-methoxy-propyl)-amide

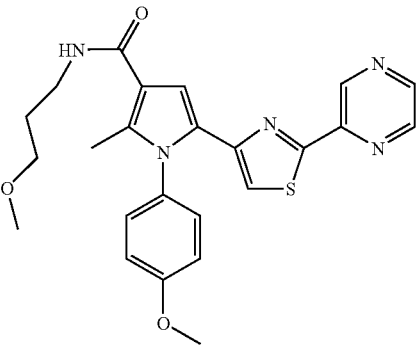

The title compound was obtained using methoxypropylamine as $R^1R^2NH$, 4-methoxybenzylamine as $R^3—(CH_2)_m—NH_2$ and pyrazine-2-carbothioamide as $R^4C(S)NH_2$, MS(ES+) 478 (M+H)+.

Example 293

5-[2-(2-Chloro-phenyl)-thiazol-4-yl]-2-methyl-1-thiophen-2-ylmethyl-1H-pyrrole-3-carboxylic acid (3-methoxy-propyl)-amide

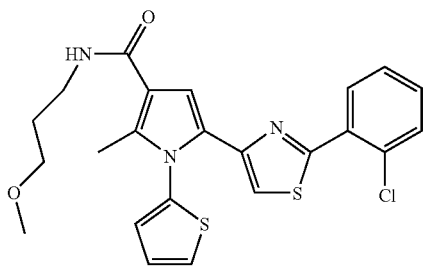

The title compound was obtained using methoxypropylamine as R¹R²NH, 3-(aminomethyl)thiophene as R₃—(CH₂)ₘ—NH₂ and 2-chloro-phenyl thioamide as R⁴C(S)NH₂, MS(ES+) 486 (M+H)⁺.

Example 294

5-[2-(4-Methoxy-phenyl)-thiazol-4-yl]-2-methyl-1-thiophen-2-ylmethyl-1H-pyrrole-3-carboxylic acid (3-methoxy-propyl)-amide

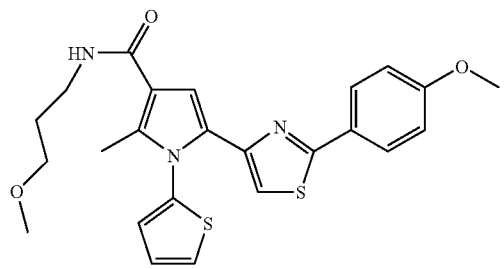

The title compound was obtained using methoxypropylamine as R¹R²NH, 3-(aminomethyl)thiophene as R₃—(CH₂)ₘ—NH₂ and 4-methoxyphenyl thioamide as R⁴C(S)NH₂, MS(ES+) 482 (M+H)⁺.

Example 295

5-[2-(2-Ethyl-pyridin-4-yl)-thiazol-4-yl]-2-methyl-1-thiophen-2-ylmethyl-1H-pyrrole-3-carboxylic acid (3-methoxy-propyl)-amide

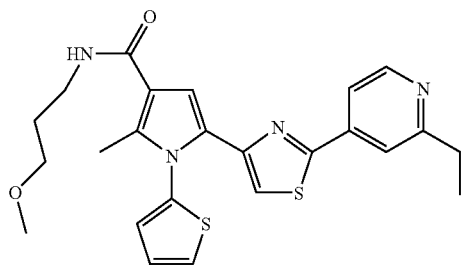

The title compound was obtained using methoxypropylamine as R¹R²NH, 3-(aminomethyl)thiophene as R₃—(CH₂)ₘ—NH₂ and 2-ethyl-4-pyridine carbothiamide as R⁴C(S)NH₂, MS(ES+) 481 (M+H)⁺.

Example 296

1-[2-(3,4-Dimethoxy-phenyl)-ethyl]-5-[2-(4-methoxy-phenoxymethyl)-thiazol-4-yl]-2-methyl-1H-pyrrole-3-carboxylic acid (3-methoxy-propyl)-amide

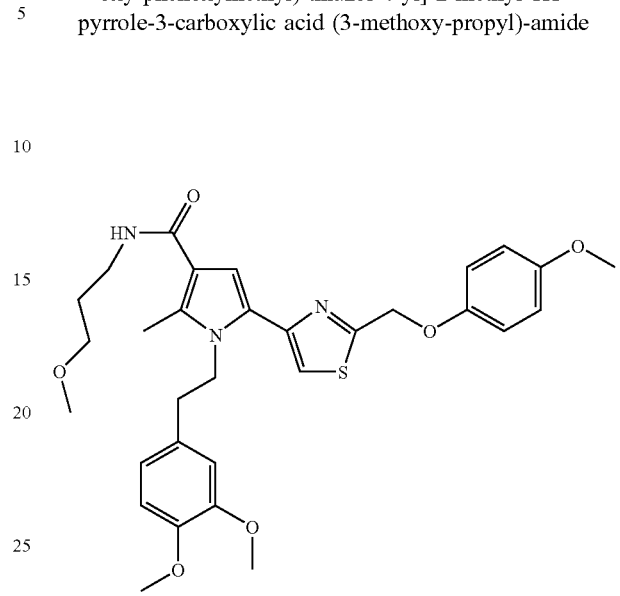

The title compound was obtained using methoxypropylamine as R¹R²NH, homoveratrylamine as R₃—(CH₂)ₘ—NH₂ and 2-(4-methoxyphenoxy)ethanethioamide as R⁴C(S)NH₂, MS(ES+) 580 (M+H)⁺.

Example 297

4-[1-[2-(3,4-Dimethoxy-phenyl)-ethyl]-4-(3-methoxy-propylcarbamoyl)-5-methyl-1H-pyrrol-2-yl]-thiazole-2-carboxylic acid ethyl ester

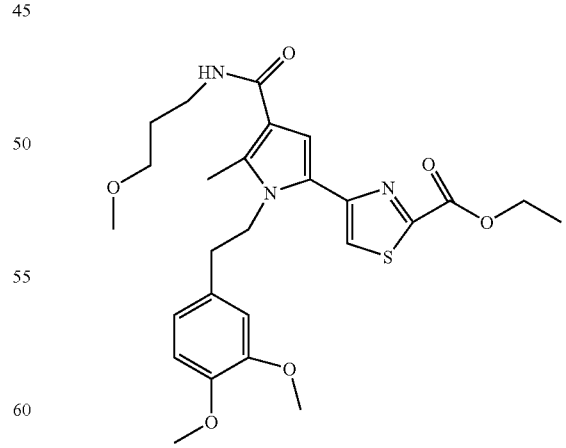

The title compound was obtained using methoxypropylamine as R¹R²NH, homoveratrylamine as R₃—(CH₂)ₘ—NH₂ and ethylthiooxamate as R⁴C(S)NH₂, MS(ES+) 516 (M+H)⁺.

Example 298

Cyclohexylmethyl-5-[2-(4-methoxy-phenyl)-thiazol-4-yl]-2-methyl-1H-pyrrole-3-carboxylic acid morpholin-4-ylamide

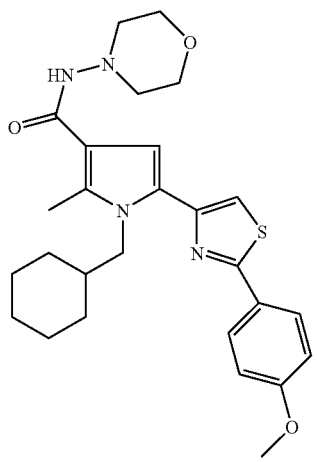

The title compound was obtained using 1-amino-morpholine as $R^1R^2NH$, aminomethylcyclohexane as $R^3$—$(CH_2)_m$—$NH_2$ and 4-methoxyphenyl thioamide as $R^4C(S)NH_2$, MS(ISP) 495.3 (M+H)$^+$.

Example 299

Cyclohexylmethyl-5-[2-(4-methoxy-phenyl)-thiazol-4-yl]-2-methyl-1H-pyrrole-3-carboxylic acid piperidin-1-ylamide

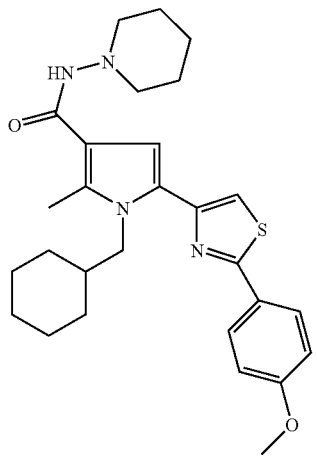

The title compound was obtained using 1-amino-piperidine as $R^1R^2NH$, aminomethylcyclohexane as $R^3$—$(CH_2)_m$—$NH_2$ and 4-methoxyphenyl thioamide as $R^4C(S)NH_2$, MS(ISP) 493.4 (M+H)$^+$.

Example 300

1-(4-Chloro-phenyl)-5-[2-(4-methoxy-phenyl)-thiazol-4-yl]-2-methyl-1H-pyrrole-3-carboxylic acid butylamide

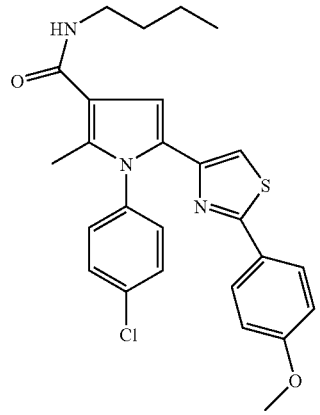

The title compound was obtained using butylamine as $R^1R^2NH$, 4-chloroaniline as $R^3$—$(CH_2)_m$—$NH_2$ and 4-methoxyphenyl thioamide as $R^4C(S)NH_2$, MS(ISP) 480.3 (M+H)$^+$.

Example 301

Cyclohexylmethyl-5-[2-(4-methoxy-phenyl)-thiazol-4-yl]-2-methyl-1H-pyrrole-3-carboxylic acid (3,4-dimethoxy-phenyl)-amide

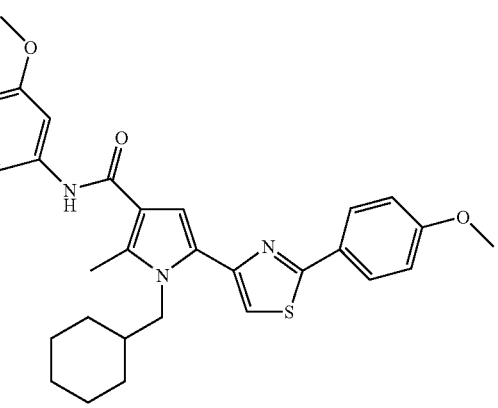

The title compound was obtained using 3,4-dimethoxy aniline as $R^1R^2NH$, aminomethylcyclohexane as $R^3$—$(CH_2)_m$—$NH_2$ and 4-methoxyphenyl thioamide as $R^4C(S)NH_2$, MS(ISP) 546.3 (M+H)$^+$.

Example 302

Cyclohexylmethyl-5-[2-(4-methoxy-phenyl)-thiazol-4-yl]-2-methyl-1H-pyrrole-3-carboxylic acid (2-nitro-phenyl)-amide

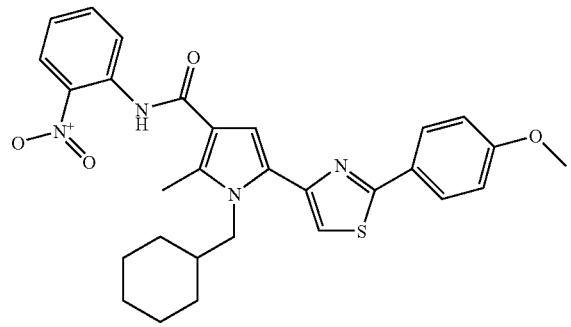

The title compound was obtained using 2-nitroaniline as $R^1R^2NH$, aminomethylcyclohexane as $R^3$—$(CH_2)_m$—$NH_2$ and 4-methoxyphenyl thioamide as $R^4C(S)NH_2$, MS(ISP) 531.3 (M+H)$^+$.

Example 303

Cyclohexylmethyl-5-[2-(4-methoxy-phenyl)-thiazol-4-yl]-2-methyl-1H-pyrrole-3-carboxylic acid (4-trifluoromethyl-phenyl)-amide

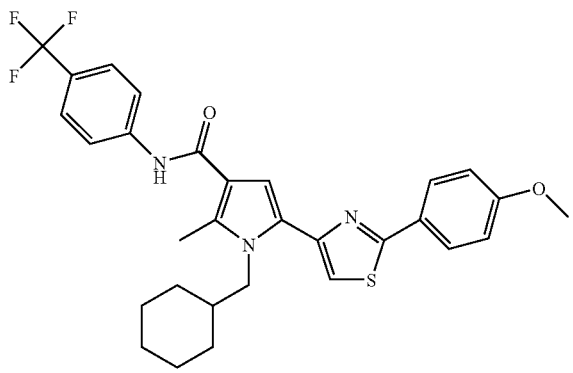

The title compound was obtained using 4-trifluoromethylaniline as $R^1R^2NH$, aminomethylcyclohexane as $R^3$—$(CH_2)_m$—$NH_2$ and 4-methoxyphenyl thioamide as $R^4C(S)NH_2$, MS(ISP) 554.3 (M+H)$^+$.

Example 304

N'-{1-Cyclohexylmethyl-5-[2-(4-methoxy-phenyl)-thiazol-4-yl]-2-methyl-1H-pyrrole-3-carbonyl}-hydrazinecarboxylic acid ethyl ester

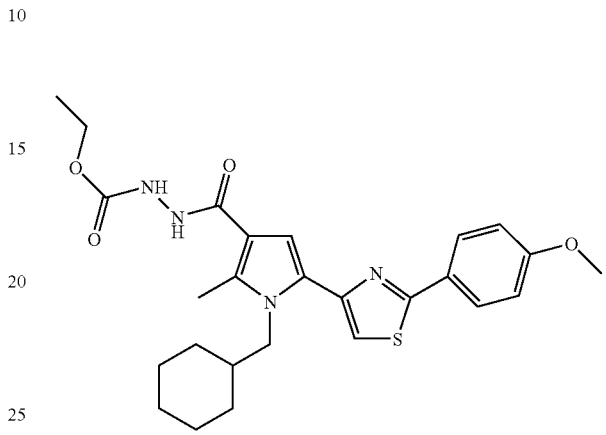

The title compound was obtained using ethyl carbazate as $R^1R^2NH$, aminomethylcyclohexane as $R^3$—$(CH_2)_m$—$NH_2$ and 4-methoxyphenyl thioamide as $R^4C(S)NH_2$, MS(ISP) 497.4 (M+H)$^+$.

Example 305

Cyclohexylmethyl-5-[2-(4-methoxy-phenyl)-thiazol-4-yl]-2-methyl-1H-pyrrole-3-carboxylic acid (pyridin-2-ylmethyl)-amide

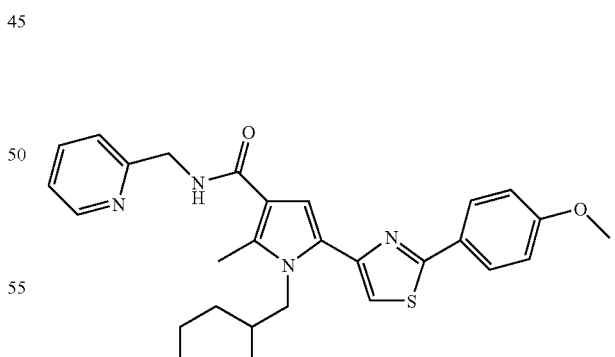

The title compound was obtained using 2-(aminomethyl)pyridine as $R^1R^2NH$, aminomethylcyclohexane as $R^3$—$(CH_2)_m$—$NH_2$ and 4-methoxyphenyl thioamide as $R^4C(S)NH_2$, MS(ISP) 501.3 (M+H)$^+$.

Example 306

Cyclohexylmethyl-5-[2-(4-methoxy-phenyl)-thiazol-4-yl]-2-methyl-1H-pyrrole-3-carboxylic acid (4-chloro-phenyl)-amide

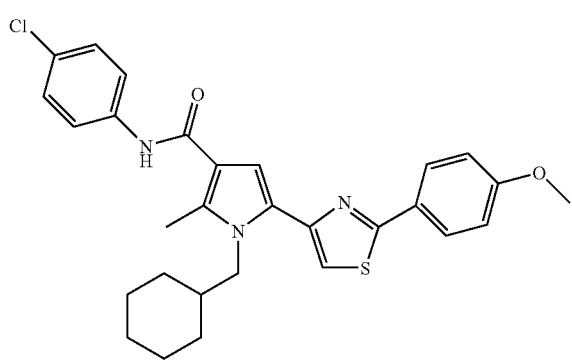

The title compound was obtained using 4-chloro-aniline as $R^1R^2NH$, aminomethylcyclohexane as $R^3$—$(CH_2)_m$—$NH_2$ and 4-methoxyphenyl thioamide as $R^4C(S)NH_2$, MS(ISP) 520.3 $(M+H)^+$.

Example 307

Cyclohexylmethyl-5-[2-(4-methoxy-phenyl)-thiazol-4-yl]-2-methyl-1H-pyrrole-3-carboxylic acid (3,4-dichloro-phenyl)-amide

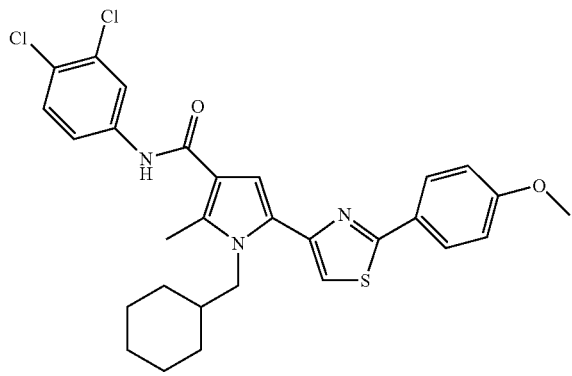

The title compound was obtained using 3,4-dichloroaniline as $R^1R^2NH$, aminomethylcyclohexane as $R^3$—$(CH_2)_m$—$NH_2$ and 4-methoxyphenyl thioamide as $R^4C(S)NH_2$, MS(ISP) 554.3 $(M+H)^+$.

Example 308 rac-1-Cyclohexylmethyl-5-[2-(4-methoxy-phenyl)-thiazol-4-yl]-2-methyl-1H-pyrrole-3-carboxylic acid sec-butylamide

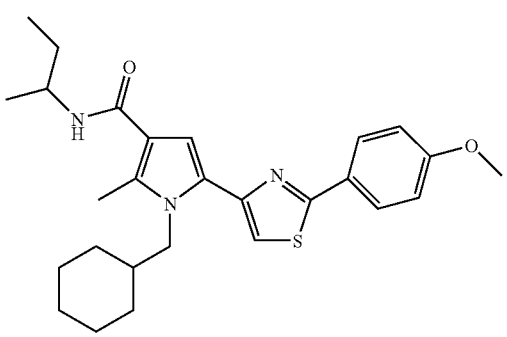

The title compound was obtained using sec-butylamine as $R^1R^2NH$, aminomethylcyclohexane as $R^3$—$(CH_2)_m$—$NH_2$ and 4-methoxyphenyl thioamide as $R^4C(S)NH_2$, MS(ISP) 466.4 $(M+H)^+$.

Example 309

{1-Cyclohexylmethyl-5-[2-(4-methoxy-phenyl)-thiazol-4-yl]-2-methyl-1H-pyrrol-3-yl}-morpholin-4-yl-methanone

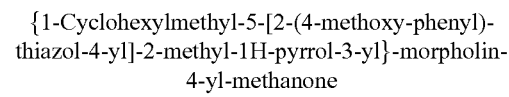

The title compound was obtained using morpholine as $R^1R^2NH$, aminomethylcyclohexane as $R^3$—$(CH_2)_m$—$NH_2$ and 4-methoxyphenyl thioamide as $R^4C(S)NH_2$, MS(ISP) 480.3 $(M+H)^+$.

Example 310

Methyl-isoxazole-3-carboxylic acid N'-{1-cyclohexylmethyl-5-[2-(4-methoxy-phenyl)-thiazol-4-yl]-2-methyl-1H-pyrrole-3-carbonyl}-hydrazide

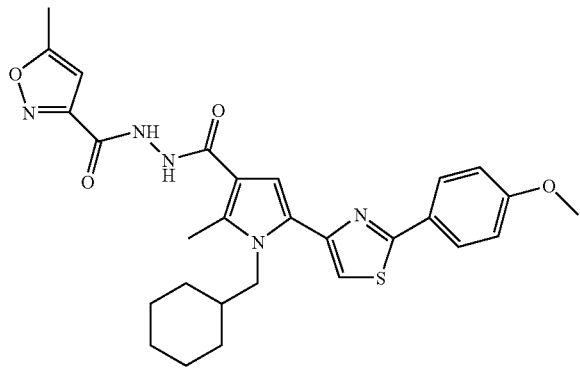

The title compound was obtained using 5-methylisoxazole-3-carbohydrazide as $R^1R^2NH$, aminomethylcyclohexane as $R^3$—$(CH_2)_m$—$NH_2$ and 4-methoxyphenyl thioamide as $R^4C(S)NH_2$, MS(ISP) 534.3 (M+H)$^+$.

Example 311

{1-Cyclohexylmethyl-5-[2-(4-methoxy-phenyl)-thiazol-4-yl]-2-methyl-1H-pyrrol-3-yl}-piperidin-1-yl-methanone

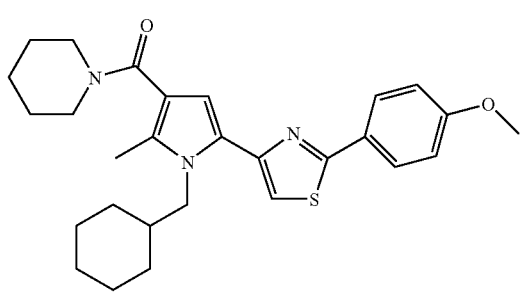

The title compound was obtained using piperidine as $R^1R^2NH$, aminomethylcyclohexane as $R^3$—$(CH_2)_m$—$NH_2$ and 4-methoxyphenyl thioamide as $R^4C(S)NH_2$, MS(ISP) 478.3 (M+H)$^+$.

Example 312

5-[2-(4-Methoxy-phenyl)-thiazol-4-yl]-2-methyl-1-phenethyl-1H-pyrrole-3-carboxylic acid butylamide

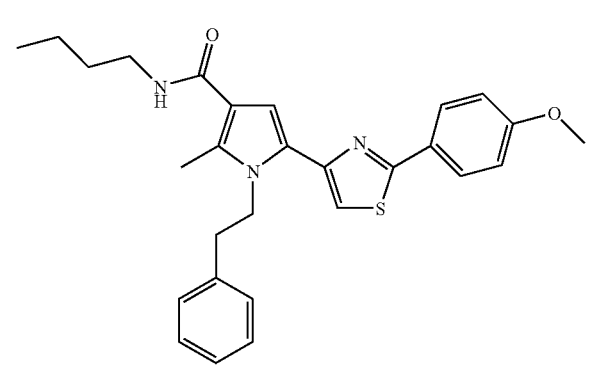

The title compound was obtained using butylamine as $R^1R^2NH$, phenethylamine as $R^3$—$(CH_2)_m$—$NH_2$ and 4-methoxyphenyl thioamide as $R^4C(S)NH_2$, MS(ISP) 474.3 (M+H)$^+$.

Example 313

1-(2-Cyclohexyl-ethyl)-5-[2-(4-methoxy-phenyl)-thiazol-4-yl]-2-methyl-1H-pyrrole-3-carboxylic acid butylamide

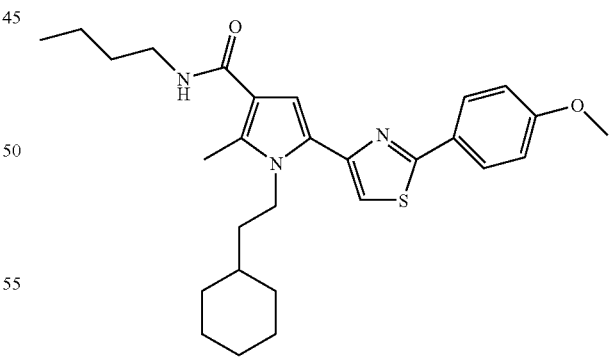

The title compound was obtained using butylamine as $R^1R^2NH$, 2-cyclohexyl-ethylamine as $R^3$—$(CH_2)_m$—$NH_2$ and 4-methoxyphenyl thioamide as $R^4C(S)NH_2$, MS(ISP) 480.4 (M+H)$^+$.

Example 314

1-(3,5-Dimethyl-benzyl)-5-[2-(4-methoxy-phenyl)-thiazol-4-yl]-2-methyl-1H-pyrrole-3-carboxylic acid butylamide

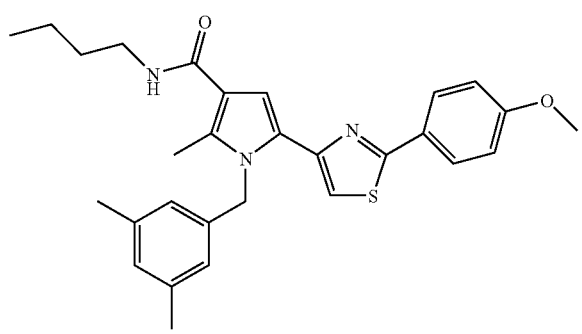

The title compound was obtained using butylamine as $R^1R^2NH$, 3,5-dimethylbenzylamine as $R^3$—$(CH_2)_m$—$NH_2$ and 4-methoxyphenyl thioamide as $R^4C(S)NH_2$, MS(ISP) 488.3 (M+H)$^+$.

Example 315

Cyclohexylmethyl-5-[2-(4-methoxy-phenyl)-thiazol-4-yl]-2-methyl-1H-pyrrole-3-carboxylic acid phenylamide

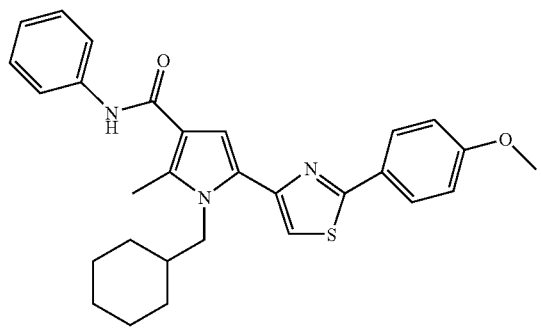

The title compound was obtained using aniline as $R^1R^2NH$, aminomethylcyclohexane as $R^3$—$(CH_2)_m$—$NH_2$ and 4-methoxyphenyl thioamide as $R^4C(S)NH_2$, MS(ISP) 486.4 (M+H)$^+$.

Example 316

5-[2-(4-Methoxy-phenyl)-thiazol-4-yl]-2-methyl-1-(4-phenyl-butyl)-1H-pyrrole-3-carboxylic acid butylamide

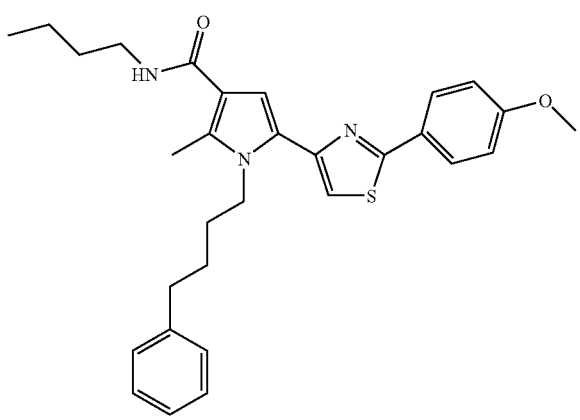

The title compound was obtained using butylamine as $R^1R^2NH$, 4-phenylbutylamine as $R^3$—$(CH_2)_m$—$NH_2$ and 4-methoxyphenyl thioamide as $R^4C(S)NH_2$, MS(ISP) 502.3 (M+H)$^+$.

Example 317

1-(1-Ethyl-pyrrolidin-2-ylmethyl)-5-[2-(4-methoxy-phenyl)-thiazol-4-yl]-2-methyl-1H-pyrrole-3-carboxylic acid butylamide

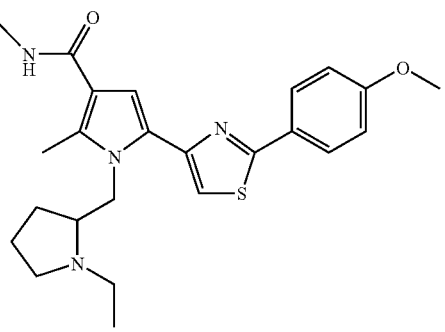

The title compound was obtained using butylamine as $R^1R^2NH$, 2-(aminomethyl)-1-ethylpyrrolidine as $R^3$—$(CH_2)_m$—$NH_2$ and 4-methoxyphenyl thioamide as $R^4C(S)NH_2$, MS(ISP) 481.3 (M+H)$^+$.

Example 318

Cyclohexylmethyl-5-[2-(4-methoxy-phenyl)-thiazol-4-yl]-2-methyl-1H-pyrrole-3-carboxylic acid amide

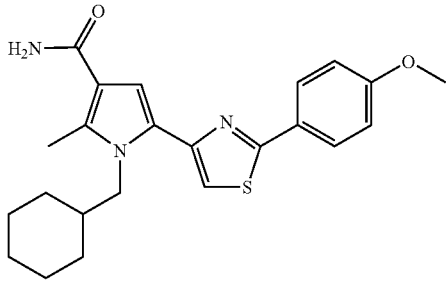

The title compound was obtained using aminomethylcyclohexane as $R^3$—$(CH_2)_m$—$NH_2$ and 4-methoxyphenyl thioamide as $R^4C(S)NH_2$, MS(ISP) 410.3 (M+H)$^+$.

Example 319

5-[2-(4-Methoxy-phenyl)-thiazol-4-yl]-2-methyl-1-(2-morpholin-4-yl-ethyl)-1H-pyrrole-3-carboxylic acid butylamide

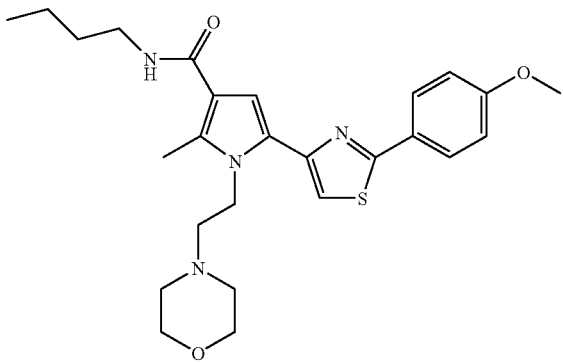

The title compound was obtained using butylamine as $R^1R^2NH$, 4-(2-aminoethyl)morpholine as $R^3$—$(CH_2)_m$—$NH_2$ and 4-methoxyphenyl thioamide as $R^4C(S)NH_2$, MS(ISP) 483.3 (M+H)$^+$.

Example 320

Cyclohexylmethyl-5-[2-(4-methoxy-phenyl)-thiazol-4-yl]-2-methyl-1H-pyrrole-3-carboxylic acid (4-methyl-thiazol-2-yl)-amide

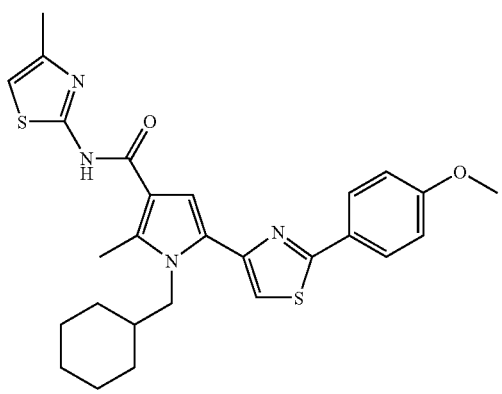

The title compound was obtained using 2-amino-4-methylthiazole as $R^1R^2NH$, aminomethylcyclohexane as $R^3$—$(CH_2)_m$—$NH_2$ and 4-methoxyphenyl thioamide as $R^4C(S)NH_2$, MS(ISP) 507.3 (M+H)$^+$.

Example 321

1-(3-Methoxy-benzyl)-5-[2-(4-methoxy-phenyl)-thiazol-4-yl]-2-methyl-1H-pyrrole-3-carboxylic acid butylamide

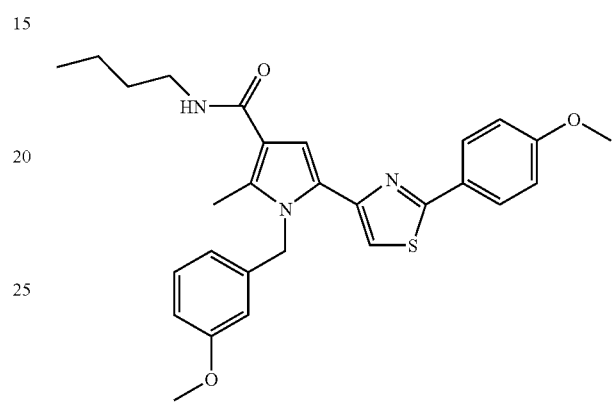

The title compound was obtained using butylamine as $R^1R^2NH$, 3-methoxybenzylamine as $R^3$—$(CH_2)_m$—$NH_2$ and 4-methoxyphenyl thioamide as $R^4C(S)NH_2$, MS(ISP) 490.3 (M+H)$^+$.

Example 322

1-(3,5-Dichloro-benzyl)-5-[2-(4-methoxy-phenyl)-thiazol-4-yl]-2-methyl-1H-pyrrole-3-carboxylic acid butylamide

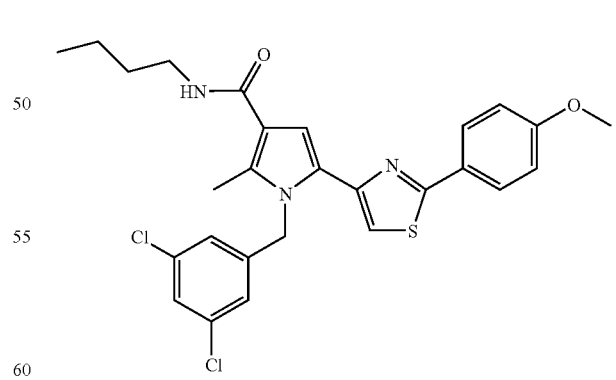

The title compound was obtained using butylamine as $R^1R^2NH$, 3,5-dichloroaniline as $R^3$—$(CH_2)_m$—$NH_2$ and 4-methoxyphenyl thioamide as $R^4C(S)NH_2$, MS(ISP) 528.2 (M+H)$^+$.

Example 323

Indan-2-yl-5-[2-(4-methoxy-phenyl)-thiazol-4-yl]-2-methyl-1H-pyrrole-3-carboxylic acid butylamide

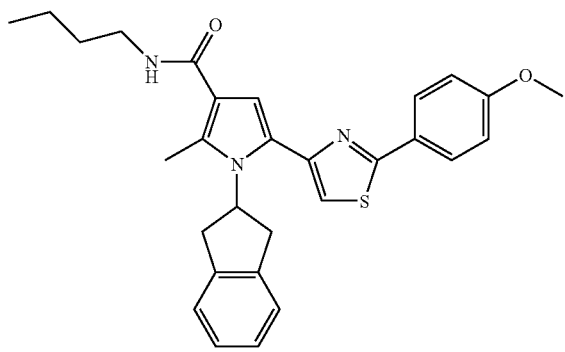

The title compound was obtained using butylamine as $R^1R^2NH$, 2-aminoindane as $R^3$—$(CH_2)_m$—$NH_2$ and 4-methoxyphenyl thioamide as $R^4C(S)NH_2$, MS(ISP) 486.4 (M+H)+.

Example 324

Cyclohexylmethyl-5-[2-(4-methoxy-phenyl)-thiazol-4-yl]-2-methyl-1H-pyrrole-3-carboxylic acid pyrimidin-2-ylamide

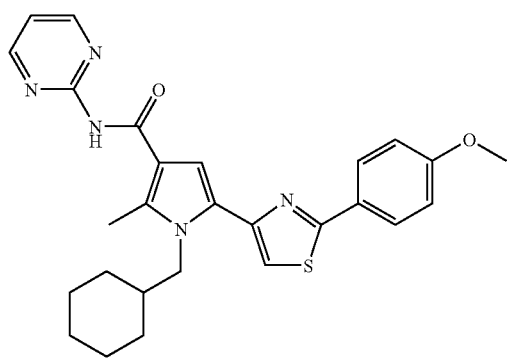

The title compound was obtained using 2-aminopyrimidine as $R^1R^2NH$, aminomethylcyclohexane as $R^3$—$(CH_2)_m$—$NH_2$ and 4-methoxyphenyl thioamide as $R^4C(S)NH_2$, MS(ISP) 488.3 (M+H)+.

Example 325

1-(3,4-Dihydroxy-benzyl)-5-[2-(4-methoxy-phenyl)-thiazol-4-yl]-2-methyl-1H-pyrrole-3-carboxylic acid butylamide

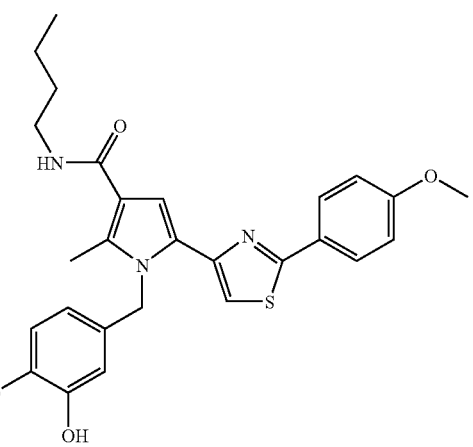

The title compound was obtained using butylamine as $R^1R^2NH$, 3,4-dihydroxybenzylamine as $R^3$—$(CH_2)_m$—$NH_2$ and 4-methoxyphenyl thioamide as $R^4C(S)NH_2$, MS(ISP) 492.3 (M+H)+.

Example 326

5-[2-(4-Methoxy-phenyl)-thiazol-4-yl]-2-methyl-1-(3-piperidin-1-yl-propyl)-1H-pyrrole-3-carboxylic acid butylamide

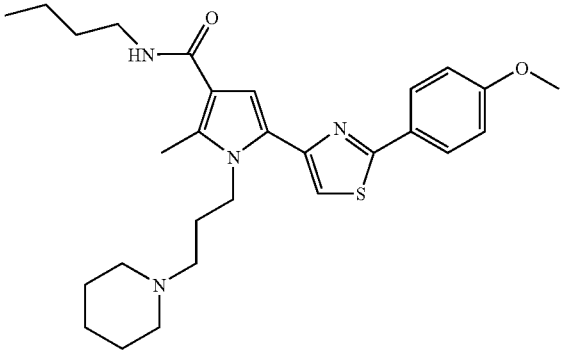

The title compound was obtained using butylamine as $R^1R^2NH$, 3-piperidino-propylamine as $R^3$—$(CH_2)_m$—$NH_2$ and 4-methoxyphenyl thioamide as $R^4C(S)NH_2$, MS(ISP) 495.4 (M+H)+.

Example 327 rac-1-Cyclohexylmethyl-5-[2-(4-methoxy-phenyl)-thiazol-4-yl]-2-methyl-1H-pyrrole-3-carboxylic acid (5-hydroxy-2,2,6-trimethyl-cyclohexylmethyl)-amide

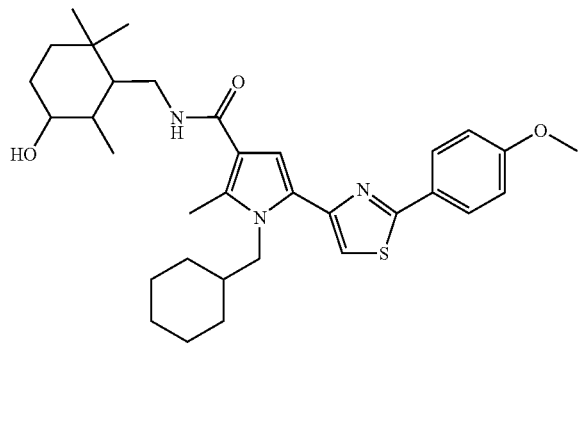

The title compound was obtained using aminomethylcyclohexane as $R^3$—$(CH_2)_m$—$NH_2$ and 4-methoxyphenyl thioamide as $R^4C(S)NH_2$, MS(ISP) 564.4 (M+H)$^+$.

Example 328

5-[2-(4-Methoxy-phenyl)-thiazol-4-yl]-2-methyl-1-(3-trifluoromethoxy-benzyl)-1H-pyrrole-3-carboxylic acid butylamide

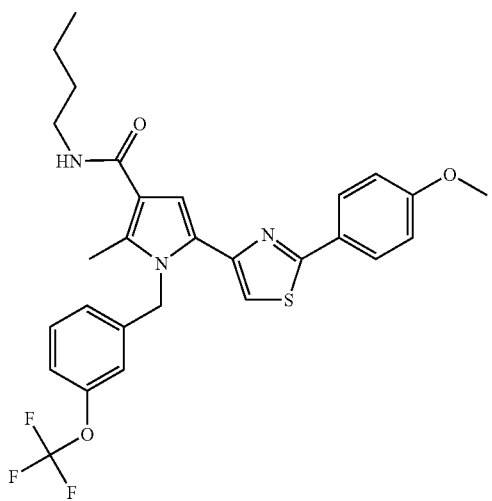

The title compound was obtained using butylamine as $R^1R^2NH$, 3-(trifluoromethoxy)benzylamine as $R^3$—$(CH_2)_m$—$NH_2$ and 4-methoxyphenyl thioamide as $R^4C(S)NH_2$, MS(ISP) 544.4 (M+H)$^+$.

Example 329

5-[2-(4-Methoxy-phenyl)-thiazol-4-yl]-2-methyl-1-(4-trifluoromethoxy-benzyl)-1H-pyrrole-3-carboxylic acid butylamide

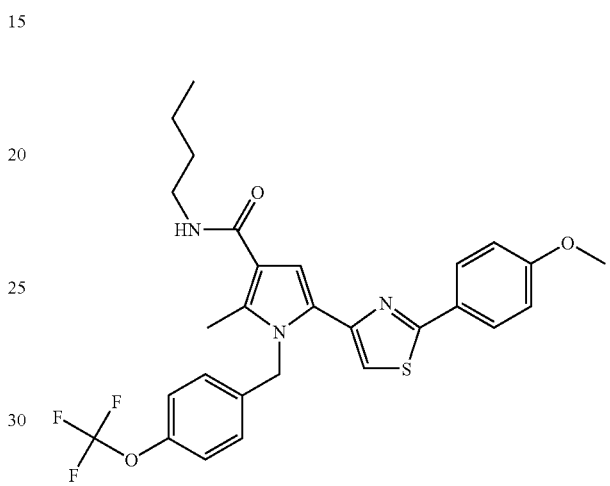

The title compound was obtained using butylamine as $R^1R^2NH$, 4-(trifluoromethoxy)benzylamine as $R^3$—$(CH_2)_m$—$NH_2$ and 4-methoxyphenyl thioamide as $R^4C(S)NH_2$, MS(ISP) 544.3 (M+H)$^+$.

Example 330

5-[2-(4-Methoxy-phenyl)-thiazol-4-yl]-2-methyl-1-(3-methyl-thiophen-2-ylmethyl)-1H-pyrrole-3-carboxylic acid butylamide

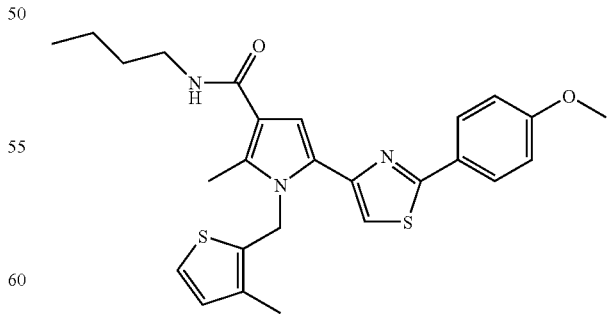

The title compound was obtained using butylamine as $R^1R^2NH$, (3-methyl-2-thienyl)methylamine as $R^3$—$(CH_2)_m$—$NH_2$ and 4-methoxyphenyl thioamide as $R^4C(S)NH_2$, MS(ISP) 480.3 (M+H)$^+$.

Example 331

5-[2-(4-Methoxy-phenyl)-thiazol-4-yl]-2-methyl-1-(4-nitro-benzyl)-1H-pyrrole-3-carboxylic acid butylamide

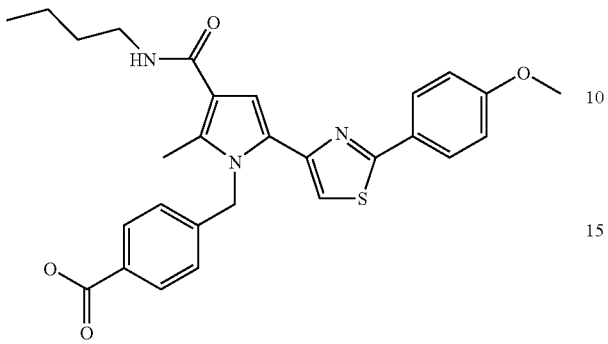

The title compound was obtained using butylamine as $R^1R^2NH$, 4-nitrobenzylamine as $R^3$—$(CH_2)_m$—$NH_2$ and 4-methoxyphenyl thioamide as $R^4C(S)NH_2$, MS(ISP) 505.4 $(M+H)^+$.

Example 332

Benzhydryl-5-[2-(4-methoxy-phenyl)-thiazol-4-yl]-2-methyl-1H-pyrrole-3-carboxylic acid butylamide

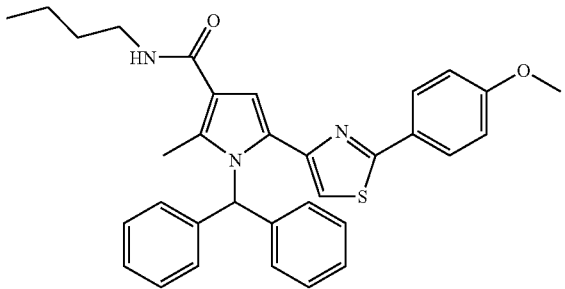

The title compound was obtained using butylamine as $R^1R^2NH$, benzhydrylamine as $R^3$—$(CH_2)_m$—$NH_2$ and 4-methoxyphenyl thioamide as $R^4C(S)NH_2$, MS(ISP) 536.4 $(M+H)^+$.

Example 333

Benzyl-5-[2-(4-methoxy-phenyl)-thiazol-4-yl]-2-methyl-1H-pyrrole-3-carboxylic acid butylamide

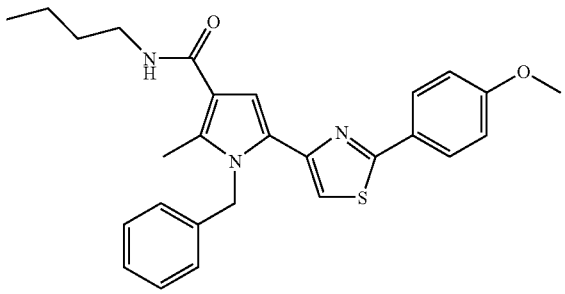

The title compound was obtained using butylamine as $R^1R^2NH$, benzylamine as $R^3$—$(CH_2)_m$—$NH_2$ and 4-methoxyphenyl thioamide as $R^4C(S)NH_2$, MS(ISP) 560.3 $(M+H)^+$.

Example 334

5-[2-(4-Methoxy-phenyl)-thiazol-4-yl]-2-methyl-1-(2-pyridin-2-yl-ethyl)-1H-pyrrole-3-carboxylic acid butylamide

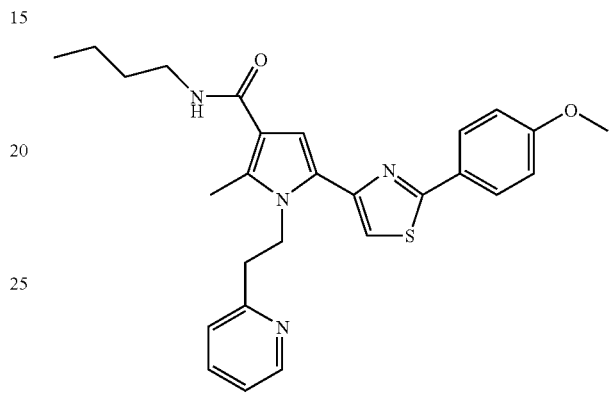

The title compound was obtained using butylamine as $R^1R^2NH$, 2-(2-aminoethyl)pyridine as $R^3$—$(CH_2)_m$—$NH_2$ and 4-methoxyphenyl thioamide as $R^4C(S)NH_2$, MS(ISP) 475.3 $(M+H)^+$.

Example 335

{1-Cyclohexylmethyl-5-[2-(4-methoxy-phenyl)-thiazol-4-yl]-2-methyl-1H-pyrrol-3-yl}-pyrrolidin-1-yl-methanone

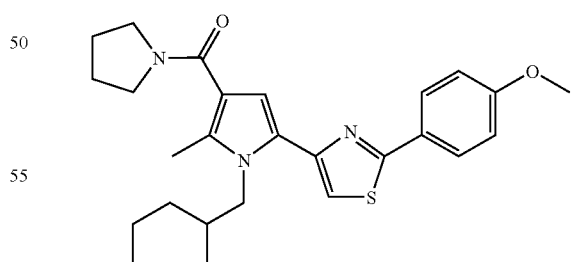

The title compound was obtained using pyrrolidine as $R^1R^2NH$, aminomethylcyclohexane as $R^3$—$(CH_2)_m$—$NH_2$ and 4-methoxyphenyl thioamide as $R^4C(S)NH_2$, MS(ISP) 464.3 $(M+H)^+$.

Example 336

Cyclohexylmethyl-5-[2-(3,4-dimethoxy-phenyl)-thiazol-4-yl]-2-methyl-1H-pyrrole-3-carboxylic acid butylamide

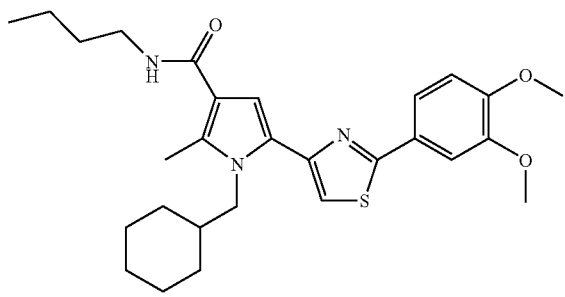

The title compound was obtained using butylamine as $R^1R^2NH$, aminomethylcyclohexane as $R^3$—$(CH_2)_m$—$NH_2$ and 3,4-dimethoxyphenyl thioamide as $R^4C(S)NH_2$, MS(ISP) 496.4 (M+H)$^+$.

Example 337

Cyclohexylmethyl-5-[2-(2-methoxy-phenyl)-thiazol-4-yl]-2-methyl-1H-pyrrole-3-carboxylic acid butylamide

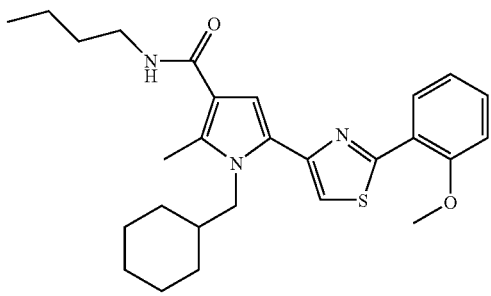

The title compound was obtained using butylamine as $R^1R^2NH$, aminomethylcyclohexane as $R^3$—$(CH_2)_m$—$NH_2$ and 3,4-dimethoxyphenyl thioamide as $R^4C(S)NH_2$, MS(ISP) 466.3 (M+H)$^+$.

Example 338

Cyclohexylmethyl-2-methyl-5-[2-(4-trifluoromethyl-phenyl)-thiazol-4-yl]-1H-pyrrole-3-carboxylic acid butylamide

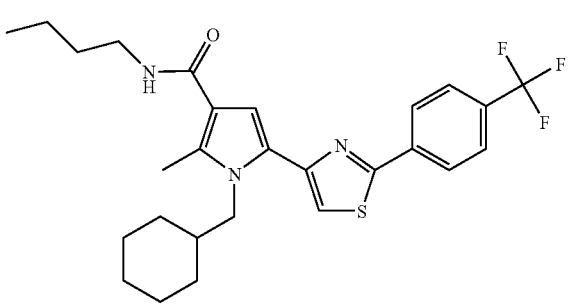

The title compound was obtained using butylamine as $R^1R^2NH$, aminomethylcyclohexane as $R^3$—$(CH_2)_m$—$NH_2$ and 4-trifluoromethylphenyl thioamide as $R^4C(S)NH_2$, MS(ISP) 504.2 (M+H)$^+$.

Example 339

Cyclohexylmethyl-5-[2-(3-methoxy-phenyl)-thiazol-4-yl]-2-methyl-1H-pyrrole-3-carboxylic acid butylamide

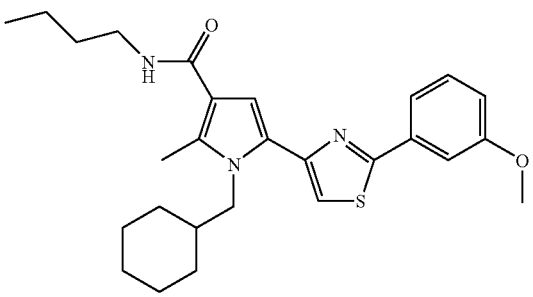

The title compound was obtained using butylamine as $R^1R^2NH$, aminomethylcyclohexane as $R^3$—$(CH_2)_m$—$NH_2$ and 3-methoxyphenyl thioamide as $R^4C(S)NH_2$, MS(ISP) 466.3 (M+H)$^+$.

Example 340

5-(2-Benzo[1,3]dioxol-5-yl-thiazol-4-yl)-1-cyclohexylmethyl-2-methyl-1H-pyrrole-3-carboxylic acid butylamide

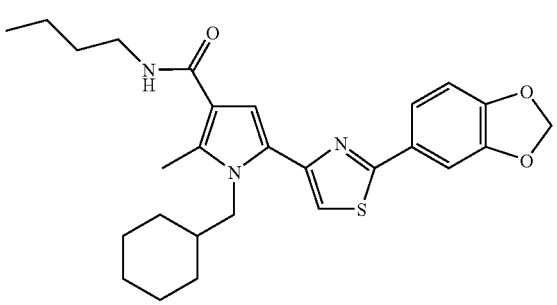

The title compound was obtained using butylamine as $R^1R^2NH$, aminomethylcyclohexane as $R^3$—$(CH_2)_m$—$NH_2$ and 1,3-benzodioxole-5-carbothiamide as $R^4C(S)NH_2$, MS(ISP) 480.3 (M+H)$^+$.

Example 341

Cyclohexylmethyl-5-[2-(4-fluoro-phenyl)-thiazol-4-yl]-2-methyl-1H-pyrrole-3-carboxylic acid butylamide

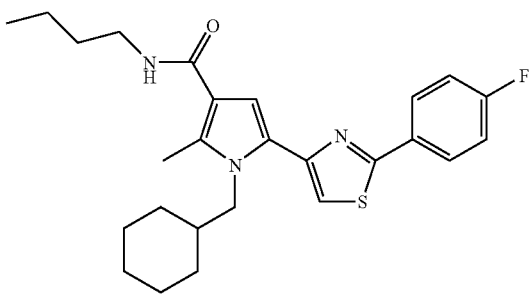

The title compound was obtained using butylamine as R$^1$R$^2$NH, aminomethylcyclohexane as R$^3$—(CH$_2$)$_m$—NH$_2$ and 4-fluorophenyl thioamide as R$^4$C(S)NH$_2$, MS(ISP) 454.3 (M+H)$^+$.

Example 342

Cyclohexylmethyl-5-[2-(2-fluoro-phenyl)-thiazol-4-yl]-2-methyl-1H-pyrrole-3-carboxylic acid butylamide

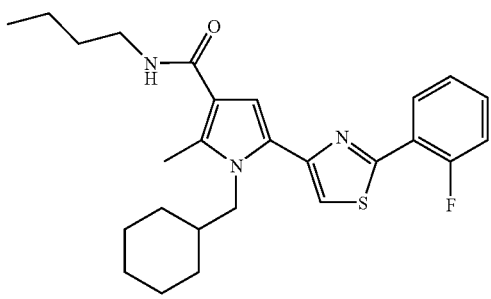

The title compound was obtained using butylamine as R$^1$R$^2$NH, aminomethylcyclohexane as R$^3$—(CH$_2$)$_m$—NH$_2$ and 2-fluorophenyl thioamide as R$^4$C(S)NH$_2$, MS(ISP) 454.3 (M+H)$^+$.

Example 343

Cyclohexylmethyl-2-methyl-5-[2-(4-trifluoromethoxy-phenyl)-thiazol-4-yl]-1H-pyrrole-3-carboxylic acid butylamide

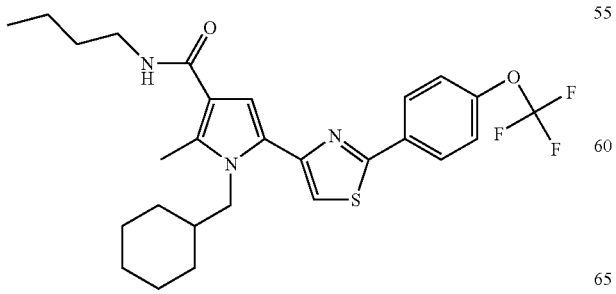

The title compound was obtained using butylamine as R$^1$R$^2$NH, aminomethylcyclohexane as R$^3$—(CH$_2$)$_m$—NH$_2$ and 4-(trifluoromethoxy)phenyl thioamide as R$^4$C(S)NH$_2$, MS(ISP) 520.3 (M+H)$^+$.

Example 344

Cyclohexylmethyl-5-[2-(3,5-dimethoxy-phenyl)-thiazol-4-yl]-2-methyl-1H-pyrrole-3-carboxylic acid butylamide

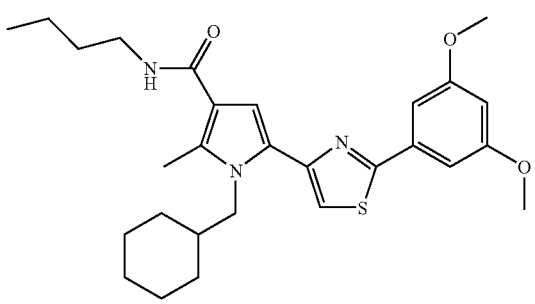

The title compound was obtained using butylamine as R$^1$R$^2$NH, aminomethylcyclohexane as R$^3$—(CH$_2$)$_m$—NH$_2$ and 3,5-dimethoxyphenyl thioamide as R$^4$C(S)NH$_2$, MS(ISP) 496.4 (M+H)$^+$.

Example 345

Cyclohexylmethyl-2-methyl-5-(2-m-tolyl-thiazol-4-yl)-1H-pyrrole-3-carboxylic acid butylamide

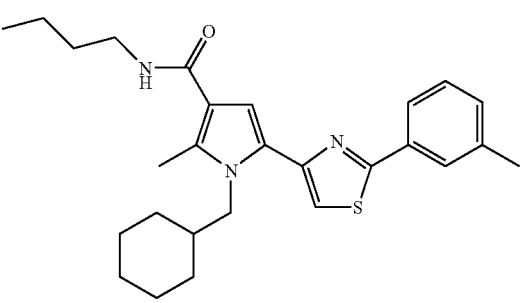

The title compound was obtained using butylamine as R$^1$R$^2$NH, aminomethylcyclohexane as R$^3$—(CH$_2$)$_m$—NH$_2$ and 3-methylphenyl thioamide as R$^4$C(S)NH$_2$, MS(ISP) 450.3 (M+H)$^+$.

Example 346

Cyclohexylmethyl-2-methyl-5-(2'-methyl-[2,4']bithiazolyl-4-yl)-1H-pyrrole-3-carboxylic acid butylamide

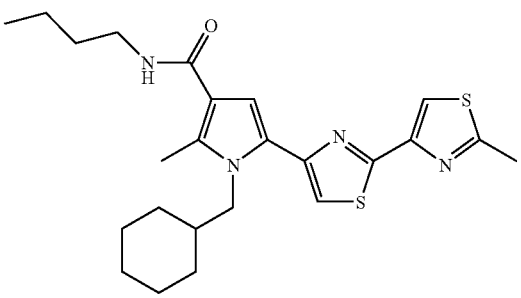

The title compound was obtained using butylamine as $R^1R^2NH$, aminomethylcyclohexane as $R^3$—$(CH_2)_m$—$NH_2$ and 2-methyl-1,3-thiazole-4-carbothioamide as $R^4C(S)NH_2$, MS(ISP) 457.3 (M+H)$^+$.

Example 347

Cyclohexylmethyl-5-[2-(4-ethyl-phenyl)-thiazol-4-yl]-2-methyl-1H-pyrrole-3-carboxylic acid butylamide

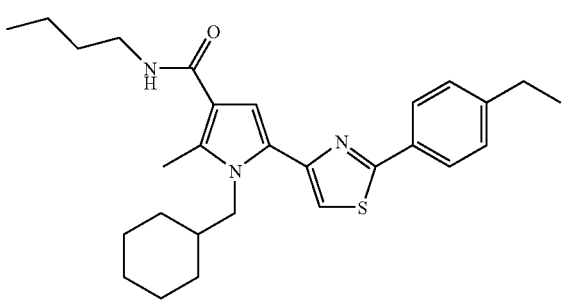

The title compound was obtained using butylamine as $R^1R^2NH$, aminomethylcyclohexane as $R^3$—$(CH_2)_m$—$NH_2$ and 4-ethylphenyl thioamide as $R^4C(S)NH_2$, MS(ISP) 464.3 (M+H)$^+$.

Example 348

5-[2-(4-Chloro-phenyl)-thiazol-4-yl]-1-cyclohexylmethyl-2-methyl-1H-pyrrole-3-carboxylic acid butylamide

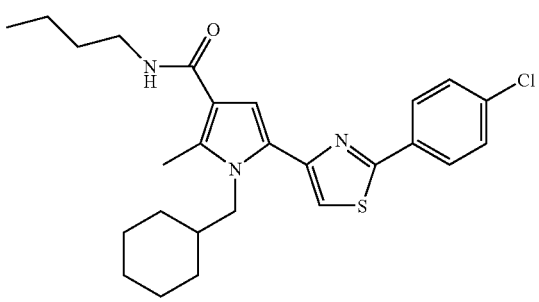

The title compound was obtained using butylamine as $R^1R^2NH$, aminomethylcyclohexane as $R^3$—$(CH_2)_m$—$NH_2$ and 4-chlorophenyl thioamide as $R^4C(S)NH_2$, MS(ISP) 470.3 (M+H)$^+$.

Example 349

5-[2-(4-tert-Butyl-phenyl)-thiazol-4-yl]-1-cyclohexylmethyl-2-methyl-1H-pyrrole-3-carboxylic acid butylamide

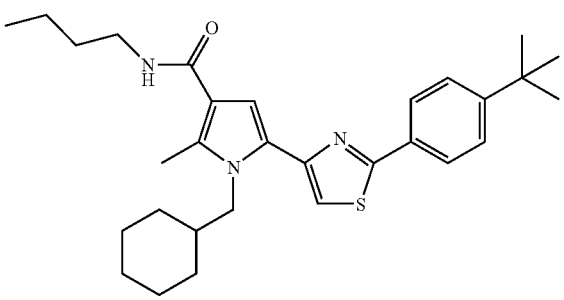

The title compound was obtained using butylamine as $R^1R^2NH$, aminomethylcyclohexane as $R^3$—$(CH_2)_m$—$NH_2$ and 4-tertbutylphenyl thioamide as $R^4C(S)NH_2$, MS(ISP) 492.4 (M+H)$^+$.

Example 350

Cyclohexylmethyl-5-[2-(2,3-dihydro-benzofuran-5-yl)-thiazol-4-yl]-2-methyl-1H-pyrrole-3-carboxylic acid butylamide

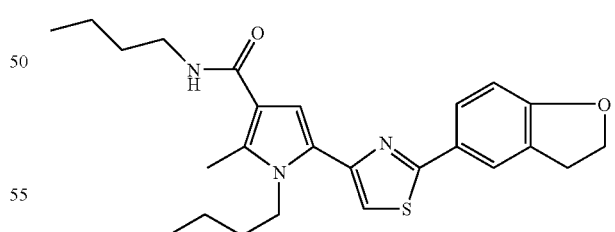

The title compound was obtained using butylamine as $R^1R^2NH$, aminomethylcyclohexane as $R^3$—$(CH_2)_m$—$NH_2$ and 2,3-dihydrobenzo[b]furan-5-carbothioamide as $R^4C(S)NH_2$, MS(ISP) 478.3 (M+H)$^+$.

Example 351

Cyclohexylmethyl-2-methyl-5-(2-p-tolyl-thiazol-4-yl)-1H-pyrrole-3-carboxylic acid butylamide

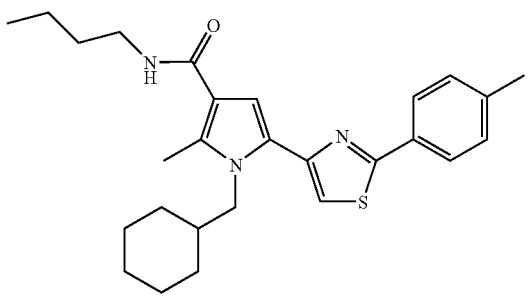

The title compound was obtained using butylamine as $R^1R^2NH$, aminomethylcyclohexane as $R^3$—$(CH_2)_m$—$NH_2$ and 4-methylphenyl thioamide as $R^4C(S)NH_2$, MS(ISP) 450.3 $(M+H)^+$.

Example 352

Cyclohexylmethyl-5-[2-(6-methoxy-pyridin-3-yl)-thiazol-4-yl]-2-methyl-1H-pyrrole-3-carboxylic acid butylamide

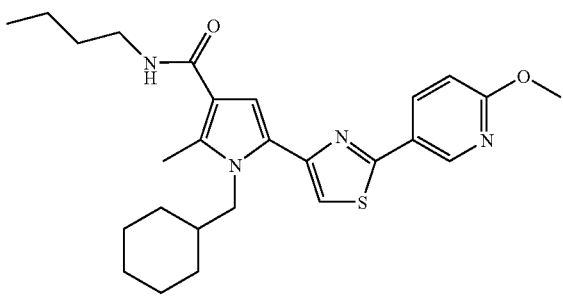

The title compound was obtained using butylamine as $R^1R^2NH$, aminomethylcyclohexane as $R^3$—$(CH_2)_m$—$NH_2$ and 6-methoxy-nicotamide as $R^4C(S)NH_2$, MS(ISP) 467.3 $(M+H)^+$.

Example 353

Cyclohexylmethyl-5-[2-(2,4-dichloro-phenyl)-thiazol-4-yl]-2-methyl-1H-pyrrole-3-carboxylic acid butylamide

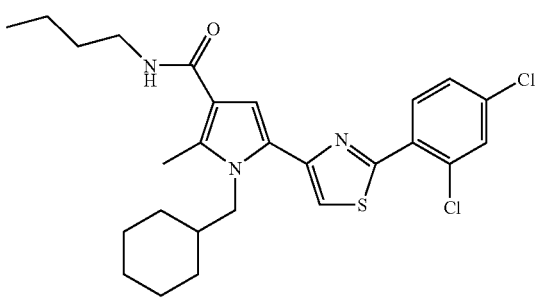

The title compound was obtained using butylamine as $R^1R^2NH$, aminomethylcyclohexane as $R^3$—$(CH_2)_m$—$NH_2$ and 2,4-dichlorophenyl thioamide as $R^4C(S)NH_2$, MS(ISP) 504.2 $(M+H)^+$.

Example 354

Cyclohexylmethyl-5-[2-(4-methoxy-phenyl)-thiazol-4-yl]-2-methyl-1H-pyrrole-3-carboxylic acid pentylamide

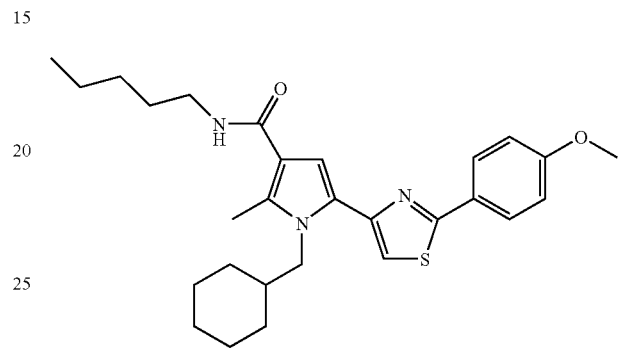

The title compound was obtained using pentylamine as $R^1R^2NH$, aminomethylcyclohexane as $R^3$—$(CH_2)_m$—$NH_2$ and 4-methoxyphenyl thioamide as $R^4C(S)NH_2$, MS(ISP) 481.3 $(M+H)^+$.

Example 355

Cyclohexylmethyl-5-[2-(4-methoxy-phenyl)-thiazol-4-yl]-2-methyl-1H-pyrrole-3-carboxylic acid propylamide

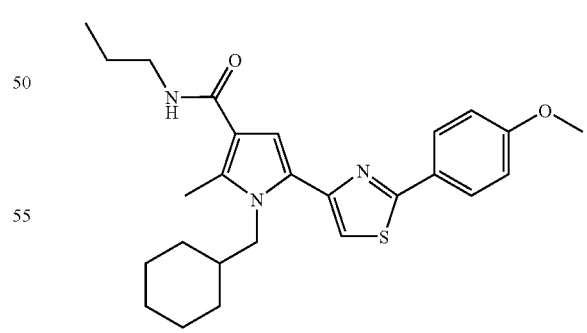

The title compound was obtained using propylamine as $R^1R^2NH$, aminomethylcyclohexane as $R^3$—$(CH_2)_m$—$NH_2$ and 4-methoxyphenyl thioamide as $R^4C(S)NH_2$, MS(ISP) 452.3 $(M+H)^+$.

Example 356

Cyclohexylmethyl-5-[2-(4-methoxy-phenyl)-thiazol-4-yl]-2-methyl-1H-pyrrole-3-carboxylic acid cyclohexylamide

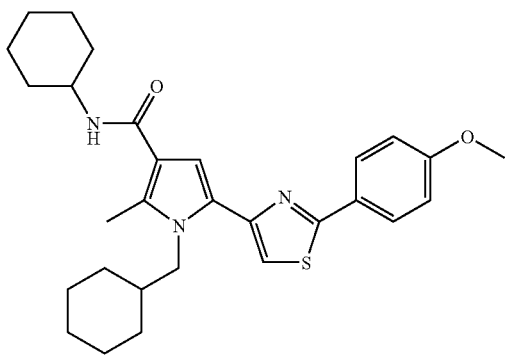

The title compound was obtained using cyclohexylamine as $R^1R^2NH$, aminomethylcyclohexane as $R^3-(CH_2)_m-NH_2$ and 4-methoxyphenyl thioamide as $R^4C(S)NH_2$, MS(ISP) 492.3 (M+H)$^+$.

Example 357

Cyclohexylmethyl-5-[2-(4-methoxy-phenyl)-thiazol-4-yl]-2-methyl-1H-pyrrole-3-carboxylic acid cyclopentylamide

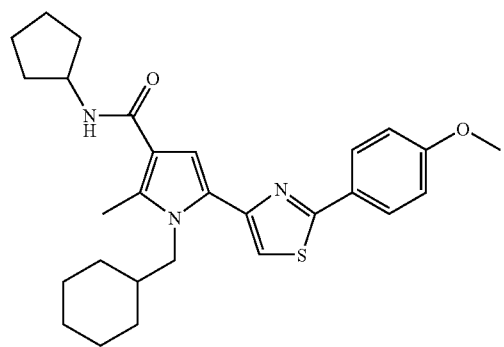

The title compound was obtained using cyclopentylamine as $R^1R^2NH$, aminomethylcyclohexane as $R^3-(CH_2)_m-NH_2$ and 4-methoxyphenyl thioamide as $R^4C(S)NH_2$, MS(ISP) 478.3 (M+H)$^+$.

Example 358

Cyclohexylmethyl-5-[2-(4-methoxy-phenyl)-thiazol-4-yl]-2-methyl-1H-pyrrole-3-carboxylic acid cyclopropylamide

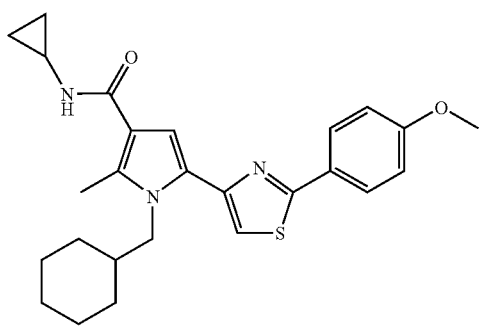

The title compound was obtained using cyclopropylamine as $R^1R^2NH$, aminomethylcyclohexane as $R^3-(CH_2)_m-NH_2$ and 4-methoxyphenyl thioamide as $R^4C(S)NH_2$, MS(ISP) 450.3 (M+H)$^+$.

Example 359

Cyclohexylmethyl-5-[2-(4-methoxy-phenyl)-thiazol-4-yl]-2-methyl-1H-pyrrole-3-carboxylic acid cyclobutylamide

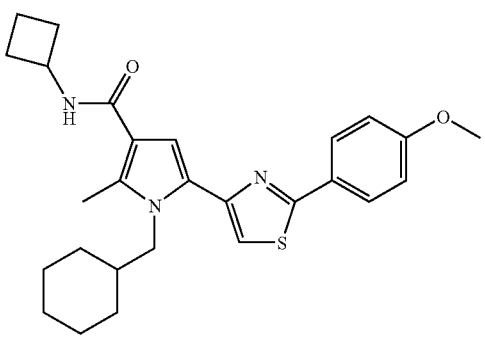

The title compound was obtained using cyclobutylamine as $R^1R^2NH$, aminomethylcyclohexane as $R^3-(CH_2)_m-NH_2$ and 4-methoxyphenyl thioamide as $R^4C(S)NH_2$, MS(ISP) 464.3 (M+H)$^+$.

Example 360

(trans) rac-1-Cyclohexylmethyl-5-[2-(4-methoxy-phenyl)-thiazol-4-yl]-2-methyl-1H-pyrrole-3-carboxylic acid (2-hydroxy-cyclopentyl)-amide

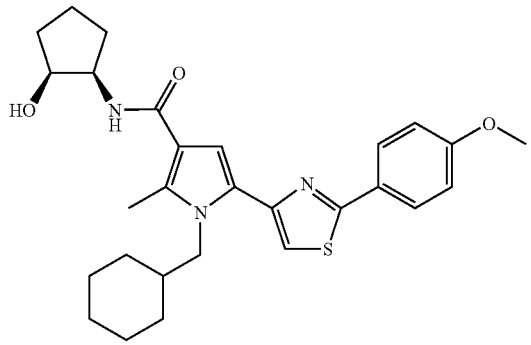

The title compound was obtained using trans-2-aminocyclopentanol as $R^1R^2NH$, aminomethylcyclohexane as $R^3$—$(CH_2)_m$—$NH_2$ and 4-methoxyphenyl thioamide as $R^4C(S)NH_2$, MS(ISP) 494.3 (M+H)$^+$.

Example 361

1-(4-Chloro-benzyl)-5-[2-(4-methoxy-phenyl)-thiazol-4-yl]-2-methyl-1H-pyrrole-3-carboxylic acid butylamide

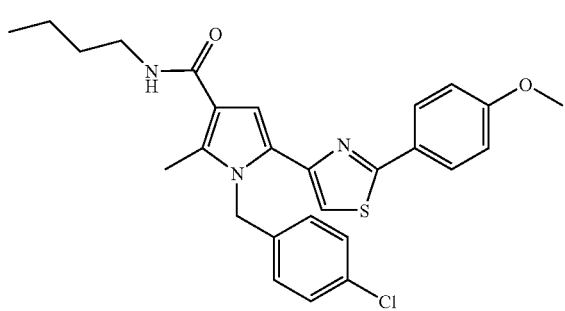

The title compound was obtained using butylamine as $R^1R^2NH$, 4-chloroaniline as $R^3$—$(CH_2)_m$—$NH_2$ and 4-methoxyphenyl thioamide as $R^4C(S)NH_2$, MS(ISP) 494.2 (M+H)$^+$.

Example 362

1-(3,4-Dichloro-benzyl)-5-[2-(4-methoxy-phenyl)-thiazol-4-yl]-2-methyl-1H-pyrrole-3-carboxylic acid butylamide

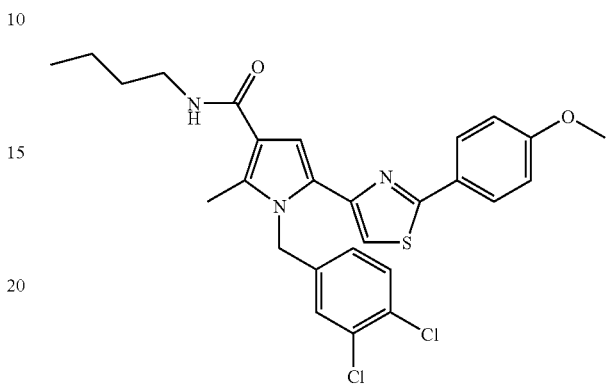

The title compound was obtained using butylamine as $R^1R^2NH$, 3,4-dichloroaniline as $R^3$—$(CH_2)_m$—$NH_2$ and 4-methoxyphenyl thioamide as —$R^4C(S)NH_2$, MS(ISP) 527.2 (M+H)$^+$.

Example 363

1-(4-Chloro-3-trifluoromethyl-benzyl)-5-[2-(4-methoxy-phenyl)-thiazol-4-yl]-2-methyl-1H-pyrrole-3-carboxylic acid butylamide

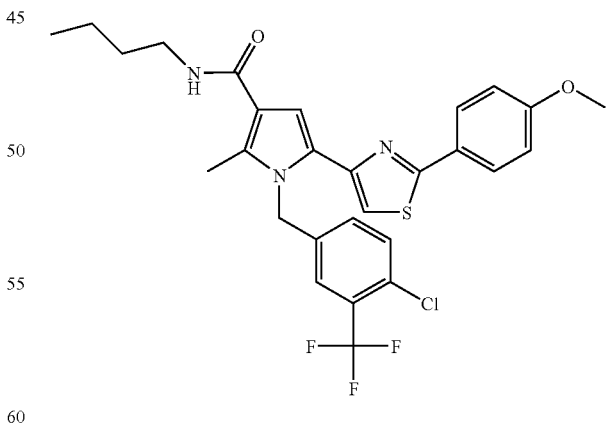

The title compound was obtained using butylamine as $R^1R^2NH$, 3-trifluoromethyl,4-chloro aniline as $R^3$—$(CH_2)_m$—$NH_2$ and 4-methoxyphenyl thioamide as $R^4C(S)NH_2$, MS(ISP) 562.2 (M+H)$^+$.

Example 364

1-(3,4-Dimethyl-benzyl)-5-[2-(4-methoxy-phenyl)-thiazol-4-yl]-2-methyl-1H-pyrrole-3-carboxylic acid butylamide

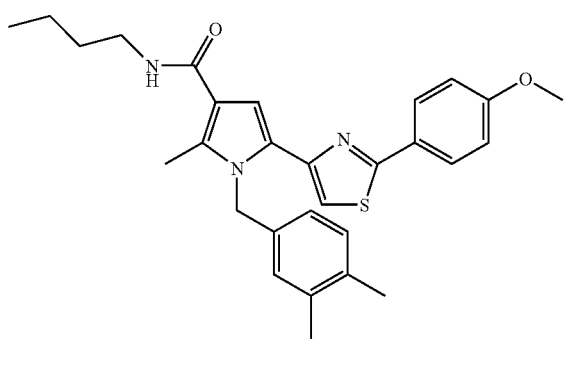

The title compound was obtained using butylamine as $R^1R^2NH$, 3,4-dimethylbenzylamine as $R^3$—$(CH_2)_m$—$NH_2$ and 4-methoxyphenyl thioamide as $R^4C(S)NH_2$, MS(ISP) 488.3 $(M+H)^+$.

Example 365

5-[2-(4-Methoxy-phenyl)-thiazol-4-yl]-2-methyl-1-(2-methyl-benzyl)-1H-pyrrole-3-carboxylic acid butylamide

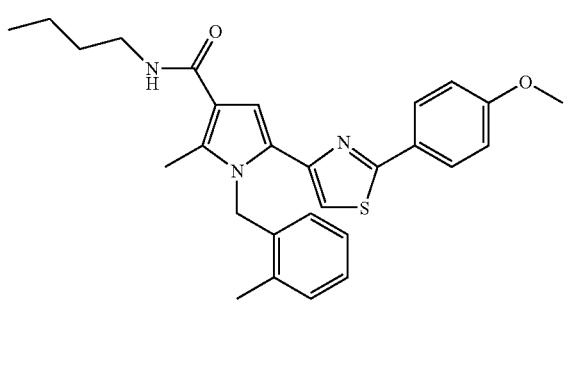

The title compound was obtained using butylamine as $R^1R^2NH$, 2-methylbenzylamine as $R^3$—$(CH_2)_m$—$NH_2$ and 4-methoxyphenyl thioamide as $R^4C(S)NH_2$, MS(ISP) 474.3 $(M+H)^+$.

Example 366

1-(3,4-Dimethoxy-benzyl)-5-[2-(4-methoxy-phenyl)-thiazol-4-yl]-2-methyl-1H-pyrrole-3-carboxylic acid butylamide

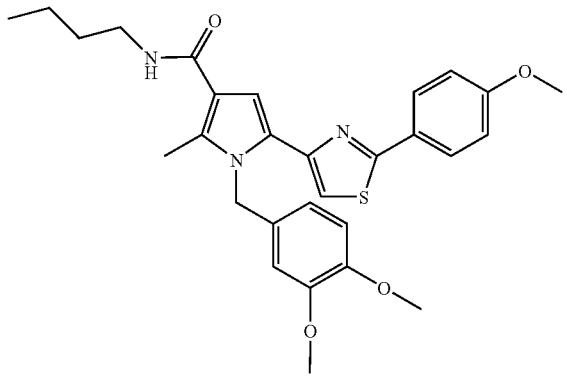

The title compound was obtained using butylamine as $R^1R^2NH$, 3,4-dimethoxybenzyl-amine as $R^3$—$(CH_2)_m$—$NH_2$ and 4-methoxyphenyl thioamide as $R^4C(S)NH_2$, MS(ISP) 520.4 $(M+H)^+$.

Example 367

1-(3,4-Dimethyl-benzyl)-5-[2-(4-methoxy-phenyl)-thiazol-4-yl]-2-methyl-1H-pyrrole-3-carboxylic acid butylamide

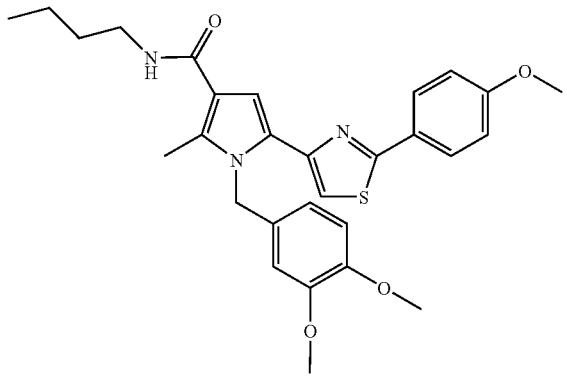

The title compound was obtained using butylamine as $R^1R^2NH$, 2,4-dimethoxybenzylamine as $R^3$—$(CH_2)_m$—$NH_2$ and 4-methoxyphenyl thioamide as $R^4C(S)NH_2$, MS(ISP) 520.3 $(M+H)^+$.

Example 368

1-(3,5-Dimethoxy-benzyl)-5-[2-(4-methoxy-phenyl)-thiazol-4-yl]-2-methyl-1H-pyrrole-3-carboxylic acid butylamide

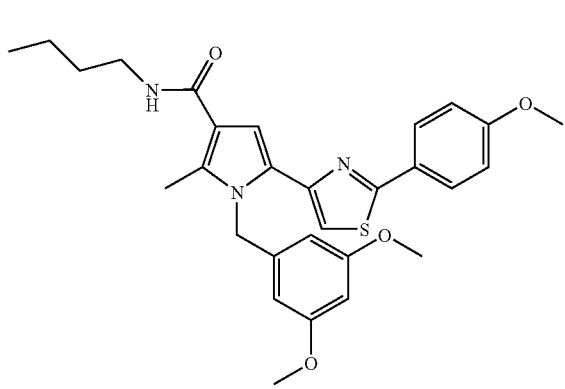

The title compound was obtained using butylamine as $R^1R^2NH$, 3,5-methoxybenzylamine as $R^3$—$(CH_2)_m$—$NH_2$ and 4-methoxyphenyl thioamide as $R^4C(S)NH_2$, MS(ISP) 520.3 (M+H)$^+$.

Example 369

Cyclohexylmethyl-5-[2-(4-hydroxy-phenyl)-thiazol-4-yl]-2-methyl-1H-pyrrole-3-carboxylic acid butylamide

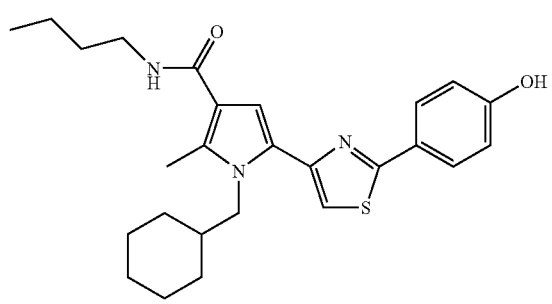

The title compound was obtained using butylamine as $R^1R^2NH$, aminomethylcyclohexane as $R^3$—$(CH_2)_m$—$NH_2$ and 4-hydroxyphenyl thioamide as $R^4C(S)NH_2$, MS(ISP) 452.3 (M+H)$^+$.

Example 370

1-(4-Isopropyl-benzyl)-5-[2-(4-methoxy-phenyl)-thiazol-4-yl]-2-methyl-1H-pyrrole-3-carboxylic acid butylamide

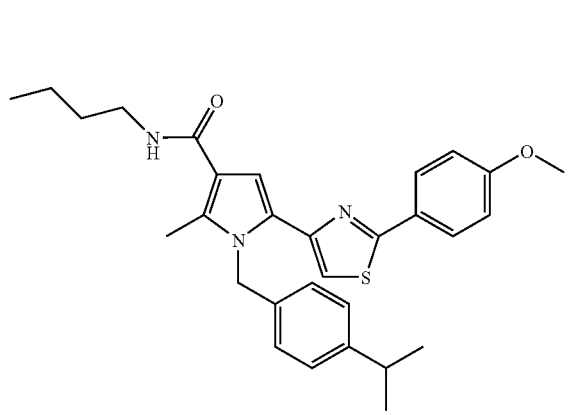

The title compound was obtained using butylamine as $R^1R^2NH$, 4-isopropylbenzylamine as $R^3$—$(CH_2)_m$—$NH_2$ and 4-methoxyphenyl thioamide as $R^4C(S)NH_2$, MS(ISP) 502.3 (M+H)$^+$.

Example 371

5-[2-(4-Methoxy-phenyl)-thiazol-4-yl]-2-methyl-1-pyridin-2-ylmethyl-1H-pyrrole-3-carboxylic acid butylamide

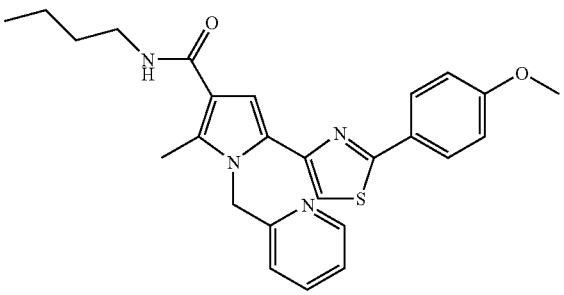

The title compound was obtained using butylamine as $R^1R^2NH$, 2-(aminomethyl)pyridine as $R^3$—$(CH_2)_m$—$NH_2$ and 4-methoxyphenyl thioamide as $R^4C(S)NH_2$, MS(ISP) 461.3 (M+H)$^+$.

Example 372

Cyclohexylmethyl-5-[2-(4-methoxy-phenyl)-thiazol-4-yl]-2-methyl-1H-pyrrole-3-carboxylic acid (4-trifluoromethoxy-phenyl)-amide

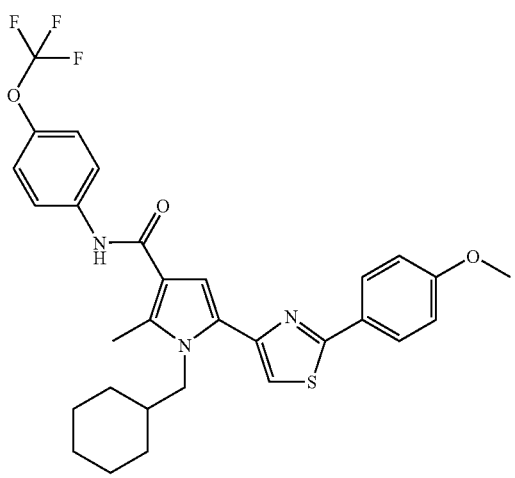

The title compound was obtained using 4-(trifluoromethoxy)aniline as $R^1R^2NH$, aminomethylcyclohexane as $R^3$—$(CH_2)_m$—$NH_2$ and 4-methoxyphenyl thioamide as $R^4C(S)NH_2$. MS(ISP) 569.6 (M+H)$^+$.

Example 373

5-[2-(4-Methoxy-phenyl)-thiazol-4-yl]-2-methyl-1-(3,4,5-trimethoxy-benzyl)-1H-pyrrole-3-carboxylic acid butylamide

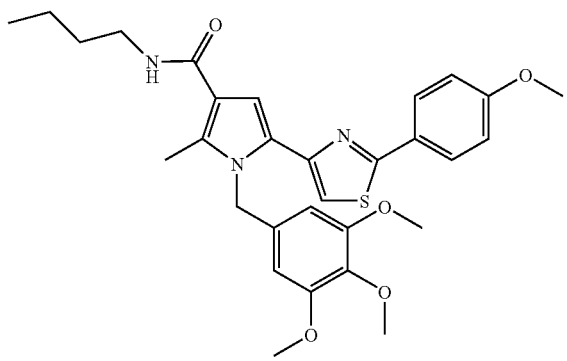

The title compound was obtained using butylamine as $R^1R^2NH$, 3,4,5-trimethoxy-benzylamine as $R^3$—$(CH_2)_m$—$NH_2$ and 4-methoxyphenyl thioamide as $R^4C(S)NH_2$. MS(ISP) 549.2 (M+H)$^+$.

Example 374

5-[2-(4-Methoxy-phenyl)-thiazol-4-yl]-2-methyl-1-(2-p-tolyl-ethyl)-1H-pyrrole-3-carboxylic acid butylamide

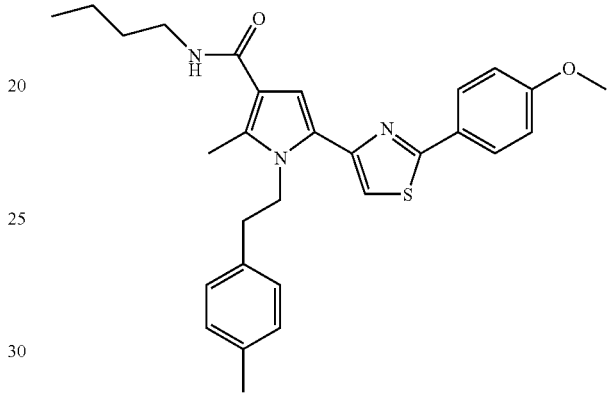

The title compound was obtained using butylamine as $R^1R^2NH$, 2-(p-tolyl)ethylamine as $R^3$—$(CH_2)_m$—$NH_2$ and 4-methoxyphenyl thioamide as $R^4C(S)NH_2$. MS(ISP) 487.6 (M+H)$^+$.

Example 375

Cyclohexylmethyl-5-(2-cyclohexyl-thiazol-4-yl)-2-methyl-1H-pyrrole-3-carboxylic acid butylamide

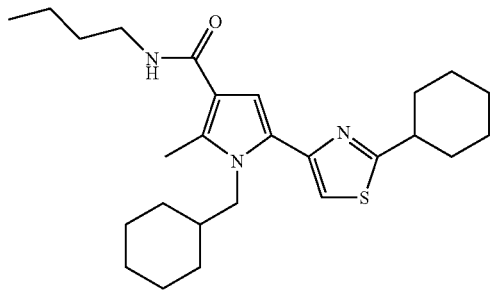

The title compound was obtained using butylamine as $R^1R^2NH$, aminomethylcyclohexane as $R^3$—$(CH_2)_m$—$NH_2$ and cyclohexane carbothioamide as $R^4C(S)NH_2$. MS(ISP) 441.68 (M+H)$^+$.

Example 376

Cyclohexyl-5-[2-(4-methoxy-phenyl)-thiazol-4-yl]-2-methyl-1H-pyrrole-3-carboxylic acid cyclopropyl-methyl-amide

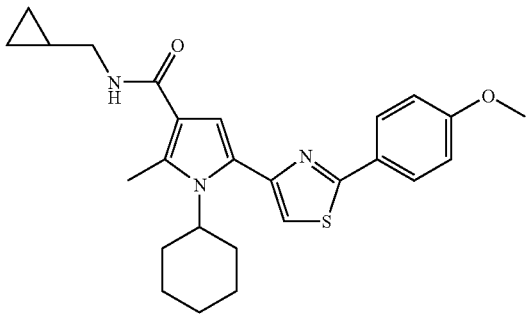

The title compound was obtained using cyclopropylmethylamine as $R^1R^2NH$, cyclohexylamine as $R^3-(CH_2)_m-NH_2$ and 4-methoxyphenyl thioamide as $R^4C(S)NH_2$. MS(ISP) 450.3 (M+H)$^+$.

Example 377 rac -1-(5-Hydroxy-1,3,3-trimethyl-cyclohexylmethyl)-5-[2-(4-methoxy-phenyl)-thiazol-4-yl]-2-methyl-1H-pyrrole-3-carboxylic acid butylamide

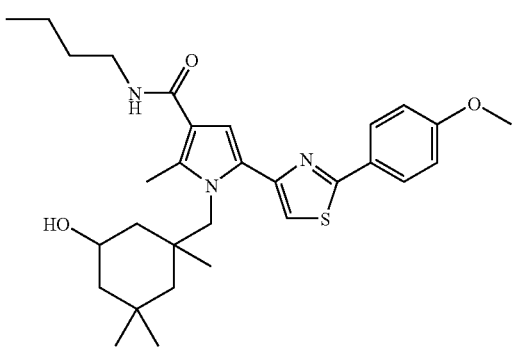

The title compound was obtained using butylamine as $R^1R^2NH$, 3-aminomethyl-3,5,5-trimethyl-cyclohexanol as $R^3-(CH_2)_m-NH_2$ and 4-methoxyphenyl thioamide as $R^4C(S)NH_2$. MS(ISP) 524.4 (M+H)$^+$.

GALENICAL EXAMPLES

Example A

Film coated tablets containing the following ingredients can be manufactured in a conventional manner:

| Ingredients | Per tablet | |
| --- | --- | --- |
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magesium stearate and compressed to yield kernels of 120 or 350 mg respectively. The kernels are lacquered with an aq. solution/suspension of the above mentioned film coat.

Example B

Capsules containing the following ingredients can be manufactured in a conventional manner:

| Ingredients | Per capsule |
| --- | --- |
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
| --- | --- |
| Compound of formula (I) | 3.0 mg |
| Polyethylene glycol 400 | 150.0 mg |
| Acetic acid | q.s. ad pH 5.0 |
| Water for injection solutions | ad 1.0 ml |

The active ingredient is dissolved in a mixture of Polyethylene glycol 400 and water for injection (part). The pH is adjusted to 5.0 by addition of acetic acid. The volume is adjusted to 1.0 ml by addition of the residual amount of water. The solution is filtered, filled into vials using an appropriate overage and sterilized.

What is claimed is:

1. A compound of formula (I):

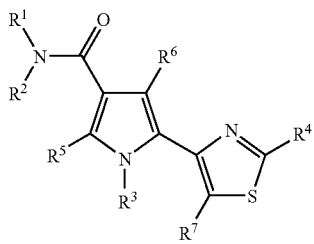

wherein:
(a) $R^1$ and $R^2$ are defined as follows:
  (1) $R^1$ is hydrogen or lower alkyl; and $R^2$ is selected from the group consisting of hydrogen, lower alkyl, lower alkenyl, lower alkoxy-lower alkyl, lower alkoxycarbonylamino, —$(CH_2)_m$—$R^{2a}$ and —NHC(O)—$R^{2a}$; or
  (2) $R^1$ and $R^2$ together with the nitrogen atom to which they are attached form a 5- or 6-membered, saturated heterocyclic ring optionally containing one or two further heteroatom(s) independently selected from the group consisting of: nitrogen, oxygen and sulfur, said heterocyclic ring being optionally mono-, di- or tri-substituted, independently, by a substituent selected from the group consisting of hydroxy, lower alkyl, lower alkoxy, amino, lower alkylamino, fluorinated lower alkyl and fluorinated lower alkoxy;
(b) $R^{2a}$ is selected from the group consisting of:
  (1) cycloalkyl, optionally mono-, di-, tri- or tetra-substituted, independently, by a substituent selected from the group consisting of hydroxy, lower alkyl, lower alkoxy, fluorinated lower alkyl and fluorinated lower alkoxy;
  (2) cycloalkenyl, optionally mono-, di- or tri-substituted, independently, by a substituent selected from the group consisting of hydroxy, lower alkyl, lower alkoxy, fluorinated lower alkyl and fluorinated lower alkoxy;
  (3) a 5- or 6-membered monovalent saturated heterocyclic ring containing one to three heteroatoms independently selected from the group consisting of nitrogen, oxygen and sulfur, said heterocyclic ring being optionally mono-, di- or tri-substituted, independently, by a substituent selected from the group consisting of: hydroxy, lower alkyl, lower alkoxy, amino, lower alkylamino, fluorinated lower alkyl and fluorinated lower alkoxy;
  (4) a 5- or 6-membered monovalent heteroaromatic ring containing one to three heteroatoms independently selected from the group consisting of nitrogen, oxygen and sulfur, said heteroaromatic ring being optionally mono-, di- or tri-substituted, independently, by a substituent selected from the group consisting of hydroxy, lower alkyl, lower alkoxy, halogen, amino, and lower alkylamino; and
  (5) phenyl, which may optionally be mono-, di- or tri-substituted, independently, by a substituent selected from the group consisting of hydroxy, lower alkyl, lower alkoxy, halogen, lower alkylamino, halogenated lower alkyl, halogenated lower alkoxy and nitro;
(c) $R^3$ is selected from the group consisting of: lower alkyl, lower alkenyl, lower alkoxy-lower alkyl, diphenyl-lower alkyl, and —$(CH_2)_n$—$R^{3a}$;
(d) $R^{3a}$ is selected from the group consisting of:
  (1) cycloalkyl, which may optionally be fused to a phenyl ring; or cycloalkyl which may optionally be mono-, di- or tri-substituted, independently, by a substituent selected from the group consisting of hydroxy, lower alkyl, lower alkoxy, fluorinated lower alkyl and fluorinated lower alkoxy;
  (2) cycloalkenyl, which may optionally be mono-, di- or tri-substituted, independently, by a substituent selected from the group consisting of hydroxy, lower alkyl, lower alkoxy, fluorinated lower alkyl and fluorinated lower alkoxy;
  (3) a 5- or 6-membered monovalent saturated heterocyclic ring containing one to three heteroatoms independently selected from the group consisting of nitrogen, oxygen and sulfur, said heterocyclic ring being optionally mono-, di- or tri-substituted, independently, by a substituent selected from the group consisting of hydroxy, lower alkyl, lower alkoxy, amino, lower alkylamino, fluorinated lower alkyl and fluorinated lower alkoxy;
  (4) a 5- or 6-membered monovalent heteroaromatic ring containing one to three heteroatoms independently selected from the group consisting of nitrogen, oxygen and sulfur, said heteroaromatic ring being optionally mono-, di- or tri-substituted, independently, by a substituent selected from the group consisting of hydroxy, lower alkyl, lower alkoxy, halogen, amino and lower alkylamino; and
  (5) phenyl, which may optionally be mono-, di- or tri-substituted, independently, by a substituent selected from the group consisting of hydroxy, lower alkyl, lower alkoxy, halogen, lower alkylamino, halogenated lower alkyl, halogenated lower alkoxy and nitro;
(e) $R^4$ is selected from the group consisting of:
  (1) lower alkyl;
  (2) lower alkoxycarbonyl;
  (3) cycloalkyl, which may optionally be mono-, di- or tri-substituted, independently, by a substituent selected from the group consisting of hydroxy, lower alkyl, lower alkoxy, fluorinated lower alkyl and fluorinated lower alkoxy;
  (4) a 5- or 6-membered monovalent heteroaromatic ring containing one to three heteroatoms independently selected from the group consisting of nitrogen, oxygen and sulfur, said heteroaromatic ring being optionally mono-, di- or tri-substituted, independently, by a substituent selected from the group consisting of hydroxy, lower alkyl, lower alkoxy, halogen, amino, and lower alkylamino;
  (5) phenoxy-lower alkyl, wherein the phenyl moiety may optionally be mono-, di- or tri-substituted, independently, by a substituent selected from the group consisting of hydroxy, lower alkyl, lower alkoxy, halogen, lower alkylamino, halogenated lower alkyl, halogenated lower alkoxy and nitro; and
  (6) phenyl, which may optionally be mono-, di- or tri-substituted, independently, by a substituent selected from the group consisting of hydroxy, lower alkyl, lower alkoxy, halogen, lower alkylamino, halogenated lower alkyl, halogenated lower alkoxy and nitro; or two adjacent substituents of the said phenyl residue together are —O—(CH$_2$)$_p$—O— or —(CH$_2$)$_2$—O—;

(f) R$^5$ and R$^6$ are each independently selected from the group consisting of hydrogen, lower alkyl, halogen and fluorinated methyl;

(g) R$^7$ is hydrogen, lower alkyl or halogen;

(h) m is 0, 1, 2 or 3;

(i) n is 0, 1, 2, 3 or 4;

(j) p is 1, 2 or 3;

or a pharmaceutically acceptable salt thereof.

2. A compound according to claim 1, wherein R$^1$ is hydrogen.

3. A compound according to claim 1, wherein R$^2$ is lower alkyl or —(CH$_2$)$_m$—R$^{2a}$ or —NHC(O)—R$^{2a}$.

4. A compound according to claim 1, wherein R$^2$ is —(CH$^2$)$_m$—R$^{2a}$ or —NHC(O)—R$^{2a}$.

5. A compound according to claim 4, wherein R$^{2a}$ is a cycloalkyl with three to six carbon atoms, which may optionally be mono- or tetra-substituted, independently, by lower alkyl and/or hydroxy.

6. A compound according to claim 4, wherein R$^{2a}$ is cyclohexenyl.

7. A compound according to claim 4, wherein R$^{2a}$ is an unsubstituted 5-membered monovalent saturated heterocyclic ring containing one or two heteroatoms independently selected from the group consisting of nitrogen and oxygen.

8. A compound according to claim 7, wherein R$^{2a}$ is piperidinyl, morpholino or tetrahydrofuranyl.

9. A compound according to claim 4, wherein R$^{2a}$ is a 5- or 6-membered monovalent heterocyclic ring containing one or two heteroatoms independently selected from the group consisting nitrogen and sulfur, said heteroaromatic ring being optionally substituted by lower alkyl.

10. A compound according to claim 9, wherein R$^{2a}$ is pyridinyl, pyrimidinyl, thiazolyl or isoxazolyl, optionally substituted by lower alkyl.

11. A compound according to claim 4, wherein R$^{2a}$ is a phenyl which is optionally mono- or di-substituted, independently, by lower alkoxy, halogen, halogenated lower alkyl, halogenated lower alkoxy or nitro.

12. A compound according to claim 1, wherein m is 0 or 1.

13. A compound according to claim 1, wherein R$^1$ and R$^2$ together with the nitrogen atom to which they are attached form a 5- or 6-membered, saturated heterocyclic ring optionally containing an oxygen atom in the ring.

14. A compound according to claim 13, wherein R$^1$ and R$^2$ together with the nitrogen atom to which they are attached are unsubstituted pyrrolidinyl, piperidinyl or morpholino.

15. A compound according to claim 1, wherein R$^3$ is —(CH$_2$)$_n$—R$^{3a}$.

16. A compound according to claim 15, wherein R$^{3a}$ is cycloalkyl fused to a phenyl ring.

17. A compound according to claim 15, wherein R$^{3a}$ is an unsubstituted cycloalkyl with five or six carbon atoms.

18. A compound according to claim 15, wherein R$^{3a}$ is a 5- or 6-membered heterocyclic ring containing one or two heteroatoms independently selected from the group consisting of nitrogen and oxygen, said heterocyclic ring being optionally mono-, di- or tri-substituted, independently, by lower alkyl.

19. A compound according to claim 15, wherein R$^{3a}$ is a 5- or 6-membered heteroaromatic ring containing one heteroatom selected from the group consisting of nitrogen, oxygen and sulfur, said heteroaromatic ring being optionally mono-substituted by lower alkyl.

20. A compound according to claim 15, wherein R$^{3a}$ is phenyl optionally mono- or di-substituted, independently, by a substituent selected from the group consisting of hydroxy, lower alkyl, lower alkoxy, halogen, halogenated lower alkyl, halogenated lower alkoxy and nitro.

21. A compound according to claim 15, wherein n is 1 or 2.

22. A compound according to claim 1, wherein R$^4$ is unsubstituted cyclohexyl.

23. A compound according to claim 1, wherein R$^4$ is a 5- or 6-membered heteroaromatic ring containing one or two heteroatoms independently selected from the group consisting of nitrogen and sulfur, said heteroaromatic ring being optionally mono-substituted by lower alkyl.

24. A compound according to claim 1, wherein R$^4$ is phenyl mono- or di-substituted, independently, by a substituent selected from the group consisting of hydroxy, lower alkyl, lower alkoxy, halogen, halogenated lower alkyl, halogenated lower alkoxy and nitro.

25. A compound according to claim 1, wherein R$^4$ is phenyl with two adjacent substituents which together are —O—(CH$_2$)—O— or —(CH$_2$)$_2$—O—.

26. A compound according to claim 1, selected from the group consisting of:

(a) 1-Cyclohexylmethyl-5-[2-(4-methoxy-phenyl)-thiazol-4-yl]-2-methyl-1H-pyrrole-3-carboxylic acid butylamide, (b) 1-(4-Methoxy-benzyl)-5-[2-(4-methoxy-phenyl)-thiazol-4-yl]-2-methyl-1H-pyrrole-3-carboxylic acid butylamide, (c) rac-1-Cyclohexylmethyl-5-[2-(4-methoxy-phenyl)-thiazol-4-yl]-2-methyl-1H-pyrrole-3-carboxylic acid sec-butylamide, (d) rac-1-Cyclohexylmethyl-5-[2-(4-methoxy-phenoxymethyl)-thiazol-4-yl]-2-methyl-1H-pyrrole-3-carboxylic acid sec-butylamide, (e) 1-Cyclohexylmethyl-5-[2-(4-methoxy-phenyl)-thiazol-4-yl]-2-methyl-1H-pyrrole-3-carboxylic acid isobutylamide, (f) 1-Furan-2-ylmethyl-5-[2-(4-methoxy-phenyl)-thiazol-4-yl]-2-methyl-1H-pyrrole-3-carboxylic acid isobutylamide, (g) 1-(4-Methoxy-benzyl)-5-[2-(4-methoxy-phenyl)-thiazol-4-yl]-2-methyl-1H-pyrrole-3-carboxylic acid isobutylamide, (h) 1-Cyclohexylmethyl-5-[2-(4-methoxy-phenyl)-thiazol-4-yl]-2-methyl-1H-pyrrole-3-carboxylic acid allylamide, (i) 1-Cyclohexylmethyl-5-[2-(4-methoxy-phenyl)-thiazol-4-yl]-2-methyl-1H-pyrrole-3-carboxylic acid cyclohexylmethyl-amide, (j) 1-Cyclohexylmethyl-2-methyl-5-(2-pyrazin-2-yl-thiazol-4-yl)-1H-pyrrole-3-carboxylic acid cyclohexylmethyl-amide, and (k) pharmaceutically acceptable salt thereof.

27. A compound according to claim 1, selected from the group consisting of:

(a) 1-(4-Methoxy-benzyl)-5-[2-(4-methoxy-phenyl)-thiazol-4-yl]-2-methyl-1H-pyrrole-3-carboxylic acid cyclohexylmethyl-amide, (b) 5-[2-(4-Methoxy-phenoxymethyl)-thiazol-4-yl]-1-(3-methoxy-propyl)-2-methyl-1H-pyrrole-3-carboxylic acid cyclohexylmethyl-amide, (c) 4-[1-[2-(3,4-Dimethoxy-phenyl)-ethyl]-4-(3-methoxy-propylcarbamoyl)-5-methyl-1H-pyrrol-2-yl]-thiazole-2-carboxylic acid ethyl ester, (d) 1-Cyclohexylmethyl-5-[2-(4-methoxy-phenyl)-thiazol-4-yl]-2-methyl-1H-pyrrole-3-carboxylic acid piperidin-1-ylamide,
(e) N'-{1-Cyclohexylmethyl-5-[2-(4-methoxy-phenyl)-thiazol-4-yl]-2-methyl-1H-pyrrole-3-carbonyl}-hydrazinecarboxylic acid ethyl ester,
(f) rac-1-Cyclohexylmethyl-5-[2-(4-methoxy-phenyl)-thiazol-4-yl]-2-methyl-1H-pyrrole-3-carboxylic acid sec-butylamide,
(g) {1-Cyclohexylmethyl-5-[2-(4-methoxy-phenyl)-thiazol-4-yl]-2-methyl-1H-pyrrol-3-yl}-piperidin-1-yl-methanone,
(h) 1-Cyclohexylmethyl-5-[2-(4-methoxy-phenyl)-thiazol-4-yl]-2-methyl-1H-pyrrole-3-carboxylic acid phenylamide,
(i) 1-Cyclohexylmethyl-5-[2-(4-methoxy-phenyl)-thiazol-4-yl]-2-methyl-1H-pyrrole-3-carboxylic acid pyrimidin-2-ylamide,
(j) rac-1-Cyclohexylmethyl-5-[2-(4-methoxy-phenyl)-thiazol-4-yl]-2-methyl-1H-pyrrole-3-carboxylic acid (5-hydroxy-2,2,6-trimethyl-cyclohexylmethyl)-amide, and
(k) pharmaceutically acceptable salt thereof.

28. A compound according to claim 1, selected from the group consisting of:
(a) 5-[2-(4-Methoxy-phenyl)-thiazol-4-yl]-2-methyl-1-(3-trifluoromethoxy-benzyl)-1H-pyrrole-3-carboxylic acid butylamide,
(b) 1-Benzyl-5-[2-(4-methoxy-phenyl)-thiazol-4-yl]-2-methyl-1H-pyrrole-3-carboxylic acid butylamide,
(c) {1-Cyclohexylmethyl-5-[2-(4-methoxy-phenyl)-thiazol-4-yl]-2-methyl-1H-pyrrol-3-yl}-pyrrolidin-1-yl-methanone,
(d) 1-Cyclohexylmethyl-5-[2-(3,4-dimethoxy-phenyl)-thiazol-4-yl]-2-methyl-1H-pyrrole-3-carboxylic acid butylamide,
(e) 1-Cyclohexylmethyl-5-[2-(3-methoxy-phenyl)-thiazol-4-yl]-2-methyl-1H-pyrrole-3-carboxylic acid butylamide,
(f) 5-(2-Benzo[1,3]dioxol-5-yl-thiazol-4-yl)-1-cyclohexylmethyl-2-methyl-1H-pyrrole-3-carboxylic acid butylamide,
(g) 1-Cyclohexylmethyl-5-[2-(4-fluoro-phenyl)-thiazol-4-yl]-2-methyl-1H-pyrrole-3-carboxylic acid butylamide,
(h) 1-Cyclohexylmethyl-5-[2-(2-fluoro-phenyl)-thiazol-4-yl]-2-methyl-1H-pyrrole-3-carboxylic acid butylamide,
(i) 1-Cyclohexylmethyl-2-methyl-5-[2-(4-trifluoromethoxy-phenyl)-thiazol-4-yl]-1H-pyrrole-3-carboxylic acid butylamide,
(j) 1-Cyclohexylmethyl-5-[2-(3,5-dimethoxy-phenyl)-thiazol-4-yl]-2-methyl-1H-pyrrole-3-carboxylic acid butylamide,
(k) pharmaceutically acceptable salt thereof.

29. A compound according to claim 1, selected from the group consisting of:
(a) 1-Cyclohexylmethyl-2-methyl-5-(2-m-tolyl-thiazol-4-yl)-1H-pyrrole-3-carboxylic acid butylamide,
(b) 1-Cyclohexylmethyl-2-methyl-5-(2'-methyl-[2,4']bithiazolyl-4-yl)-1H-pyrrole-3-carboxylic acid butylamide,
(c) 1-Cyclohexylmethyl-5-[2-(4-ethyl-phenyl)-thiazol-4-yl]-2-methyl-1H-pyrrole-3-carboxylic acid butylamide,
(d) 5-[2-(4-Chloro-phenyl)-thiazol-4-yl]-1-cyclohexylmethyl-2-methyl-1H-pyrrole-3-carboxylic acid butylamide,
(e) 5-[2-(4-tert-Butyl-phenyl)-thiazol-4-yl]-1-cyclohexylmethyl-2-methyl-1H-pyrrole-3-carboxylic acid butylamide,
(f) 1-Cyclohexylmethyl-5-[2-(2,3-dihydro-benzofuran-5-yl)-thiazol-4-yl]-2-methyl-1H-pyrrole-3-carboxylic acid butylamide,
(g) 1-Cyclohexylmethyl-2-methyl-5-(2-p-tolyl-thiazol-4-yl)-1H-pyrrole-3-carboxylic acid butylamide,
(h) 1-Cyclohexylmethyl-5-[2-(6-methoxy-pyridin-3-yl)-thiazol-4-yl]-2-methyl-1H-pyrrole-3-carboxylic acid butylamide,
(i) 1-Cyclohexylmethyl-5-[2-(2,4-dichloro-phenyl)-thiazol-4-yl]-2-methyl-1H-pyrrole-3-carboxylic acid butylamide,
(j) 1-Cyclohexylmethyl-2-methyl-5-[2-(4-nitro-phenyl)-thiazol-4-yl]-1H-pyrrole-3-carboxylic acid butylamide,
(k) pharmaceutically acceptable salt thereof.

30. A compound according to claim 1, selected from the group consisting of:
(a) 1-Cyclohexylmethyl-5-[2-(4-methoxy-phenyl)-thiazol-4-yl]-2-methyl-1H-pyrrole-3-carboxylic acid pentylamide,
(b) 1-Cyclohexylmethyl-5-[2-(4-methoxy-phenyl)-thiazol-4-yl]-2-methyl-1H-pyrrole-3-carboxylic acid propylamide,
(c) 1-Cyclohexylmethyl-5-[2-(4-methoxy-phenyl)-thiazol-4-yl]-2-methyl-1H-pyrrole-3-carboxylic acid cyclohexylamide,
(d) 1-Cyclohexylmethyl-5-[2-(4-methoxy-phenyl)-thiazol-4-yl]-2-methyl-1H-pyrrole-3-carboxylic acid cyclopentylamide,
(e) 1-Cyclohexylmethyl-5-[2-(4-methoxy-phenyl)-thiazol-4-yl]-2-methyl-1H-pyrrole-3-carboxylic acid cyclopropylamide,
(f) 1-Cyclohexylmethyl-5-[2-(4-methoxy-phenyl)-thiazol-4-yl]-2-methyl-1H-pyrrole-3-carboxylic acid cyclobutylamide,
(g) (trans) rac-1-Cyclohexylmethyl-5-[2-(4-methoxy-phenyl)-thiazol-4-yl]-2-methyl-1H-pyrrole-3-carboxylic acid (2-hydroxy-cyclopentyl)-amide, and
(h) pharmaceutically acceptable salt thereof.

31. A compound according to claim 1, selected from the group consisting of:
(a) 1-(4-Chloro-benzyl)-5-[2-(4-methoxy-phenyl)-thiazol-4-yl]-2-methyl-1H-pyrrole-3-carboxylic acid butylamide,
(b) 1-(3,4-Dichloro-benzyl)-5-[2-(4-methoxy-phenyl)-thiazol-4-yl]-2-methyl-1H-pyrrole-3-carboxylic acid butylamide,
(c) 1-(3,4-Dimethyl-benzyl)-5-[2-(4-methoxy-phenyl)-thiazol-4-yl]-2-methyl-1H-pyrrole-3-carboxylic acid butylamide,
(d) 1-(3,4-Dimethoxy-benzyl)-5-[2-(4-methoxy-phenyl)-thiazol-4-yl]-2-methyl-1H-pyrrole-3-carboxylic acid butylamide,
(e) 1-Cyclohexylmethyl-5-[2-(4-hydroxy-phenyl)-thiazol-4-yl]-2-methyl-1H-pyrrole-3-carboxylic acid butylamide,
(f) 1-(4-Isopropyl-benzyl)-5-[2-(4-methoxy-phenyl)-thiazol-4-yl]-2-methyl-1H-pyrrole-3-carboxylic acid butylamide,
(g) 5-[2-(4-Methoxy-phenyl)-thiazol-4-yl]-2-methyl-1-pyridin-2-ylmethyl-1H-pyrrole-3-carboxylic acid butylamide,
(h) 1-Cyclohexylmethyl-5-(2-cyclohexyl-thiazol-4-yl)-2-methyl-1H-pyrrole-3-carboxylic acid butylamide, and
(i) pharmaceutically acceptable salt thereof.

32. A process for the manufacture of compounds of formula (I) as defined in claim 1, which process comprises reaction of an enamine of formula A:

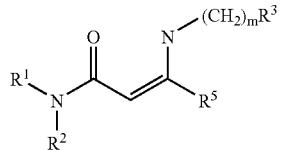

wherein $R^1$, $R^2$, $R^3$, $R^5$ and m are as defined claim 1; with an alfa-bromoketone of formula B:

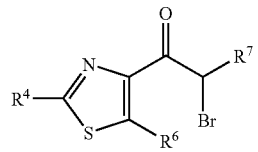

wherein $R^4$, $R^6$ and $R^7$ are as defined claim 1.

33. A compound manufactured by a process according to claim 32.

34. A pharmaceutical composition comprising a therapeutically effective amount of a compound of claim 1 and a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 7,135,488 B2 | Page 1 of 1 |
| APPLICATION NO. | : 10/743403 | |
| DATED | : November 14, 2006 | |
| INVENTOR(S) | : Wolfgang Guba et al. | |

It is certified that error appears in the above-identified patent and that said Letters Patent is hereby corrected as shown below:

On Title Page, (75) Inventors: "Wolfgang Guba, Muellheim (DE);" should be
-- Wolfgang Guba, Muellheim (DE): --

Signed and Sealed this

Twenty-first Day of August, 2007

JON W. DUDAS
*Director of the United States Patent and Trademark Office*